US010220088B2

(12) United States Patent
Hess et al.

(10) Patent No.: US 10,220,088 B2
(45) Date of Patent: Mar. 5, 2019

(54) FOWL ADENOVIRUS VACCINE

(71) Applicant: VETERINARMEDIZINISCHE UNIVERSITÄT WIEN, Vienna (AT)

(72) Inventors: Michael Hess, Klosterneuburg (AT); Anna Schachner, Vienna (AT); Ana Marek, Vienna (AT); Barbara Jaskulska, Vienna (AT)

(73) Assignee: VETERINARMEDIZINISCHE UNIVERSITÄT WIEN, Vienna (AT)

( * ) Notice: Subject to any disclaimer, the term of this patent is extended or adjusted under 35 U.S.C. 154(b) by 0 days.

(21) Appl. No.: 14/913,204

(22) PCT Filed: Aug. 19, 2014

(86) PCT No.: PCT/EP2014/067647
§ 371 (c)(1),
(2) Date: Feb. 19, 2016

(87) PCT Pub. No.: WO2015/024929
PCT Pub. Date: Feb. 26, 2015

(65) Prior Publication Data
US 2016/0199484 A1 Jul. 14, 2016

(30) Foreign Application Priority Data
Aug. 19, 2013 (EP) .................................. 13180860

(51) Int. Cl.
*A61K 39/235* (2006.01)
*A61K 39/39* (2006.01)
*C12N 7/00* (2006.01)
*A61K 39/12* (2006.01)
*A61K 39/00* (2006.01)

(52) U.S. Cl.
CPC ............ *A61K 39/235* (2013.01); *A61K 39/12* (2013.01); *A61K 39/39* (2013.01); *C12N 7/00* (2013.01); *A61K 2039/552* (2013.01); *A61K 2039/5555* (2013.01); *A61K 2039/55505* (2013.01); *A61K 2039/55544* (2013.01); *A61K 2039/55555* (2013.01); *A61K 2039/55566* (2013.01); *A61K 2039/55577* (2013.01); *C12N 2710/10234* (2013.01); *C12N 2710/10271* (2013.01)

(58) Field of Classification Search
None
See application file for complete search history.

(56) References Cited

U.S. PATENT DOCUMENTS

| 2007/0105193 A1* | 5/2007 | Vilalta | A61K 39/215 |
| | | | 435/69.1 |
| 2011/0165224 A1* | 7/2011 | Gomis | A61K 39/235 |
| | | | 424/450 |
| 2016/0199484 A1* | 7/2016 | Hess | A61K 39/235 |
| | | | 424/186.1 |

FOREIGN PATENT DOCUMENTS

| EP | 2839841 | 2/2015 |
| JP | 2016-528270 | 9/1916 |
| WO | WO 2003/039593 | 5/2003 |
| WO | WO 2004/078977 | * 9/2004 |
| WO | WO 2015/024929 | 2/2015 |

OTHER PUBLICATIONS

Sequence alignment of SEQ ID No. 31 with UniProt database access No. H8WQW9_ADEN by Marek et al in Vet Microbiol 2012 vol. 156 pp. 411-417.*
Sequence alignment of SEQ ID No. 37 with UniProt database access No. SPIK2_ADEG1 by Chiocca et al in J of Virology 1996 vol. 79 pp. 2939-2949.*
Sequence alignment of SEQ ID No. 39 with UniProt database access No. Q77VH5 by Ojkic et al in J of General Virology 2000 vol. 81 ppl 833-1837.*
Sequence alignment of SEQ ID No. 40 with UniProt database access No. E9KLB3_9ADEN by Grgic et al in Virus Research 2011 vol. 156 pp. 91-97.*
Sequence alignment of SEQ ID No. 41 with UniProt database access No. H8WR01_9ADEN by Marek et al in Vet Micribiol 2012 vol. 156 pp. 411-417.*
Marek et al. (Veterinary Microbiology. 2013; 166: 250-256).*
Schachner et al. "Fowl adenovirus-induced diseases and strategies for their control—a review on the current global situation." Avian Pathology (2017): 1-16.*
Harrach et al. (Virology. 1997; 229: 302-306).*
Raue and Hess (Journal of Virological Methods. 1998; 73: 211-217).*
Grafi et al. "Fowl aviadenovirus serotype 1 confirmed as the aetiological agent of gizzard erotions in replacement pullets and layer flocks in Great Britain by laboratory and in vivo studies". Avian Pathology (2017): 1-10).*
Alvarado et al., "Genetic Characterization, Pathogenicity, and Protection Studies with an Avian Adenovirus Isolate Associated with Inclusion Body Hepatitis", *Avian Diseases*, 51: 27-32, 2007.
Anjum, "Experimental Transmission of Hydropericardium Syndrome and Protection Against itin Commercial Broiler Chickens", *Avian Pathology*, 19: 655-660, 1990.
European Office Communication issued in Corresponding European Application No. 13180860.2, dated May 8, 2014.
Fingerut et al., "A subunit vaccine against the adenovirus egg-drop syndrome using part of its fiber protein", *Vaccine*, 21: 2761-66, 2003.

(Continued)

*Primary Examiner* — Shanon A. Foley
(74) *Attorney, Agent, or Firm* — Norton Rose Fulbright US LLP

(57) ABSTRACT

Disclosed is a vaccine comprising a fiber protein, selected from fiber-2 protein of Fowl Adenovirus C (FAdV-C), fiber-2 protein of Fowl Adenovirus A (FAdV-A), fiber protein of Fowl Adenovirus B, D and E (FAdV-B, FAdV-D and FAdV-E), or an immunogenic fragment thereof for use in preventing hepatitis-hydropericardium Syndrome (HHS) or inclusion body hepatitis (IBH) or Gizzard Erosion (GE) in birds, preferably in poultry, especially in broilers.

Figure 1:
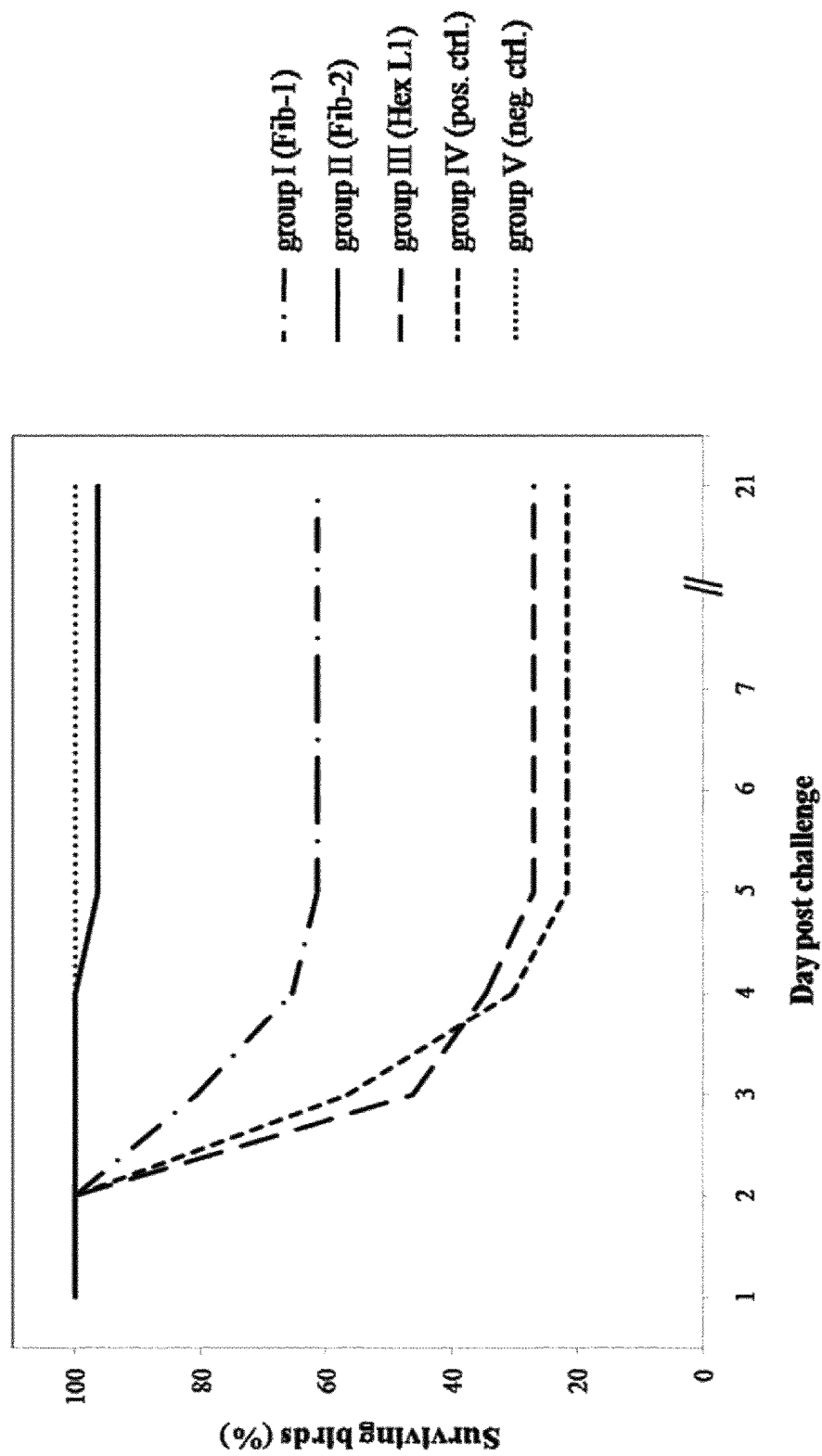

23 Claims, 17 Drawing Sheets
Specification includes a Sequence Listing.

(56) References Cited

OTHER PUBLICATIONS

Grgic et al., "Pathogenicity and Cytokine Gene Expression Pattern of a Serotype 4 Fowl Adenovirus Isolate", PLoS ONE, 8(10): e77601, 2013.
Griffin et al., "Coding potential and transcript analysis of fowl adenovirus 4: insight into upstream ORFs as common sequence features in adenoviral transcripts", Journal of General Virology, 92: 1260-1272, 2011.
Gunes et al., "Realtime PCR assay for universal detection and quantitation of all five species of fowl adenoviruses (FAdVA to FAdVE)", Journal of Virological Methods, 183: 147-153, 2012.
Hess et al., "The Avian Adenovirus Penton: Two Fibres and One Base", J. Mol. Biol., 252: 379-385, 1995.
Huo et al., "Prediction and Identification of T Cell Epitopes in the H5N1 Influenza Virus Nucleoprotein in Chicken", PLoS ONE, 7(6): e39344, 2012.
International Search Report and Written Opinion issued in PCT/EP2014/067647, dated Mar. 25, 2015.
Marek et al., "Two fiber genes of nearly equal lengths are a common and distinctive feature of Fowl adenovirus C members", Veterinary Microbiology, 156: 411-417, 2012.
Mazaheri et al., "Some strains of serotype 4 fowl adenoviruses cause inclusion body hepatitis and hydropericardium syndrome in chickens", Avian Pathology, 27: 269-276, 1998.
Meulemans et al., "Polymerase chain reaction combined with restriction enzyme analysis for detection and differentiation of fowl adenoviruses", Avian Pathology, 30: 655-660, 2001.
Schachner et al., "Recombinant FAdV-4 fiber-2 protein protects chickens against hepatitis-hydropericardium syndrome (HHS)", Vaccine, 32: 1086-1092, 2014.
Schat et al., Cell-Culture Methods, chapter 43, 2008.
Schonewille et al., "Specific-Pathogen-Free Chickens Vaccinated with a Live FAdV-4 Vaccine Are Fully Protected Against a Severe Challenge Even in the Absence of Neutralizing Antibodies", Avian Diseases, 54: 905-910, 2010.
Shah et al., "A subunit vaccine against hydropericardium syndrome using adenovirus penton capsid protein", Vaccine, 30: 7153-56, 2012.
Song et al., "Human adenovirus type 41 possesses different amount of short and long fibers in the virion", Virology, 432: 336-342, 2012.
Tan et al., "Defining CAR as a cellular receptor for the avian adenovirus CELO using a genetic analysis of the two viral fibre proteins", Journal of General Virology, 82: 1465-72, 2001.
Wallny et al., "Peptide motifs of the single dominantly expressed class I molecule explain the striking MHC-determined response to Rous sarcoma virus in chickens", PNAS, 103(5): 1434-39, 2006.
Chiocca et al., "The Complete DNA Sequence and Genomic Organization of the Avian Adenovirus CELO", Journal of Virology, vol. 70, No. 5, (1996), pp. 2939-2949.
Chroboczek et al., "Adenovirus Fiber", Current Topics in Microbiology and Immunology, 199, (1995), pp. 163-200.
Gahery-Segard et al., "Immune Response to Recombinant Capsid Proteins of Adenovirus in Humans: Antifiber and Anti-Penton Base Antibodies Have a Synergistic Effect on Neutralizing Activity", Journal of Virology, vol. 72, No. 3 (1998), pp. 2388-2397.

Gelderblom et al., "The Fibers of Fowl Adenoviruses", Archives of Virology, Vo. 72, No. 4, (1982), pp. 289-298.
Harrach et al., "Family Adenoviridae", Virus Taxonomy: Ninth Report of the International Committee on Taxonomy of Viruses, (2012), pp. 125-141.
Hong et al., "The 100K-Chaperone Protein from Adenovirus Serotype 2 (Subgroup C) Assists in Trimerization and Nuclear Localization of Hexons from Subgroups C and B Adenoviruses", Journal of Molecular Biology, vol. 352, (2005), pp. 125-138.
Norrby, "The Structural and Functional Diversity of Adenovirus Capsid Components", Journal of General Virology, vol. 5, No. 2, (1969), pp. 221-236.
Ojkic et al., "The Complete Nucleotide Sequence of Fowl Adenovirus Type 8", Journal of General Virology, vol. 81, (2000), pp. 1833-1837.
Guardad-Calvo et al., "Structure of the C-terminal head domain long fiber," Journal of General Virology, (2007), 88:2407-2416. of the fowl adenovirus type 1.
Office Action issued in Corresponding Japanese Patent Application No. 2016-535460, dated Apr. 10, 2018.
Choi et al., "Epidemiological investigation of outbreaks of fowl adenovirus infection in commercial chickens in Korea," Poultry Science, 91(1):2502-2506, (2012).
Farkas et al., "Completion of the reptilian lineage of genome analysis of snake adenovirus type 1, a representative within the novel genus Atadenovirus," Virus Research, 132(1):132-139, (2008).
Lauring et al., "Rationalizing the development of live attenuated virus vaccines," Nature Biotechnology, 28(6): 573-579, (2010).
Mareck et al., "Classification of fowl adenoviruses by use of phylogenetic analysis and high-resolution melting-curve analysis of the hexon L1 gene region," Journal of Virological Methods, 170(1):147-154, (2010).
McFerran et al., "Avian adenoviruses," Revue Scientifique et Technique—Office International Despizooties/Scientific and Technoical Review, 19(2):589-601, (2000).
Nakamura et al., "Pathologic Study of Specific-Pathogen-Free Chicks and Hens Inoculated with Adenovirus Isolated from Hydropericardium Syndrome," Avian Diseases, 43(3):414, (1999).
Office Action issued in corresponding European Application No. 14793022.6, dated Oct. 19, 2017.
Schade et al., "Adenoviral Gizzard Erosion in Broiler Chickens in Germany," Avian Diseases, 57(1): 159-163, (2013).
Steer et al., "Application of high-resolution melting curve analysis for typing of fowl adenoviruses in field cases of inclusion body hepatitis," Australian Veterinary Journal, 89(5): 184-192, (2011).
U.S. National Institutes of Health NIH website, downloaded from: http://www.niaid.nih.gov/topics/vaccines/Pages/typesVaccines.aspx, last updated on Apr. 3, 2012.
Uniprot: "Alignment FAdV Fiber 2," 2017, Retrieved from the Internet URL: http://www.uniprot.org/align/A20140920A7434721E10EE6586998A056CCD0537E009819V.
Grgic et al., "Pathogenicity and complete genome sequence of a fowl adenovirus serotype 8 isolate", Virus Research, 156 (2011), pp. 91-97.
Japanese Office Action dated Dec. 4, 2018, issued in corresponding Application No. JP 2016-535459.

* cited by examiner

| group | description | day of life=study day | | | | | | | | | | | | | | | | | | | | | | | | | | |
|---|---|---|---|---|---|---|---|---|---|---|---|---|---|---|---|---|---|---|---|---|---|---|---|---|---|---|---|---|
| | | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 |
| I (n=10) | vacc. w/ FAdV-D Fib SR48 and chall w/ FAdV-D 08/18926 | V | | | | | | | | | | | | | | | | | | | | C | | | | | | | N |
| II (n=10) | challenge control FAdV-D 08/18926 | A | | | | | | | | | | | | | | | | | | | | C | | | | | | | N |
| III (n=10) | vacc. w/ FAdV-E Fib YR36 and chall w/ FAdV-E 08/17832 | V | | | | | | | | | | | | | | | | | | | | C | | | | | | | N |
| IV (n=10) | challenge control FAdV-E 08/17832 | A | | | | | | | | | | | | | | | | | | | | C | | | | | | | N |
| V (n=10) | negative control | A | | | | | | | | | | | | | | | | | | | | A | | | | | | | N |

V = vaccination.
C = challenge.
A = administration of placebo (mock-injection).
N = necropsy of all birds, including cloacal swab and liver tissue sampling for histology and rt PCR.

Fig. 6

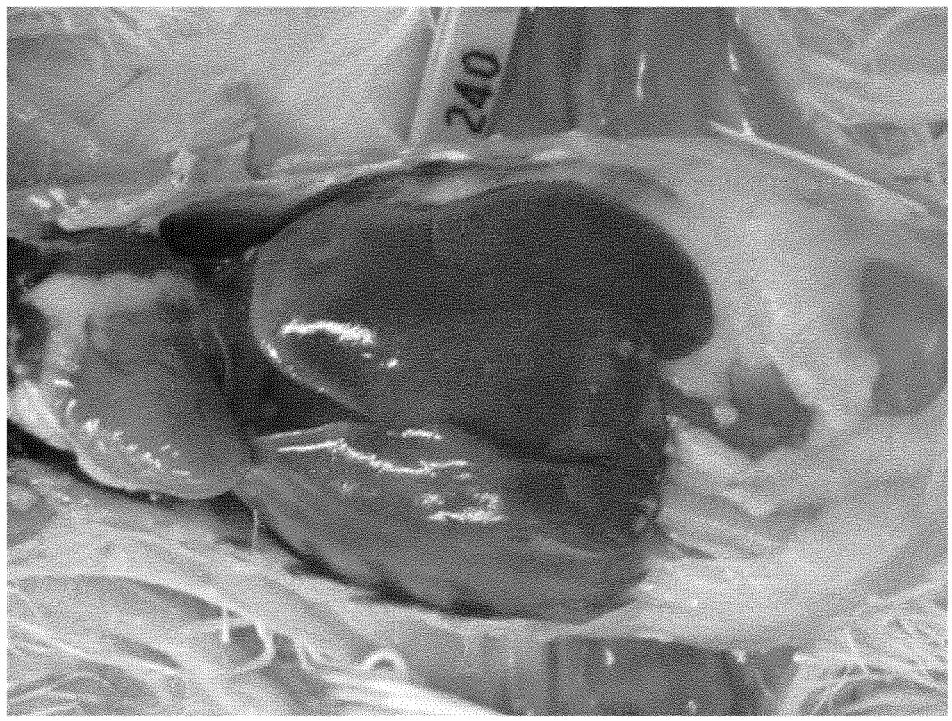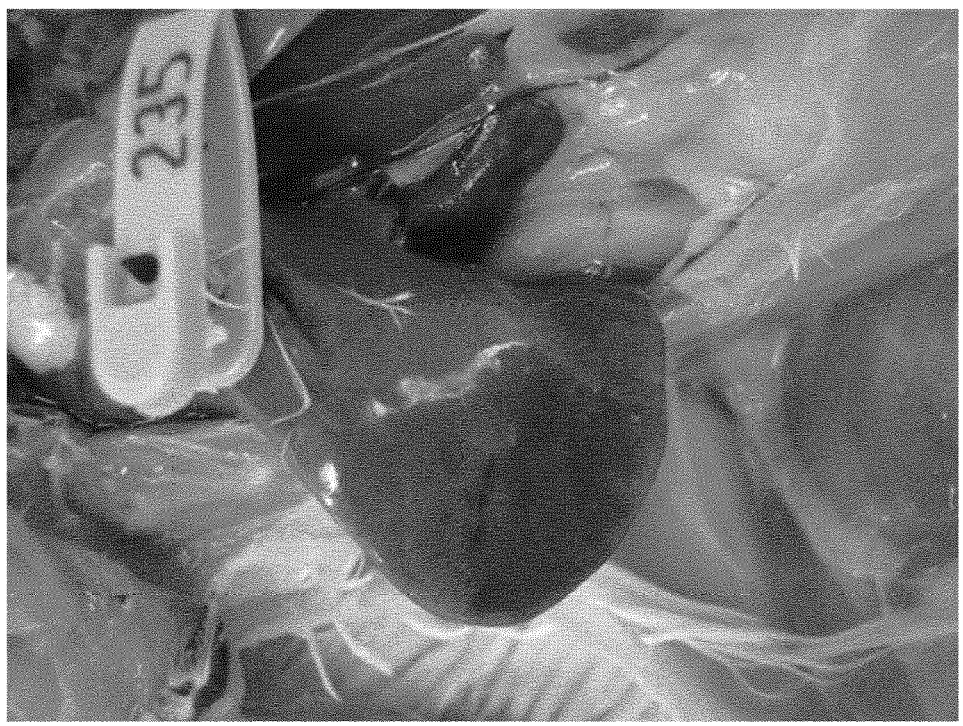
Fig. 7A

Fig. 7B

FOWL ADENOVIRUS VACCINE

CROSS-REFERENCE TO RELATED APPLICATIONS

This application is a national phase application under 35 U.S.C. § 371 of International Application No. PCT/EP2014/067647 filed 19 Aug. 2014, which claims priority to European Patent Application No. 13180860.2 filed 19 Aug. 2013. The entire contents of each of the above-referenced disclosures is specifically incorporated by reference herein without disclaimer.

The invention relates to methods and compositions (formulations) for the prevention of hepatitis-hydropericardium syndrome (HHS), inclusion body hepatitis (IBH) and gizzard erosion (GE).

HHS is an infectious disease of chickens, characterized by high mortality and severe economic losses, mainly in broiler flocks. After first reports of the disease in 1987 from Pakistan, outbreaks have been documented mainly in Asian countries, Central and South America. Initial assumptions pointed towards the involvement of an unknown agent in addition to an adenovirus which was later revised by reproducing the disease in specific pathogen-free birds following oral infection with virulent fowl adenovirus (FAdV) species C strains.

The viral inclusion body hepatitis (IBH) is an adenovirus infection which is very similar to HHS, except that the viruses leading to IBH are less virulent. Both diseases are characterized by haemorrhages and dystrophic necrobiotic changes in the liver and kidneys, accompanied by intranuclear inclusion bodies. A characteristic pathological finding is the enlarged, dystrophic liver with yellowish colour and crumbly texture. More rarely, macroscopically visible necrotic foci could be detected in the liver. The kidneys are enlarged, pale and mottled with multiple haemorrhages. Sometimes, the skin is icteric. Often ecchymoses and striated haemorrhages in skeletal muscles are observed. Microscopically, extensive dystrophic changes and necroses of liver parenchyma are detected. In the nuclei of hepatocytes, basophilic or eosinophilic inclusion bodies are detected.

The diagnosis is based upon the typical gross lesions and the history records. In a number of cases, the dominant lesions are the prominent mottled or striated haemorrhages of the liver. In addition to those lesions HHS is characterized by a yellowish straw colored fluid in the hydropericard. Outbreaks are encountered primarily in meat type chickens, most commonly at the age of 1-8 weeks. In comparison to HHS various serotypes, predominantly seroytpes 2-11, are reported in the cause of IBH outbreaks.

Clinical signs can be observed only several hours prior to death occurrence. They consist in pale comb and wattles, depression and apathy. IBH is characterized by a sudden onset and a sharply increased death rate that reaches peak values by the 3rd-4th day and returns back within the normal range by the 6th-7th day. The total death rate is usually under 10% but can attain up to 30%, with up to 70% in case of HHS.

Gizzard erosion (GE) is characterized by discoloration and erosion of the gizzard koilin layer and is confirmed by histological investigations documenting adenoviral intranuclear inclusion bodies in gizzard epithelial cells and/or isolation of FAdV-1 from affected gizzard samples. The disease could influence the performance of a broiler flock with influence on body weight and condemnation rate at slaughter house.

Fowl adenoviruses are resistant to many environmental factors and could be easily transmitted by a mechanical route. Sick chickens carry the virus in their excreta, kidneys, tracheal and nasal mucosa. Transmission of adenoviruses occurs vertically by breeder eggs. With regard to preventing and control a FAdV infection, protection of the breeders, in addition to broilers, has a high priority. The most important steps in HHS, IBH and GE prevention is the control of vertical transmission. Furthermore, the access of wild birds should be prevented as they are potential carriers and distributors of the virus. There are some vaccines against HHS and IBH but none against GE. There is no effective treatment against any of these diseases.

Fowl adenoviruses are members of the family Adenoviridae and genus Aviadenovirus. Five species (FAdV-A to FAdV-E) and 12 serotypes (FAdV-1 to 8a and 8b to 11), identified by cross-neutralization test, have so far been recognized.

Adenoviruses are non-enveloped particles with a double-stranded DNA genome and a diameter of 70-90 nm.

The major structural proteins of an adenovirus are hexons and pentons, constituting an icosahedral capsid of 252 subunits (capsomers), with hexons forming the facets and pentons capping the vertices of the icosahedron. The penton base anchors the antenna-like fiber protein, whose distal head domain, termed knob, harbors the receptor-binding site and is thus essential for initiating virus attachment to the host cell.

The FAdV capsid is characterized by a morphological peculiarity of two fiber proteins associated with each penton base, whereas mammalian adenoviruses feature only one fiber protein per vertex. Although the existence of dual fibers is common to all FAdVs, two fibers distinct in sequence and length, each encoded by a separate gene, are a specific feature of FAdV-(FAdV-A) (Hess et al., J. Mol. Biol. 252 (1995), 379-385). Based on the novel finding of two separate fiber-encoding genes in an FAdV-C isolate, it was recently demonstrated that this reflects, among all FAdV species with equally long fiber proteins, a feature exclusively attributed to members of FAdV-C (Marek et al., Vet. Microbiol. 156 (2012), 411-417).

Characterization of the knob as receptor-binding domain has established the fiber molecule as a critical factor associated with infection properties of adenoviruses, such as alterations in tissue tropism and virulence. However, many questions are still open in regard to the individual functionality of the dual fibers present in FAdVs, particularly in the context of interaction with host cell receptors.

As major surface-exposed capsid structures, fiber and hexon are key mediators of antigenicity in adenoviruses and carriers of a panoply of epitopes of subgroup- and type-specificity. It has also been shown that hexon- and fiber-specific antibodies account for most of the neutralizing activity in mammalian humoral response against adenovirus. Recently, in vitro trials demonstrated different degrees of neutralizing capacity of antibodies raised against recombinant hexon and fiber proteins of the egg-drop syndrome virus (EDSV (DAdV-A=DAdV-1)).

Owing to their antigenic properties, adenovirus capsid structures have been proposed as potential candidates for the design of epitope-based vaccines.

Strategies to combat HHS or IBH have concentrated on the prevention of infection and on the provision of attenuated fowl adenovirus vaccines (WO 03/039593) or inactivated vaccines from infected liver homogenates (Anjum et al. 1990) or grown up virus on primary cells (Alvarado et al. 2007). Due to the ubiquitous occurrence of FAdVs, however, applying such conventional vaccines and verification of effectiveness of the vaccination is of limited use due to the lack of discrimination between vaccination and infection. A subunit vaccine against HHS based on the penton base (expressed in *E. coli*) was recently suggested (Shah et al., 2012); however it is usually difficult to detect antibodies as an indicator of successful immunization because of the omnipresence of other fowl adenoviruses. No specific prophylaxis is reported for GE.

US 2011/165224 A1 discloses isolated FAdV strains of specific serotypes for inducing protective immunity. These compositions contain whole (live or killed) viruses, no subunit vaccines or isolated FAdV proteins. Schonewille et al. (Avian Dis. 54 (2010), 905-910 also disclose live FAdV-4 vaccines used in SPF chicken. Again, no subunit vaccine or isolated FAdV proteins are disclosed. Grgic et al. (PLoS ONE 8 (2013), e77601 disclose pathogenicity and cytokine expression pattern of a FAdV-4 isolate. Griffin et al. (J. Gen. Virol. 92 (2011); 1260-1272) disclose coding potential and transcript analysis of FAdV-4. It is speculated that FAdV-4 fiber 2 (short fiber) which is "predicted to be protein-coding" (but not shown to be expressed) might bind a receptor and determine the tissue tropism of FAdV-4, "perhaps leading to the unique clinical features associated with infection of virulent FadV-4". The authors correctly point out that both, avian FAdV-1 and the human enteric serotypes HAdV-40 and HAdV-41 (=HADV-F), contain two fiber genes. However, there are significant differences: Whereas in FAdV-1, as in all fowl AdVs, always two fibers per penton base are assembled together, there is only one fiber in the HAdV-Fs. Moreover, different quantities of both fibers are assembled into the HAdV-F virion although expression is the same on mRNA level (Song et al., Virology 432 (2012), 336-342). This shows that both fibers have different functions in the assembled virion (this has been verified in receptor studies). Moreover, Tan et al. (J. Gen. Virol. 82 (2001), 1465-1472) have shown that fiber 2 is involved in virus assembly and in the interaction with an unknown cellular receptor. Since FAdV-1 comprises—in contrast to all other FAdVs—two fibers of completely different lengths, such results cannot be transferred to other serotypes. Marek et al. (Vet. Microbiol. 156 (2012); 411-417) discloses the fact that two fiber genes of nearly equal length are present in FAdV-C whereas other serotypes have only one fiber gene. Although it is mentioned that "fibers of FAdV play an important role in infectivity and pathogenicity of FAdV" (demonstrated in 1996!), this statement was identified by Marek et al. as "purely speculative" as far as FAdV-C is concerned. Furthermore, the likelihood that fiber proteins are involved in infectivity and pathogenicity does not automatically implicate the successful application of recombinant proteins as a vaccine.

Fingerut et al. (Vaccine 21 (2003); 2761-2766) disclose a subunit vaccine against the adenovirus egg-drop syndrome using part of its fiber protein.

It is an object of the present invention to provide a safe and specific vaccine for efficient prevention of HHS and/or IBD and/or GE in birds, especially in poultry. The vaccine should be easy and cost-effective to produce and be suitable for administration on an industrial basis. Successful immunization with the vaccine should be easily detectable and confirmable.

Therefore, the present invention discloses a vaccine comprising a fiber protein, selected from fiber-2 protein of Fowl Adenovirus C (FAdV-C), fiber-2 protein of Fowl Adenovirus A (FAdV-A), fiber protein of Fowl Adenovirus B, D and E (FAdV-B, FAdV-D and FAdV-E), or an immunogenic fragment thereof for use in preventing hepatitis-hydropericardium syndrome (HHS) or inclusion body hepatitis (IBH) or Gizzard erosion (GE) in birds, preferably in poultry, especially in broilers.

The present invention provides the teaching that the fiber-2 protein of FAdV-C (and FAdV-A and the Fiber protein of FAdV-B, FAdV-D and FAdV-E) represent effective subunit vaccines that protects birds, especially chicken, completely from HHS. This finding was remarkable because fiber-1 protein of FAdV-C as well as hexon-derived subunit vaccines (hexon loop 1) did not show protective effect. It is evident that the present vaccines with isolated subunits, i.e. isolated single proteins or protein fragments, essentially differ from vaccines that are based on live, attenuated or killed (whole) viruses. Accordingly, the present invention provides a completely novel and—in view of the teachings present in the present field for fiber and hexon-derived proteins in FAdVs—surprisingly effective strategy for vaccinating birds to manage prevention of HHS, IBH and GE.

Figure 5A:
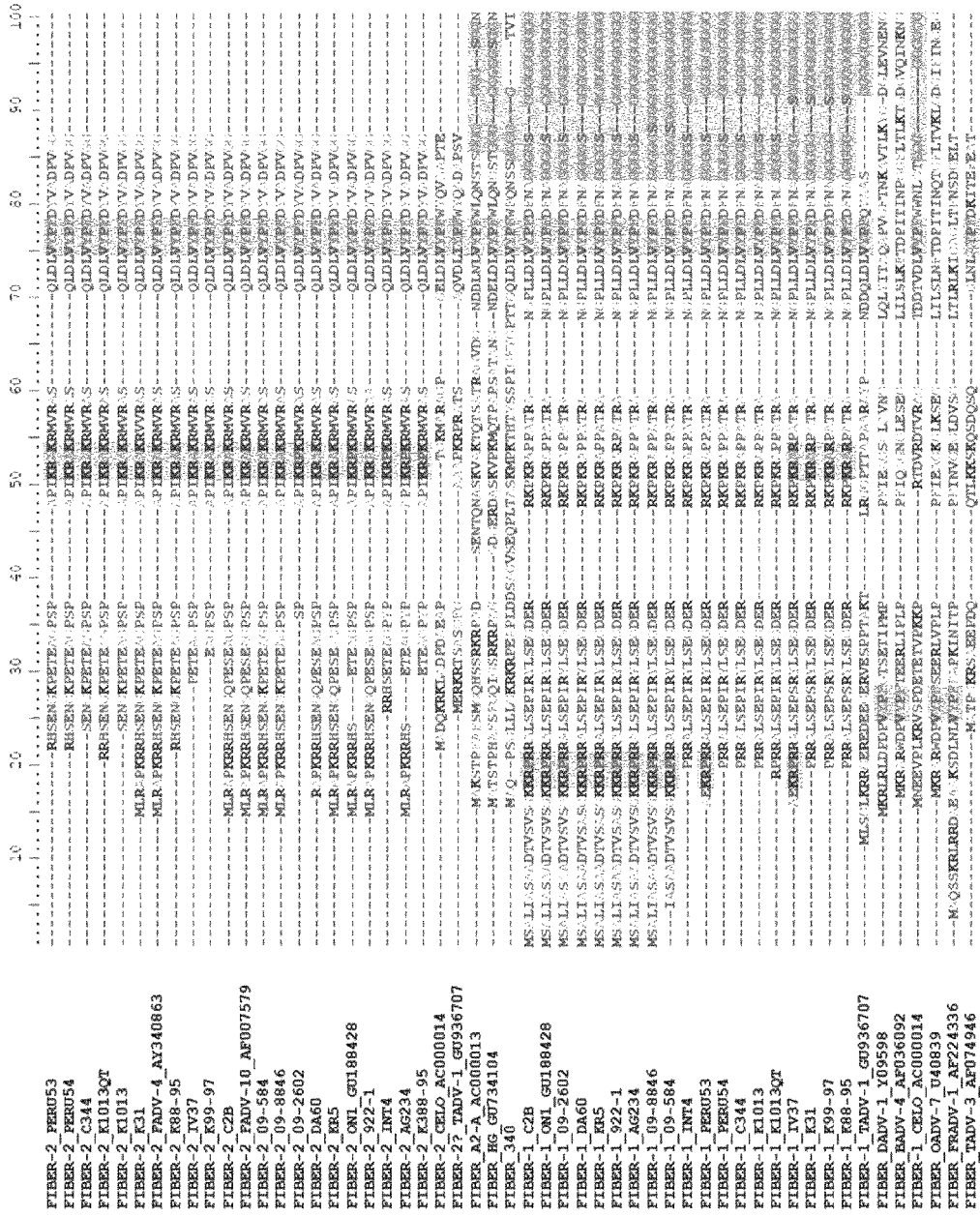
Figure 5B:
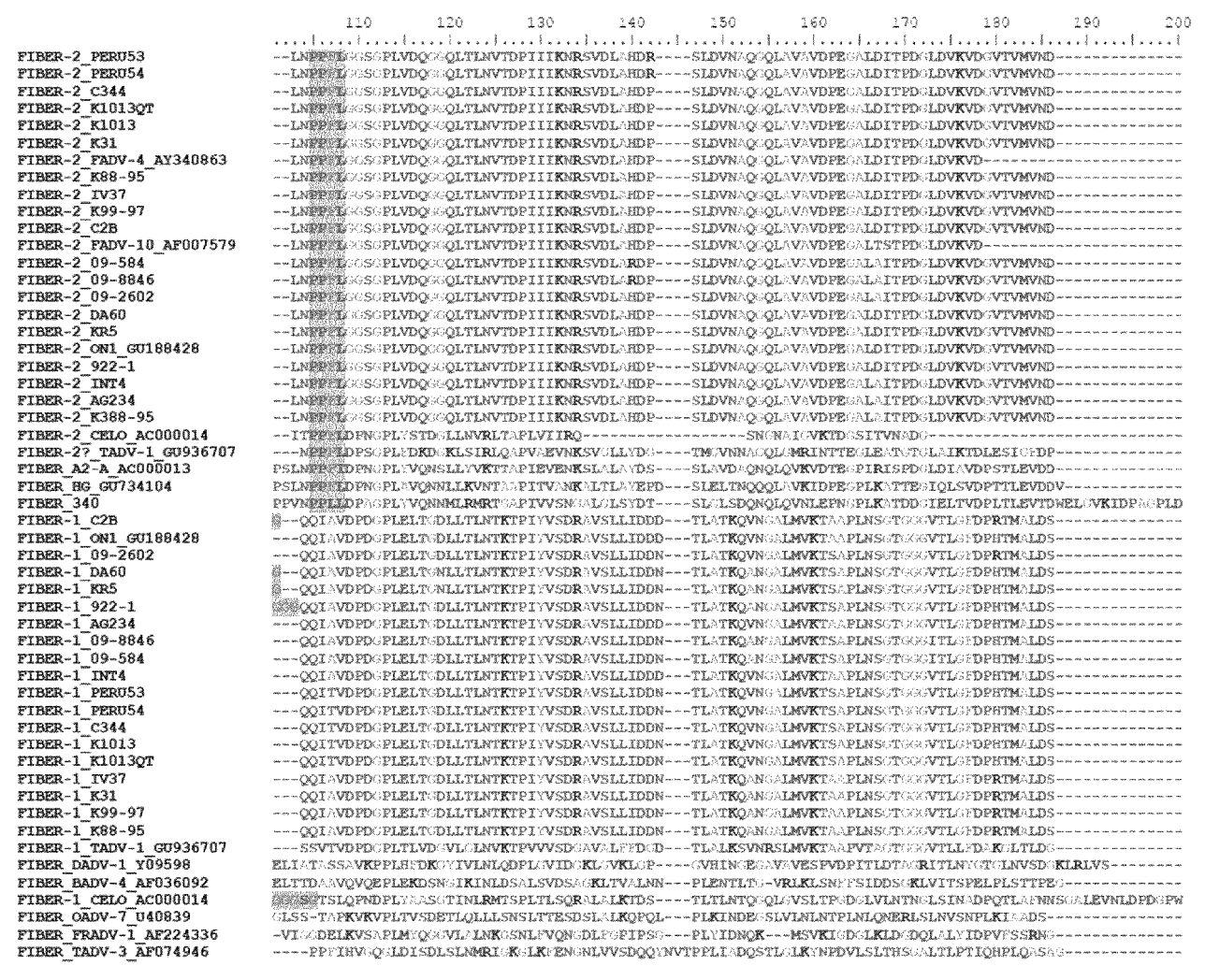
Figure 5C:
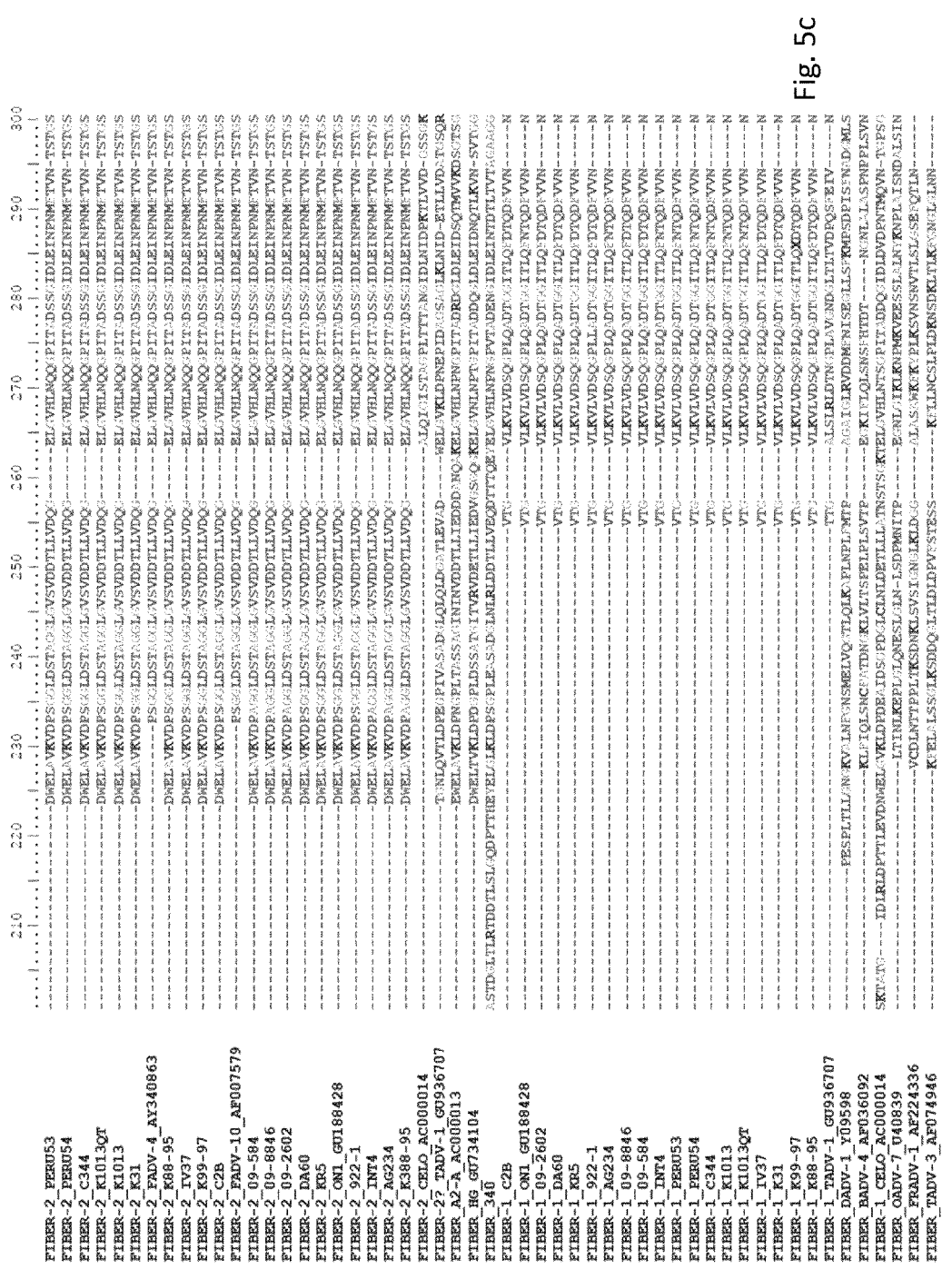
Figure 5D:
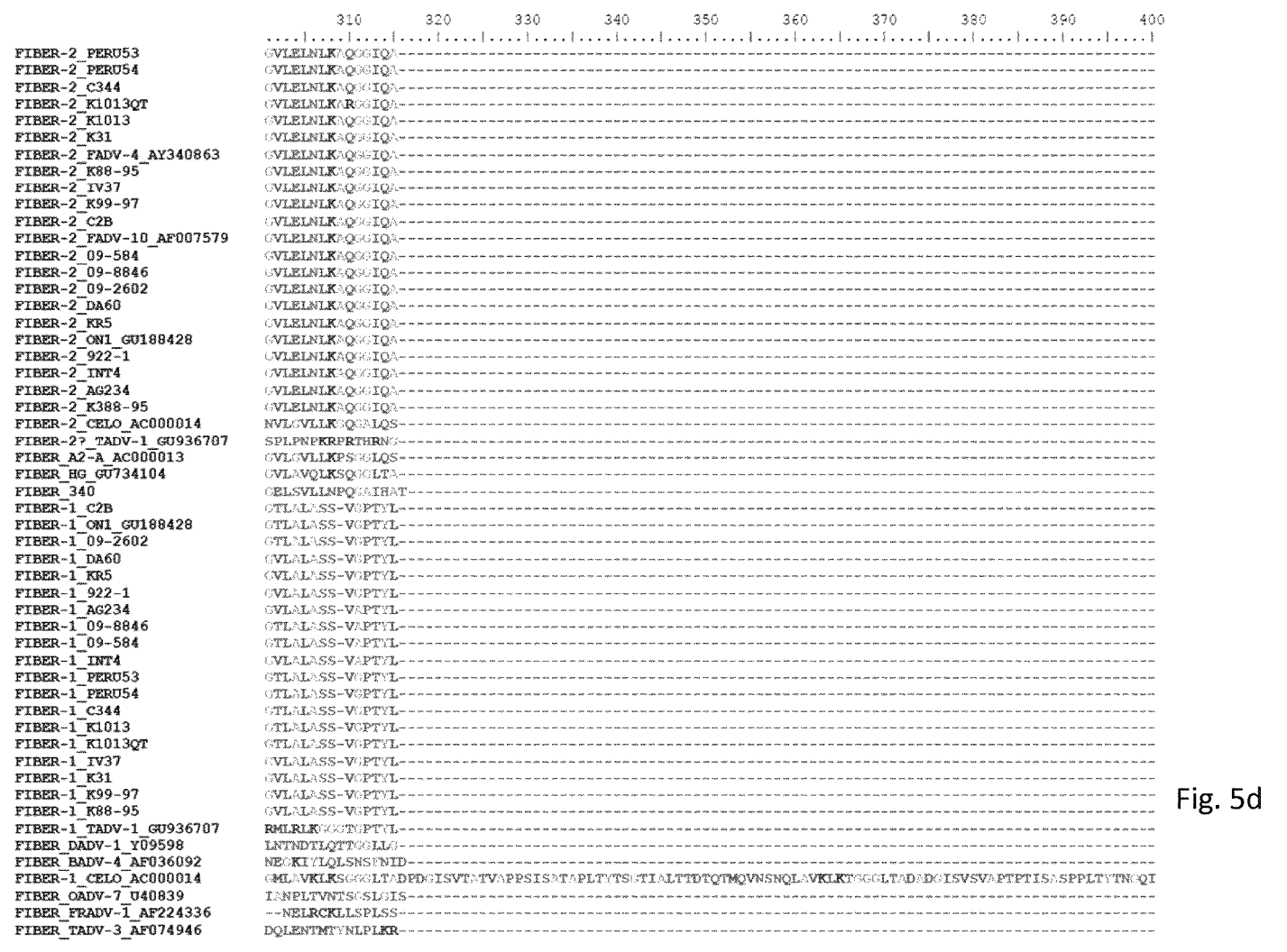
Figure 5E:
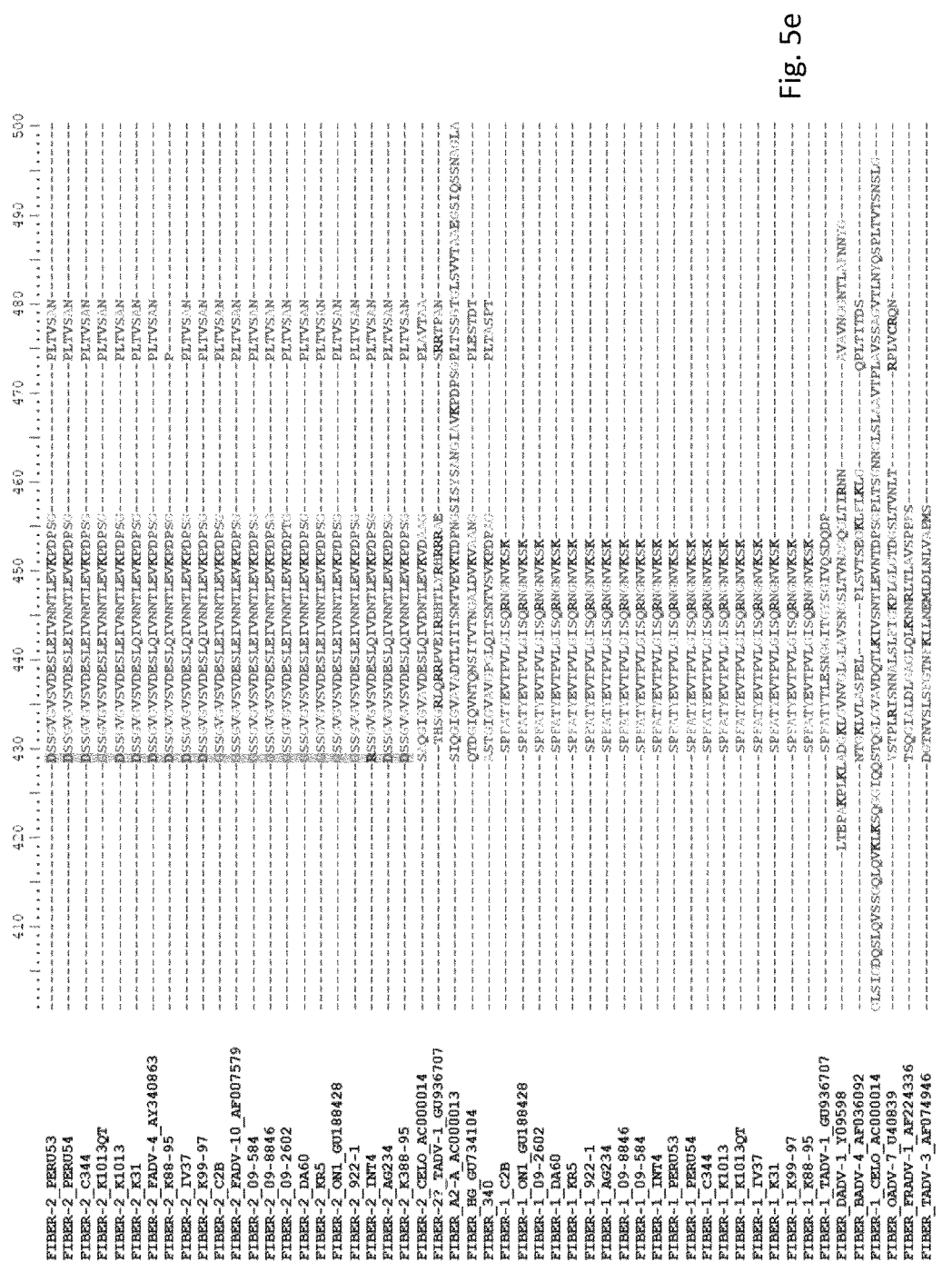
Figure 5F:
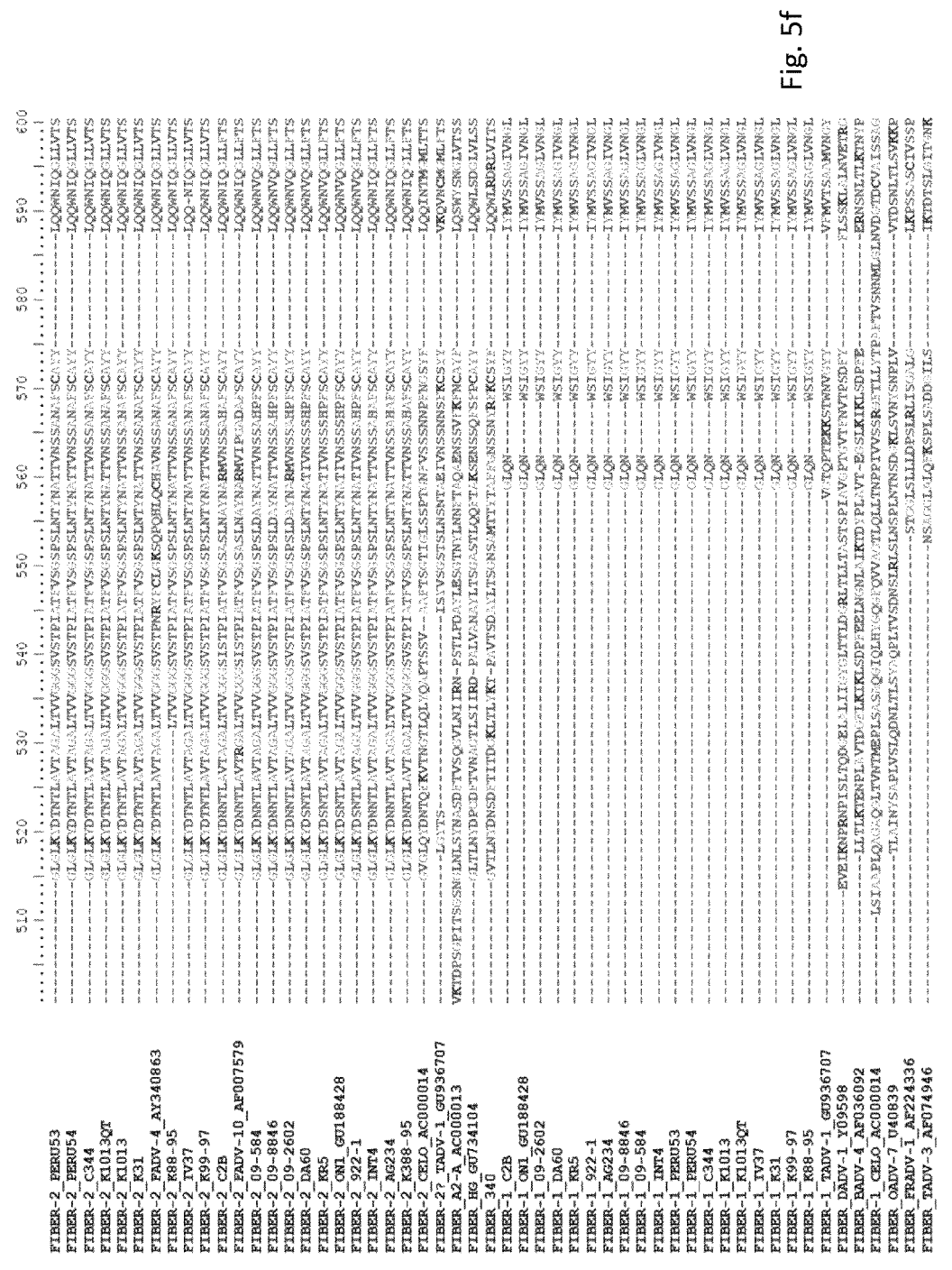
Figure 5G:
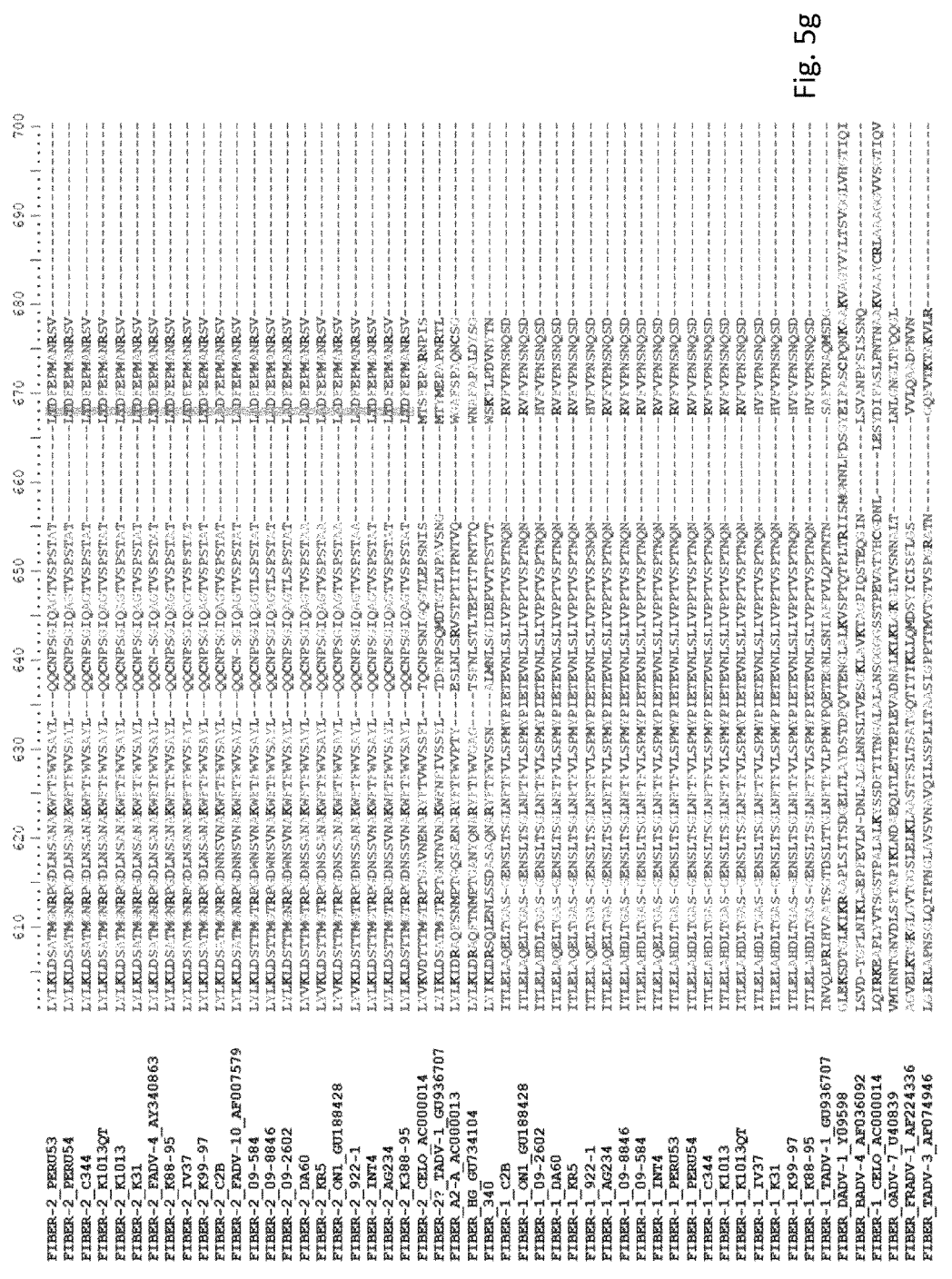
Figure 5H:
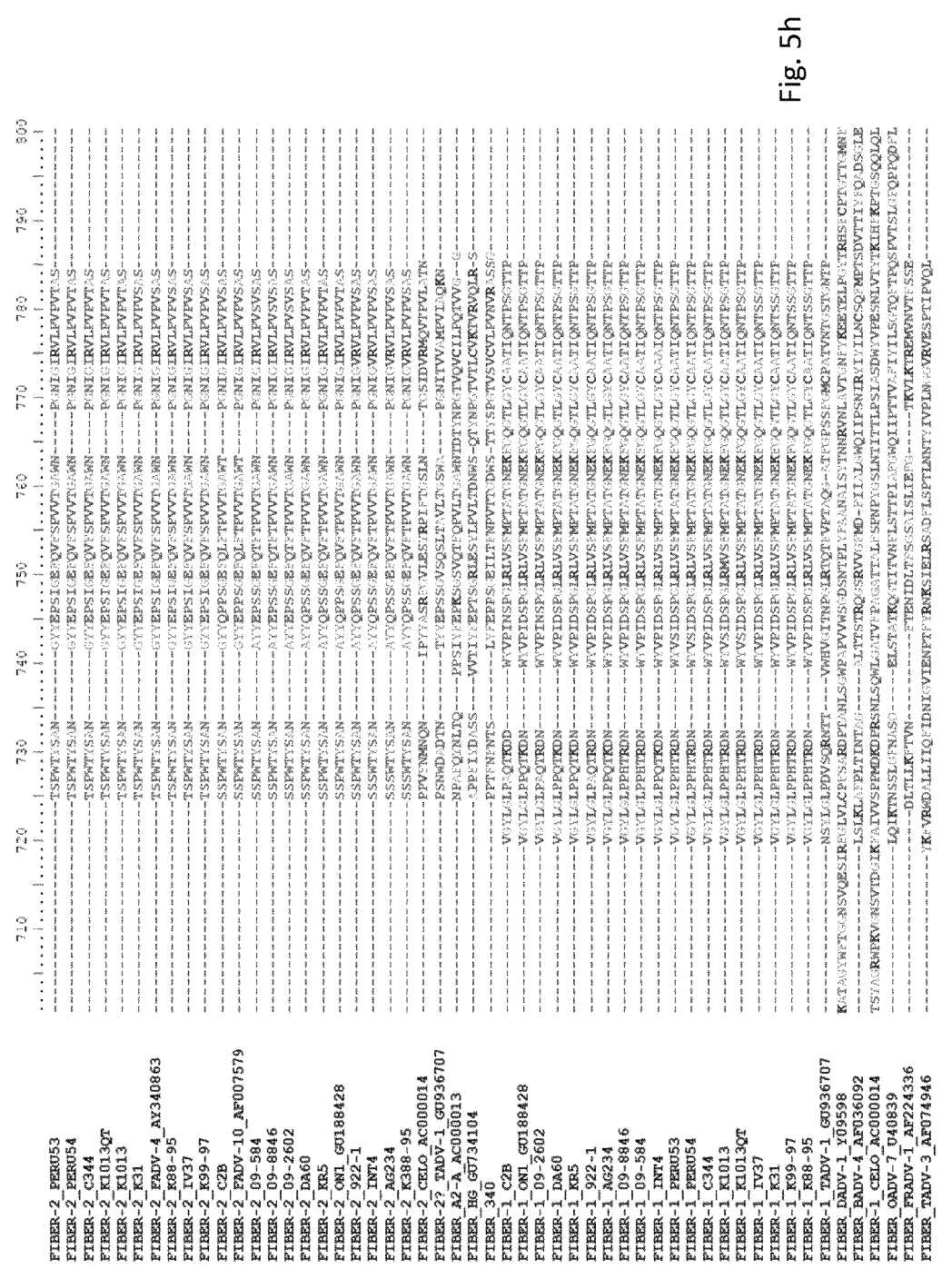
Figure 5I:
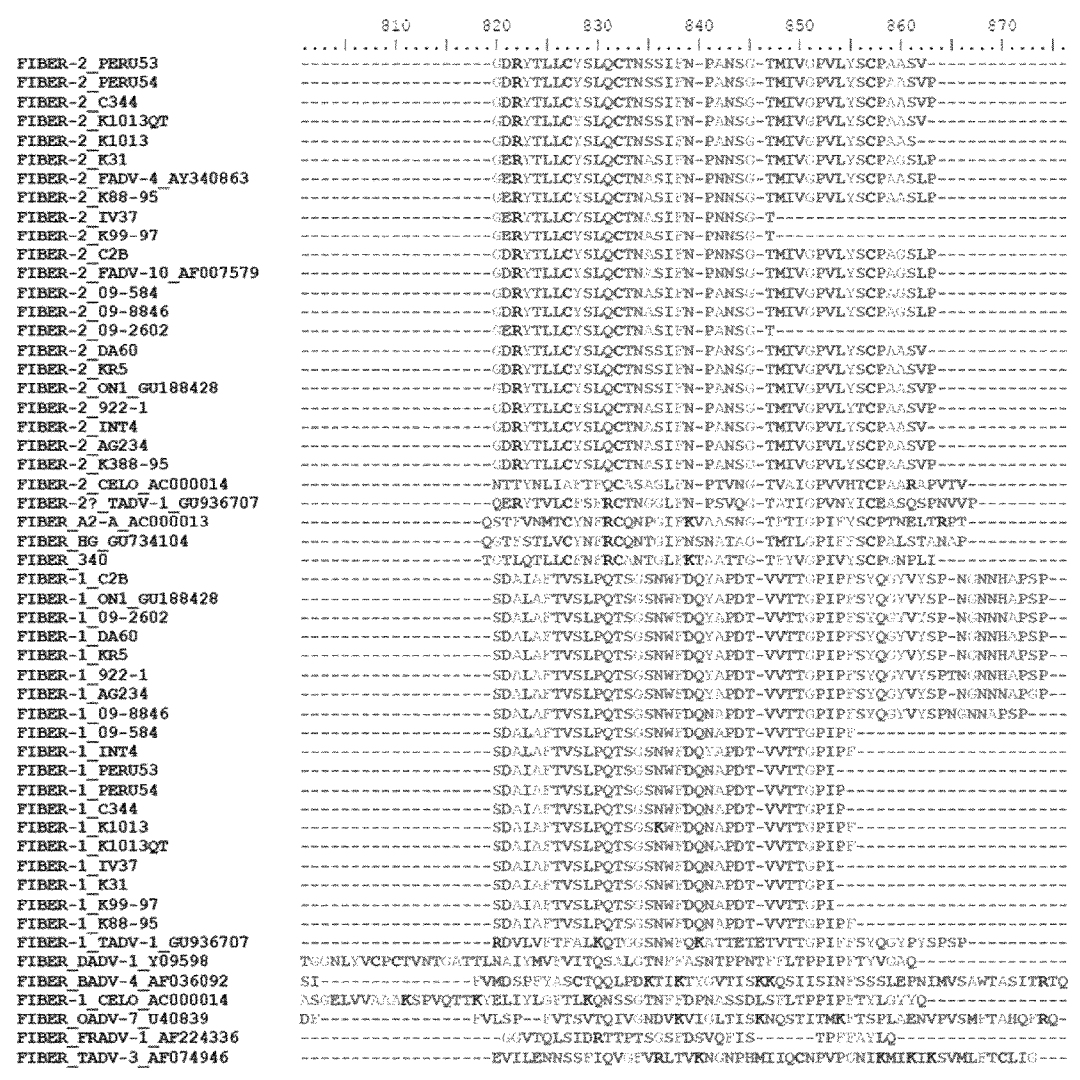

For the present invention, any fiber-2 protein of FAdV-C and FAdV-A as well as the related fiber protein of FAdV-B, FAdV-D and FAdV-E can be used. Preferably, vaccine protection according to the present invention is provided in homologous form, i.e. that the vaccination against a given serotype or species is performed with a fiber protein (or immunogenic fragment thereof) of the corresponding serotype (e.g. fiber 2 of FAdV-C is used for vaccination for prevention of infection with an FAdV-C). In the examples of the present invention, fiber-2 protein from reference strain KR5 was used as reference (UniProt entry H8WQW9) (SEQ ID NO.31); however, also other fiber-2 protein sequences of FAdV-C and FAdV-A as well as the fiber protein sequences of FAdV-B, FAdV-D and FAdV-E can be used, e.g. from reference strains ON1 (GU188428=NC 015323) (SEQ ID NO.32) or CFA20 (AF160185) (SEQ ID NO:) or any other FAdV-C field isolates, e.g. isolates IV37 (SEQ ID NO.23), K99-97 (SEQ ID NO.24), K388-95 (SEQ ID NO:36), K88-95 (SEQ ID NO.22), K31 (SEQ ID NO.20), Peru53 (SEQ ID NO:15), Peru54 (SEQ ID NO.16), c344 (SEQ ID NO.17), K1013 (SEQ ID NO.19), AG234 (SEQ ID NO.35), C2B (SEQ ID NO.25), 09-584 (SEQ ID NO.27), 09-8846 (SEQ ID NO.28), 09-2602 (SEQ ID NO.29), 922-1 (SEQ ID NO.33), Da60 (SEQ ID NO.30), K1013QT (SEQ ID NO.18) and INTO (SEQ ID NO.34) (as disclosed by Marek et al., Vet. Microbiol. 156 (2012), 411-417); and CELO (FAdV-A; Q64787) (SEQ ID NO.64) 340 (FAdV-B) (SEQ ID NO.41), A2-A (FAdV-D; AC000013) (SEQ ID NO.39), HG (FAdV-E; GU734104) (SEQ ID NO.40); corresponding to UniProt entries H8WG65 (SEQ ID NO.25), H8WG69 (SEQ ID NO.17), H8WG72 (SEQ ID NO.15), H8WG77 (SEQ ID NO.28), H8WG70 (SEQ ID NO.23), H8WG73 (SEQ ID NO.16), H8WG66 (SEQ ID NO.33), H8WG76 (SEQ ID NO.27), H8WG60 (SEQ ID NO.20), H8WG61 (SEQ ID NO.35), H8WG62 (SEQ ID NO.34), H8WG75 (SEQ ID NO.29), H8WG67 (SEQ ID NO.19), H8WG78 (SEQ ID NO.36), H8WG63 (SEQ ID NO.68), H8WG68 (SEQ ID NO.18), H8WG64 (SEQ ID NO.30), H8WG74 (SEQ ID NO.24), H8WG71 (SEQ ID NO.22), H8WQZ7 (SEQ ID NO.69), H8WQZ2 (SEQ ID NO. 70), H8WQW9 (SEQ ID NO.31), QOGH78 (SEQ ID NO.71), O55281 (SEQ ID NO.26), and F2VJI5 (SEQ ID NO.32). Further examples are listed in Table 3 or FIG. 5 of the present specification.

Instead of using the whole fiber-2 protein of FAdV-C and FAdV-A as well as the whole fiber protein sequences of FAdV-B, FAdV-D and FAdV-E, only immunogenic fragments of fiber-2 protein can be used as vaccines according to the present invention. Immunogenic fragments can be any polypeptide from a fiber-2 protein of a naturally occurring FAdV-C or FAdV-A or Fiber protein of FAdV-B, FAdV-D and FAdV-E isolate with a minimum length of 7 amino acid residues, preferably with a minimum length of 8 amino acid residues, especially with a minimum length of 9 amino acid residues. These minimum lengths provide sufficient MHC binding. Suitable motifs can be verified experimentally or via computer prediction (see e.g. Wallny et al., PNAS 103(2006), 1434-1439; Huo et al., PLoS ONE 7 (2012): e39344. doi:10.1371). Preferred lengths of the immunogenic fragments are therefore 7 to 100 amino acids, preferably 8 to 50 amino acids, more preferred 8 to 20 amino acids, especially 8 to 16 amino acids. For example, the immunogenic fragments according to the present invention may contain octapeptides or nonapeptides based on the peptide-binding motifs of chicken MHC class I molecules belonging to the B4, B12, B15, and B19 haplotypes (Wallny et al., 2006; Huo et al., 2012). The motifs were as follows: B4: x-(D or E)-x-x-(D or E)-x-x-E; B12: x-x-x-x-(V or I)-x-x-V and x-x-x-x-(V or I)-x-x-x(V); B15: (K or R)-R-x-x-x-x-x-Y and (K or)-R-x-x-x-xx-x-Y; B19: x-R-x-x-x-x-x-(Y, P, L, F) and x-R-x-x-x-x-x-(Y, P, L, F).

The fiber-2 protein has a tail domain (amino acid 1 to 65), a shaft domain (amino acid 66 to 276) and a head domain (amino acid 277 to 479; all amino acid sequence numbers in this general specification are based on the fiber-2 protein of the KR5 reference strain (UniProt H8WQW9; Marek et al., 2012)). The fiber protein of FAdV-B, FAdV-D and FAdV-E has a corresponding structure. An alignment of examples for protein sequences according to the present invention is shown in FIG. 5. Preferred immunogenic fragments of the present invention contain the following motifs (based on amino acid numbering according to fiber-2 of KR5): 400 to 450, preferably 410 to 440, more preferred 420-440; 70 to 95, preferably 75 to 93, especially 75 to 90; 20 to 70, preferably 25 to 65, especially 45 to 65 and 25 to 47; 200 to 225, 265 to 290, 350 to 385, 460 to 480, 165 to 190, 320 to 350 and 290 to 320.

Examples of immunogenic fragments are fragments comprising one or more of the following amino acid sequences of fiber-2 protein (or Fiber in -B, -D and -E) (again according to the amino acid sequence of fiber-2 of KR5 and corresponding to the alignment in FIG. 5):

| Most preferred: | 427 to 441 | 407 to 421 | 51 to 65 |
|---|---|---|---|
| 23 to 37 | 423 to 437 | 408 to 422 | 326 to 340 |
| 24 to 38 | 253 to 267 | 409 to 423 | 255 to 269 |
| 22 to 36 | 425 to 439 | 69 to 83 | 326 to 340 |
| 25 to 39 | 254 to 268 | 255 to 269 | |
| 21 to 35 | 78 to 92 | 20 to 34 | |
| 424 to 438 | 424 to 438 | 325 to 339 | |
| 254 to 268 | 424 to 438 | 355 to 369 | |
| 423 to 437 | 79 to 93 | 425 to 439 | |
| 424 to 438 | 77 to 91 | 423 to 437 | |
| 421 to 435 | 423 to 437 | 45 to 59 | |
| 422 to 436 | 26 to 40 | 46 to 60 | |
| 423 to 437 | 403 to 417 | 47 to 61 | |
| 424 to 438 | 404 to 418 | 48 to 62 | |
| 425 to 439 | 405 to 419 | 49 to 63 | |
| 426 to 440 | 406 to 420 | 50 to 64 | |
| Highly preferred: | 207 to 221 | 426 to 440 | 308 to 322 |
| 424 to 438 | 208 to 222 | 324 to 338 | 283 to 297 |
| 26 to 40 | 209 to 223 | 167 to 181 | 71 to 85 |
| 27 to 41 | 210 to 224 | 168 to 182 | 425 to 439 |
| 28 to 42 | 267 to 281 | 169 to 183 | 426 to 440 |
| 29 to 43 | 268 to 282 | 170 to 184 | 77 to 91 |
| 30 to 44 | 269 to 283 | 171 to 185 | 422 to 436 |
| 31 to 45 | 270 to 284 | 172 to 186 | 68 to 82 |
| 32 to 46 | 271 to 285 | 173 to 187 | 426 to 440 |
| 75 to 89 | 272 to 286 | 356 to 370 | 282 to 296 |
| | 273 to 287 | 70 to 84 | 426 to 440 |
| 76 to 90 | 353 to 367 | 353 to 367 | 356 to 370 |
| 77 to 91 | 354 to 368 | 192 to 206 | 281 to 295 |
| 78 to 92 | 355 to 369 | 54 to 68 | 284 to 298 |
| 79 to 93 | 356 to 370 | 55 to 69 | 78 to 92 |
| 80 to 94 | 357 to 371 | 322 to 336 | 310 to 324 |
| 81 to 95 | 358 to 372 | 323 to 337 | 311 to 325 |
| 354 to 368 | 359 to 373 | 324 to 338 | 53 to 67 |
| 283 to 297 | 69 to 83 | 325 to 339 | 183 to 197 |
| 425 to 439 | 76 to 90 | 326 to 340 | 313 to 327 |
| 422 to 436 | 425 to 439 | 422 to 436 | 314 to 328 |
| 325 to 339 | 327 to 341 | 422 to 436 | 315 to 329 |
| 282 to 296 | 68 to 82 | 327 to 341 | 316 to 330 |
| 422 to 436 | 252 to 266 | 56 to 70 | 317 to 331 |
| 253 to 267 | 309 to 323 | 294 to 308 | 318 to 332 |
| 423 to 437 | 442 to 456 | 295 to 309 | 319 to 333 |
| 322 to 336 | 256 to 270 | 296 to 310 | 52 to 66 |
| 323 to 337 | 426 to 440 | 297 to 311 | 252 to 266 |
| 324 to 338 | 68 to 82 | 298 to 312 | 183 to 197 |
| 325 to 339 | 69 to 83 | 299 to 313 | 297 to 311 |
| 326 to 340 | 70 to 84 | 300 to 314 | 422 to 436 |
| 327 to 341 | 71 to 85 | 355 to 369 | 328 to 342 |
| 328 to 342 | 72 to 86 | 325 to 339 | 59 to 73 |
| 70 to 84 | 73 to 87 | 191 to 205 | 60 to 74 |
| 425 to 439 | 74 to 88 | 355 to 369 | 61 to 75 |
| 423 to 437 | 464 to 478 | 71 to 85 | 62 to 76 |
| 424 to 438 | 465 to 479 | 441 to 455 | 63 to 77 |
| 204 to 218 | 310 to 324 | 421 to 435 | 64 to 78 |
| 205 to 219 | 80 to 94 | 256 to 270 | 65 to 79 |
| 206 to 220 | 443 to 457 | 79 to 93 | 463 to 477 |
| 184 to 198 | 188 to 202 | | |
| 254 to 268 | 76 to 90 | | |
| 309 to 323 | 194 to 208 | | |
| 207 to 221 | 77 to 91 | | |
| 43 to 57 | 326 to 340 | | |
| 324 to 338 | 193 to 207 | | |
| 52 to 66 | 79 to 93 | | |
| 53 to 67 | 282 to 296 | | |
| 54 to 68 | 69 to 83 | | |
| 55 to 69 | 184 to 198 | | |
| 56 to 70 | 298 to 312 | | |
| 57 to 71 | 23 to 37 | | |
| 58 to 72 | 70 to 84 | | |
| 185 to 199 | 379 to 393 | | |
| 323 to 337 | 283 to 297 | | |
| 444 to 458 | 296 to 310 | | |
| 324 to 338 | 283 to 297 | | |
| 356 to 370 | | | |
| 78 to 92 | | | |
| 206 to 220 | | | |
| 364 to 378 | | | |
| 376 to 390 | | | |
| 377 to 391 | | | |
| 378 to 392 | | | |
| 379 to 393 | | | |
| 380 to 394 | | | |
| 381 to 395 | | | |
| 382 to 396 | | | |
| 71 to 85 | | | |
| 192 to 206 | | | |
| 378 to 392 | | | |
| 421 to 435 | | | |
| 192 to 206 | | | |
| 297 to 311 | | | |
| 182 to 196 | | | |
| 183 to 197 | | | |
| 184 to 198 | | | |
| 185 to 199 | | | |
| 186 to 200 | | | |
| 187 to 201 | | | |
| Preferred: | 283 to 297 | 127 to 141 | 355 to 369 |
| 424 to 438 | 284 to 298 | 186 to 200 | 425 to 439 |
| 354 to 368 | 285 to 299 | 465 to 479 | 421 to 435 |
| 27 to 41 | 286 to 300 | 310 to 324 | 206 to 220 |
| 426 to 440 | 284 to 298 | 257 to 271 | 283 to 297 |
| 255 to 269 | 440 to 454 | 421 to 435 | 80 to 94 |
| 282 to 296 | 261 to 275 | 323 to 337 | 308 to 322 |
| 357 to 371 | 310 to 324 | 208 to 222 | 312 to 326 |
| 193 to 207 | 251 to 265 | 378 to 392 | 91 to 105 |
| 261 to 275 | 363 to 377 | 72 to 86 | 92 to 106 |

-continued

| | | | |
|---|---|---|---|
| 307 to 321 | 207 to 221 | 93 to 107 | 93 to 107 |
| 352 to 366 | 24 to 38 | 207 to 221 | 94 to 108 |
| 354 to 368 | 319 to 333 | 320 to 334 | 95 to 109 |
| 75 to 89 | 282 to 296 | 86 to 100 | 96 to 110 |
| 261 to 275 | 182 to 196 | 458 to 472 | 97 to 111 |
| 295 to 309 | 260 to 274 | 459 to 473 | 69 to 83 |
| 44 to 58 | 22 to 36 | 460 to 474 | 424 to 438 |
| 207 to 221 | 293 to 307 | 461 to 475 | 169 to 183 |
| 169 to 183 | 428 to 442 | 462 to 476 | 165 to 179 |
| 253 to 267 | 429 to 443 | 281 to 295 | 166 to 180 |
| 311 to 325 | 296 to 310 | 280 to 294 | 101 to 115 |
| 292 to 306 | 168 to 182 | 281 to 295 | 102 to 116 |
| 185 to 199 | 260 to 274 | 77 to 91 | 103 to 117 |
| 464 to 478 | 318 to 332 | 205 to 219 | 104 to 118 |
| 465 to 479 | 78 to 92 | 308 to 322 | 105 to 119 |
| 283 to 297 | 309 to 323 | 193 to 207 | 106 to 120 |
| 423 to 437 | 79 to 93 | 204 to 218 | 107 to 121 |
| 206 to 220 | 191 to 205 | 261 to 275 | 191 to 205 |
| 42 to 56 | 192 to 206 | 260 to 274 | 298 to 312 |
| 287 to 301 | 193 to 207 | 170 to 184 | 259 to 273 |
| 288 to 302 | 194 to 208 | 377 to 391 | 423 to 437 |
| 289 to 303 | 195 to 209 | 282 to 296 | 309 to 323 |
| 290 to 304 | 196 to 210 | 167 to 181 | 205 to 219 |
| 291 to 305 | 197 to 211 | 190 to 204 | 261 to 275 |
| 292 to 306 | 282 to 296 | 310 to 324 | 357 to 371 |
| 293 to 307 | 28 to 42 | 189 to 203 | 256 to 270 |
| 357 to 371 | 317 to 331 | 190 to 204 | 291 to 305 |
| 280 to 294 | 245 to 259 | 309 to 323 | 295 to 309 |
| 281 to 295 | 206 to 220 | 284 to 298 | 327 to 341 |
| 282 to 296 | 67 to 81 | 76 to 90 | 294 to 308 |
| 170 to 184 | 258 to 272 | 443 to 457 | 161 to 175 |
| 283 to 297 | 328 to 342 | 307 to 321 | 162 to 176 |
| 347 to 361 | 203 to 217 | 81 to 95 | 163 to 177 |
| 421 to 435 | 322 to 336 | 29 to 43 | 355 to 369 |
| 208 to 222 | 128 to 142 | 94 to 108 | 204 to 218 |
| 281 to 295 | 262 to 276 | 311 to 325 | 421 to 435 |
| 191 to 205 | 85 to 99 | 284 to 298 | 406 to 420 |
| 244 to 258 | 55 to 69 | 421 to 435 | 118 to 132 |
| 464 to 478 | 452 to 466 | 80 to 94 | 71 to 85 |
| 57 to 71 | 75 to 89 | 72 to 86 | 294 to 308 |
| 58 to 72 | 422 to 436 | 202 to 216 | 346 to 360 |
| 425 to 439 | 77 to 91 | 79 to 93 | 426 to 440 |
| 348 to 362 | 353 to 367 | 323 to 337 | 280 to 294 |
| 349 to 363 | 321 to 335 | 281 to 295 | 45 to 59 |
| 350 to 364 | 28 to 42 | 312 to 326 | 290 to 304 |
| 351 to 365 | 78 to 92 | 87 to 101 | 297 to 311 |
| 352 to 366 | 262 to 276 | 28 to 42 | 320 to 334 |
| 284 to 298 | 453 to 467 | 281 to 295 | 119 to 133 |
| 379 to 393 | 123 to 137 | 285 to 299 | 20 to 34 |
| 311 to 325 | 124 to 138 | 465 to 479 | 21 to 35 |
| 327 to 341 | 125 to 139 | 356 to 370 | 22 to 36 |
| 260 to 274 | 126 to 140 | 194 to 208 | 23 to 37 |
| 182 to 196 | 127 to 141 | 309 to 323 | 24 to 38 |
| 445 to 459 | 128 to 142 | 306 to 320 | 25 to 39 |
| 262 to 276 | 129 to 143 | 252 to 266 | 404 to 418 |
| 422 to 436 | 265 to 279 | 306 to 320 | 442 to 456 |
| 55 to 69 | 266 to 280 | 443 to 457 | 289 to 303 |
| 450 to 464 | 320 to 334 | 405 to 419 | 281 to 295 |
| 451 to 465 | 321 to 335 | 54 to 68 | 170 to 184 |
| 452 to 466 | 366 to 380 | 41 to 55 | 258 to 272 |
| 453 to 467 | 367 to 381 | 204 to 218 | 259 to 273 |
| 454 to 468 | 368 to 382 | 24 to 38 | 260 to 274 |
| 455 to 469 | 369 to 383 | 380 to 394 | 261 to 275 |
| 456 to 470 | 370 to 384 | 251 to 265 | 262 to 276 |
| 310 to 324 | 371 to 385 | 208 to 222 | 263 to 277 |
| 70 to 84 | 372 to 386 | 348 to 362 | 264 to 278 |
| 208 to 222 | 284 to 298 | 157 to 171 | 442 to 456 |
| 353 to 367 | 322 to 336 | 158 to 172 | 443 to 457 |
| 205 to 219 | 246 to 260 | 159 to 173 | 444 to 458 |
| 328 to 342 | 260 to 274 | 160 to 174 | 445 to 459 |
| 446 to 460 | 262 to 276 | 308 to 322 | 117 to 131 |
| 447 to 461 | 376 to 390 | 444 to 458 | 70 to 84 |
| 448 to 462 | 21 to 35 | 254 to 268 | 346 to 360 |
| 347 to 361 | 311 to 325 | 195 to 209 | 310 to 324 |
| 186 to 200 | 170 to 184 | 126 to 140 | 25 to 39 |
| 68 to 82 | 294 to 308 | 189 to 203 | 29 to 43 |
| 403 to 417 | 54 to 68 | 93 to 107 | 465 to 479 |
| 213 to 227 | 29 to 43 | 295 to 309 | 292 to 306 |
| 25 to 39 | 298 to 312 | 192 to 206 | 345 to 359 |
| 27 to 41 | 364 to 378 | 194 to 208 | 164 to 178 |
| 259 to 273 | 290 to 304 | 227 to 241 | 137 to 151 |
| 27 to 41 | 259 to 273 | 71 to 85 | 263 to 277 |
| 169 to 183 | 205 to 219 | 70 to 84 | 209 to 223 |
| 407 to 421 | 92 to 106 | 23 to 37 | 305 to 319 |
| 321 to 335 | 280 to 294 | 316 to 330 | 171 to 185 |
| 365 to 379 | 28 to 42 | 1 to 15 | 136 to 150 |
| 442 to 456 | 33 to 47 | 206 to 220 | 280 to 294 |
| 299 to 313 | 34 to 48 | 293 to 307 | 66 to 80 |
| 227 to 241 | 35 to 49 | 56 to 70 | 67 to 81 |
| 308 to 322 | 36 to 50 | 1 to 15 | 181 to 195 |
| 309 to 323 | 37 to 51 | 243 to 257 | 358 to 372 |
| 310 to 324 | 38 to 52 | 369 to 383 | 284 to 298 |
| 311 to 325 | 205 to 219 | 325 to 339 | 295 to 309 |
| 312 to 326 | 80 to 94 | 225 to 239 | 325 to 339 |
| 377 to 391 | 39 to 53 | 226 to 240 | 129 to 143 |
| 72 to 86 | 40 to 54 | 227 to 241 | 94 to 108 |
| 29 to 43 | 245 to 259 | 228 to 242 | 307 to 321 |
| 348 to 362 | 262 to 276 | 229 to 243 | 291 to 305 |
| 307 to 321 | 426 to 440 | 230 to 244 | 251 to 265 |
| 345 to 359 | 69 to 83 | 231 to 245 | 252 to 266 |
| 346 to 360 | 280 to 294 | 76 to 90 | 253 to 267 |
| 347 to 361 | 312 to 326 | 349 to 363 | 254 to 268 |
| 361 to 375 | 464 to 478 | 378 to 392 | 255 to 269 |
| 362 to 376 | 319 to 333 | 451 to 465 | 256 to 270 |
| 363 to 377 | 354 to 368 | 296 to 310 | 257 to 271 |
| 364 to 378 | 187 to 201 | 69 to 83 | 288 to 302 |
| 365 to 379 | 322 to 336 | 356 to 370 | 285 to 299 |
| 169 to 183 | 325 to 339 | 228 to 242 | 254 to 268 |
| 311 to 325 | 308 to 322 | 76 to 90 | 228 to 242 |
| 168 to 182 | 67 to 81 | 71 to 85 | 257 to 271 |
| 319 to 333 | | | |
| 440 to 454 | | | |

The vaccine according to the present invention preferably contains a fiber-2 protein of FAdV-C or FAdV-A or a fiber protein of FAdV-B, FAdV-D and FAdV-E, selected from the sequences UniProt entries H8WG65 (SEQ ID NO.25), H8WG69 (SEQ ID NO.17), H8WG72 (SEQ ID NO.15), H8WG77 (SEQ ID NO.28), H8WG70 (SEQ ID NO.23), H8WG73 (SEQ ID NO.16), H8WG66 (SEQ ID NO.33), H8WG76 (SEQ ID NO.27), H8WG60 (SEQ ID NO.20), H8WG61 (SEQ ID NO.35), H8WG62 (SEQ ID NO.34), H8WG75 (SEQ ID NO.29), H8WG67 (SEQ ID NO.19), H8WG78 (SEQ ID NO.36), H8WG63 (SEQ ID NO.68), H8WG68 (SEQ ID NO.18), H8WG64 (SEQ ID NO.30), H8WG74 (SEQ ID NO.24), H8WG71 (SEQ ID NO.22), H8WQZ7 (SEQ ID NO.69), H8WQZ2 (SEQ ID NO. 70), H8WQW9 (SEQ ID NO.31), Q0GH78 (SEQ ID NO.71), O55281 (SEQ ID NO.26), and F2VJI5 (SEQ ID NO.32), as well as the protein sequences provided in Table 3, especially H8WQW9 (SEQ ID NO.31), or immunogenic fragments thereof; or immunogenic sequences with at least 80, preferably at least 90, especially at least 95% amino acid identity, or immunogenic fragments thereof (based on alignment with the Clustal Omega program; identity is calculated by the ratio of identical amino acids divided by the total number of amino acids (of the shorter sequence, if sequences are not of the same length), times 100 (for %)). For example, amino acid residues on position (based on the KR5 sequence H8WQW9 (SEQ ID NO.31)) 29, 31, 36, 91, 93, 114, 115, 213, 219, 232, 235, 279, 291, 294, 295, 299, 300, 302 to 307, 319, 324, 329, 343, 338, 343 to 346, 372, 378, 380, 391, 393, 400, 403, 405, 406, 411, 413, 421, 427, 433, 435, 439, 453, 459, 476, or 478 can be changed (as evidenced by the isolates of UniProt sequences H8WG65 (SEQ ID NO.25), H8WG69 (SEQ ID NO.17), H8WG72 (SEQ ID NO.15), H8WG77 (SEQ ID NO.28), H8WG70 (SEQ ID NO.23), H8WG73 (SEQ ID NO.16), H8WG66 (SEQ ID NO.33), H8WG76 (SEQ ID NO.27), H8WG60 (SEQ ID NO.20), H8WG61 (SEQ ID NO.35), H8WG62 (SEQ ID NO.34), H8WG75 (SEQ ID NO.29), H8WG67 (SEQ ID NO.19), H8WG78 (SEQ ID NO.36), H8WG63 (SEQ ID NO.68), H8WG68 (SEQ ID NO.18), H8WG64 (SEQ ID NO.30), H8WG74 (SEQ ID NO.24), H8WG71 (SEQ ID NO.22), H8WQZ7 (SEQ ID NO.69), H8WQZ2 (SEQ ID NO. 70), H8WQW9 (SEQ ID NO.31), QOGH78 (SEQ ID NO.71), O55281 (SEQ ID NO.26), and F2VJI5 (SEQ ID NO.32); or deletion of sequences, such as at the N-terminus (e.g. up to position 21), 123 to 139, 250 to 272, 364, or at the C-terminus, e.g. positions 464 to 479 (as also evidenced by the above UniProt sequences; alignments made by the UniProt alignment software (Clustal Omega program)). Further naturally occurring amino acid variations, deletions and insertions are exemplified in FIG. 5 and derivable from the sequences in Table 3.

Preferably, the vaccine according to the present invention further comprises an adjuvant, preferably selected from the group consisting of Freund's complete adjuvant, Freund's incomplete adjuvant, aluminum hydroxide, *Bordetella pertussis*, saponin, muramyl dipeptide, ethylene vinyl acetate copolymer, oil, a vegetable oil or a mineral oil, in particular peanut oil or silicone oil, and combinations thereof.

Adjuvants are substances that enhance the immune response to immunogens. Adjuvants, can include aluminum hydroxide and aluminum phosphate, saponins e.g., Quil A, water-in-oil emulsion, oil-in-water emulsion, water-in-oil-in-water emulsion. The emulsion can be based in particular on light liquid paraffin oil (European Pharmacopea type); isoprenoid oil such as squalane or squalene; oil resulting from the oligomerization of alkenes, in particular of isobutene or decene; esters of acids or of alcohols containing a linear alkyl group, more particularly plant oils, ethyl oleate, propylene glycol di(caprylate/caprate), glyceryl tri (caprylate/caprate) or propylene glycol dioleate; esters of branched fatty acids or alcohols, in particular isostearic acid esters. The oil is used in combination with emulsifiers to form the emulsion. The emulsifiers are preferably nonionic surfactants, in particular esters of sorbitan, of mannide (e.g. anhydromannitol oleate), of glycerol, of polyglycerol, of propylene glycol and of oleic, isostearic, ricinoleic or hydroxystearic acid, which are optionally ethoxylated, and polyoxypropylene-polyoxyethylene copolymer blocks, in particular the Pluronic® products, especially L121. For example the adjuvant-containing vaccine is prepared in the following way: 50 to 90 v/v of aqueous phase comprising the immunogen are emulsified in 1 to 10% w/v of anhydromannitol oleate, 1 to 10% w/v of oleic acid ethoxylated with 11 EO (ethylene oxide) and 5 to 40% v/v of light liquid paraffin oil (European Pharmacopea type) with the aid of an emulsifying turbomixer. An alternative method for preparing the emulsion consists in emulsifying, by passages through a high-pressure homogenizer, a mixture of 1 to 10% w/v squalane, 1 to 10% w/v Pluronic® L121, 0.05 to 1% w/v of an ester of oleic acid and of anhydrosorbitol ethoxylated with 20 EO, 50 to 95% v/v of the aqueous phase comprising the immunogen. It is also possible to formulate with synthetic polymers (e.g., homo- and copolymers of lactic and glycolic acid, which have been used to produce microspheres that encapsulate immunogens, e.g., biodegradable microspheres). A further instance of an adjuvant is a compound chosen from the polymers of acrylic or methacrylic acid and the copolymers of maleic anhydride and alkenyl derivative. Advantageous adjuvant compounds are the polymers of acrylic or methacrylic acid which are cross-linked, especially with polyalkenyl ethers of sugars or polyalcohols. These compounds are known by the term carbomer, e.g. acrylic polymers cross-linked with a polyhydroxylated compound having at least 3 hydroxyl groups, preferably not more than 8, the hydrogen atoms of at least three hydroxyls being replaced by unsaturated aliphatic radicals having at least 2 carbon atoms. The preferred radicals are those containing from 2 to 4 carbon atoms, e.g. vinyls, allyls and other ethylenically unsaturated groups. The unsaturated radicals may themselves contain other substituents, such as methyl. The products sold under the name Carbopol® (BF Goodrich, Ohio, USA) are particularly appropriate. They are cross-linked with an allyl sucrose or with allyl pentaerythritol. Among then, there may be mentioned Carbopol® 974P, 934P and 971P. Among the copolymers of maleic anhydride and alkenyl derivative, the copolymers EMA® (Monsanto) which are copolymers of maleic anhydride and ethylene, linear or cross-linked, for example cross-linked with divinyl ether, are preferred. The dissolution of these polymers in water leads to an acid solution that will be neutralized, preferably to physiological pH, in order to give the adjuvant solution into which the immunogenic, immunological or vaccine composition itself will be incorporated. The carboxyl groups of the polymer are then partly in COO⁻ form.

Preferably, a solution of adjuvant according to the invention, is prepared in distilled water, preferably in the presence of sodium chloride, the solution obtained being at acidic pH. This stock solution is diluted by adding it to the desired quantity (for obtaining the desired final concentration), or a substantial part thereof, of water charged with NaCl, preferably physiological saline (NaCl 9 g/l) all at once in several portions with concomitant or subsequent neutralization (pH 7.3 to 7.4), preferably with NaOH. This solution at physiological pH will be used as it is for mixing with the vaccine, which may be especially stored in freeze-dried, liquid or frozen form. From this disclosure and the knowledge in the art, the skilled artisan can select a suitable adjuvant, if desired, and the amount thereof to employ in an immunological, immunogenic or vaccine composition according to the invention, without undue experimentation.

Accordingly, the vaccine according to the present invention preferably comprises a pharmaceutically acceptable diluent and/or carrier, preferably selected from the group consisting of water-for-injection, physiological saline, tissue culture medium, propylene glycol, polyethylene glycol, vegetable oils, especially olive oil, and injectable organic esters such as ethyl oleate.

The Fiber 2 protein of FAdV-C or FAdV-A or Fiber protein sequences of FAdV-B, FAdV-D and FAdV-E can be produced by any suitable expression system. Preferably, production is effected in a eukaryotic expression system. Specifically preferred expression systems are a baculovirus expression system, an *E. coli* expression system, or a *Pichia pastoris* expression system. However, virtually any suitable expression system or vector can be used in the production of the vaccine provided by this invention. By way of illustration, said suitable expression or vector systems can be selected, according to the conditions and needs of each specific case, from plasmids, bacmids, yeast artificial chromosomes (YACs), bacteria artificial chromosomes (BACs), bacteriophage P1-based artificial chromosomes (PACs), cosmids, or viruses, which can further have a heterologous replication origin, for example, bacterial or of yeast, so that it may be amplified in bacteria or yeasts, as well as a marker usable for selecting the transfected cells different from the gene or genes of interest. These expression systems or vectors can be obtained by conventional methods known by persons skilled in the art.

The vaccines according to the present invention can be produced in industrial amounts; the individual vaccine dose given to the animals can be in the ranges also applied for other vaccines. Preferably, the fiber-2 protein of FAdV-C or FAdV-A or fiber protein of FAdV-B, FAdV-D or FAdV-E or an immunogenic fragment thereof is contained in the vaccine in an amount of 0.1 µg/ml to 10 mg/ml, preferably of 1 µg/ml to 1 mg/ml, especially of 10 to 100 µg/ml.

In a preferred form, the vaccine according to the present invention consists of fiber-2 protein of FAdV-C or FAdV-A or fiber protein of FAdV-B, FAdV-D or FAdV-E or an immunogenic fragment thereof, preferably in an amount of 0.1 µg to 10 mg, preferably of 1 µg to 1 mg, especially of 10 to 100 µg; and a pharmaceutically acceptable carrier and/or diluent and/or adjuvant.

The vaccine according to the present invention preferably comprises a pharmaceutically acceptable vehicle, especially if provided as commercially sold vaccine product. The suitable vehicles may be both aqueous and non-aqueous. Examples of non-aqueous solvents are propylene glycol, polyethylene glycol, vegetable oils such as olive oil, and injectable organic esters such as ethyl oleate.

With the present invention, an efficient method for preventing HHS, IBH and GE in birds is provided. Accordingly, the present invention relates to another aspect to a method for preventing HHS, IBH or GE in birds, preferably in poultry, especially in broilers, comprising administering to poultry, especially to the parent flock, a vaccine containing fiber-2 protein of FAdV-C or FAdV-A or fiber protein of FAdV-B, FAdV-D or FAdV-E or an immunogenic fragment thereof. The vaccine is administered to the birds in an effective amount at a suitable point in time. Typical ways of administration are intravenous, subcutaneous, intramuscular, oral, in ovo or intracloacal administration. Preferably, vaccination in chicken is effected in week 17 to 19, especially in week 18 of life.

A specific advantage of the present invention is that vaccination of the parent flock provides sufficient protection for the progeny, especially to broilers, to safeguard sufficient protection e.g. up to at least 30, preferably at least 40, especially at least 60 days, to the progeny of vaccinated animals. It is therefore advantageous that the present invention provides sufficient protection of the broilers by vaccination of the parent animals. Accordingly, protection of broilers is effected by immunization of the parental animal in poultry, especially in chicken.

According to another aspect, the present invention also provides a kit comprising a fiber-2 protein of FAdV-C or FAdV-A or fiber protein of FAdV-B, FAdV-D or FAdV-E or an immunogenic fragment thereof immobilised on a solid surface. Preferably, the kit is a serological kit for detection of anti-fiber-2 antibodies (within the meaning of the present invention) in samples, especially blood samples of animals. This kit is specifically suitable for the present invention to detect the successful vaccination by determining specific anti-fiber-2 or anti-fiber antibodies in the vaccinated animals. In the course of establishing the present invention it was found that specific detection of anti-fiber-2 or anti-fiber antibodies in the vaccinated animals is difficult or even impossible by commercially available FAdV-test kits, especially FAdV-ELISAs, or by usual serum neutralization tests (SNTs). It was observed that only detection with fiber-2 or fiber-specific tests (e.g. Fib-2 or Fib ELISAs and the like) was possible. This was due to type specificity and the non-neutralizing capacity of the antibodies elicited by the vaccination according to the present invention. Nevertheless ((and even more remarkable)), sufficient protection is provided with the vaccine according to the present invention.

This shows that there was also a need to provide a specific test and test system to establish whether protection is given (by the determining the presence of specific antibodies against fibre-2 protein of FAdV-C or FAdV-A or against fiber protein of FAdV-B, FAdV-D or FAdV-E). This could be provided by the kit according to the present invention that—in contrast to the commercially available FAdV-ELISAs and SNTs (that might produce false negative results)—successfully and reliably confirm successful vaccination. The kit of the present invention also provides a means for detecting infection with FAdV viruses, because fiber-2 protein of FAdV-C or FAdV-A or fiber protein of FAdV-B, FAdV-D or FAdV-E is very specific for the individual viruses. Moreover, the kit according to the present invention is also suitable for determining whether antibody protection is still present in progeny of vaccinated animals or whether an active immunization of the progeny is indicated.

Preferably, the kit according to the present invention further comprises means for detection of the binding of an antibody to the immobilised fiber-2 protein of FAdV-C or FAdV-A or immobilised fiber protein of FAdV-B, FAdV-D or FAdV-E or the immobilised immunogenic fragment thereof, preferably an antibody being specific for bird antibodies, especially an anti-chicken IgG antibody or an anti-turkey IgG antibody. Of course, any suitable detection (capturing) means for the binding event between fiber-2 protein or fiber protein and an antibody from the vaccinated bird is suitable for the present kit; however, (secondary) antibodies or suitable (secondary) antibody fragments that are able to bind to the anti-fiber-2 antibodies or anti-fiber antibodies to be detected in a (blood) sample of the vaccinated bird are specifically preferred.

It is specifically preferable to provide a solid phase test kit with a labelled agent that detects the binding event to the immobilised fiber-2 or fiber protein. Accordingly, detection agent for the binding event, especially the anti-chicken IgG antibody or the anti-turkey IgG antibody, is a labelled agent, especially a labelled antibody. For example, the agent (antibody/antibody fragment) is labelled with a colourigenic, fluorescent, luminescent or radioactive label.

Suitable labels are therefore e.g. fluorescent compounds, isotopic compounds, chemiluminescent compounds, quantum dot labels, biotin, enzymes, electron-dense reagents, and haptens or proteins for which antisera or monoclonal antibodies are available. The various means of detection include but are not limited to spectroscopic, photochemical, radiochemical, biochemical, immunochemical, or chemical means.

The label may be of a chemical, peptide or nucleic acid molecule nature although it is not so limited. Other detectable labels include radioactive isotopes such as $^{32}$P, luminescent markers such as fluorochromes, optical or electron density markers, etc., or epitope tags such as the FLAG epitope or the HA epitope, biotin, avidin, and enzyme tags such as horseradish peroxidase, β-galactosidase, etc. The label may be bound to a peptide during or following its synthesis. There are many different labels and methods of labeling known to those of ordinary skill in the art. Examples of the types of labels that can be used in the present invention include enzymes, radioisotopes, fluorescent compounds, colloidal metals, chemiluminescent compounds, and bioluminescent compounds. Those of ordinary skill in the art will know of other suitable labels for the agents (antibodies/antibody fragments) described herein, Or will be able to ascertain such, using routine experimentation. Furthermore, the coupling or conjugation of these labels to the peptides of the invention can be performed using standard techniques common to those of ordinary skill in the art.

The invention is further illustrated by the following examples and figures, yet without being restricted thereto.

FIG. 1. Example 1: Survival rates of birds of group I (Fib-1 vaccinated), group II (Fib-2 vaccinated) and group III (Hex L1 vaccinated), together with groups IV (positive control) and V (negative control), after infection with virulent FAdV strain AG234.

Figure 2:

FIG. 2. Example 1: Pathologic lesions as manifested by focal necroses in the liver and pericardial sac filled with straw-coloured fluid in a bird from the positive control group IV that died 3 days post challenge (d.p.c.).

Figure 3:
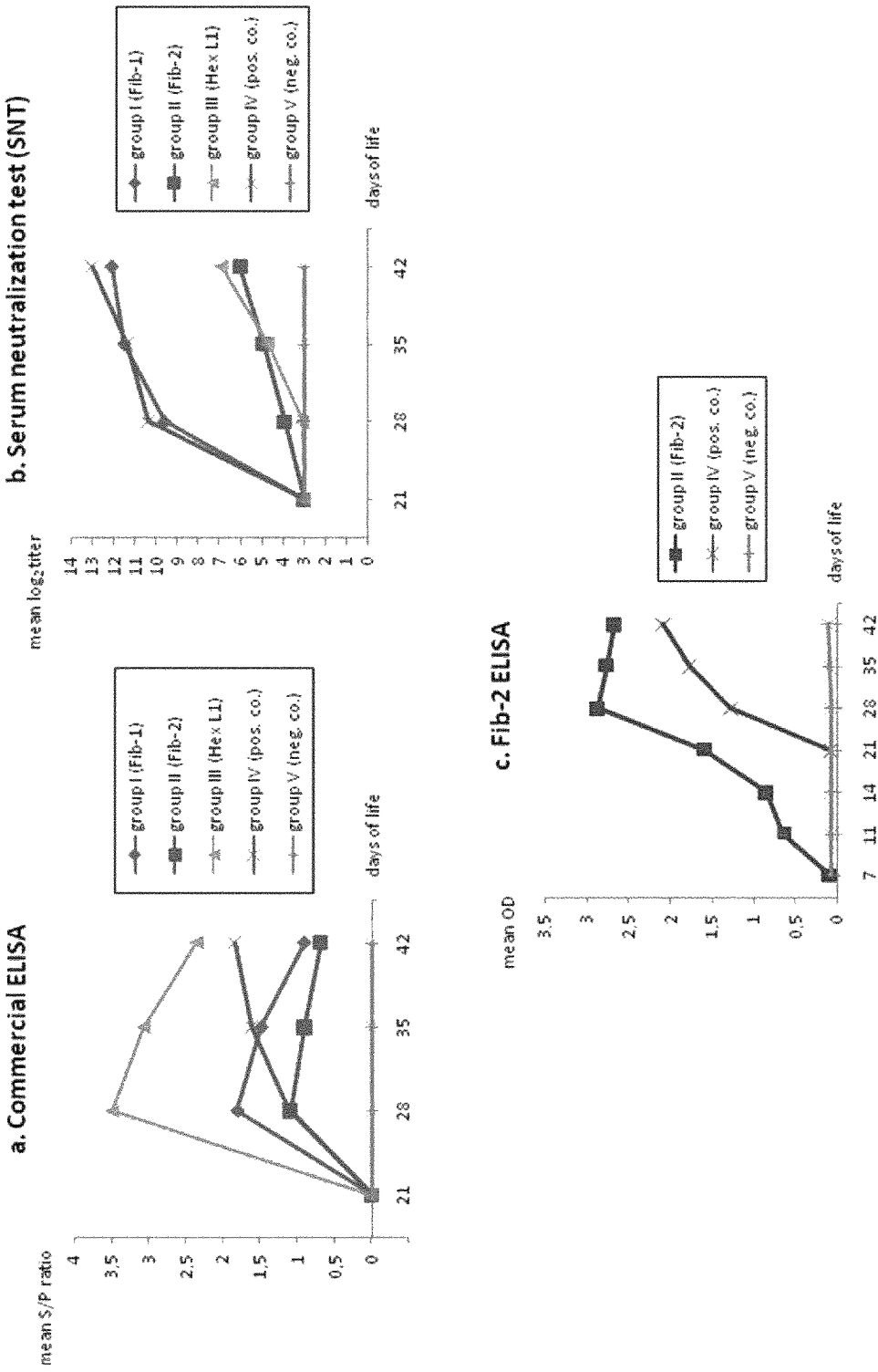

FIG. 3. Example 1: Results of antibody investigation as detected by (a) commercial FAdV Group-1 ELISA (results indicated as Sample to Positive (S/P) ratio of the mean OD value of maximum ten tested sera from each group, starting measurements on day 21 (before challenge), (b) Serum neutralization test (SNT) (results indicated as $\log_2$ transformed mean titers of maximum ten tested sera from each group, starting measurements on day 21; titres 3 were considered negative), and (c) custom-made ELISA using recombinant Fib-2 protein (results indicated as mean OD values measured from sera of all Fib-2 vaccinated birds as well as positive and negative control birds, starting on day 7).

Figure 4:
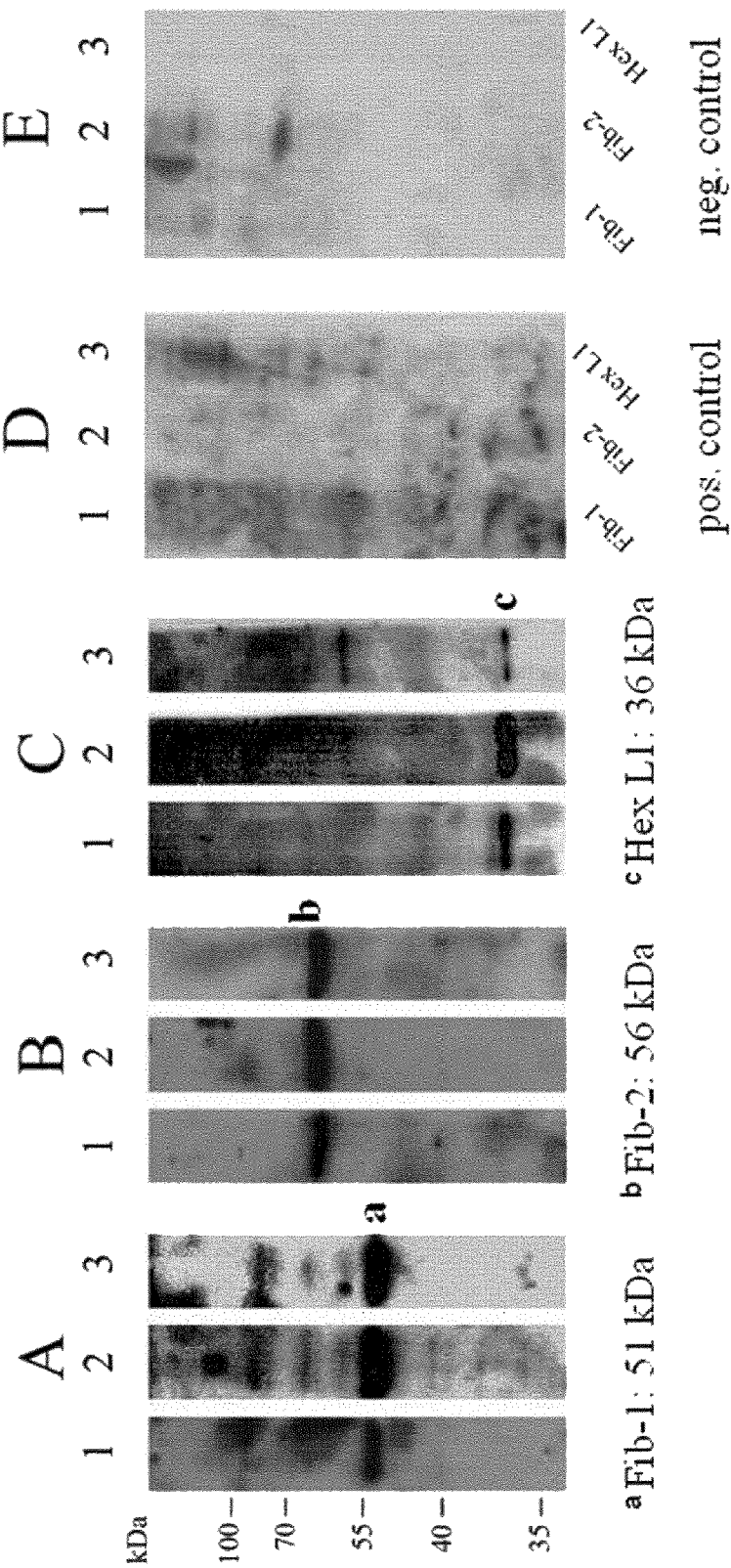

FIG. 4. Example 1: Immunoblots of purified recombinant KR5 proteins incubated with chicken sera collected on 21st day of life (preabsorbed with insect cell powder, diluted 1:2000). A, lanes 1, 2 and 3 purified Fib-1 incubated with sera from Fib-1 vaccinated birds. B, lanes 1, 2 and 3 purified Fib-2 incubated with sera from Fib-2 vaccinated birds. C, lanes 1, 2 and 3 purified Hex L1 incubated with sera from Hex L1 vaccinated birds. D, lane 1 purified Hex L1, lane 2 purified Fib-1, lane 3 purified Fib-2, incubated with serum from a bird of the positive control group (vaccinated with purified, non-infected insect cell material). E, lane 1 purified Hex L1, lane 2 purified Fib-1, lane 3 purified Fib-2, incubated with serum from a bird of the negative control group (non-vaccinated). Proteins are detected by serum antibodies as bands migrated to estimated molecular weight sizes of 51 kDa (Fib-1), 56 kDa (Fib-2) and 36 kDa (Hex L1).

FIGS. 5a-5i. Alignment of fiber proteins according to the present invention (Fib-2 of FAdV-A and FAdV-C and Fib of FAdV-B, -D and -E) (SEQ ID NOs: 15-67, respectively)

FIG. 6. Example 2: Design of the animal experiment, indicating the five different groups of birds and the respective treatment intervals FIG. 7. Example 2: Macroscopic lesions in organs of birds of the challenge control groups, as indicated by (A) spots in the livers found in two birds of group II, and (B) spots in the spleens found in birds of groups I, II and IV.

Figure 8:
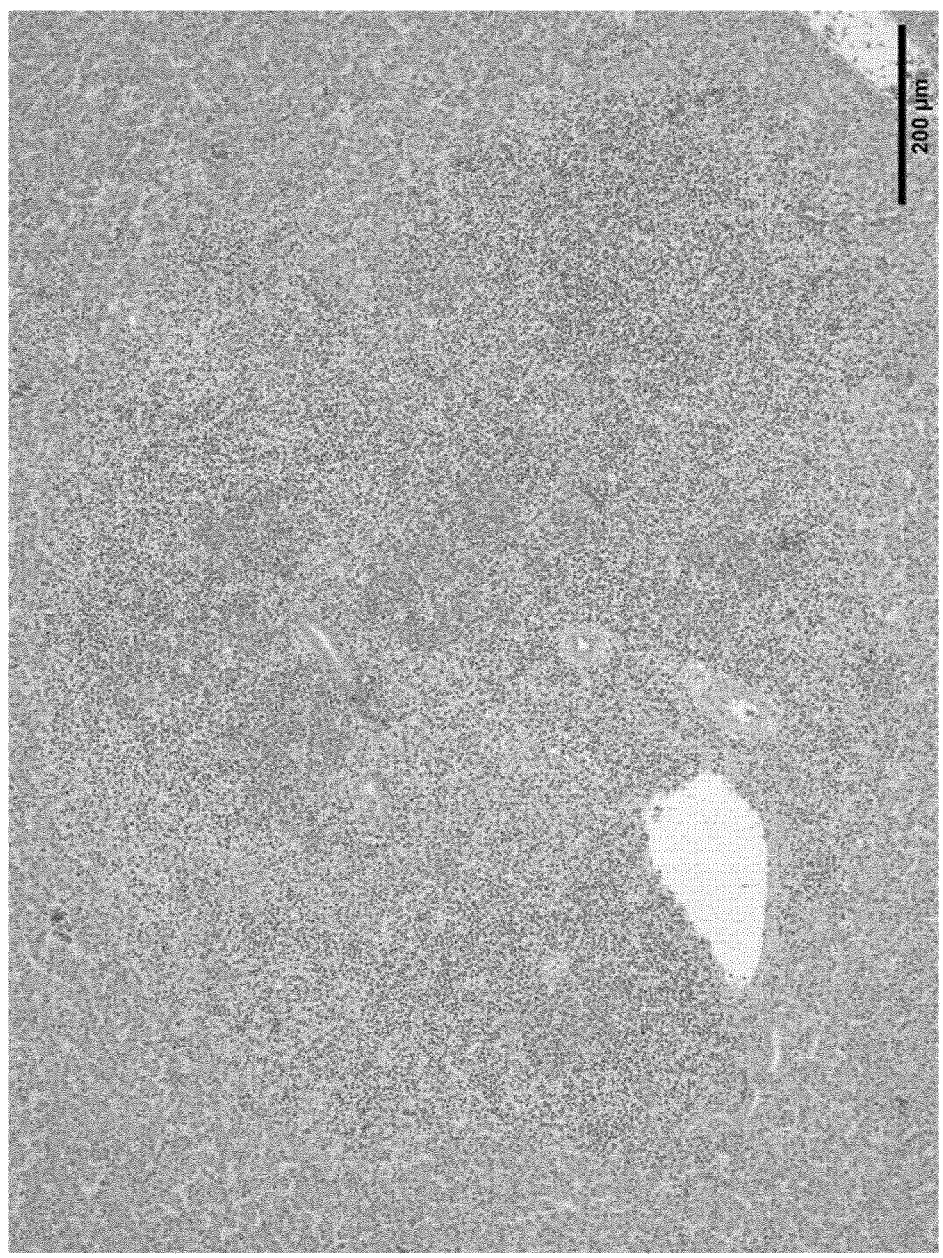

FIG. 8. Example 2: Histological section of the liver from bird 237 of the challenge control group II, taken 7 days after challenge, displaying a large site of lymphocyte infiltration of approximately 1200 μm in diameter and, as indicated by the arrow, proliferation of bile duct epithelial cells characteristic for the histopathological picture of hepatitis. The bar represents 200 μm.

EXAMPLES

Example 1

In Example 1 of the present invention, fiber-1, fiber-2 and the loop-1 region of hexon of an FAdV-C reference strain (KR5), were recombinantly expressed in the baculovirus system. In a vaccination trial, the efficacy of these capsid components to induce protective immunity in chickens was assessed by challenging birds with virulent FAdV. Hence, this is the first study of its kind to employ both fiber proteins individually in an in vivo experiment with the aim to further elucidate the functional significance of the investigated FAdV capsid proteins in the infection process and to address their potential use as candidate subunit vaccines for the control of HHS.

1. MATERIALS AND METHODS 1.1. Virus Propagation and DNA Extraction

FAdV-C(=FAdV-4) reference strain KR5 and the challenge virus AG234 were propagated on primary chicken-embryo liver (CEL) cells according to a protocol described by Schat and Sellers, A Laboratory Manual for the Isolation and Identification of Avian Pathogens, (2008), 195-203). Viral titer was determined according to the method of Reed and Muench (Am. J. Hyg. 27 (1938), 493-497) by endpoint titration. DNA extraction from cell culture supernatant was carried out with the DNeasy Blood & Tissue Kit (Qiagen, Hilden, Germany).

1.2. Cloning and initial protein expression

Primers were designed on the basis of the complete genomic KR5 sequence (GenBank accession number HE608152) and contained 5'-terminal restriction sites for cloning into the pFastBac transfer vector (Invitrogen, Vienna, Austria) (Table 1). The entire encoding regions for fiber-1 and fiber-2 (nucleotides 30438 to 31739 and 31723 to 33162, respectively) and the hexon loop-1 region (nucleotides 20481 to 21366) were amplified from the FAdV-C reference strain KR5 using a proofreading DNA polymerase (Invitrogen, Vienna, Austria). Following intermediate cloning into the pCR4Blunt-TOPO vector (Invitrogen) and digestion with BamHI/StuI (Fib-1), StuI/XbaI (Fib-2) and NcoI/XhoI (Hex L1) fragments were ligated into the cleaved pFastBac vector at the respective restriction sites. After determining the correct insertion of each product into pFastBac by sequencing, the construct was transformed into competent *E. coli* DH10Bac cells (Invitrogen, Vienna, Austria). Recombinant baculovirus DNA was isolated from transformed colonies using the S.N.A.P. Miniprep Kit (Invitrogen, Vienna, Austria). The genes of interest were expressed in *Spodoptera frugiperda* Sf9 cells (Invitrogen, Vienna, Austria) as His-tag fusion proteins according to the manufacturer's protocol.

1.3. Identification of Recombinant Proteins

To verify expression of the recombinant proteins and to optimize the expression conditions, SDS-PAGE was performed on the soluble and membrane-bound fractions of the cell lysate, collected from infected Sf9 monolayer cultures at different time intervals (24, 48, 72, 96 h) post-infection. Recombinant proteins were identified by immunoblot using anti polyhistidine antibody (Sigma-Aldrich, Vienna, Austria). Non-infected Sf9 cells were processed in the same way to serve as negative control.

1.4. Expression and Purification of Recombinant Proteins

For expression, Sf9 suspension cultures (50 ml) were infected with amplified recombinant baculovirus at an MOI of 3. Cultures collected after 72 h inoculation in a shaking incubator were concentrated by centrifugation for 5 min at 3500 rpm. The resulting cell pellet was disrupted by resuspension in lysis buffer (containing 20 mM sodium phosphate, 0.5 M NaCl, 20-40 mM imidazole, 0.2 mg/ml lysozyme, 20 μg/ml DNAse, 1 mM $MgCl_2$, 1 mM PMSF and proteinase inhibitors) and sonication, with subsequent incubation on ice for 1 h. Clarified supernatants obtained by centrifugation of the crude cell lysates at 14000 rpm for 20 min at 4° C. were used for purification on affinity chromatography columns (His GraviTrap, GE Healthcare, Freiburg, Germany). Hexon L1 protein presented as insoluble material in the pellet fraction was solubilised with phosphate buffer containing 8 M urea. The 0.45 µm-filtered sample was loaded on columns equilibrated with phosphate buffer containing 8 M urea, and the protein was eluted after step-washing the columns with decreasing concentrations of urea. Samples from each purification fraction were subsequently analyzed for presence of the proteins of interest by SDS-PAGE and immunoblotting.

Prior to in vivo administration, the recombinant proteins were transferred into sterile PBS (Gibco/Invitrogen, Vienna, Austria) by buffer exchange in Slide-A-Lyzer 7K Dialysis Cassettes (Thermo Scientific, Vienna, Austria). Protein Hex L1 was additionally processed through Amicon Ultra-15 size exclusion spin columns (Millipore, Vienna, Austria) to remove eluted insect cell proteins and to concentrate the target protein. Protein concentrations were determined by Bradford assay (Thermo Scientific, Vienna, Austria).

1.5. Animal Experiment

A total of 112 SPF (specific pathogen-free) chickens (VALO, Lohmann Tierzucht GmbH, Cuxhaven, Germany) were divided into five groups that were housed separately in isolator units (Montair Andersen bv, HM 1500, Sevenum, Netherlands). At first day of life, a 500 µl injection was administered intramuscularly to each animal, containing 50 µg of the recombinant protein, with group I (n=26) receiving fiber-1 (Fib-1), group II (n=28) receiving fiber-2 (Fib-2) and group III (n=26) receiving hexon loop-1 (Hex L1), mixed 1:1 with GERBU Adjuvant LQ #3000 (GERBU Biotechnik GmbH, Heidelberg, Germany; a sterile aqueous suspension of lipid particles with excipients and emulsifiers).

Equally, birds of group IV (n=23) were injected with purified and dialysed material from non-infected insect cells to serve as a positive control. Birds of group V (n=9) were treated as a negative control and received an injection of 500 µl sterile PBS.

At day 21 of life, animals of groups I to IV were intramuscularly challenged with 200 µl of $10^7$ 50% tissue culture infective dose ($TCID_{50}$)/ml of the virulent FAdV-C virus AG234. Birds of the negative control group were administered the same amount of sterile PBS intramuscularly.

Upon challenge, the birds were monitored daily for clinical signs. Necropsy was performed on all animals that died or had to be euthanized in the course of the study. Samples taken at regular intervals included blood (collected on days 7, 11, 14, 21, 28, 35 and 42) for detection of antibodies and cloacal swabs (collected on days 21, 28 and 35) or tissue from the large intestine (taken on day 42) for detection of virus excretion at regular intervals.

All remaining birds were killed at the termination of the experiment on day 42 of life.

The trial and all of the included procedures on experimental birds were discussed and approved by the institutional ethics committee and licensed by the Austrian government (license number BMWF-68.205/0196-II/3b/2012).

1.6. Antibody Response

Commercial FAdV Enzyme-Linked Immunosorbent Assay (ELISA)

Commercially available FAdV Group 1 Antibody Test Kit was obtained from BioChek (Reeuwijk, Holland) to test antibody levels in sera of each group before (day 21) and after challenge (days 28, 35 and 42).

Serum Neutralization Test (SNT)

Test sera were inactivated at 56° C. for 30 min. CEL cells were prepared from 14-day-old chicken embryos and plated in 96-well plates (Sarstedt, Wiener Neudorf, Austria) with a density of $1 \times 10^6$ cells/ml. The assay was performed according to a constant virus diluted serum method using 100 $TCID_{50}$/100 µl KR5. The plates were inoculated at 37° C. in 5% $CO_2$ and investigated for CPE after 5 days.

Fib-2 ELISA

After predetermining optimal virus- and serum-dilutions by checker-board titrations, 96-well ELISA plates (Nunc Medisorb, Roskilde, Denmark) were coated with 100 µl recombinant affinity-purified Fib-2 protein per well, diluted in coating buffer (0.015 M $Na_2CO_3$, 0.035 M $NaHCO_3$, pH 8.4) to a final concentration of 0.05 µg/ml. After 24 h, plates were washed and 100 µl of the test sera, diluted 1:100 in blocking buffer (Starting Block T20 PBS, Thermo Scientific), were added to each well for 1 h. Following a washing step, 100 µl Goat-Anti-Chicken-IgG-HRP (Southern Biotechnology, Birmingham, USA) diluted 1:5000 in PBS-0.05% v/v Tween 20 (Calbiochem, Darmstadt, Germany) were added to each well and incubated for 1 h. After another washing step, 100 µl TMB (tetramethylbenzidine) substrate (Calbiochem, Darmstadt, Germany) were added to each well and the plates were incubated for 15 min in the dark. The reaction was stopped with 100 µl 0.5 M sulphuric acid/well and the optical density (OD) of each well was measured with an ELISA reader (Sunrise-Basic, Tecan, Grodig, Austria) at a wavelength of 450 nm.

On each plate, a positive and a negative control were included. All sera were tested in duplicate and the OD is indicated as the mean value of the duplicates. A tentative cut-off value was established as the arithmetic mean of all OD values plus three times the standard deviation determined from serum samples from the negative control group.

1.7. Western Blot Analysis

Purified recombinant Fib-1, Fib-2 and Hex L1 proteins were boiled for 5 min in sample buffer containing 4% SDS and 10% mercaptoethanol, separated by 12% SDS-PAGE and electrotransferred onto BioTrace PVDF Transfer Membrane (Pall, Vienna, Austria). After 3 h of blocking with 3% (w/v) skim milk, the membrane was cut into strips which were incubated separately in the test sera (preabsorbed with 1% Sf9 cell powder, diluted 1:2000) for 1 h. After several washes with PBS-0.05% Tween 20, the membrane strips were incubated for 1 h with rabbit anti-chicken IgG-HRP conjugate (Sigma-Aldrich, Vienna, Austria) diluted 1:2500, followed by several washes and incubation with Clarity Western ECL substrate (Bio-Rad Laboratories GmbH, Vienna, Austria). Visualization was performed on x-ray film (Super RX, Fuji, Japan) after exposure for 12 sec.

1.8. Real-Time (Rt) PCR from Cloacal Swabs and Intestine

Excretion of challenge virus was investigated from cloacal swabs taken on days 7 and 14 post challenge (p.c.) and tissue samples taken from the large intestine at termination of the study (day 21 p.c.) from five birds of each group, using an rt PCR assay based on the 52K gene, following DNA extraction with a commercial system (Qiagen, Hilden, Germany) (Günes et al., J. Virol. Meth. 183 (2012), 147-153).

2. RESULTS 2.1. Expression of Proteins

Characteristic morphologic changes were exhibited by Sf9 cell cultures within 48-96 h after inoculation with recombinant baculovirus. Recombinant proteins were detected by SDS-PAGE and Western blot as bands migrated to estimated molecular weight sizes of 51 kDa (Fib-1), 56 kDa (Fib-2) and 35 kDa (Hex L1) with peak expression around 72 h after inoculation. Furthermore, expression analysis showed that large fractions of Fib-1 and Fib-2 were expressed as soluble proteins in the supernatant, whereas Hex L1 protein was preferentially found in the pellet.

2.2. Protection of Recombinant Proteins Against Virulent FAdV

Following challenge, clear-cut differences in severity of clinical signs and mortality rates were noticed between individual groups (FIG. 1). The difference in mortality between the groups was found to be highly significant by chi-square analysis ($\chi^2=46$; $p<0.01$) and significant differences were also indicated in the pairwise comparison of mortality between the Fib-2 vaccinated group and all other challenged groups (Bonferroni corrected chi-square test).

Onset of mortality was recorded on day 3 p.c., in coincidence with the overall peak of mortality. Dead birds were observed until day 5 p.c., and after that no more animals died. After infection with the virulent virus, birds of group IV (positive control) showed severe clinical depression as manifested by huddling together with ruffled feathers, and 18 out of 23 animals (78%) died. In contrast, birds in group II (Fib-2 vaccinated) displayed no apparent clinical symptoms and only one dead animal out of 28 on day 3 p.c. after the challenge was recorded. Birds of group I (Fib-1 vaccinated) partially showed clinical symptoms and 10 out of 26 animals died resulting in an overall mortality of 38%. In group III (Hex L1 vaccinated), severity of clinical affection was comparable to the positive control group, and 19 out of 26 animals (73%) died. Necropsy revealed severe lesions in heart and liver of all animals found dead or those which had to be euthanized during the experiment. Characteristic findings included straw-colored fluid in the pericardial sac and focal necrosis in the livers (FIG. 2).

Surviving animals of clinically affected groups experienced full recovery by 26 days of life. No more lesions were recorded in any of the surviving animals at termination of the experiment on day 42 of life. In group V (negative control), no clinical signs were observed at any time of the experiment and no pathological lesions were noticed at termination of the study.

2.3. Detection of Antibodies

Commercial FAdV ELISA and SNT

No antibodies were detected with the commercial ELISA and the SNT prior to challenge at day 21 in any of the groups (FIGS. 3a and 3b). Following challenge, birds of groups I-IV developed an increase in antibody levels detectable by both commercial ELISA and SNT. In the vaccinated groups, antibodies measured by commercial ELISA increased until 7 d.p.c. and after that gradually declined, whereas antibody levels in the positive control group display a continuous increase until termination of the experiment. Development of neutralizing antibodies p.c. continuously increased in groups I-IV with highest titres obtained in non-vaccinated birds No antibodies were detected in negative control animals at any of the tested time points during the experiment.

Fib-2 ELISA

To investigate a specific antibody response against Fib- prior to and after challenge a custom-made ELISA using recombinant purified protein was developed. Starting measurements in Fib-2 vaccinated birds on day 7, the ELISA first detected an increase in mean OD value above the determined cut-off on day 11 and peaked at 7 d.p.c. (FIG. 3b). Until termination of the experiment, mean Fib-2 antibody levels declined only slightly. Of note, the antibody response of the bird that did not survive challenge was only 0.21 and differed significantly from all other birds.

Birds of the positive control group were tested negative for Fib-2 antibodies on day 21. Survivors, however, developed a strong anti-Fib-2 response p.c., reaching the level of vaccinated birds by the end of the experiment.

Sera obtained from the negative control group before and after challenge were tested negative in the Fib-2 ELISA (FIG. 3c), similarly to sera from Fib-1 and Hex L1 vaccinated groups.

2.4. Western Blot

Immunoblots with sera from three birds of each group I-III obtained on day 21 after administration of recombinant proteins confirmed the presence of antibodies against Fib-1, Fib-2 and Hex L1, respectively (FIG. 4). No antibodies were detected in sera from one bird of the positive and negative control group when tested against each of the purified recombinant proteins in the immunoblot.

2.5. Virus Excretion

No virus excretion was detected in any of the samples taken from negative control animals (Table 2). Following challenge, viral excretion was noticed in all tested birds of groups I-IV, at 7 d.p.c with no evident difference in viral load between protein-vaccinated and positive control birds. Shedding was verified until termination of the experiment and the majority of birds were recorded positive for virus excretion in the faeces. The large intestine of half of the infected birds was positive at termination of the study, with positive birds in each of the groups I-IV.

3. DISCUSSION

While human adenoviruses are well studied on a molecular basis for their use as vaccine and gene therapy vectors, current understanding of FAdV-host interaction and molecules involved is still limited. Interaction between capsomer and host cell has been established as the critical factor in formation of host immunity, rendering adenovirus capsid proteins interesting candidates for subunit vaccine development. In regard to the prevention of HHS, E. coli expressed penton base was recently proposed as a potential subunit antigen. In the present study, the efficacy of fiber subunit immunization derived from FAdV-C was investigated by utilizing for the first time the novel finding of two distinct fiber-encoding genes in FAdV-C. In addition, hexon loop-1, a surface-exposed structure with immunogenic potential, was investigated.

The choice of the baculovirus expression system was based on evidence for possible post-translational modifications of such adenovirus proteins.

Upon challenge with the virulent strain AG234, different degrees of protection were observed in chickens vaccinated with recombinant FAdV capsid proteins. Although Hex L1-specific antibodies were detected prior to challenge, this protein could not be proven as an effective subunit antigen in our study. In comparison, an immune response directed against Fib-2 is highly efficacious as it prevents any clinical signs of disease. This could indicate a key role of the Fib-2 protein in the initial steps of infection, possibly by mediating attachment to host cell receptors. Cellular attachment via binding of fiber to the ubiquitously present coxsackievirus-adenovirus receptor (CAR) is a well-known mechanism in human adenoviruses. However, knowledge about CAR-fiber interaction is primarily derived from in vitro studies and the role of CAR as primary receptor for adenovirus entry into the host cell is increasingly questioned. In this context, binding to primary receptors specific for avian—but not mammalian, —cells was suggested to be mediated by the short fiber of CELO. Previous phylogenetic data show a higher degree of relatedness of FAdV-C Fib-2 with the short fiber gene of CELO and the single fiber gene found in other FAdV species, as compared to Fib-1. Based on these informations, together with the actual finding of highly efficacious immune response directed against FAdV-C Fib-2, Fib-2 could serve as the primary ligand for induction of a host-cell dependent infection pathway.

Antibodies raised against Fib-2 following vaccination were detected with the exception of one bird, indicating a correlation with protection, in contrast to the commercial ELISA which failed to detect antibodies before challenge. Obviously, the type specificity of the fiber antigen results in a binding incompatibility of the induced antibodies within the commercial ELISA test system. The results obtained from SNT indicate that antibodies directed against Fib-2 do not possess neutralizing capacity, which is in agreement with previously reported observations of weak or lacking serum neutralization activity elicited by fiber if administered as an isolated virus component.

The challenge virus was detected in cloacal swabs of groups I-IV alike, demonstrating that vaccination does not prevent virus excretion and shedding, even in birds protected from clinical disease. This finding is supported by a previous study that reports excretion of challenge virus even in birds clinically fully protected by a live attenuated FAdV vaccine (Schonewille et al., Avian Dis. 54 (2010), 905-910).

In summary, identification of virulent strains of FAdV-C as causative agents of HHS together with the limitations faced by currently employed inactivated vaccines argue for the development of next-generation immunization strategies. The findings presented in the present invention shows high efficacy of recombinant Fib-2 protein for the development of an effective and safe subunit vaccine.

Tables

TABLE 1

Primers used.

| Primer name | Sequence (5'-3') | Position | Purpose |
|---|---|---|---|
| KR5-b Fib-1 f | 5'-GGATCCATGTCGGCCCTAATCG-3' SEQ ID NO.: 1 | 30438-30453 | [a] Amplification of the fiber-1 gene of strain KR5 and cloning into the pFastBac vector |
| KR5-b Fib-1 r | 5'-AGGCCTTTAGGGGCTCGGAGC-3' SEQ ID NO.: 2 | 31725-31739 | [a] Amplification of the fiber-1 gene of strain KR5 and cloning into the pFastBac vector |
| KR5-b Fib-2 f | 5'-AGGCCTATGCTCCGAGCCCCTA-3' SEQ ID NO.: 3 | 31723-31738 | [a] Amplification of the fiber-2 gene of strain KR5 and cloning into the pFastBac vector |
| KR5-b Fib-2 r | 5'-TCTAGATTACGGGACGGAGGCTG-3' SEQ ID NO.: 4 | 33146-33162 | [a] Amplification of the fiber-2 gene of strain KR5 and cloning into the pFastBac vector |
| FAV f | 5'-AATTCCATGGACAAGTTCAGGCAGAC-GGTCGT-3' SEQ ID NO.: 5 | 20481-20502 | [a] Amplification of the hexon loop-1 gene region of strain KR5 and cloning into the pFastBac vector |
| FAV r | 5'-TAACTCGAGCTAGTGATGCCGG-GACATCAT-3' SEQ ID NO.: 6 | 21347-21366 | [a] Amplification of the hexon loop-1 gene region of strain KR5 and cloning into the pFastBac vector |
| 52K-fw | 5'-ATGGCKCAGATGGCYAAGG-3' SEQ ID NO.: 7 | 13075-13093 | [b] Amplification of the 52k gene in rt-PCR |
| 52K-rv | 5'-AGCGCCTGGGTCAAACCGA-3' SEQ ID NO.: 8 | 13250-13232 | [b] Amplification of the 52k gene in rt-PCR |

[a] Position is indicated for the complete genomic KR5 sequence (HE608152).
[b] Position is indicated for the complete genomic CELO sequence (U46933).

TABLE 2

Detection of viral excretion in cloacal swab samples (taken on days 21, 28 and 35) and tissue from the large intestine (taken on day 42) by real-time PCR from five birds of each group. Results are shown as number of positive samples/number of samples tested.

| d [a] | group I (Fib-1) | group II (Fib-2) | group III (Hex L1) | group IV (positve control) | group V (negative control) |
|---|---|---|---|---|---|
| 21 | — | — | — | — | — |
| 28 | 5/5 | 5/5 | 5/5 | 5/5 | 0/5 |
| 35 | 3/5 | 4/5 | 4/5 | 4/5 | 0/5 |
| 42 | 1/5 | 3/5 | 5/5 | 1/5 | 0/5 |

[a] Day of life

TABLE 3

List of examples of fiber proteins useable according to the present invention:

Fowl adenovirus 8 serotype 8 pVIII (pVIII), fiber (fiber), and fiber genes, complete cds; and unknown genes
4,011 bp linear DNA
U40587.1 GI:1497858
Fowl adenovirus 8 serotype 8 pVIII (pVIII), ORF-6, fiber, ORF-5, ORF-4, and ORF-3 genes, complete cds
4,005 bp linear DNA
U40588.1 GI:1497867
Fowl adenovirus 4 isolate Punjab 1 fiber gene, complete cds
1,386 bp linear DNA TABLE 3-continued List of examples of fiber proteins useable according to the present invention:

DQ864436.1 GI:112735223
Fowl adenovirus 1 isolate Punjab 1 fiber gene, partial cds
345 bp linear DNA
DQ864435.1 GI:112735221
Fowl adenovirus 4 isolate Punjab 2 fiber gene, complete cds
1,386 bp linear DNA
DQ864434.1 GI:112735219
Fowl adenovirus D, complete genome
45,063 bp linear DNA
AC_000013.1 GI:56160703
Fowl adenovirus 5 strain 340, complete genome
45,781 bp linear DNA
NC_021221.1 GI:501000341
Fowl adenovirus 5 strain 340, complete genome
45,781 bp linear DNA
KC493646.1 GI:494114569
Fowl adenovirus B pVIII gene, U-exon gene, fiber gene and ORF22, isolate 340
3,286 bp linear DNA
HE608155.1 GI:381214079
Fowl adenovirus B partial fiber gene, isolate 340
1,665 bp linear DNA
FR872928.1 GI:381214015
Fowl adenovirus 8 isolate 05-50052-3180 fiber protein gene, complete cds
1,575 bp linear DNA
JQ034221.1 GI:380039470
Fowl adenovirus 11 isolate 05-17766 fiber protein gene, complete cds
1,719 bp linear DNA
JQ034220.1 GI:380039468
Fowl adenovirus 11 isolate 06-25854-1 fiber protein gene, complete cds
1,719 bp linear DNA
JQ034219.1 GI:380039466
Fowl adenovirus 11 isolate 05-50052-3181 fiber protein gene, complete cds
1,719 bp linear DNA
JQ034218.1 GI:380039464
Fowl adenovirus 11 isolate 05-50052-2924-1 fiber protein gene, complete cds
1,719 bp linear DNA
JQ034217.1 GI:380039462
Fowl adenovirus 8 isolate 06-41265-07 fiber protein gene, complete cds
1,572 bp linear DNA
JQ034216.1 GI:380039460
Fowl adenovirus 8 isolate 04-53357-125 fiber protein gene, complete cds
1,572 bp linear DNA
JQ034215.1 GI:380039458
Fowl adenovirus 8 isolate 06-16340-336 fiber protein gene, complete cds
1,575 bp linear DNA
JQ034214.1 GI:380039456
Fowl adenovirus A short fiber gene, serotype 4
1,437 bp linear DNA
HE649966.1 GI:372285271
Fowl adenovirus 4 short fiber gene, complete cds
1,482 bp linear DNA
AY340863.1 GI:33359662
Fowl adenovirus 10 short fiber protein gene, complete cds
1,496 bp linear DNA
AF007579.1 GI:2674070
Fowl adenovirus 4 isolate Kr-Yeoju short fiber gene, complete cds
1,425 bp linear DNA
HQ709232.1 GI:318040046
Fowl adenovirus 4 isolate Kr-Gunwi short fiber gene, complete cds
1,425 bp linear DNA
HQ709231.1 GI:318040044
Fowl adenovirus 4 isolate Kr-Andong short fiber gene, complete cds
1,425 bp linear DNA
HQ709230.1 GI:318040042
Fowl adenovirus 4 isolate Kr-Changnyeong short fiber gene, complete cds
1,425 bp linear DNA
HQ709229.1 GI:318040040
Fowl adenovirus partial sf gene for short fiber protein, isolate OTE
1,197 bp linear DNA
FN557186.1 GI:315455213
Fowl adenovirus partial sf gene for short fiber protein, isolate 08-5769
1,197 bp linear DNA
FN557185.1 GI:315455211
Fowl adenovirus partial sf gene for short fiber protein, isolate 08-3622
1,197 bp linear DNA
FN557184.1 GI:315455209
Fowl adenovirus 8 100 kDa protein homolog gene, partial cds; pVIII homolog, short fiber homolog, and triacylglycerol lipase homolog genes, complete cds; and unknown genes
19,056 bp linear DNA
AF155911.1 GI:6572643
Fowl adenovirus 1 strain PL/060/08 short fiber protein gene, partial cds
1,153 bp linear DNA
GU952108.1 GI:294992185
Fowl adenovirus 4 isolate Bareilly fiber protein gene, complete cds
1,437 bp linear DNA
FJ949088.1 GI:238683632
Fowl adenovirus A, complete genome
43,804 bp linear DNA
NC_001720.1 GI:9628835
Fowl adenovirus D, complete genome
45,063 bp linear DNA
NC_000899.1 GI:9633173
Fowl adenovirus 9, complete genome
45,063 bp linear DNA
AF083975.2 GI:6466454
Fowl adenovirus 1 two fibers, protein pVIII and 7 unknown genes
7,359 bp linear DNA
X84724.1 GI:780165
Fowl adenovirus E, complete genome
44,055 bp linear DNA
NC_014969.1 GI:320202734
Fowl adenovirus E isolate HG, complete genome
44,055 bp linear DNA
GU734104.1 GI:293627422
Fowl adenovirus C pVIII gene, U-exon gene, fiber-1 gene, fiber-2 gene and ORF22, isolate C2B
4,345 bp linear DNA
HE608154.1 GI:381214073
Fowl adenovirus C pVIII gene, U-exon gene, fiber-1 gene, fiber-2 gene and ORF22, isolate AG234
4,321 bp linear DNA
HE608153.1 GI:381214067
Fowl adenovirus C complete genome, isolate KR5
45,810 bp linear DNA
HE608152.1 GI:381214017
Fowl adenovirus C partial fiber-2 gene, isolate K388-95
1,395 bp linear DNA
FR872927.1 GI:381214013
Fowl adenovirus C partial fiber-2 gene, isolate 09/8846
1,440 bp linear DNA
FR872926.1 GI:381214011
Fowl adenovirus C partial fiber-2 gene, isolate 09/584
1,440 bp linear DNA
FR872925.1 GI:381214009
Fowl adenovirus C partial fiber-2 gene, isolate 09/2602
1,329 bp linear DNA
FR872924.1 GI:381213952
Fowl adenovirus C partial fiber-2 gene, isolate K99-97
1,340 bp linear DNA
FR872923.1 GI:381213950
Fowl adenovirus C partial fiber-2 gene, isolate Peru54
1,421 bp linear DNA

TABLE 3-continued

List of examples of fiber proteins useable according to the present invention:

FR872922.1 GI:381213948
Fowl adenovirus C partial fiber-2 gene, isolate Peru53
1,416 bp linear DNA
FR872921.1 GI:381213946
Fowl adenovirus C partial fiber-1 gene, isolate K1013
1,184 bp linear DNA
FR872898.1 GI:381213900
Fowl adenovirus C partial fiber-1 gene, isolate 922/1
1,311 bp linear DNA
FR872897.1 GI:381213898
Fowl adenovirus C partial fiber-1 gene, isolate C2B
1,302 bp linear DNA
FR872896.1 GI:381213896
Fowl adenovirus C partial fiber-1 gene, isolate Da60
1,302 bp linear DNA
FR872895.1 GI:381213894
Fowl adenovirus C partial fiber-1 gene, isolate KR5
1,302 bp linear DNA
FR872894.1 GI:381213892
Fowl adenovirus C partial fiber-1 gene, isolate INT4
(QT-cell passaged AG234)
1,188 bp linear DNA
FR872893.1 GI:381213890
Fowl adenovirus C partial fiber-1 gene, isolate AG234
1,302 bp linear DNA
FR872892.1 GI:381213888
Fowl adenovirus C partial fiber-1 gene, isolate K31
1,181 bp linear DNA
FR872891.1 GI:381213886
Fowl adenovirus A short fiber gene, serotype 4
1,437 bp linear DNA
HE649966.1 GI:372285271
Fowl adenovirus 4 isolate Kr-Yeoju short fiber gene,
complete cds
1,425 bp linear DNA
HQ709232.1 GI:318040046
Fowl adenovirus 4 isolate Kr-Gunwi short fiber gene,
complete cds
1,425 bp linear DNA
HQ709231.1 GI:318040044
Fowl adenovirus 4 isolate Kr-Andong short fiber gene,
complete cds
1,425 bp linear DNA
HQ709230.1 GI:318040042
Fowl adenovirus 4 isolate Kr-Changnyeong short fiber gene,
complete cds
1,425 bp linear DNA
HQ709229.1 GI:318040040
Fowl adenovirus partial sf gene for short fiber protein,
isolate OTE
1,197 bp linear DNA
FN557186.1 GI:315455213
Fowl adenovirus partial sf gene for short fiber protein,
isolate 08-5769
1,197 bp linear DNA
FN557185.1 GI:315455211
Fowl adenovirus partial sf gene for short fiber protein,
isolate 08-3622
1,197 bp linear DNA
FN557184.1 GI:315455209
Fowl adenovirus E isolate HG, complete genome
44,055 bp linear DNA
GU734104.1 GI:293627422
Fowl adenovirus 8 serotype 8 pVIII (pVIII), ORF-6, fiber,
ORF-5, ORF-4, and ORF-3 genes, complete cds
4,005 bp linear DNA
U40588.1 GI:1497867
Fowl adenovirus 8 serotype 8 pVIII (pVIII), fiber (fiber),
and fiber genes, complete cds; and unknown genes
4,011 bp linear DNA
U40587.1 GI:1497858
Fowl adenovirus 4 isolate Bareilly fiber protein gene,
complete cds
1,437 bp linear DNA
FJ949088.1 GI:238683632
Fowl adenovirus 4 short fiber gene, complete cds
1,482 bp linear DNA
AY340863.1 GI:33359662
Fowl adenovirus 4 isolate Punjab 1 fiber gene, complete cds
1,386 bp linear DNA
DQ864436.1 GI:112735223
Fowl adenovirus 1 isolate Punjab 1 fiber gene, partial cds
345 bp linear DNA
DQ864435.1 GI:112735221
Fowl adenovirus 4 isolate Punjab 2 fiber gene, complete cds
1,386 bp linear DNA
DQ864434.1 GI:112735219
Fowl adenovirus 8 100 kDa protein homolog gene, partial cds;
pVIII homolog, short fiber homolog, and triacylglycerol
lipase homolog genes, complete cds; and unknown genes
19,056 bp linear DNA
AF155911.1 GI:6572643
Fowl adenovirus 9, complete genome
45,063 bp linear DNA
AF083975.2 GI:6466454
Fowl adenovirus 10 short fiber protein gene, complete cds
1,496 bp linear DNA
AF007579.1 GI:2674070
Avian adenovirus CELO, complete genome
43,804 bp linear DNA
U46933.1 GI:1314432
Sequence 1 from Patent WO9740180
43,804 bp linear DNA
Fowl adenovirus 1 two fibers, protein pVIII and 7 unknown
genes
7,359 bp linear DNA
X84724.1 GI:780165

The nature of the sequence, the FAdV species/serotypes, the length of the sequence, the GenBank accession number and the version is indicated for each of the sequences.

TABLE 4

List of species in the genus Aviadenovirus:

| *Falcon adenovirus A* | | | |
|---|---|---|---|
| Falcon adenovirus | 1 | [AY683541] | (FaAdV-1) |
| *Fowl adenovirus A* | | | |
| Fowl adenovirus | 1 | (CELO) [U46933 = AC_000014] | (FAdV-1) |
| *Fowl adenovirus B* | | | |
| Fowl adenovirus | 5 | (340) [AF508952] | (FAdV-5) |
| *Fowl adenovirus C* | | | |
| Fowl adenovirus | 4 | (ON1) [GU188428 = NC_015323] | (FAdV-4) |
| Fowl adenovirus | 10 | (CFA20) [AF160185] | (FAdV-10) |
| *Fowl adenovirus D* | | | |
| Fowl adenovirus | 2 | (P7-A) [AF339915] | (FAdV-2) |
| Fowl adenovirus | 3 | (75) [AF508949] | (FAdV-3) |
| Fowl adenovirus | 9 | (A2-A) [AF083975 = AC_000013] | (FAdV-9) |
| Fowl adenovirus | 11 | (380) [AF339925] | (FAdV-11) |
| *Fowl adenovirus E* | | | |
| Fowl adenovirus | 6 | (CR119) [AF508954] | (FAdV-6) |
| Fowl adenovirus | 7 | (YR36) [AF508955] | (FAdV-7) |
| Fowl adenovirus | 8a | (CFA40) [AF155911] | (FAdV-8a) |
| Fowl adenovirus | 8b | (764) [AF508958] | (FAdV-8b) |
| *Goose adenovirus* | | | |
| Goose adenovirus | 1 | | (GoAdV-1) |

Species names are in italic script; names of types and isolates ( ) are in roman script. Sequence accession numbers [ ] and assigned abbreviations ( ) are also listed.

Example 2

1. MATERIALS AND METHODS 1.1. Virus Propagation and DNA Extraction

FAdV-D and -E reference strains SR48 and YR36 were used as cloning templates, FAdV-D and -E field isolates 08/18926 and 08/17832, both isolated from field outbreaks of inclusion body hepatitis, as challenge strains. All viruses were propagated on primary chicken-embryo liver (CEL) cells which were prepared according to a protocol described by Schat & Sellers [1]. Viral titer was determined by endpoint titration according to the method of Reed & Muench [2]. DNA extraction from cell culture supernatant was carried out with the DNeasy Blood & Tissue Kit (Qiagen, Hilden, Germany).

1.2. Cloning and Expression of Recombinant Proteins

The entire fiber encoding region was amplified from FAdV-D and -E reference strains SR48 and YR36, using primers designed on basis of the respective fiber gene sequences, containing the 5'-terminal restriction sites SStI/KpnI (primer pair FAdV-D Fib SR48 f/r) and BamHI/StuI (primer pair FAdV-E Fib YR36 f/r) for cloning the amplicons into the pFastBac transfer vector (Invitrogen, Vienna, Austria) (Table 5). Following transfection of *Spodoptera frugiperda* Sf9 cells (Invitrogen, Vienna, Austria) with recombinant baculovirus DNA isolated from transformed *E. coli* DH10Bac (Invitrogen, Vienna, Austria), the proteins of interest, thereupon termed FAdV-D Fib SR48 and FAdV-E Fib YR36, were expressed according to the manufacturer's protocol as His-tag fusion proteins of approximately 66 and 61 kDa molecular weight size.

Subsequently, Sf9 suspension cultures (50 ml) were infected with amplified recombinant baculovirus stocks at an MOI of 3. Cultures collected after 72 h inoculation in a shaking incubator were concentrated by centrifugation (5 min at 3500 rpm). For purification of FAdV-E Fib YR36, which was identified in the soluble (cytosol) fraction, the pelleted cells were disrupted by resuspension in lysis buffer (20 mM sodium phosphate, 0.5 M NaCl, 45 mM imidazole, 0.2 mg/ml lysozyme, 20 µg/ml DNAse, 1 mM $MgCl_2$, 1 mM PMSF and proteinase inhibitors) and sonication, with subsequent incubation on ice for 1 h. Clarified supernatants obtained by centrifugation of the crude cell lysates at 14000 rpm for 20 min at 4° C. were applied on affinity chromatography columns (His GraviTrap, GE Healthcare, Freiburg, Germany). FAdV-D Fib SR48 protein, presented as insoluble material in the pellet fraction, was solubilized with phosphate buffer (20 mM sodium phosphate, 0.5 M NaCl, 20 mM imidazole) containing 8 M urea. The 0.45 µm-filtered sample was loaded on columns equilibrated with phosphate buffer containing 8 M urea, and the protein was eluted after step-washing the columns with decreasing (8 M-0 M) concentrations of urea.

The eluates were analyzed for presence and purity of the proteins of interest by SDS-PAGE and immunoblotting, followed by measurements of the protein concentration by Bradford assay (Thermo Scientific, Vienna, Austria).

1.3. Animal Experiment

Fifty SPF (specific pathogen free) one-day-old chickens were divided into five groups containing 10 birds each, separately housed in isolator units. For individual identification, the birds were marked with subcutaneous tags. The design of the experiment is shown in FIG. 6.

At first day of life, each animal was administered a 500 µl intramuscular injection. Birds of the vaccination groups I (n=10) and III (n=10) received FAdV-D Fib SR48 and FAdV-E Fib YR36, respectively, containing a dose of 50 µg recombinant protein/bird mixed 1:1 with GERBU Adjuvant LQ #3000 (GERBU Biotechnik GmbH, Heidelberg, Germany). In contrast, non-vaccinated birds (challenge controls) in groups II (n=10) and IV (n=10), as well as birds of the negative control group V (n=10) were injected sterile PBS mixed 1:1 with adjuvant.

At day 21 of life, animals of groups I and II were intramuscularly challenged with 200 µl of $10^7$ 50% tissue culture infective dose ($TCID_{50}$)/ml of virus strain 08/18926, birds of groups III and IV were likewise challenged with the same dose of virus strain 08/17832. Group V was administered 200 µl of sterile PBS instead.

Upon challenge, the birds were monitored daily for clinical signs. All birds were killed at termination of the experiment on day 28 of life and subjected to necropsy and collection of cloacal swab and liver tissue samples.

1.4. Histological Investigation of Liver Tissue

Livers from 5 birds from groups I-IV and 2 negative control birds were used for detailed histological investigation. Birds were selected based upon body weight at time of killing and those birds with the lowest body weight/group were chosen. Livers were placed in 10% formalin and embedded in paraffin-wax. Tissue slices of 4 µm thickness were prepared using the microtom Microm HM 360 (Microm Laborgeräte GmbH, Walldorf, Germany) and mounted on glass slides. Dewaxing and dehydration of the tissue slices was performed followed by routine staining using haematoxylin and eosin.

The threshold value for a significant lesion size was determined as 247.6 µm diameter, according to the diameter of the largest spot of lymphocyte infiltration observed in livers of negative control birds (group V). Consequently, all spots exceeding this size were counted in tissue sections of nearly equal size.

1.5. Real-Time (Rt) PCR from Liver Tissue and Cloacal Swabs

At termination of the study (day 7 post challenge) the presence of challenge virus and viral load were determined in all liver samples and from cloacal swabs of 5 challenged birds (groups I-IV). For comparison, 2 negative control birds were investigated. In any case, processed cloacal swabs originated from those birds whose livers were investigated by histology. Following DNA extraction with the DNeasy Blood & Tissue Kit (Qiagen, Hilden, Germany), an rt PCR assay based on the 52K gene [3] was applied.

1.6. Statistical Analysis

Statistical analysis of data was performed with Microsoft Excel 2007 (MS Office, Microsoft Corporation, Redmond, Wash., USA) and the statistical software package SPSS Version 20 (IBM SPSS Statistics, IBM Corporation, Somers, N.Y., USA).

2. RESULTS 2.1. Clinical and Pathological Findings

Two birds, one in group I and one in group IV, died due to cannibalism and were therefore excluded from the study. With the exception the body weight, none of the challenged birds showed clinical symptoms pathognomonic for a fowl adenovirus infection.

At termination of the study on day 7 post challenge (p.c.), it was noted that higher mean body weights were achieved in the protein-vaccinated groups, as compared to their respective control groups. Applying t-test, the difference in body weight was found to be statistically significant between the FAdV-D Fib SR48-vaccinated group (group I) and the corresponding challenge control group II (p=0.03; α=0.05) (Table 6).

Pathomorphological lesions noticed during post mortem investigations included tiny hemorrhagic spots in the liver, recorded in two birds of the challenge control group II, as well as in the spleen, found in three birds of group II and in two birds of each of the groups I and IV (FIG. 7). As a consequence such organs appeared with a marbled surface structure.

2.2. Histological Investigation of Liver Tissue

Applying histological scoring it was noted that livers of both challenge control groups II and IV differed from livers of protein-vaccinated groups. In such organs, an overall more pronounced appearance of lymphocyte infiltration sites was recorded, however most of which were disregarded due to the determined lesion size threshold (>247.6 μm diameter in size). However, in addition to such smaller-sized lesions, a significantly higher number of spots of lymphocyte infiltration above the threshold size was detected in the livers of the non-vaccinated birds of groups II and IV, as compared to the respective protein-vaccinated groups I and III (Table 6; FIG. 8).

2.3. Real-Time (Rt) PCR from Liver Tissue and Cloacal Swabs

Rt PCR performed on liver tissue and cloacal swab samples from two birds of the negative control group yielded negative results. Applying rt PCR, presence of viral DNA could be detected in the livers of some challenged birds in groups I-IV, however 5/9 and 3/10 vaccinated birds remained negative in vaccinated groups I and III, respectively. In contrast to this, liver samples of only 2/10 and 1/9 non-vaccinated birds in groups II and IV were negative (Table 6). Performing groupwise comparison, the difference in the number of birds that showed presence of viral DNA in the liver could not be confirmed as statistically significant using Chi-square test ($\chi^2$=2.574, p=0.109 and $\chi^2$=1.017, p=0.313 for α=0.05), although in both cases there was an obvious tendency for an elevated number of positive birds in the non-vaccinated groups, as compared to the corresponding protein-vaccinated groups (numbers given above). Owing to the circumstance that viral quantity in liver tissue was below the detection limit in most birds, a statistical analysis was not attempted for these data. However highest virus loads were consistently recorded in birds from non-vaccinated groups II and IV, and exceeded measured virus loads in vaccinated birds tenfold.

Rt PCR investigation of cloacal swabs showed that all tested birds from groups I-IV excreted the challenge virus at termination of the study. Despite a statistically non-significant difference in viral quantity in cloacal swabs of protein-vaccinated groups as compared to their respective non-vaccinated groups when applying t-test (p=0.124 and p=0.194 for α=0.05), it was noted that higher mean virus loads were consistently found in non-vaccinated groups, with mean group values differing tenfold in the case of groups I and II.

3. DISCUSSION

Fowl adenoviruses (FAdVs) represent a structural peculiarity as they possess two fiber proteins per penton base, leading to an unusual penton at the viral capsid. Only FAdV-A and FAdV-C type viruses have two fiber-coding genes whereas fibers of other FAdVs are transcribed from a single gene [4]. It was recently demonstrated by Schachner et al. [5] that FAdV-C fibers differ in their biological function e.g. their capability to protect chickens from deadly hepatitis-hydropericardium syndrome. Whereas baculovirus expressed fiber-1 protein offered only partial protection, birds were fully protected following vaccination with fiber-2 protein. Considering that fiber proteins of FAdV-D and FAdV-E show a somewhat higher phylogenetic relationship with fiber-2 protein of FAdV-C [4], it was hypothesized that fiber proteins of FAdV-D and FAdV-E are also suitable to protect birds from the respective disease. FAdV-D and FAdV-E viruses are less virulent than FAdV-C but they are the etiological agents of inclusion body hepatitis in young chicks, reported in several parts of the world.

Therefore, in the actual experiment the efficacy of baculovirus expressed fiber proteins of FAdV-D and -E was tested for their ability to protect SPF chickens from challenge with pathogenic field isolates inducing inclusion body hepatitis. The experimental set-up was chosen based upon a recent study in which the recombinant fiber-2 protein of Fowl adenovirus C (FAdV-C) was able to prevent hepatitis-hydropericardium syndrome [5]. However, it needs to be considered that FAdV-D and FAdV-E type viruses are less virulent and older birds—a common feature for all fowl adenoviruses—are less susceptible, as demonstrated exemplarily for virulent FAdV-C [6].

In agreement with the previous statement, no adverse clinical signs, with the exception of an influence on body weight, were noticed in the challenged birds. Non-vaccinated birds challenged with FAdV-D field virus showed a significantly reduced body weight in comparison to vaccinated birds. Tiny hemorrhagic spots could be noticed in livers and spleens of some challenged birds. To assess the protective efficacy of recombinant FAdV-D and FAdV-E fiber proteins, detailed histological investigations and molecular studies for viral DNA detection were performed. As a few small spots of lymphocyte infiltration were noticed in control birds (without challenge) the diameter of the biggest spot was taken as threshold for assessing livers of challenged birds. Investigating livers of 5 birds from each of the challenged groups, the overall number of spots was clearly increased, while the number of spots above the threshold size was more than doubled in non-vaccinated birds compared to vaccinated ones. From the premise that spots above the threshold size served as a characteristic indicator for hepatitis, it can be concluded that recombinant fiber proteins were able to reduce severity of lesions.

Interestingly, the histological findings correlated well with the presence of challenge virus in liver tissue determined by real time PCR, with highest viral loads found in livers of individual birds with elevated number of lymphocyte infiltration spots, while the three birds from group I and III that were tested negative showed only minor or no histological lesions.

Rt PCR investigations of the livers indicated a reduced presence of challenge virus in vaccinated versus non-vaccinated birds, and in both sample categories—liver tissue and cloacal swabs—it was consistently found that viral quantity was notably reduced in the vaccinated groups. This finding was most pronounced in birds challenged with FAdV-D virus displaying a tenfold decrease of viral load in both livers and cloacal swabs investigated from vaccinated versus non-vaccinated birds.

In conclusion, influence on body weight, presence of morphological and histological lesions and viral load in liver samples together with virus excretion in feces demonstrate the benefit of FAdV-D and -E fiber proteins as recombinant vaccines.

4. REFERENCES

[1] Schat K, Sellers H S. Cell Culture Methods. In: Dufour-Zavala L, Swayne D E, Glisson J R, Pearson J E, Reed W M, Jackwood M W, Woolcock P R, editors. A Laboratory Manual for the Isolation and Identification of Avian Pathogens. 5th ed. Madison, Wis., OmniPress, Inc., 2008: p. 195-203.

[2] Reed L J, Muench H. A simple method of estimating fifty percent endpoints. Am J Hyg 1938; 27:493-7.

[3] Günes A, Marek A, Grafl B, Berger E, Hess M. Real-time PCR assay for universal detection and quantitation of all five species of fowl adenoviruses (FAdV-A to FAdV-E). J Virol Methods 2012; 183(2):147-53.

[4] Marek A, Nolte V, Schachner A, Berger E, Schlotterer C, Hess M. Two fiber genes of nearly equal lengths are a common and distinctive feature of Fowl adenovirus C members. Vet Microbiol 2012; 156(3-4):411-7.

[5] Schachner A, Marek A, Jaskulska B, Bilic I, Hess M. Recombinant FAdV-4 fiber-2 protein protects chickens against hepatitis-hydropericardium syndrome (HHS). Vaccine 2014; 32:1086-92.

[6] Mazaheri A, Prusas C, Voss M, Hess M. Some strains of serotype 4 fowl adenoviruses cause inclusion body hepatitis and hydropericardium syndrome in chickens. Avian Pathol 1998; 27(3):269-76.

[7] Meulemans G, Boschmans M, Berg T P, Decaesstecker M. Polymerase chain reaction combined with restriction enzyme analysis for detection and differentiation of fowl adenoviruses. Avian Pathol 2001; 30(6):655-60.

TABLE 5

Primers used in this study.

| Primer name | Sequence (5'-3') [a] | Position | Purpose | Reference |
|---|---|---|---|---|
| FAdV-D Fib SR48 f | 5'-<u>GAGCTC</u>ATGGCGAAATCGACTCC-3' SEQ ID NO.: 9 | 1-17 [b] | Amplification of the fiber gene of strain SR48 and cloning into the pFastBac vector | this study |
| FAdV-D Fib SR48 r | 5'-<u>GGTACC</u>TTAGGGTTGTGTTAATTTATTGG-3' SEQ ID NO.: 10 | 1713-1691 [b] | Amplification of the fiber gene of strain SR48 and cloning into the pFastBac vector | this study |
| FAdV-E Fib YR36 f | 5'-<u>GGATCC</u>ATGGCGACCTCGACTC-3' SEQ ID NO.: 11 | 1-16 [c] | Amplification of the fiber gene of strain YR36 and cloning into the pFastBac vector | this study |
| FAdV-E Fib YR36 r | 5'-<u>AGGCCT</u>TTAAGGAGCGTTGACGG-3' SEQ ID NO.: 12 | 1559-1575 [b] | Amplification of the fiber gene of strain YR36 and cloning into the pFastBac vector | this study |
| 52K-fw | 5'-ATGGCKCAGATGGCYAAGG-3' SEQ ID NO.: 13 | 13075-13093 [d] | Amplification of the 52K gene in rt-PCR | [7] |
| 52K-rv | 5'-AGCGCCTGGGTCAAACCGA-3' SEQ ID NO.: 14 | 13250-13232 [d] | Amplification of the 52K gene in rt-PCR | [7] |

[a] Underlined nucleotides indicate restriction sites.
[b] Position is indicated for the fiber gene sequence of SR48.
[c] Position is indicated for the fiber gene sequence of YR36.
[d] Position is indicated for the complete genomic sequence of CELO (U46933).

TABLE 6

Summary of the results from clinical and pathological investigation, as well as histological investigation of liver tissue and rt PCR performed on liver tissue and cloacal swab samples from birds of all groups.

| Group | Tag no. | Body weight (g) | Macroscopic lesions in organs | No. of lymphocyte infiltration spots in liver tissue (above threshold size) | Viral load in liver samples | Viral load in cloacal swab samples |
|---|---|---|---|---|---|---|
| I | 221 | 312 | | 1 | neg. | 7.44 × 10³ |
| | 222 | 378 | | nt [b] | 0 [c] | nt |
| | 223 | 390 | | nt | neg. | nt |
| | 224 | 438 | | nt | neg. | nt |
| | 225 | 460 | | nt | neg. | nt |
| | 226 | 392 | spot in | 1 | 5.33 | 2.41 × 10² |
| | 227 | * [a] | | nt, * | nt, * | nt, * |
| | 228 | 372 | | 1 | neg. | 4.79 × 10² |
| | 229 | 370 | spot in | 0 | 0 | 7.14 × 10⁴ |
| | 230 | 354 | | 3 | 3.97 | 9.91 × 10³ |
| | Mean | 385.1 ± | | 1.2 ± 1.1 | nd [d] | 1.79 × 10⁴ ± |
| II | 231 | 345 | spot in | 0 | 0 | 4.88 × 10³ |
| | 232 | 330 | | nt | neg. | nt |
| | 233 | 366 | | nt | neg. | nt |
| | 234 | 348 | | nt | 0 | nt |
| | 235 | 365 | spot in liver | nt, * | 0 | 1.09 × 10⁶ |

TABLE 6-continued

Summary of the results from clinical and pathological investigation, as well as histological investigation of liver tissue and rt PCR performed on liver tissue and cloacal swab samples from birds of all groups.

| Group | Tag no. | Body weight (g) | Macroscopic lesions in organs | No. of lymphocyte infiltration spots in liver tissue (above threshold size) | Viral load in liver samples | Viral load in cloacal swab samples |
|---|---|---|---|---|---|---|
|  | 236 | 324 | spot in | 6 | $2.79 \times 10^1$ | $1.94 \times 10^5$ |
|  | 237 | 322 |  | 5 | 3.73 | $2.41 \times 10^6$ |
|  | 238 | 329 | spot in | 2 | 0 | $3.47 \times 10^5$ |
|  | 239 | 372 |  | nt | 0 | nt |
|  | 240 | 356 | spot in liver | 7 | 0 | $2.43 \times 10^5$ |
|  | Mean | 345.7 ± |  | 4 ± 2.9 | nd | $7.15 \times 10^5$ ± |
| III | 241 | 380 |  | nt | 0 | nt |
|  | 242 | 382 |  | nt | neg. | nt |
|  | 243 | 316 |  | 1 | 0 | $2.03 \times 10^6$ |
|  | 244 | 356 |  | 1 | 0 | $2.62 \times 10^6$ |
|  | 245 | 364 |  | nt | neg. | nt |
|  | 246 | 345 |  | 0 | neg. | $3.46 \times 10^4$ |
|  | 247 | 350 |  | 6 | 1.09 | $4.03 \times 10^5$ |
|  | 248 | 418 |  | nt | 0 | nt |
|  | 249 | 356 |  | 0 | 0 | $3.78 \times 10^3$ |
|  | 250 | 390 |  | nt | 0 | nt |
|  | Mean | 365.7 ± |  | 1.6 ± 2.5 | nd | $1.02 \times 10^6$ ± |
| IV | 251 | * |  | nt, * | nt, * | nt, * |
|  | 252 | 366 |  | 1 | 0 | $1.05 \times 10^5$ |
|  | 253 | 317 | spot in | 0 | 0 | $1.01 \times 10^7$ |
|  | 254 | 368 |  | nt | 0 | nt |
|  | 255 | 408 |  | nt | 0 | nt |
|  | 256 | 380 |  | nt | 0 | nt |
|  | 257 | 315 | spot in | 4 | $5.33 \times 10^1$ | $5.38 \times 10^6$ |
|  | 258 | 346 |  | 8 | 0 | $1.37 \times 10^6$ |
|  | 259 | 390 |  | nt | neg. | nt |
|  | 260 | 318 |  | 4 | 0 | $1.62 \times 10^6$ |
|  | Mean ± | 356.4 ± |  | 3.4 ± 3.1 | nd | $3.72 \times 10^6$ ± |
| V | 261 | 350 |  | 0 | neg. | neg. |
|  | 262 | 426 |  | nt | nt | nt |
|  | 263 | 354 |  | nt | nt | nt |
|  | 264 | 352 |  | nt | nt | nt |
|  | 265 | 374 |  | nt | nt | nt |
|  | 266 | 418 |  | nt | nt | nt |
|  | 267 | 308 |  | nt | nt | nt |
|  | 268 | 350 |  | 0 | neg. | neg. |
|  | 269 | 378 |  | nt | nt | nt |
|  | 270 | 384 |  | nt | nt | nt |
|  | Mean | 369.4 ± |  |  |  |  |

[a] bird dead due to cannibalism or sample lost.
[b] nt = not tested.
[c] sample tested positive but viral load below the quantification limit.
[d] nd = not determined.

The invention claimed is:

1. A vaccine comprising a fiber protein further defined as:
   fiber-2 protein of Fowl Adenovirus C (FAdV-C);
   fiber-2 protein of Fowl Adenovirus A (FAdV-A); or
   fiber protein of Fowl Adenovirus B, D, or E (FAdV-B, FAdV-D, or FAdV-E),
   wherein the vaccine is further defined as a subunit vaccine, and
   wherein the vaccine further comprises an immuno-effective amount of an adjuvant.

2. The vaccine of claim 1, wherein the adjuvant is Freund's complete adjuvant, Freund's incomplete adjuvant, aluminum hydroxide, *Bordetella pertussis*, saponin, muramyl dipeptide, ethylene vinyl acetate copolymer, oil, a vegetable oil or a mineral oil.

3. The vaccine of claim 1, wherein the fiber protein has a sequence of:
   UniProt entries H8WG65 (SEQ ID NO: 25), H8WG69 (SEQ ID NO: 17), H8WG72 (SEQ ID NO: 15), H8WG77 (SEQ ID NO: 28), H8WG70 (SEQ ID NO: 23), H8WG73 (SEQ ID NO: 16), H8WG66 (SEQ ID NO: 33), H8WG76 (SEQ ID NO: 27), H8WG60 (SEQ ID NO: 20), H8WG61 (SEQ ID NO: 35), H8WG62 (SEQ ID NO: 34), H8WG75 (SEQ ID NO: 29), H8WG67 (SEQ ID NO: 19), H8WG78 (SEQ ID NO: 36), H8WG63 (SEQ ID NO: 68), H8WG68 (SEQ ID NO: 18), H8WG64 (SEQ ID NO: 30), H8WG74 (SEQ ID NO: 24), H8WG71 (SEQ ID NO: 22), H8WQZ7 (SEQ ID NO: 69), H8WQZ2 (SEQ ID NO: 70), H8WQW9 (SEQ ID NO: 31), QOGH78 (SEQ ID NO: 71), O55281 (SEQ ID NO: 26), or F2VJI5 (SEQ ID NO: 32).

4. The vaccine of claim 3, wherein the fiber protein has a sequence of UniProt entry H8WQW9 (SEQ ID NO: 31).

5. The vaccine of claim 1, further comprising a pharmaceutically acceptable diluent and/or carrier.

6. The vaccine of claim 5, wherein the pharmaceutically acceptable diluent and/or carrier comprises a water-for-injection, physiological saline, tissue culture medium, propylene glycol, polyethylene glycol, vegetable oil, or an injectable organic ester.

7. The vaccine of claim 1, wherein the fiber protein has been recombinantly produced in a baculovirus expression system or a *Pichia pastoris* expression system.

8. The vaccine of claim 1, wherein the fiber protein is contained in an amount of 0.1 µg/ml to 10 mg/ml.

9. The vaccine of claim 8, of wherein the fiber protein is contained in an amount 1 µg/ml to 1 mg/ml.

10. The vaccine of claim 9, wherein the fiber protein is contained in an amount of 10 to 100 µg/ml.

11. The vaccine of claim 1, consisting of:
    the fiber protein in an amount of 0.1 µg to 10 mg;
    an immuno-effective amount of an adjuvant; and
    a pharmaceutically acceptable carrier and/or diluent.

12. The vaccine of claim 11, wherein the fiber protein is in an amount of 1 µg to 1 mg.

13. The vaccine of claim 12, wherein the fiber protein is in an amount of 10 to 100 µg.

14. The vaccine of claim 1, consisting of:
    the fiber protein in an amount of 0.1 µg to 10 mg; and
    an immuno-effective amount of an adjuvant.

15. The vaccine of claim 1, wherein the fiber protein is a fiber-2 protein of FAdV-C or a fiber protein of FAdV-D or FAdV-E.

16. A vaccine suitable for vaccinating against a FAdV infection in birds, comprising a fiber protein further defined as:
    fiber-2 protein of FAdV-C; or
    fiber protein of FAdV-D or FAdV-E,
    wherein the vaccine is further defined as a subunit vaccine, and wherein the vaccine further comprises an immuno-effective amount of an adjuvant.

17. A method of vaccinating a bird against a FAdV infection, comprising administering to the bird the vaccine of claim 1.

18. The method of claim 17, wherein the bird is poultry.

19. The method of claim 18, wherein the poultry is a broiler.

20. The method of claim 17, wherein risk of the bird developing hepatitis-hydropericardium syndrome (HHS) is reduced, wherein the fiber protein of the vaccine is a fiber-2 protein of FAdV-C.

21. The method of claim 17, wherein risk of the bird developing inclusion body hepatitis (IBH) is reduced, wherein the fiber protein of the vaccine is a fiber protein of FAdV-D or FAdV-E.

22. The method of claim 17, wherein risk of a FAdV infection is reduced.

23. The method of claim 22, wherein the fiber protein of the vaccine is a fiber-2 protein of FAdV-C or a fiber protein of FAdV-D or FAdV-E.

* * * * *

SEQUENCE LISTING

<160> NUMBER OF SEQ ID NOS: 71

<210> SEQ ID NO 1
<211> LENGTH: 22
<212> TYPE: DNA
<213> ORGANISM: Artificial Sequence
<220> FEATURE:
<223> OTHER INFORMATION: Synthetic Primer

<400> SEQUENCE: 1
ggatccatgt cggccctaat cg                                              22

<210> SEQ ID NO 2
<211> LENGTH: 21
<212> TYPE: DNA
<213> ORGANISM: Artificial Sequence
<220> FEATURE:

<223> OTHER INFORMATION: Synthetic Primer

<400> SEQUENCE: 2
aggcctttag gggctcggag c                                              21

<210> SEQ ID NO 3
<211> LENGTH: 22
<212> TYPE: DNA
<213> ORGANISM: Artificial Sequence
<220> FEATURE:
<223> OTHER INFORMATION: Synthetic Primer

<400> SEQUENCE: 3
aggcctatgc tccgagcccc ta                                             22

<210> SEQ ID NO 4
<211> LENGTH: 23
<212> TYPE: DNA
<213> ORGANISM: Artificial Sequence
<220> FEATURE:
<223> OTHER INFORMATION: Synthetic Primer

<400> SEQUENCE: 4
tctagattac gggacggagg ctg                                            23

<210> SEQ ID NO 5
<211> LENGTH: 32
<212> TYPE: DNA
<213> ORGANISM: Artificial Sequence
<220> FEATURE:
<223> OTHER INFORMATION: Synthetic Primer

<400> SEQUENCE: 5
aattccatgg acaagttcag gcagacggtc gt                                  32

<210> SEQ ID NO 6
<211> LENGTH: 30
<212> TYPE: DNA
<213> ORGANISM: Artificial Sequence
<220> FEATURE:
<223> OTHER INFORMATION: Synthetic Primer

<400> SEQUENCE: 6
taactcgagc tagtgatgcc gggacatcat                                     30

<210> SEQ ID NO 7
<211> LENGTH: 19
<212> TYPE: DNA
<213> ORGANISM: Artificial Sequence
<220> FEATURE:
<223> OTHER INFORMATION: Synthetic Primer

<400> SEQUENCE: 7
atggckcaga tggcyaagg                                                 19

<210> SEQ ID NO 8
<211> LENGTH: 19
<212> TYPE: DNA
<213> ORGANISM: Artificial Sequence
<220> FEATURE:
<223> OTHER INFORMATION: Synthetic Primer

<400> SEQUENCE: 8
agcgcctggg tcaaaccga                                                 19

```
<210> SEQ ID NO 9
<211> LENGTH: 23
<212> TYPE: DNA
<213> ORGANISM: Artificial Sequence
<220> FEATURE:
<223> OTHER INFORMATION: Synthetic Primer

<400> SEQUENCE: 9
gagctcatgg cgaaatcgac tcc                                            23

<210> SEQ ID NO 10
<211> LENGTH: 29
<212> TYPE: DNA
<213> ORGANISM: Artificial Sequence
<220> FEATURE:
<223> OTHER INFORMATION: Synthetic Primer

<400> SEQUENCE: 10
ggtaccttag ggttgtgtta atttattgg                                      29

<210> SEQ ID NO 11
<211> LENGTH: 22
<212> TYPE: DNA
<213> ORGANISM: Artificial Sequence
<220> FEATURE:
<223> OTHER INFORMATION: Synthetic Primer

<400> SEQUENCE: 11
ggatccatgg cgacctcgac tc                                             22

<210> SEQ ID NO 12
<211> LENGTH: 23
<212> TYPE: DNA
<213> ORGANISM: Artificial Sequence
<220> FEATURE:
<223> OTHER INFORMATION: Synthetic Primer

<400> SEQUENCE: 12
aggcctttaa ggagcgttga cgg                                            23

<210> SEQ ID NO 13
<211> LENGTH: 19
<212> TYPE: DNA
<213> ORGANISM: Artificial Sequence
<220> FEATURE:
<223> OTHER INFORMATION: Synthetic Primer

<400> SEQUENCE: 13
atggckcaga tggcyaagg                                                 19

<210> SEQ ID NO 14
<211> LENGTH: 19
<212> TYPE: DNA
<213> ORGANISM: Artificial Sequence
<220> FEATURE:
<223> OTHER INFORMATION: Synthetic Primer

<400> SEQUENCE: 14
agcgcctggg tcaaaccga                                                 19

<210> SEQ ID NO 15
<211> LENGTH: 471
<212> TYPE: PRT
<213> ORGANISM: fowl adenovirus

<400> SEQUENCE: 15
```

-continued

```
Arg His Ser Glu Asn Gly Lys Pro Glu Thr Glu Ala Gly Pro Ser Pro
 1               5                  10                 15

Ala Pro Ile Lys Arg Ala Lys Arg Met Val Arg Ala Ser Gln Leu Asp
             20                  25                 30

Leu Val Tyr Pro Phe Asp Tyr Val Ala Asp Pro Val Gly Gly Leu Asn
         35                  40                  45

Pro Pro Phe Leu Gly Gly Ser Gly Pro Leu Val Asp Gln Gly Gly Gln
 50                  55                  60

Leu Thr Leu Asn Val Thr Asp Pro Ile Ile Lys Asn Arg Ser Val
 65                  70                  75                 80

Asp Leu Ala His Asp Arg Ser Leu Asp Val Asn Ala Gln Gly Gln Leu
                 85                  90                  95

Ala Val Ala Val Asp Pro Glu Gly Ala Leu Asp Ile Thr Pro Asp Gly
             100                 105                 110

Leu Asp Val Lys Val Asp Gly Val Thr Val Met Val Asn Asp Asp Trp
             115                 120                 125

Glu Leu Ala Val Lys Val Asp Pro Ser Gly Leu Asp Ser Thr Ala
 130                 135                 140

Gly Gly Leu Gly Val Ser Val Asp Asp Thr Leu Leu Val Asp Gln Gly
145                 150                 155                 160

Glu Leu Gly Val His Leu Asn Gln Gln Gly Pro Ile Thr Ala Asp Ser
                 165                 170                 175

Ser Gly Ile Asp Leu Glu Ile Asn Pro Asn Met Phe Thr Val Asn Thr
             180                 185                 190

Ser Thr Gly Ser Gly Val Leu Glu Leu Asn Leu Lys Ala Gln Gly Gly
             195                 200                 205

Ile Gln Ala Asp Ser Ser Gly Val Gly Val Ser Val Asp Glu Ser Leu
 210                 215                 220

Glu Ile Val Asn Asn Thr Leu Glu Val Lys Pro Asp Pro Ser Gly Pro
225                 230                 235                 240

Leu Thr Val Ser Ala Asn Gly Leu Gly Leu Lys Tyr Asp Thr Asn Thr
             245                 250                 255

Leu Ala Val Thr Ala Gly Ala Leu Thr Val Val Gly Gly Ser Val
             260                 265                 270

Ser Thr Pro Ile Ala Thr Phe Val Ser Gly Ser Pro Ser Leu Asn Thr
             275                 280                 285

Tyr Asn Ala Thr Thr Val Asn Ser Ser Ala Asn Ala Phe Ser Cys Ala
             290                 295                 300

Tyr Tyr Leu Gln Gln Trp Asn Ile Gln Gly Leu Leu Val Thr Ser Leu
305                 310                 315                 320

Tyr Leu Lys Leu Asp Ser Ala Thr Met Gly Asn Arg Pro Gly Asp Leu
             325                 330                 335

Asn Ser Ala Asn Ala Lys Trp Phe Thr Phe Trp Val Ser Ala Tyr Leu
             340                 345                 350

Gln Gln Cys Asn Pro Ser Gly Ile Gln Ala Gly Thr Val Ser Pro Ser
             355                 360                 365

Thr Ala Thr Leu Thr Asp Phe Glu Pro Met Ala Asn Arg Ser Val Thr
             370                 375                 380

Ser Pro Trp Thr Tyr Ser Ala Asn Gly Tyr Tyr Glu Pro Ser Ile Gly
385                 390                 395                 400

Glu Phe Gln Val Phe Ser Pro Val Val Thr Gly Ala Trp Asn Pro Gly
             405                 410                 415

Asn Ile Gly Ile Arg Val Leu Pro Val Pro Val Thr Ala Ser Gly Asp
```

```
                        420             425             430
Arg Tyr Thr Leu Leu Cys Tyr Ser Leu Gln Cys Thr Asn Ser Ser Ile
                435             440             445

Phe Asn Pro Ala Asn Ser Gly Thr Met Ile Val Gly Pro Val Leu Tyr
    450             455             460

Ser Cys Pro Ala Ala Ser Val
465             470

<210> SEQ ID NO 16
<211> LENGTH: 472
<212> TYPE: PRT
<213> ORGANISM: fowl adenovirus

<400> SEQUENCE: 16

Arg His Ser Glu Asn Gly Lys Pro Glu Thr Glu Ala Gly Pro Ser Pro
1               5                   10                  15

Ala Pro Ile Lys Arg Ala Lys Arg Met Val Arg Ala Ser Gln Leu Asp
                20                  25                  30

Leu Val Tyr Pro Phe Asp Tyr Val Ala Asp Pro Val Gly Gly Leu Asn
            35                  40                  45

Pro Pro Phe Leu Gly Gly Ser Gly Pro Leu Val Asp Gln Gly Gly Gln
        50                  55                  60

Leu Thr Leu Asn Val Thr Asp Pro Ile Ile Lys Asn Arg Ser Val
65                  70                  75                  80

Asp Leu Ala His Asp Arg Ser Leu Asp Val Asn Ala Gln Gly Gln Leu
                85                  90                  95

Ala Val Ala Val Asp Pro Glu Gly Ala Leu Asp Ile Thr Pro Asp Gly
            100                 105                 110

Leu Asp Val Lys Val Asp Gly Val Thr Val Met Val Asn Asp Asp Trp
        115                 120                 125

Glu Leu Ala Val Lys Val Asp Pro Ser Gly Gly Leu Asp Ser Thr Ala
130                 135                 140

Gly Gly Leu Gly Val Ser Val Asp Asp Thr Leu Leu Val Asp Gln Gly
145                 150                 155                 160

Glu Leu Gly Val His Leu Asn Gln Gln Gly Pro Ile Thr Ala Asp Ser
                165                 170                 175

Ser Gly Ile Asp Leu Glu Ile Asn Pro Asn Met Phe Thr Val Asn Thr
            180                 185                 190

Ser Thr Gly Ser Gly Val Leu Glu Leu Asn Leu Lys Ala Gln Gly Gly
        195                 200                 205

Ile Gln Ala Asp Ser Ser Gly Val Gly Val Ser Val Asp Glu Ser Leu
    210                 215                 220

Glu Ile Val Asn Asn Thr Leu Glu Val Lys Pro Asp Pro Ser Gly Pro
225                 230                 235                 240

Leu Thr Val Ser Ala Asn Gly Leu Gly Leu Lys Tyr Asp Thr Asn Thr
                245                 250                 255

Leu Ala Val Thr Ala Gly Ala Leu Thr Val Val Gly Gly Gly Ser Val
            260                 265                 270

Ser Thr Pro Ile Ala Thr Phe Val Ser Gly Ser Pro Ser Leu Asn Thr
        275                 280                 285

Tyr Asn Ala Thr Thr Val Asn Ser Ser Ala Asn Ala Phe Ser Cys Ala
    290                 295                 300

Tyr Tyr Leu Gln Gln Trp Asn Ile Gln Gly Leu Leu Val Thr Ser Leu
305                 310                 315                 320
```

```
Tyr Leu Lys Leu Asp Ser Ala Thr Met Gly Asn Arg Pro Gly Asp Leu
            325                 330                 335

Asn Ser Ala Asn Ala Lys Trp Phe Thr Phe Trp Val Ser Ala Tyr Leu
        340                 345                 350

Gln Gln Cys Asn Pro Ser Gly Ile Gln Ala Gly Thr Val Ser Pro Ser
    355                 360                 365

Thr Ala Thr Leu Thr Asp Phe Glu Pro Met Ala Asn Arg Ser Val Thr
370                 375                 380

Ser Pro Trp Thr Tyr Ser Ala Asn Gly Tyr Tyr Glu Pro Ser Ile Gly
385                 390                 395                 400

Glu Phe Gln Val Phe Ser Pro Val Val Thr Gly Ala Trp Asn Pro Gly
                405                 410                 415

Asn Ile Gly Ile Arg Val Leu Pro Val Pro Val Thr Ala Ser Gly Asp
            420                 425                 430

Arg Tyr Thr Leu Leu Cys Tyr Ser Leu Gln Cys Thr Asn Ser Ser Ile
        435                 440                 445

Phe Asn Pro Ala Asn Ser Gly Thr Met Ile Val Gly Pro Val Leu Tyr
    450                 455                 460

Ser Cys Pro Ala Ala Ser Val Pro
465                 470

<210> SEQ ID NO 17
<211> LENGTH: 470
<212> TYPE: PRT
<213> ORGANISM: fowl adenovirus

<400> SEQUENCE: 17

Ser Glu Asn Gly Lys Pro Glu Thr Glu Ala Gly Pro Ser Pro Ala Pro
1               5                   10                  15

Ile Lys Arg Ala Lys Arg Met Val Arg Ala Ser Gln Leu Asp Leu Val
            20                  25                  30

Tyr Pro Phe Asp Tyr Val Ala Asp Pro Val Gly Gly Leu Asn Pro Pro
        35                  40                  45

Phe Leu Gly Gly Ser Gly Pro Leu Val Asp Gln Gly Gly Gln Leu Thr
50                  55                  60

Leu Asn Val Thr Asp Pro Ile Ile Lys Asn Arg Ser Val Asp Leu
65                  70                  75                  80

Ala His Asp Pro Ser Leu Asp Val Asn Ala Gln Gly Gln Leu Ala Val
                85                  90                  95

Ala Val Asp Pro Glu Gly Ala Leu Asp Ile Thr Pro Asp Gly Leu Asp
            100                 105                 110

Val Lys Val Asp Gly Val Thr Val Met Val Asn Asp Asp Trp Glu Leu
        115                 120                 125

Ala Val Lys Val Asp Pro Ser Gly Gly Leu Asp Ser Thr Ala Gly Gly
130                 135                 140

Leu Gly Val Ser Val Asp Asp Thr Leu Leu Val Asp Gln Gly Glu Leu
145                 150                 155                 160

Gly Val His Leu Asn Gln Gln Gly Pro Ile Thr Ala Asp Ser Ser Gly
                165                 170                 175

Ile Asp Leu Glu Ile Asn Pro Asn Met Phe Thr Val Asn Thr Ser Thr
            180                 185                 190

Gly Ser Gly Val Leu Glu Leu Asn Leu Lys Ala Gln Gly Gly Ile Gln
        195                 200                 205

Ala Asp Ser Ser Gly Val Gly Val Ser Val Asp Glu Ser Leu Glu Ile
210                 215                 220
```

Val Asn Asn Thr Leu Glu Val Lys Pro Asp Pro Ser Gly Pro Leu Thr
225                 230                 235                 240

Val Ser Ala Asn Gly Leu Gly Leu Lys Tyr Asp Thr Asn Thr Leu Ala
            245                 250                 255

Val Thr Ala Gly Ala Leu Thr Val Val Gly Gly Ser Val Ser Thr
            260                 265                 270

Pro Ile Ala Thr Phe Val Ser Gly Ser Pro Ser Leu Asn Thr Tyr Asn
            275                 280                 285

Ala Thr Thr Val Asn Ser Ser Ala Asn Ala Phe Ser Cys Ala Tyr Tyr
            290                 295                 300

Leu Gln Gln Trp Asn Ile Gln Gly Leu Leu Val Thr Ser Leu Tyr Leu
305                 310                 315                 320

Lys Leu Asp Ser Ala Thr Met Gly Asn Arg Pro Gly Asp Leu Asn Ser
            325                 330                 335

Ala Asn Ala Lys Trp Phe Thr Phe Trp Val Ser Ala Tyr Leu Gln Gln
            340                 345                 350

Cys Asn Pro Ser Gly Ile Gln Ala Gly Thr Val Ser Pro Ser Thr Ala
            355                 360                 365

Thr Leu Thr Asp Phe Glu Pro Met Ala Asn Arg Ser Val Thr Ser Pro
370                 375                 380

Trp Thr Tyr Ser Ala Asn Gly Tyr Tyr Glu Pro Ser Ile Gly Glu Phe
385                 390                 395                 400

Gln Val Phe Ser Pro Val Val Thr Gly Ala Trp Asn Pro Gly Asn Ile
            405                 410                 415

Gly Ile Arg Val Leu Pro Val Pro Val Thr Ala Ser Gly Asp Arg Tyr
            420                 425                 430

Thr Leu Leu Cys Tyr Ser Leu Gln Cys Thr Asn Ser Ser Ile Phe Asn
            435                 440                 445

Pro Ala Asn Ser Gly Thr Met Ile Val Gly Pro Val Leu Tyr Ser Cys
            450                 455                 460

Pro Ala Ala Ser Val Pro
465                 470

<210> SEQ ID NO 18
<211> LENGTH: 472
<212> TYPE: PRT
<213> ORGANISM: fowl adenovirus

<400> SEQUENCE: 18

Arg Arg His Ser Glu Asn Gly Lys Pro Glu Thr Glu Ala Gly Pro Ser
1               5                   10                  15

Pro Ala Pro Ile Lys Arg Ala Lys Arg Met Val Arg Ala Ser Gln Leu
            20                  25                  30

Asp Leu Val Tyr Pro Phe Asp Tyr Val Ala Asp Pro Val Gly Gly Leu
            35                  40                  45

Asn Pro Pro Phe Leu Gly Gly Ser Gly Pro Leu Val Asp Gln Gly Gly
            50                  55                  60

Gln Leu Thr Leu Asn Val Thr Asp Pro Ile Ile Ile Lys Asn Arg Ser
65                  70                  75                  80

Val Asp Leu Ala His Asp Pro Ser Leu Asp Val Asn Ala Gln Gly Gln
            85                  90                  95

Leu Ala Val Ala Val Asp Pro Glu Gly Ala Leu Asp Ile Thr Pro Asp
            100                 105                 110

Gly Leu Asp Val Lys Val Asp Gly Val Thr Val Met Val Asn Asp Asp

```
                   115                 120                 125
Trp Glu Leu Ala Val Lys Val Asp Pro Ser Gly Gly Leu Asp Ser Thr
130                 135                 140

Ala Gly Leu Gly Val Ser Val Asp Asp Thr Leu Leu Val Asp Gln
145                 150                 155                 160

Gly Glu Leu Gly Val His Leu Asn Gln Gln Gly Pro Ile Thr Ala Asp
                165                 170                 175

Ser Ser Gly Ile Asp Leu Glu Ile Asn Pro Asn Met Phe Thr Val Asn
            180                 185                 190

Thr Ser Thr Gly Ser Gly Val Leu Glu Leu Asn Leu Lys Ala Arg Gly
        195                 200                 205

Gly Ile Gln Ala Gly Ser Ser Gly Val Gly Val Ser Val Asp Glu Ser
    210                 215                 220

Leu Glu Ile Val Asn Asn Thr Leu Glu Val Lys Pro Asp Pro Ser Gly
225                 230                 235                 240

Pro Leu Thr Val Ser Ala Asn Gly Leu Gly Leu Lys Tyr Asp Thr Asn
                245                 250                 255

Thr Leu Ala Val Thr Ala Gly Ala Leu Thr Val Val Gly Gly Gly Ser
            260                 265                 270

Val Ser Thr Pro Ile Ala Thr Phe Val Ser Gly Ser Pro Ser Leu Asn
        275                 280                 285

Thr Tyr Asn Ala Thr Thr Val Asn Ser Ser Ala Asn Ala Phe Ser Cys
    290                 295                 300

Ala Tyr Tyr Leu Gln Gln Trp Asn Ile Gln Gly Leu Leu Val Thr Ser
305                 310                 315                 320

Leu Tyr Leu Lys Leu Asp Ser Ala Thr Met Gly Asn Arg Pro Gly Asp
                325                 330                 335

Leu Asn Ser Ala Asn Ala Lys Trp Phe Thr Phe Trp Val Ser Ala Tyr
            340                 345                 350

Leu Gln Gln Cys Asn Pro Ser Gly Ile Gln Ala Gly Thr Val Ser Pro
        355                 360                 365

Ser Thr Ala Thr Leu Thr Asp Phe Glu Pro Met Ala Asn Arg Ser Val
    370                 375                 380

Thr Ser Pro Trp Thr Tyr Ser Ala Asn Gly Tyr Tyr Glu Pro Ser Ile
385                 390                 395                 400

Gly Glu Phe Gln Val Phe Ser Pro Val Val Thr Gly Ala Trp Asn Pro
                405                 410                 415

Gly Asn Ile Gly Ile Arg Val Leu Pro Val Pro Val Thr Ala Ser Gly
            420                 425                 430

Asp Arg Tyr Thr Leu Leu Cys Tyr Ser Leu Gln Cys Thr Asn Ser Ser
        435                 440                 445

Ile Phe Asn Pro Ala Asn Ser Gly Thr Met Ile Val Gly Pro Val Leu
    450                 455                 460

Tyr Ser Cys Pro Ala Ala Ser Val
465                 470

<210> SEQ ID NO 19
<211> LENGTH: 468
<212> TYPE: PRT
<213> ORGANISM: fowl adenovirus

<400> SEQUENCE: 19

Ser Glu Asn Gly Lys Pro Glu Thr Glu Ala Gly Pro Ser Pro Ala Pro
1               5                   10                  15
```

```
Ile Lys Arg Ala Lys Arg Met Val Arg Ala Ser Gln Leu Asp Leu Val
             20                  25                  30

Tyr Pro Phe Asp Tyr Val Ala Asp Pro Val Gly Gly Leu Asn Pro Pro
             35                  40                  45

Phe Leu Gly Gly Ser Gly Pro Leu Val Asp Gln Gly Gly Gln Leu Thr
             50                  55                  60

Leu Asn Val Thr Asp Pro Ile Ile Lys Asn Arg Ser Val Asp Leu
65                       70                  75                  80

Ala His Asp Pro Ser Leu Asp Val Asn Ala Gln Gly Gln Leu Ala Val
                     85                  90                  95

Ala Val Asp Pro Glu Gly Ala Leu Asp Ile Thr Pro Asp Gly Leu Asp
                    100                 105                 110

Val Lys Val Asp Gly Val Thr Val Met Val Asn Asp Asp Trp Glu Leu
                    115                 120                 125

Ala Val Lys Val Asp Pro Ser Gly Gly Leu Asp Ser Thr Ala Gly Gly
                    130                 135                 140

Leu Gly Val Ser Val Asp Asp Thr Leu Leu Val Asp Gln Gly Glu Leu
145                 150                 155                     160

Gly Val His Leu Asn Gln Gln Gly Pro Ile Thr Ala Asp Ser Ser Gly
                    165                 170                 175

Ile Asp Leu Glu Ile Asn Pro Asn Met Phe Thr Val Asn Thr Ser Thr
                    180                 185                 190

Gly Ser Gly Val Leu Glu Leu Asn Leu Lys Ala Gln Gly Gly Ile Gln
                    195                 200                 205

Ala Asp Ser Ser Gly Val Gly Val Ser Val Asp Glu Ser Leu Glu Ile
                    210                 215                 220

Val Asn Asn Thr Leu Glu Val Lys Pro Asp Pro Ser Gly Pro Leu Thr
225                 230                 235                 240

Val Ser Ala Asn Gly Leu Gly Leu Lys Tyr Asp Thr Asn Thr Leu Ala
                    245                 250                 255

Val Thr Ala Gly Ala Leu Thr Val Gly Gly Gly Ser Val Ser Thr
                    260                 265                 270

Pro Ile Ala Thr Phe Val Ser Gly Ser Pro Ser Leu Asn Thr Tyr Asn
                    275                 280                 285

Ala Thr Thr Val Asn Ser Ser Ala Asn Ala Phe Ser Cys Ala Tyr Tyr
                    290                 295                 300

Leu Gln Gln Trp Asn Ile Gln Gly Leu Leu Val Thr Ser Leu Tyr Leu
305                 310                 315                 320

Lys Leu Asp Ser Ala Thr Met Gly Asn Arg Pro Gly Asp Leu Asn Ser
                    325                 330                 335

Ala Asn Ala Lys Trp Phe Thr Phe Trp Val Ser Ala Tyr Leu Gln Gln
                    340                 345                 350

Cys Asn Pro Ser Gly Ile Gln Ala Gly Thr Val Ser Pro Ser Thr Ala
                    355                 360                 365

Thr Leu Thr Asp Phe Glu Pro Met Ala Asn Arg Ser Val Thr Ser Pro
                    370                 375                 380

Trp Thr Tyr Ser Ala Asn Gly Tyr Tyr Glu Pro Ser Ile Gly Glu Phe
385                 390                 395                 400

Gln Val Phe Ser Pro Val Val Thr Gly Ala Trp Asn Pro Gly Asn Ile
                    405                 410                 415

Gly Ile Arg Val Leu Pro Val Pro Val Thr Ala Ser Gly Asp Arg Tyr
                    420                 425                 430

Thr Leu Leu Cys Tyr Ser Leu Gln Cys Thr Asn Ser Ser Ile Phe Asn
```

```
              435                 440                 445
Pro Ala Asn Ser Gly Thr Met Ile Val Gly Pro Val Leu Tyr Ser Cys
        450                 455                 460
Pro Ala Ala Ser
465

<210> SEQ ID NO 20
<211> LENGTH: 479
<212> TYPE: PRT
<213> ORGANISM: fowl adenovirus

<400> SEQUENCE: 20

Met Leu Arg Ala Pro Lys Arg Arg His Ser Glu Asn Gly Lys Pro Glu
1               5                   10                  15

Thr Glu Ala Gly Pro Ser Pro Ala Pro Ile Lys Arg Ala Lys Arg Val
            20                  25                  30

Val Arg Ala Ser Gln Leu Asp Leu Val Tyr Pro Phe Asp Tyr Val Ala
        35                  40                  45

Asp Pro Val Gly Gly Leu Asn Pro Pro Phe Leu Gly Gly Ser Gly Pro
    50                  55                  60

Leu Val Asp Gln Gly Gly Gln Leu Thr Leu Asn Val Thr Asp Pro Ile
65                  70                  75                  80

Ile Ile Lys Asn Arg Ser Val Asp Leu Ala His Asp Pro Ser Leu Asp
                85                  90                  95

Val Asn Ala Gln Gly Gln Leu Ala Val Ala Val Asp Pro Glu Gly Ala
            100                 105                 110

Leu Asp Ile Thr Pro Asp Gly Leu Asp Val Lys Val Asp Gly Val Thr
        115                 120                 125

Val Met Val Asn Asp Asp Trp Glu Leu Ala Val Lys Val Asp Pro Ser
    130                 135                 140

Gly Gly Leu Asp Ser Thr Ala Gly Gly Leu Gly Val Ser Val Asp Asp
145                 150                 155                 160

Thr Leu Leu Val Asp Gln Gly Glu Leu Gly Val His Leu Asn Gln Gln
                165                 170                 175

Gly Pro Ile Thr Ala Asp Ser Ser Gly Ile Asp Leu Glu Ile Asn Pro
            180                 185                 190

Asn Met Phe Thr Val Asn Thr Ser Thr Gly Ser Gly Val Leu Glu Leu
        195                 200                 205

Asn Leu Lys Ala Gln Gly Gly Ile Gln Ala Asp Ser Ser Gly Val Gly
    210                 215                 220

Val Ser Val Asp Glu Ser Leu Gln Ile Val Asn Asn Thr Leu Glu Val
225                 230                 235                 240

Lys Pro Asp Pro Ser Gly Pro Leu Thr Val Ser Ala Asn Gly Leu Gly
                245                 250                 255

Leu Lys Tyr Asp Thr Asn Thr Leu Ala Val Thr Ala Gly Ala Leu Thr
            260                 265                 270

Val Val Gly Gly Gly Ser Val Ser Thr Pro Ile Ala Thr Phe Val Ser
        275                 280                 285

Gly Ser Pro Ser Leu Asn Thr Tyr Asn Ala Thr Thr Val Asn Ser Ser
    290                 295                 300

Ala Asn Ala Phe Ser Cys Ala Tyr Tyr Leu Gln Gln Trp Asn Ile Gln
305                 310                 315                 320

Gly Leu Leu Val Thr Ser Leu Tyr Leu Lys Leu Asp Ser Ala Thr Met
                325                 330                 335
```

```
Gly Asn Arg Pro Gly Asp Leu Asn Ser Ala Asn Ala Lys Trp Phe Thr
            340                 345                 350

Phe Trp Val Ser Ala Tyr Leu Gln Gln Cys Asn Pro Ser Gly Ile Gln
        355                 360                 365

Ala Gly Thr Val Ser Pro Ser Thr Ala Thr Leu Thr Asp Phe Glu Pro
    370                 375                 380

Met Ala Asn Arg Ser Val Thr Ser Pro Trp Thr Tyr Ser Ala Asn Gly
385                 390                 395                 400

Tyr Tyr Glu Pro Ser Ile Gly Glu Phe Gln Val Phe Ser Pro Val Val
            405                 410                 415

Thr Gly Ala Trp Asn Pro Gly Asn Ile Gly Ile Arg Val Leu Pro Val
        420                 425                 430

Pro Val Ser Ala Ser Gly Glu Arg Tyr Thr Leu Leu Cys Tyr Ser Leu
    435                 440                 445

Gln Cys Thr Asn Ala Ser Ile Phe Asn Pro Asn Asn Ser Gly Thr Met
450                 455                 460

Ile Val Gly Pro Val Leu Tyr Ser Cys Pro Ala Gly Ser Leu Pro
465                 470                 475

<210> SEQ ID NO 21
<211> LENGTH: 461
<212> TYPE: PRT
<213> ORGANISM: fowl adenovirus

<400> SEQUENCE: 21

Met Leu Arg Ala Pro Lys Arg Arg His Ser Glu Asn Gly Lys Pro Glu
1               5                   10                  15

Thr Glu Ala Gly Pro Ser Pro Ala Pro Ile Lys Arg Ala Lys Arg Met
            20                  25                  30

Val Arg Ala Ser Gln Leu Asp Leu Val Tyr Pro Phe Asp Tyr Val Ala
        35                  40                  45

Asp Pro Val Gly Gly Leu Asn Pro Pro Phe Leu Gly Gly Ser Gly Pro
    50                  55                  60

Leu Val Asp Gln Gly Gly Gln Leu Thr Leu Asn Val Thr Asp Pro Ile
65                  70                  75                  80

Ile Ile Lys Asn Arg Ser Val Asp Leu Ala His Asp Pro Ser Leu Asp
                85                  90                  95

Val Asn Ala Gln Gly Gln Leu Ala Val Ala Val Asp Pro Glu Gly Ala
            100                 105                 110

Leu Asp Ile Thr Pro Asp Gly Leu Asp Val Lys Val Asp Pro Ser Gly
        115                 120                 125

Gly Leu Asp Ser Thr Ala Gly Gly Leu Gly Val Ser Val Asp Asp Thr
    130                 135                 140

Leu Leu Val Asp Gln Gly Glu Leu Gly Val His Leu Asn Gln Gln Gly
145                 150                 155                 160

Pro Ile Thr Ala Asp Ser Ser Gly Ile Asp Leu Glu Ile Asn Pro Asn
                165                 170                 175

Met Phe Thr Val Asn Thr Ser Thr Gly Ser Gly Val Leu Glu Leu Asn
            180                 185                 190

Leu Lys Ala Gln Gly Gly Ile Gln Ala Asp Ser Ser Gly Val Gly Val
        195                 200                 205

Ser Val Asp Glu Ser Leu Gln Ile Val Asn Asn Thr Leu Glu Val Lys
    210                 215                 220

Pro Asp Pro Ser Gly Pro Leu Thr Val Ser Ala Asn Gly Leu Gly Leu
225                 230                 235                 240
```

-continued

Lys Tyr Asp Thr Asn Thr Leu Ala Val Thr Ala Gly Ala Leu Thr Val
            245                 250                 255

Val Gly Gly Gly Ser Val Ser Thr Pro Asn Arg Tyr Phe Cys Leu Gly
        260                 265                 270

Lys Ser Gln Pro Gln His Leu Gln Cys His Ala Val Asn Ser Ser Ala
    275                 280                 285

Asn Ala Phe Ser Cys Ala Tyr Tyr Leu Gln Gln Trp Asn Ile Gln Gly
    290                 295                 300

Leu Leu Val Thr Ser Leu Tyr Leu Lys Leu Asp Ser Ala Thr Met Gly
305                 310                 315                 320

Asn Arg Pro Gly Asp Leu Asn Ser Ala Asn Ala Lys Trp Phe Thr Phe
                325                 330                 335

Trp Val Ser Ala Tyr Leu Gln Gln Cys Asn Ser Gly Ile Gln Ala Gly
            340                 345                 350

Thr Val Ser Pro Ser Thr Ala Thr Leu Thr Asp Phe Glu Pro Met Ala
        355                 360                 365

Asn Arg Ser Val Thr Ser Pro Trp Thr Tyr Ser Ala Asn Gly Tyr Tyr
    370                 375                 380

Glu Pro Ser Ile Gly Glu Phe Gln Val Phe Ser Pro Val Val Thr Gly
385                 390                 395                 400

Ala Trp Asn Pro Gly Asn Ile Gly Ile Arg Val Leu Pro Val Pro Val
                405                 410                 415

Ser Ala Ser Gly Glu Arg Tyr Thr Leu Leu Cys Tyr Ser Leu Gln Cys
            420                 425                 430

Thr Asn Ala Ser Ile Phe Asn Pro Asn Asn Ser Gly Thr Met Ile Val
        435                 440                 445

Gly Pro Val Leu Tyr Ser Cys Pro Ala Ala Ser Leu Pro
    450                 455                 460

<210> SEQ ID NO 22
<211> LENGTH: 449
<212> TYPE: PRT
<213> ORGANISM: fowl adenovirus

<400> SEQUENCE: 22

Arg His Ser Glu Asn Gly Lys Pro Glu Thr Glu Ala Gly Pro Ser Pro
1               5                   10                  15

Ala Pro Ile Lys Arg Ala Lys Arg Met Val Arg Ala Ser Gln Leu Asp
            20                  25                  30

Leu Val Tyr Pro Phe Asp Tyr Val Ala Asp Pro Val Gly Gly Leu Asn
        35                  40                  45

Pro Pro Phe Leu Gly Gly Ser Gly Pro Leu Val Asp Gln Gly Gly Gln
    50                  55                  60

Leu Thr Leu Asn Val Thr Asp Pro Ile Ile Ile Lys Asn Arg Ser Val
65                  70                  75                  80

Asp Leu Ala His Asp Pro Ser Leu Asp Val Asn Ala Gln Gly Gln Leu
                85                  90                  95

Ala Val Ala Val Asp Pro Glu Gly Ala Leu Asp Ile Thr Pro Asp Gly
            100                 105                 110

Leu Asp Val Lys Val Asp Gly Val Thr Val Met Val Asn Asp Asp Trp
        115                 120                 125

Glu Leu Ala Val Lys Val Asp Pro Ser Gly Gly Leu Asp Ser Thr Ala
    130                 135                 140

Gly Gly Leu Gly Val Ser Val Asp Asp Thr Leu Leu Val Asp Gln Gly

-continued

```
                145                 150                 155                 160
            Glu Leu Gly Val His Leu Asn Gln Gln Gly Pro Ile Thr Ala Asp Ser
                                165                 170                 175

Ser Gly Ile Asp Leu Glu Ile Asn Pro Asn Met Phe Thr Val Asn Thr
                            180                 185                 190

Ser Thr Gly Ser Gly Val Leu Glu Leu Asn Leu Lys Ala Gln Gly Gly
                        195                 200                 205

Ile Gln Ala Asp Ser Ser Gly Val Gly Val Ser Val Asp Glu Ser Leu
                    210                 215                 220

Gln Ile Val Asn Asn Thr Leu Glu Val Lys Pro Asp Pro Ser Gly Pro
            225                 230                 235                 240

Leu Thr Val Val Gly Gly Ser Val Ser Thr Pro Ile Ala Thr Phe
                                245                 250                 255

Val Ser Gly Ser Pro Ser Leu Asn Thr Tyr Asn Ala Thr Thr Val Asn
                            260                 265                 270

Ser Ser Ala Asn Ala Phe Ser Cys Ala Tyr Tyr Leu Gln Gln Trp Asn
                        275                 280                 285

Ile Gln Gly Leu Leu Val Thr Ser Leu Tyr Leu Lys Leu Asp Ser Ala
                    290                 295                 300

Thr Met Gly Asn Arg Pro Gly Asp Leu Asn Ser Ala Asn Ala Lys Trp
            305                 310                 315                 320

Phe Thr Phe Trp Val Ser Ala Tyr Leu Gln Gln Cys Asn Pro Ser Gly
                                325                 330                 335

Ile Gln Ala Gly Thr Val Ser Pro Ser Thr Ala Thr Leu Thr Asp Phe
                            340                 345                 350

Glu Pro Met Ala Asn Arg Ser Val Thr Ser Pro Trp Thr Tyr Ser Ala
                        355                 360                 365

Asn Gly Tyr Tyr Glu Pro Ser Ile Gly Glu Phe Gln Val Phe Ser Pro
                    370                 375                 380

Val Val Thr Gly Ala Trp Asn Pro Gly Asn Ile Gly Ile Arg Val Leu
            385                 390                 395                 400

Pro Val Pro Val Ser Ala Ser Gly Glu Arg Tyr Thr Leu Leu Cys Tyr
                                405                 410                 415

Ser Leu Gln Cys Thr Asn Ala Ser Ile Phe Asn Pro Asn Asn Ser Gly
                            420                 425                 430

Thr Met Ile Val Gly Pro Val Leu Tyr Ser Cys Pro Ala Ala Ser Leu
                        435                 440                 445

Pro

<210> SEQ ID NO 23
            <211> LENGTH: 449
            <212> TYPE: PRT
            <213> ORGANISM: fowl adenovirus

<400> SEQUENCE: 23

Pro Glu Thr Glu Ala Gly Pro Ser Pro Ala Pro Ile Lys Arg Ala Lys
            1               5                   10                  15

Arg Met Val Arg Ala Ser Gln Leu Asp Leu Val Tyr Pro Phe Asp Tyr
                            20                  25                  30

Val Ala Asp Pro Val Gly Gly Leu Asn Pro Pro Phe Leu Gly Gly Ser
                        35                  40                  45

Gly Pro Leu Val Asp Gln Gly Gly Gln Leu Thr Leu Asn Val Thr Asp
                    50                  55                  60

Pro Ile Ile Ile Lys Asn Arg Ser Val Asp Leu Ala His Asp Pro Ser
```

```
            65                   70                  75                  80
Leu Asp Val Asn Ala Gln Gly Gln Leu Ala Val Ala Val Asp Pro Glu
                    85                  90                  95
Gly Ala Leu Asp Ile Thr Pro Asp Gly Leu Asp Val Lys Val Asp Gly
                100                 105                 110
Val Thr Val Met Val Asn Asp Trp Glu Leu Ala Val Lys Val Asp
            115                 120                 125
Pro Ser Gly Gly Leu Asp Ser Thr Ala Gly Gly Leu Gly Val Ser Val
        130                 135                 140
Asp Asp Thr Leu Leu Val Asp Gln Gly Glu Leu Gly Val His Leu Asn
145                 150                 155                 160
Gln Gln Gly Pro Ile Thr Ala Asp Ser Ser Gly Ile Asp Leu Glu Ile
                165                 170                 175
Asn Pro Asn Met Phe Thr Val Asn Thr Ser Thr Gly Ser Gly Val Leu
            180                 185                 190
Glu Leu Asn Leu Lys Ala Gln Gly Gly Ile Gln Ala Asp Ser Ser Gly
                195                 200                 205
Val Gly Val Ser Val Asp Glu Ser Leu Gln Ile Val Asn Asn Thr Leu
        210                 215                 220
Glu Val Lys Pro Asp Pro Ser Gly Pro Leu Thr Val Ser Ala Asn Gly
225                 230                 235                 240
Leu Gly Leu Lys Tyr Asp Thr Asn Thr Leu Ala Val Thr Ala Gly Ala
                245                 250                 255
Leu Thr Val Val Gly Gly Gly Ser Val Ser Thr Pro Ile Ala Thr Phe
            260                 265                 270
Val Ser Gly Ser Pro Ser Leu Asn Thr Tyr Asn Ala Thr Val Asn
        275                 280                 285
Ser Ser Ala Asn Ala Phe Ser Cys Ala Tyr Tyr Leu Gln Gln Trp Asn
        290                 295                 300
Ile Gln Gly Leu Leu Val Thr Ser Leu Tyr Leu Lys Leu Asp Ser Ala
305                 310                 315                 320
Thr Met Gly Asn Arg Pro Gly Asp Leu Asn Ser Ala Asn Ala Lys Trp
                325                 330                 335
Phe Thr Phe Trp Val Ser Ala Tyr Leu Gln Gln Cys Asn Pro Ser Gly
            340                 345                 350
Ile Gln Ala Gly Thr Val Ser Pro Ser Thr Ala Thr Leu Thr Asp Phe
        355                 360                 365
Glu Pro Met Ala Asn Arg Ser Val Thr Ser Pro Trp Thr Tyr Ser Ala
    370                 375                 380
Asn Gly Tyr Tyr Glu Pro Ser Ile Gly Glu Phe Gln Val Phe Ser Pro
385                 390                 395                 400
Val Val Thr Gly Ala Trp Asn Pro Gly Asn Ile Gly Ile Arg Val Leu
                405                 410                 415
Pro Val Pro Val Ser Ala Ser Gly Glu Arg Tyr Thr Leu Leu Cys Tyr
            420                 425                 430
Ser Leu Gln Cys Thr Asn Ala Ser Ile Phe Asn Pro Asn Asn Ser Gly
        435                 440                 445
Thr

<210> SEQ ID NO 24
<211> LENGTH: 446
<212> TYPE: PRT
<213> ORGANISM: fowl adenovirus
```

<400> SEQUENCE: 24

Glu Ala Gly Pro Ser Pro Ala Pro Ile Lys Arg Ala Lys Arg Met Val
1               5                   10                  15

Arg Ala Ser Gln Leu Asp Leu Val Tyr Pro Phe Asp Tyr Val Ala Asp
            20                  25                  30

Pro Val Gly Gly Leu Asn Pro Pro Phe Leu Gly Gly Ser Gly Pro Leu
        35                  40                  45

Val Asp Gln Gly Gln Leu Thr Leu Asn Val Thr Asp Pro Ile Ile
50                  55                  60

Ile Lys Asn Arg Ser Val Asp Leu Ala His Asp Pro Ser Leu Asp Val
65                  70                  75                  80

Asn Ala Gln Gly Gln Leu Ala Val Ala Val Asp Pro Glu Gly Ala Leu
                85                  90                  95

Asp Ile Thr Pro Asp Gly Leu Asp Val Lys Val Asp Gly Val Thr Val
            100                 105                 110

Met Val Asn Asp Asp Trp Glu Leu Ala Val Lys Val Asp Pro Ser Gly
        115                 120                 125

Gly Leu Asp Ser Thr Ala Gly Gly Leu Gly Val Ser Val Asp Asp Thr
130                 135                 140

Leu Leu Val Asp Gln Gly Glu Leu Gly Val His Leu Asn Gln Gln Gly
145                 150                 155                 160

Pro Ile Thr Ala Asp Ser Ser Gly Ile Asp Leu Glu Ile Asn Pro Asn
                165                 170                 175

Met Phe Thr Val Asn Thr Ser Thr Gly Ser Gly Val Leu Glu Leu Asn
            180                 185                 190

Leu Lys Ala Gln Gly Gly Ile Gln Ala Asp Ser Ser Gly Val Gly Val
        195                 200                 205

Ser Val Asp Glu Ser Leu Gln Ile Val Asn Asn Thr Leu Glu Val Lys
210                 215                 220

Pro Asp Pro Ser Gly Pro Leu Thr Val Ser Ala Asn Gly Leu Gly Leu
225                 230                 235                 240

Lys Tyr Asp Thr Asn Thr Leu Ala Val Thr Ala Gly Ala Leu Thr Val
                245                 250                 255

Val Gly Gly Gly Ser Val Ser Thr Pro Ile Ala Thr Phe Val Ser Gly
            260                 265                 270

Ser Pro Ser Leu Asn Thr Tyr Asn Ala Thr Thr Val Asn Ser Ser Ala
        275                 280                 285

Asn Ala Phe Ser Cys Ala Tyr Tyr Leu Gln Gln Trp Asn Ile Gln Gly
290                 295                 300

Leu Leu Val Thr Ser Leu Tyr Leu Lys Leu Asp Ser Ala Thr Met Gly
305                 310                 315                 320

Asn Arg Pro Gly Asp Leu Asn Ser Ala Asn Ala Lys Trp Phe Thr Phe
                325                 330                 335

Trp Val Ser Ala Tyr Leu Gln Gln Cys Asn Pro Ser Gly Ile Gln Ala
            340                 345                 350

Gly Thr Val Ser Pro Ser Thr Ala Thr Leu Thr Asp Phe Glu Pro Met
        355                 360                 365

Ala Asn Arg Ser Val Thr Ser Pro Trp Thr Tyr Ser Ala Asn Gly Tyr
370                 375                 380

Tyr Glu Pro Ser Ile Gly Glu Phe Gln Val Phe Ser Pro Val Val Thr
385                 390                 395                 400

Gly Ala Trp Asn Pro Gly Asn Ile Gly Ile Arg Val Leu Pro Val Pro
                405                 410                 415

```
Val Ser Ala Ser Gly Glu Arg Tyr Thr Leu Leu Cys Tyr Ser Leu Gln
            420                 425                 430

Cys Thr Asn Ala Ser Ile Phe Asn Pro Asn Asn Ser Gly Thr
            435                 440                 445

<210> SEQ ID NO 25
<211> LENGTH: 479
<212> TYPE: PRT
<213> ORGANISM: fowl adenovirus

<400> SEQUENCE: 25

Met Leu Arg Ala Pro Lys Arg Arg His Ser Glu Asn Gly Gln Pro Glu
1               5                   10                  15

Ser Glu Ala Gly Pro Ser Pro Ala Pro Ile Lys Arg Ala Lys Arg Met
            20                  25                  30

Val Arg Ala Ser Gln Leu Asp Leu Val Tyr Pro Phe Asp Tyr Val Ala
        35                  40                  45

Asp Pro Val Gly Gly Leu Asn Pro Pro Phe Leu Gly Gly Ser Gly Pro
    50                  55                  60

Leu Val Asp Gln Gly Gly Gln Leu Thr Leu Asn Val Thr Asp Pro Ile
65                  70                  75                  80

Ile Ile Lys Asn Arg Ser Val Asp Leu Ala His Asp Pro Ser Leu Asp
                85                  90                  95

Val Asn Ala Gln Gly Gln Leu Ala Val Ala Val Asp Pro Glu Gly Ala
            100                 105                 110

Leu Asp Ile Thr Pro Asp Gly Leu Asp Val Lys Val Asp Gly Val Thr
        115                 120                 125

Val Met Val Asn Asp Asp Trp Glu Leu Ala Val Lys Val Asp Pro Ser
    130                 135                 140

Gly Gly Leu Asp Ser Thr Ala Gly Gly Leu Gly Val Ser Val Asp Asp
145                 150                 155                 160

Thr Leu Leu Val Asp Gln Gly Glu Leu Gly Val His Leu Asn Gln Gln
                165                 170                 175

Gly Pro Ile Thr Ala Asp Ser Ser Gly Ile Asp Leu Glu Ile Asn Pro
            180                 185                 190

Asn Met Phe Thr Val Asn Thr Ser Thr Gly Ser Gly Val Leu Glu Leu
        195                 200                 205

Asn Leu Lys Ala Gln Gly Gly Ile Gln Ala Gly Ser Ser Gly Val Gly
    210                 215                 220

Val Ser Val Asp Glu Ser Leu Glu Ile Val Asn Asn Thr Leu Glu Val
225                 230                 235                 240

Lys Pro Asp Pro Ser Gly Pro Leu Thr Val Ser Ala Asn Gly Leu Gly
                245                 250                 255

Leu Lys Tyr Asp Asn Asn Thr Leu Ala Val Thr Ala Gly Ala Leu Thr
            260                 265                 270

Val Val Gly Gly Gly Ser Ile Ser Thr Pro Ile Ala Thr Phe Val Ser
        275                 280                 285

Gly Ser Ala Ser Leu Asn Ala Tyr Asn Ala Arg Met Val Asn Ser Ser
    290                 295                 300

Ala His Ala Phe Ser Cys Ala Tyr Tyr Leu Gln Gln Trp Asn Ile Gln
305                 310                 315                 320

Gly Leu Leu Phe Thr Ser Leu Tyr Leu Lys Leu Asp Ser Ala Thr Met
                325                 330                 335

Gly Asn Arg Pro Gly Asp Asn Asn Ser Val Asn Ala Lys Trp Phe Thr
```

```
                340                 345                 350
Phe Trp Val Ser Ala Tyr Leu Gln Gln Cys Asn Pro Ser Gly Ile Gln
            355                 360                 365

Ala Gly Thr Val Ser Pro Ser Thr Ala Thr Leu Ala Asp Phe Glu Pro
        370                 375                 380

Met Ala Asn Arg Ser Val Ser Ser Pro Trp Thr Tyr Ser Ala Asn Gly
385                 390                 395                 400

Tyr Tyr Gln Pro Pro Ser Gly Glu Phe Gln Leu Phe Thr Pro Val Val
                405                 410                 415

Thr Gly Ala Trp Thr Pro Gly Asn Ile Gly Ile Arg Val Leu Pro Val
            420                 425                 430

Pro Val Ser Ala Ser Gly Asp Arg Tyr Thr Leu Leu Cys Tyr Ser Leu
        435                 440                 445

Gln Cys Thr Asn Ala Ser Ile Phe Asn Pro Asn Asn Ser Gly Thr Met
    450                 455                 460

Ile Val Gly Pro Val Leu Tyr Ser Cys Pro Ala Gly Ser Leu Pro
465                 470                 475

<210> SEQ ID NO 26
<211> LENGTH: 461
<212> TYPE: PRT
<213> ORGANISM: fowl adenovirus

<400> SEQUENCE: 26

Met Leu Arg Ala Pro Lys Arg Arg His Ser Glu Asn Gly Gln Pro Glu
1               5                   10                  15

Ser Glu Ala Gly Pro Ser Pro Ala Pro Ile Lys Arg Ala Lys Arg Met
            20                  25                  30

Val Arg Ala Ser Gln Leu Asp Leu Val Tyr Pro Phe Asp Tyr Val Ala
        35                  40                  45

Asp Pro Val Gly Gly Leu Asn Pro Pro Phe Leu Gly Gly Ser Gly Pro
    50                  55                  60

Leu Val Asp Gln Gly Gly Gln Leu Thr Leu Asn Val Thr Asp Pro Ile
65                  70                  75                  80

Ile Ile Lys Asn Arg Ser Val Asp Leu Ala His Asp Pro Ser Leu Asp
                85                  90                  95

Val Asn Ala Gln Gly Gln Leu Ala Val Ala Val Asp Pro Glu Gly Ala
            100                 105                 110

Leu Thr Ser Thr Pro Asp Gly Leu Asp Val Lys Val Asp Pro Ser Gly
        115                 120                 125

Gly Leu Asp Ser Thr Ala Gly Gly Leu Gly Val Ser Val Asp Asp Thr
    130                 135                 140

Leu Leu Val Asp Gln Gly Glu Leu Gly Val His Leu Asn Gln Gln Gly
145                 150                 155                 160

Pro Ile Thr Ala Asp Ser Ser Gly Ile Asp Leu Glu Ile Asn Pro Asn
                165                 170                 175

Met Phe Thr Val Asn Thr Ser Thr Gly Ser Gly Val Leu Glu Leu Asn
            180                 185                 190

Leu Lys Ala Gln Gly Gly Ile Gln Ala Gly Ser Ser Gly Val Gly Val
        195                 200                 205

Ser Val Asp Glu Ser Leu Glu Ile Val Asn Asn Thr Leu Glu Val Lys
    210                 215                 220

Pro Asp Pro Ser Gly Pro Leu Thr Val Ser Ala Asn Gly Leu Gly Leu
225                 230                 235                 240
```

```
Lys Tyr Asp Asn Asn Thr Leu Ala Val Thr Arg Gly Ala Leu Thr Val
                    245                 250                 255

Val Gly Gly Gly Ser Ile Ser Thr Pro Ile Ala Thr Phe Val Ser Gly
            260                 265                 270

Ser Ala Ser Leu Asn Ala Tyr Asn Ala Arg Met Val Ile Pro Gly Ala
        275                 280                 285

Asp Ala Phe Ser Cys Ala Tyr Tyr Leu Gln Gln Trp Asn Ile Gln Gly
    290                 295                 300

Leu Leu Phe Thr Ser Leu Tyr Leu Lys Leu Asp Ser Ala Thr Met Gly
305                 310                 315                 320

Asn Arg Pro Gly Asp Asn Asn Ser Val Asn Ala Lys Trp Phe Thr Phe
                325                 330                 335

Trp Val Ser Ala Tyr Leu Gln Gln Cys Asn Ser Gly Ile Gln Ala Gly
            340                 345                 350

Thr Val Ser Pro Ser Thr Ala Thr Leu Ala Asp Phe Glu Pro Met Ala
        355                 360                 365

Asn Arg Ser Val Ser Ser Pro Trp Thr Tyr Ser Ala Asn Gly Tyr Tyr
    370                 375                 380

Glu Pro Pro Ser Gly Glu Phe Gln Leu Phe Thr Pro Val Thr Gly
385                 390                 395                 400

Ala Trp Thr Pro Gly Asn Ile Gly Ile Arg Val Leu Pro Val Pro Val
                405                 410                 415

Ser Ala Ser Gly Asp Arg Tyr Thr Leu Leu Cys Tyr Ser Leu Gln Cys
            420                 425                 430

Thr Asn Ala Ser Ile Phe Asn Pro Asn Asn Ser Gly Thr Met Ile Val
        435                 440                 445

Gly Pro Val Leu Tyr Ser Cys Pro Ala Gly Ser Leu Pro
    450                 455                 460

<210> SEQ ID NO 27
<211> LENGTH: 479
<212> TYPE: PRT
<213> ORGANISM: fowl adenovirus

<400> SEQUENCE: 27

Met Leu Arg Ala Pro Lys Arg Arg His Ser Glu Asn Gly Lys Pro Glu
1               5                   10                  15

Thr Glu Ala Gly Pro Ser Pro Ala Pro Ile Lys Arg Ala Lys Arg Met
            20                  25                  30

Val Arg Ala Ser Gln Leu Asp Leu Val Tyr Pro Phe Asp Tyr Val Ala
        35                  40                  45

Asp Pro Val Gly Gly Leu Asn Pro Pro Phe Leu Gly Ser Gly Pro
    50                  55                  60

Leu Val Asp Gln Gly Gln Leu Thr Leu Asn Val Thr Asp Pro Ile
65                  70                  75                  80

Ile Ile Lys Asn Arg Ser Val Asp Leu Ala Arg Asp Pro Ser Leu Asp
                85                  90                  95

Val Asn Ala Gln Gly Gln Leu Ala Val Ala Val Asp Pro Glu Gly Ala
            100                 105                 110

Leu Ala Ile Thr Pro Asp Gly Leu Asp Val Lys Val Asp Gly Val Thr
        115                 120                 125

Val Met Val Asn Asp Asp Trp Glu Leu Ala Val Lys Val Asp Pro Ala
    130                 135                 140

Gly Gly Leu Asp Ser Thr Ala Gly Gly Leu Gly Val Ser Val Asp Asp
145                 150                 155                 160
```

```
Thr Leu Leu Val Asp Gln Gly Glu Leu Gly Val His Leu Asn Gln Gln
                165                 170                 175

Gly Pro Ile Thr Ala Asp Ser Ser Gly Ile Asp Leu Glu Ile Asn Pro
            180                 185                 190

Asn Met Phe Thr Val Asn Thr Ser Thr Gly Ser Gly Val Leu Glu Leu
        195                 200                 205

Asn Leu Lys Ala Gln Gly Gly Ile Gln Ala Gly Ser Ser Gly Val Gly
    210                 215                 220

Val Ser Val Asp Glu Ser Leu Glu Ile Val Asn Asn Thr Leu Glu Val
225                 230                 235                 240

Lys Pro Asp Pro Ser Gly Pro Leu Thr Val Ser Ala Asn Gly Leu Gly
                245                 250                 255

Leu Lys Tyr Asp Asn Asn Thr Leu Ala Val Thr Ala Gly Ala Leu Thr
            260                 265                 270

Val Val Gly Gly Gly Ser Val Ser Thr Pro Ile Ala Thr Phe Val Ser
        275                 280                 285

Gly Ser Pro Ser Leu Asp Ala Tyr Asn Ala Thr Thr Val Asn Ser Ser
    290                 295                 300

Ala His Pro Phe Ser Cys Ala Tyr Tyr Leu Gln Gln Trp Asn Val Gln
305                 310                 315                 320

Gly Leu Leu Phe Thr Ser Leu Tyr Leu Lys Leu Asp Ser Thr Thr Met
                325                 330                 335

Gly Thr Arg Pro Gly Asp Trp Asn Ser Val Asn Ala Lys Trp Phe Thr
            340                 345                 350

Phe Trp Val Ser Ala Tyr Leu Gln Gln Cys Asn Pro Ser Gly Ile Gln
        355                 360                 365

Ala Gly Thr Leu Ser Pro Ser Thr Ala Thr Leu Ala Asp Phe Glu Pro
    370                 375                 380

Met Ala Asn Arg Ser Val Ser Ser Pro Trp Thr Tyr Ser Ala Asn Ala
385                 390                 395                 400

Tyr Tyr Glu Pro Ser Ser Gly Glu Phe Gln Thr Phe Thr Pro Val Val
                405                 410                 415

Thr Gly Ala Trp Asn Pro Gly Asn Ile Gly Ile Arg Val Leu Pro Val
            420                 425                 430

Ser Val Ser Ala Ser Gly Asp Arg Tyr Thr Leu Leu Cys Tyr Ser Leu
        435                 440                 445

Gln Cys Thr Asn Ala Ser Ile Phe Asn Pro Ala Asn Ser Gly Thr Met
    450                 455                 460

Ile Val Gly Pro Val Leu Tyr Ser Cys Pro Ala Gly Ser Leu Pro
465                 470                 475

<210> SEQ ID NO 28
<211> LENGTH: 479
<212> TYPE: PRT
<213> ORGANISM: fowl adenovirus

<400> SEQUENCE: 28

Met Leu Arg Ala Pro Lys Arg Arg His Ser Glu Asn Gly Lys Pro Glu
1               5                   10                  15

Thr Glu Ala Gly Pro Ser Pro Ala Pro Ile Lys Arg Ala Lys Arg Met
            20                  25                  30

Val Arg Ala Ser Gln Leu Asp Leu Val Tyr Pro Phe Asp Tyr Val Ala
        35                  40                  45

Asp Pro Val Gly Gly Leu Asn Pro Pro Phe Leu Gly Gly Ser Gly Pro
```

```
              50                  55                  60
Leu Val Asp Gln Gly Gly Gln Leu Thr Leu Asn Val Thr Asp Pro Ile
 65                  70                  75                  80

Ile Ile Lys Asn Arg Ser Val Asp Leu Ala Arg Asp Pro Ser Leu Asp
                 85                  90                  95

Val Asn Ala Gln Gly Gln Leu Ala Val Ala Val Asp Pro Glu Gly Ala
                100                 105                 110

Leu Ala Ile Thr Pro Asp Gly Leu Asp Val Lys Val Asp Gly Val Thr
                115                 120                 125

Val Met Val Asn Asp Asp Trp Glu Leu Ala Val Lys Val Asp Pro Ala
                130                 135                 140

Gly Gly Leu Asp Ser Thr Ala Gly Gly Leu Gly Val Ser Val Asp Asp
145                 150                 155                 160

Thr Leu Leu Val Asp Gln Gly Glu Leu Gly Val His Leu Asn Gln Gln
                165                 170                 175

Gly Pro Ile Thr Ala Asp Ser Ser Gly Ile Asp Leu Glu Ile Asn Pro
                180                 185                 190

Asn Met Phe Thr Val Asn Thr Ser Thr Gly Ser Gly Val Leu Glu Leu
                195                 200                 205

Asn Leu Lys Ala Gln Gly Gly Ile Gln Ala Gly Ser Ser Gly Val Gly
210                 215                 220

Val Ser Val Asp Glu Ser Leu Glu Ile Val Asn Asn Thr Leu Glu Val
225                 230                 235                 240

Lys Pro Asp Pro Ser Gly Pro Leu Thr Val Ser Ala Asn Gly Leu Gly
                245                 250                 255

Leu Lys Tyr Asp Asn Asn Thr Leu Ala Val Thr Ala Gly Ala Leu Thr
                260                 265                 270

Val Val Gly Gly Ser Val Ser Thr Pro Ile Ala Thr Phe Val Ser
                275                 280                 285

Gly Ser Pro Ser Leu Asp Ala Tyr Asn Ala Thr Thr Val Asn Ser Ser
                290                 295                 300

Ala His Pro Phe Ser Cys Ala Tyr Tyr Leu Gln Gln Trp Asn Val Gln
305                 310                 315                 320

Gly Leu Leu Phe Thr Ser Leu Tyr Leu Lys Leu Asp Ser Thr Thr Met
                325                 330                 335

Gly Thr Arg Pro Gly Asp Trp Asn Ser Val Asn Ala Lys Trp Phe Thr
                340                 345                 350

Phe Trp Val Ser Ala Tyr Leu Gln Gln Cys Asn Pro Ser Gly Ile Gln
                355                 360                 365

Ala Gly Thr Leu Ser Pro Ser Thr Ala Thr Leu Ala Asp Phe Glu Pro
                370                 375                 380

Met Ala Asn Arg Ser Val Ser Ser Pro Trp Thr Tyr Ser Ala Asn Ala
385                 390                 395                 400

Tyr Tyr Glu Pro Ser Ser Gly Glu Phe Gln Thr Phe Thr Pro Val Val
                405                 410                 415

Thr Gly Ala Trp Asn Pro Gly Asn Ile Gly Ile Arg Val Leu Pro Val
                420                 425                 430

Ser Val Ser Ala Ser Gly Asp Arg Tyr Thr Leu Leu Cys Tyr Ser Leu
                435                 440                 445

Gln Cys Thr Asn Ala Ser Ile Phe Asn Pro Ala Asn Ser Gly Thr Met
                450                 455                 460

Ile Val Gly Pro Val Leu Tyr Ser Cys Pro Ala Gly Ser Leu Pro
465                 470                 475
```

<210> SEQ ID NO 29
<211> LENGTH: 442
<212> TYPE: PRT
<213> ORGANISM: fowl adenovirus

<400> SEQUENCE: 29

Ser Pro Ala Pro Ile Lys Arg Pro Lys Arg Met Val Arg Ala Ser Gln
1               5                   10                  15

Leu Asp Leu Val Tyr Pro Phe Asp Tyr Val Ala Asp Pro Val Gly Gly
            20                  25                  30

Leu Asn Pro Pro Phe Leu Gly Gly Ser Gly Pro Leu Val Asp Gln Gly
        35                  40                  45

Gly Gln Leu Thr Leu Asn Val Thr Asp Pro Ile Ile Ile Lys Asn Arg
50                  55                  60

Ser Val Asp Leu Ala His Asp Pro Ser Leu Asp Val Asn Ala Gln Gly
65                  70                  75                  80

Gln Leu Ala Val Ala Val Asp Pro Glu Gly Ala Leu Ala Ile Thr Pro
                85                  90                  95

Asp Gly Leu Asp Val Lys Val Asp Gly Val Thr Val Met Val Asn Asp
            100                 105                 110

Asp Trp Glu Leu Ala Val Lys Val Asp Pro Ala Gly Gly Leu Asp Ser
        115                 120                 125

Thr Ala Gly Gly Leu Gly Val Ser Val Asp Asp Thr Leu Leu Val Asp
130                 135                 140

Gln Gly Glu Leu Gly Val His Leu Asn Gln Gln Gly Pro Ile Thr Ala
145                 150                 155                 160

Asp Ser Ser Gly Ile Asp Leu Glu Ile Asn Pro Asn Met Phe Thr Val
                165                 170                 175

Asn Thr Ser Thr Gly Ser Gly Val Leu Glu Leu Asn Leu Lys Ala Gln
            180                 185                 190

Gly Gly Ile Gln Ala Gly Ser Ser Gly Val Gly Val Ser Val Asp Glu
        195                 200                 205

Ser Leu Glu Ile Val Asn Asn Thr Leu Glu Val Lys Pro Asp Pro Ser
210                 215                 220

Gly Pro Leu Thr Val Ser Ala Asn Gly Leu Gly Leu Lys Tyr Asp Asn
225                 230                 235                 240

Asn Thr Leu Ala Val Thr Ala Gly Ala Leu Thr Val Val Gly Gly Gly
                245                 250                 255

Ser Val Ser Thr Pro Ile Ala Thr Phe Val Ser Gly Ser Pro Ser Leu
            260                 265                 270

Asp Ala Tyr Asn Ala Arg Met Val Asn Ser Ser Ala His Pro Phe Ser
        275                 280                 285

Cys Ala Tyr Tyr Leu Gln Gln Trp Asn Val Gln Gly Leu Leu Phe Thr
290                 295                 300

Ser Leu Tyr Leu Lys Leu Asp Ser Thr Thr Met Gly Asn Arg Pro Gly
305                 310                 315                 320

Asp Trp Asn Ser Val Asn Ala Lys Trp Phe Thr Phe Trp Val Ser Ala
                325                 330                 335

Tyr Leu Gln Gln Cys Asn Pro Ser Gly Ile Gln Ala Gly Thr Leu Ser
            340                 345                 350

Pro Ser Thr Ala Thr Leu Ala Asp Phe Glu Pro Met Ala Asn Arg Ser
        355                 360                 365

Val Ser Ser Pro Trp Thr Tyr Ser Ala Asn Ala Tyr Tyr Glu Pro Ser 370                 375                 380
Ser Gly Glu Phe Gln Thr Phe Thr Pro Val Val Thr Gly Ala Trp Asn
385                 390                 395                 400

Pro Gly Asn Ile Gly Ile Arg Val Leu Pro Val Ser Val Ser Ala Ser
                405                 410                 415

Gly Glu Arg Tyr Thr Leu Leu Cys Tyr Ser Leu Gln Cys Thr Asn Ala
            420                 425                 430

Ser Ile Phe Asn Pro Ala Asn Ser Gly Thr
        435                 440

<210> SEQ ID NO 30
<211> LENGTH: 477
<212> TYPE: PRT
<213> ORGANISM: fowl adenovirus

<400> SEQUENCE: 30

Arg Ala Pro Lys Arg His Ser Glu Asn Gly Gln Pro Glu Ser Glu
1               5                   10                  15

Ala Gly Pro Ser Pro Ala Pro Ile Lys Arg Ala Lys Arg Met Val Arg
                20                  25                  30

Ala Ser Gln Leu Asp Leu Val Tyr Pro Phe Asp Tyr Val Ala Asp Pro
            35                  40                  45

Val Gly Gly Leu Asn Pro Pro Phe Leu Gly Gly Ser Gly Pro Leu Val
        50                  55                  60

Asp Gln Gly Gly Gln Leu Thr Leu Asn Val Thr Asp Pro Ile Ile Ile
65                  70                  75                  80

Lys Asn Arg Ser Val Asp Leu Ala His Asp Pro Ser Leu Asp Val Asn
                85                  90                  95

Ala Gln Gly Gln Leu Ala Val Ala Val Asp Pro Glu Gly Ala Leu Asp
            100                 105                 110

Ile Thr Pro Asp Gly Leu Asp Val Lys Val Asp Gly Val Thr Val Met
        115                 120                 125

Val Asn Asp Asp Trp Glu Leu Ala Val Lys Val Asp Pro Ser Gly Gly
130                 135                 140

Leu Asp Ser Thr Ala Gly Gly Leu Gly Val Ser Val Asp Asp Thr Leu
145                 150                 155                 160

Leu Val Asp Gln Gly Glu Leu Gly Val His Leu Asn Gln Gln Gly Pro
                165                 170                 175

Ile Thr Ala Asp Ser Ser Gly Ile Asp Leu Glu Ile Asn Pro Asn Met
            180                 185                 190

Phe Thr Val Asn Thr Ser Thr Gly Ser Gly Val Leu Glu Leu Asn Leu
        195                 200                 205

Lys Ala Gln Gly Gly Ile Gln Ala Gly Ser Ser Gly Val Gly Val Ser
210                 215                 220

Val Asp Glu Ser Leu Glu Ile Val Asn Asn Thr Leu Glu Val Lys Pro
225                 230                 235                 240

Asp Pro Ser Gly Pro Leu Thr Val Ser Ala Asn Gly Leu Gly Leu Lys
                245                 250                 255

Tyr Asp Ser Asn Thr Leu Ala Val Thr Ala Gly Ala Leu Thr Val Val
            260                 265                 270

Gly Gly Gly Ser Val Ser Thr Pro Ile Ala Thr Phe Val Ser Gly Ser
        275                 280                 285

Pro Ser Leu Asn Thr Tyr Asn Ala Thr Ile Val Asn Ser Ser Ser His
        290                 295                 300

-continued

Pro Phe Ser Cys Ala Tyr Tyr Leu Gln Gln Trp Asn Val Gln Gly Leu
305                 310                 315                 320

Leu Phe Thr Ser Leu Tyr Val Lys Leu Asp Ser Thr Thr Met Gly Thr
            325                 330                 335

Arg Pro Gly Asp Asn Ser Ser Ala Asn Ala Lys Trp Phe Thr Phe Trp
            340                 345                 350

Val Ser Ala Tyr Leu Gln Gln Cys Asn Pro Ser Gly Ile Gln Ala Gly
            355                 360                 365

Thr Val Ser Pro Ser Thr Ala Ala Leu Ala Asp Phe Glu Pro Met Ala
            370                 375                 380

Asn Arg Ser Val Ser Ser Pro Trp Thr Tyr Ser Ala Asn Ala Tyr Tyr
385                 390                 395                 400

Gln Pro Ser Ser Gly Glu Phe Gln Val Phe Thr Pro Val Val Thr Gly
                405                 410                 415

Ala Trp Asn Pro Gly Asn Ile Gly Ile Arg Val Leu Pro Val Pro Val
                420                 425                 430

Thr Ala Ser Gly Asp Arg Tyr Thr Leu Leu Cys Tyr Ser Leu Gln Cys
            435                 440                 445

Thr Asn Ser Ser Ile Phe Asn Pro Ala Asn Ser Gly Thr Met Ile Val
450                 455                 460

Gly Pro Val Leu Tyr Ser Cys Pro Ala Ala Ser Val Pro
465                 470                 475

<210> SEQ ID NO 31
<211> LENGTH: 479
<212> TYPE: PRT
<213> ORGANISM: fowl adenovirus

<400> SEQUENCE: 31

Met Leu Arg Ala Pro Lys Arg Arg His Ser Glu Asn Gly Gln Pro Glu
1               5                   10                  15

Ser Glu Ala Gly Pro Ser Pro Ala Pro Ile Lys Arg Ala Lys Arg Met
            20                  25                  30

Val Arg Ala Ser Gln Leu Asp Leu Val Tyr Pro Phe Asp Tyr Val Ala
            35                  40                  45

Asp Pro Val Gly Gly Leu Asn Pro Pro Phe Leu Gly Gly Ser Gly Pro
50                  55                  60

Leu Val Asp Gln Gly Gly Gln Leu Thr Leu Asn Val Thr Asp Pro Ile
65                  70                  75                  80

Ile Ile Lys Asn Arg Ser Val Asp Leu Ala His Asp Pro Ser Leu Asp
                85                  90                  95

Val Asn Ala Gln Gly Gln Leu Ala Val Ala Val Asp Pro Glu Gly Ala
            100                 105                 110

Leu Asp Ile Thr Pro Asp Gly Leu Asp Val Lys Val Asp Gly Val Thr
            115                 120                 125

Val Met Val Asn Asp Asp Trp Glu Leu Ala Val Lys Val Asp Pro Ser
            130                 135                 140

Gly Gly Leu Asp Ser Thr Ala Gly Gly Leu Gly Val Ser Val Asp Asp
145                 150                 155                 160

Thr Leu Leu Val Asp Gln Gly Glu Leu Gly Val His Leu Asn Gln Gln
                165                 170                 175

Gly Pro Ile Thr Ala Asp Ser Ser Gly Ile Asp Leu Glu Ile Asn Pro
            180                 185                 190

Asn Met Phe Thr Val Asn Thr Ser Thr Gly Ser Gly Val Leu Glu Leu
            195                 200                 205

Asn Leu Lys Ala Gln Gly Gly Ile Gln Ala Gly Ser Ser Gly Val Gly
            210                 215                 220

Val Ser Val Asp Glu Ser Leu Glu Ile Val Asn Asn Thr Leu Glu Val
225                 230                 235                 240

Lys Pro Asp Pro Ser Gly Pro Leu Thr Val Ser Ala Asn Gly Leu Gly
                245                 250                 255

Leu Lys Tyr Asp Ser Asn Thr Leu Ala Val Thr Ala Gly Ala Leu Thr
            260                 265                 270

Val Val Gly Gly Gly Ser Val Ser Thr Pro Ile Ala Thr Phe Val Ser
        275                 280                 285

Gly Ser Pro Ser Leu Asn Thr Tyr Asn Ala Thr Ile Val Asn Ser Ser
        290                 295                 300

Ser His Pro Phe Ser Cys Ala Tyr Tyr Leu Gln Gln Trp Asn Val Gln
305                 310                 315                 320

Gly Leu Leu Phe Thr Ser Leu Tyr Val Lys Leu Asp Ser Thr Thr Met
                325                 330                 335

Gly Thr Arg Pro Gly Asp Asn Ser Ser Ala Asn Ala Lys Trp Phe Thr
            340                 345                 350

Phe Trp Val Ser Ala Tyr Leu Gln Gln Cys Asn Pro Ser Gly Ile Gln
        355                 360                 365

Ala Gly Thr Val Ser Pro Ser Thr Ala Ala Leu Ala Asp Phe Glu Pro
    370                 375                 380

Met Ala Asn Arg Ser Val Ser Ser Pro Trp Thr Tyr Ser Ala Asn Ala
385                 390                 395                 400

Tyr Tyr Gln Pro Ser Ser Gly Glu Phe Gln Val Phe Thr Pro Val Val
                405                 410                 415

Thr Gly Ala Trp Asn Pro Gly Asn Ile Gly Ile Arg Val Leu Pro Val
            420                 425                 430

Pro Val Thr Ala Ser Gly Asp Arg Tyr Thr Leu Leu Cys Tyr Ser Leu
        435                 440                 445

Gln Cys Thr Asn Ser Ser Ile Phe Asn Pro Ala Asn Ser Gly Thr Met
    450                 455                 460

Ile Val Gly Pro Val Leu Tyr Ser Cys Pro Ala Ala Ser Val Pro
465                 470                 475

<210> SEQ ID NO 32
<211> LENGTH: 474
<212> TYPE: PRT
<213> ORGANISM: fowl adenovirus

<400> SEQUENCE: 32

Met Leu Arg Ala Pro Lys Arg Arg His Ser Glu Thr Glu Ala Gly Pro
1               5                   10                  15

Ser Pro Ala Pro Ile Lys Arg Pro Lys Arg Met Val Arg Ala Ser Gln
            20                  25                  30

Leu Asp Leu Val Tyr Pro Phe Asp Tyr Val Ala Asp Pro Val Gly Gly
        35                  40                  45

Leu Asn Pro Pro Phe Leu Gly Gly Ser Gly Pro Leu Val Asp Gln Gly
    50                  55                  60

Gly Gln Leu Thr Leu Asn Val Thr Asp Pro Ile Ile Lys Asn Arg
65                  70                  75                  80

Ser Val Asp Leu Ala His Asp Pro Ser Leu Asp Val Asn Ala Gln Gly
                85                  90                  95

Gln Leu Ala Val Ala Val Asp Pro Glu Gly Ala Leu Asp Ile Thr Pro

```
            100                 105                 110
Asp Gly Leu Asp Val Lys Val Asp Gly Val Thr Val Met Val Asn Asp
            115                 120                 125

Asp Trp Glu Leu Ala Val Lys Val Asp Pro Ser Gly Leu Asp Ser
130                 135                 140

Thr Ala Gly Gly Leu Gly Val Ser Val Asp Thr Leu Leu Val Asp
145                 150                 155                 160

Gln Gly Glu Leu Gly Val His Leu Asn Gln Gln Gly Pro Ile Thr Ala
            165                 170                 175

Asp Ser Ser Gly Ile Asp Leu Glu Ile Asn Pro Asn Met Phe Thr Val
            180                 185                 190

Asn Thr Ser Thr Gly Ser Gly Val Leu Glu Leu Asn Leu Lys Ala Gln
            195                 200                 205

Gly Gly Ile Gln Ala Gly Ser Ser Gly Val Gly Val Ser Val Asp Glu
            210                 215                 220

Ser Leu Glu Ile Val Asn Asn Thr Leu Glu Val Lys Pro Asp Pro Ser
225                 230                 235                 240

Gly Pro Leu Thr Val Ser Ala Asn Gly Leu Gly Leu Lys Tyr Asp Ser
                245                 250                 255

Asn Thr Leu Ala Val Thr Ala Gly Ala Leu Thr Val Val Gly Gly Gly
            260                 265                 270

Ser Val Ser Thr Pro Ile Ala Thr Phe Val Ser Gly Ser Pro Ser Leu
            275                 280                 285

Asn Thr Tyr Asn Ala Thr Ile Val Asn Ser Ser His Pro Phe Ser
            290                 295                 300

Cys Ala Tyr Tyr Leu Gln Gln Trp Asn Val Gln Gly Leu Leu Phe Thr
305                 310                 315                 320

Ser Leu Tyr Val Lys Leu Asp Ser Thr Thr Met Gly Thr Arg Pro Gly
                325                 330                 335

Asp Asn Ser Ser Ala Asn Ala Lys Trp Phe Thr Phe Trp Val Ser Ala
            340                 345                 350

Tyr Leu Gln Gln Cys Asn Pro Ser Gly Ile Gln Ala Gly Thr Val Ser
            355                 360                 365

Pro Ser Thr Ala Ala Leu Ala Asp Phe Glu Pro Met Ala Asn Arg Ser
370                 375                 380

Val Ser Ser Pro Trp Thr Tyr Ser Ala Asn Ala Tyr Tyr Gln Pro Pro
385                 390                 395                 400

Ser Gly Glu Phe Gln Val Phe Thr Pro Val Val Thr Gly Ala Trp Asn
                405                 410                 415

Pro Gly Asn Ile Gly Ile Arg Val Leu Pro Val Pro Val Thr Ala Ser
            420                 425                 430

Gly Asp Arg Tyr Thr Leu Leu Cys Tyr Ser Leu Gln Cys Thr Asn Ser
            435                 440                 445

Ser Ile Phe Asn Pro Ala Asn Ser Gly Thr Met Ile Val Gly Pro Val
            450                 455                 460

Leu Tyr Ser Cys Pro Ala Ala Ser Val Pro
465                 470
```

<210> SEQ ID NO 33
<211> LENGTH: 479
<212> TYPE: PRT
<213> ORGANISM: fowl adenovirus

<400> SEQUENCE: 33

-continued

```
Met Leu Arg Ala Pro Lys Arg Arg His Ser Glu Asn Gly Gln Pro Glu
1               5                   10                  15

Ser Glu Ala Gly Pro Ser Pro Ala Pro Ile Lys Arg Ala Lys Arg Met
            20                  25                  30

Val Arg Ala Ala Gln Leu Asp Leu Val Tyr Pro Phe Asp Tyr Val Ala
        35                  40                  45

Asp Pro Val Gly Gly Leu Asn Pro Pro Phe Leu Gly Gly Ser Gly Pro
    50                  55                  60

Leu Val Asp Gln Gly Gln Leu Thr Leu Asn Val Thr Asp Pro Ile
65                  70                  75                  80

Ile Ile Lys Asn Arg Ser Val Asp Leu Ala His Asp Pro Ser Leu Asp
                85                  90                  95

Val Asn Ala Gln Gly Gln Leu Ala Val Ala Val Asp Pro Glu Gly Ala
            100                 105                 110

Leu Asp Ile Thr Pro Asp Gly Leu Asp Val Lys Val Asp Gly Val Thr
        115                 120                 125

Val Met Val Asn Asp Asp Trp Glu Leu Ala Val Lys Val Asp Pro Ser
    130                 135                 140

Gly Gly Leu Asp Ser Thr Ala Gly Leu Gly Val Ser Val Asp Asp
145                 150                 155                 160

Thr Leu Leu Val Asp Gln Gly Glu Leu Gly Val His Leu Asn Gln Gln
                165                 170                 175

Gly Pro Ile Thr Ala Asp Ser Ser Gly Ile Asp Leu Glu Ile Asn Pro
            180                 185                 190

Asn Met Phe Thr Val Asn Thr Ser Thr Gly Ser Gly Val Leu Glu Leu
        195                 200                 205

Asn Leu Lys Ala Gln Gly Gly Ile Gln Ala Gly Ser Ser Gly Val Gly
    210                 215                 220

Val Ser Val Asp Glu Ser Leu Glu Ile Val Asn Asn Thr Leu Glu Val
225                 230                 235                 240

Lys Pro Asp Pro Ser Gly Pro Leu Thr Val Ser Ala Asn Gly Leu Gly
                245                 250                 255

Leu Lys Tyr Asp Ser Asn Thr Leu Ala Val Thr Ala Gly Ala Leu Thr
            260                 265                 270

Val Val Gly Gly Gly Ser Val Ser Thr Pro Ile Ala Thr Phe Val Ser
        275                 280                 285

Gly Ser Pro Ser Leu Asn Thr Tyr Asn Ala Thr Ile Val Asn Ser Ser
    290                 295                 300

Ala His Pro Phe Ser Cys Ala Tyr Tyr Leu Gln Gln Trp Asn Val Gln
305                 310                 315                 320

Gly Leu Leu Phe Thr Ser Leu Tyr Val Lys Leu Asp Ser Thr Thr Met
                325                 330                 335

Gly Thr Arg Pro Gly Asp Asn Ser Ser Ala Asn Ala Lys Trp Phe Thr
            340                 345                 350

Phe Trp Val Ser Ala Tyr Leu Gln Gln Cys Asn Pro Ser Gly Ile Gln
        355                 360                 365

Ala Gly Thr Val Ser Pro Ser Thr Ala Ala Leu Ala Asp Phe Glu Pro
    370                 375                 380

Met Ala Asn Arg Ser Val Ser Ser Pro Trp Thr Tyr Ser Ala Asn Ala
385                 390                 395                 400

Tyr Tyr Gln Pro Ser Ser Gly Glu Phe Gln Val Phe Thr Pro Val Val
                405                 410                 415

Thr Gly Ala Trp Asn Pro Gly Asn Ile Gly Val Arg Val Leu Pro Val
```

|     |     |     |     |     | 420 |     |     |     | 425 |     |     |     |     | 430 |
| --- | --- | --- | --- | --- | --- | --- | --- | --- | --- | --- | --- | --- | --- | --- |
| Pro | Val | Ser | Ala | Ser | Gly | Asp | Arg | Tyr | Thr | Leu | Leu | Cys | Tyr | Ser | Leu |

Pro Val Ser Ala Ser Gly Asp Arg Tyr Thr Leu Leu Cys Tyr Ser Leu
                            435                         440                             445

Gln Cys Thr Asn Ala Ser Ile Phe Asn Pro Ala Asn Ser Gly Thr Met
            450                             455                             460

Thr Val Gly Pro Val Leu Tyr Thr Cys Pro Ala Ala Ser Val Pro
465                             470                             475

<210> SEQ ID NO 34
<211> LENGTH: 467
<212> TYPE: PRT
<213> ORGANISM: fowl adenovirus

<400> SEQUENCE: 34

Arg Arg His Ser Glu Thr Glu Ala Gly Pro Tyr Pro Ala Pro Ile Lys
1               5                   10                  15

Arg Pro Lys Arg Met Val Arg Ala Ser Gln Leu Asp Leu Val Tyr Pro
                20                  25                  30

Phe Asp Tyr Val Ala Asp Pro Val Gly Gly Leu Asn Pro Pro Phe Leu
            35                  40                  45

Gly Gly Ser Gly Pro Leu Val Asp Gln Gly Gly Gln Leu Thr Leu Asn
    50                  55                  60

Val Thr Asp Pro Ile Ile Ile Lys Asn Arg Ser Val Asp Leu Ala His
65                  70                  75                  80

Asp Pro Ser Leu Asp Val Asn Ala Gln Gly Gln Leu Ala Val Ala Val
                85                  90                  95

Asp Pro Glu Gly Ala Leu Ala Ile Thr Pro Asp Gly Leu Asp Val Lys
            100                 105                 110

Val Asp Gly Val Thr Val Met Val Asn Asp Asp Trp Glu Leu Ala Val
        115                 120                 125

Lys Val Asp Pro Ala Gly Gly Leu Asp Ser Thr Ala Gly Gly Leu Gly
130                 135                 140

Val Ser Val Asp Asp Thr Leu Leu Val Asp Gln Gly Glu Leu Gly Val
145                 150                 155                 160

His Leu Asn Gln Gln Gly Pro Ile Thr Ala Asp Ser Ser Gly Ile Asp
                165                 170                 175

Leu Glu Ile Asn Pro Asn Met Phe Thr Val Asn Thr Ser Thr Gly Ser
            180                 185                 190

Gly Val Leu Glu Leu Asn Leu Lys Ala Gln Gly Gly Ile Gln Ala Arg
        195                 200                 205

Ser Ser Gly Val Gly Val Ser Val Asp Glu Ser Leu Gln Ile Val Asp
210                 215                 220

Asn Thr Leu Glu Val Lys Pro Asp Pro Ser Gly Pro Leu Thr Val Ser
225                 230                 235                 240

Ala Asn Gly Leu Gly Leu Lys Tyr Asp Asn Asn Thr Leu Ala Val Thr
                245                 250                 255

Ala Gly Ala Leu Thr Val Val Gly Gly Ser Val Ser Thr Pro Ile
            260                 265                 270

Ala Thr Phe Val Ser Gly Ser Pro Ser Leu Asn Thr Tyr Asn Ala Thr
        275                 280                 285

Thr Val Asn Ser Ser Ala His Ala Phe Ser Cys Ala Tyr Tyr Leu Gln
290                 295                 300

Gln Trp Asn Ile Gln Gly Leu Leu Phe Thr Ser Leu Tyr Leu Lys Leu
305                 310                 315                 320

```
Asp Ser Thr Thr Met Gly Thr Arg Pro Gly Asp Asn Ser Ser Val Asn
                325                 330                 335

Ala Lys Trp Phe Thr Phe Trp Val Ser Ala Tyr Leu Gln Gln Cys Asn
            340                 345                 350

Pro Ser Gly Ile Gln Ala Gly Thr Val Ser Pro Ser Thr Ala Thr Leu
        355                 360                 365

Thr Asp Phe Glu Pro Met Ala Asn Arg Ser Val Ser Ser Ser Trp Thr
    370                 375                 380

Tyr Ser Ala Asn Ala Tyr Tyr Gln Pro Ser Gly Glu Phe Gln Val
385                 390                 395                 400

Phe Thr Pro Val Val Thr Gly Ala Trp Asn Pro Gly Asn Ile Gly Val
                405                 410                 415

Arg Val Leu Pro Val Pro Val Ser Ala Ser Gly Asp Arg Tyr Thr Leu
            420                 425                 430

Leu Cys Tyr Ser Leu Gln Cys Thr Asn Ala Ser Ile Phe Asn Pro Ala
        435                 440                 445

Asn Ser Gly Thr Met Ile Val Gly Pro Val Leu Tyr Ser Cys Pro Ala
    450                 455                 460

Ala Ser Val
465

<210> SEQ ID NO 35
<211> LENGTH: 474
<212> TYPE: PRT
<213> ORGANISM: fowl adenovirus

<400> SEQUENCE: 35

Met Leu Arg Ala Pro Lys Arg Arg His Ser Glu Thr Glu Ala Gly Pro
1               5                   10                  15

Tyr Pro Ala Pro Ile Lys Arg Pro Lys Arg Met Val Arg Ala Ser Gln
            20                  25                  30

Leu Asp Leu Val Tyr Pro Phe Asp Tyr Val Ala Asp Pro Val Gly Gly
        35                  40                  45

Leu Asn Pro Pro Phe Leu Gly Gly Ser Gly Pro Leu Val Asp Gln Gly
    50                  55                  60

Gly Gln Leu Thr Leu Asn Val Thr Asp Pro Ile Ile Ile Lys Asn Arg
65                  70                  75                  80

Ser Val Asp Leu Ala His Asp Pro Ser Leu Asp Val Asn Ala Gln Gly
                85                  90                  95

Gln Leu Ala Val Ala Val Asp Pro Glu Gly Ala Leu Ala Ile Thr Pro
            100                 105                 110

Asp Gly Leu Asp Val Lys Val Asp Gly Val Thr Val Met Val Asn Asp
        115                 120                 125

Asp Trp Glu Leu Ala Val Lys Val Asp Pro Ala Gly Gly Leu Asp Ser
    130                 135                 140

Thr Ala Gly Gly Leu Gly Val Ser Val Asp Asp Thr Leu Leu Val Asp
145                 150                 155                 160

Gln Gly Glu Leu Gly Val His Leu Asn Gln Gln Gly Pro Ile Thr Ala
                165                 170                 175

Asp Ser Ser Gly Ile Asp Leu Glu Ile Asn Pro Asn Met Phe Thr Val
            180                 185                 190

Asn Thr Ser Thr Gly Ser Gly Val Leu Glu Leu Asn Leu Lys Ala Gln
        195                 200                 205

Gly Gly Ile Gln Ala Asp Ser Ser Gly Val Gly Val Ser Val Asp Glu
    210                 215                 220
```

Ser Leu Gln Ile Val Asn Asn Thr Leu Glu Val Lys Pro Asp Pro Ser
225                 230                 235                 240

Gly Pro Leu Thr Val Ser Ala Asn Gly Leu Gly Leu Lys Tyr Asp Asn
                245                 250                 255

Asn Thr Leu Ala Val Thr Ala Gly Ala Leu Thr Val Val Gly Gly Gly
            260                 265                 270

Ser Val Ser Thr Pro Ile Ala Thr Phe Val Ser Gly Pro Ser Leu
        275                 280                 285

Asn Thr Tyr Asn Ala Thr Thr Val Asn Ser Ser Ala His Ala Phe Ser
    290                 295                 300

Cys Ala Tyr Tyr Leu Gln Gln Trp Asn Ile Gln Gly Leu Leu Phe Thr
305                 310                 315                 320

Ser Leu Tyr Leu Lys Leu Asp Ser Thr Thr Met Gly Thr Arg Pro Gly
                325                 330                 335

Asp Asn Ser Ser Val Asn Ala Lys Trp Phe Thr Phe Trp Val Ser Ala
            340                 345                 350

Tyr Leu Gln Gln Cys Asn Pro Ser Gly Ile Gln Ala Gly Thr Val Ser
        355                 360                 365

Pro Ser Thr Ala Thr Leu Thr Asp Phe Glu Pro Met Ala Asn Arg Ser
    370                 375                 380

Val Ser Ser Ser Trp Thr Tyr Ser Ala Asn Ala Tyr Tyr Gln Pro Ser
385                 390                 395                 400

Ser Gly Glu Phe Gln Val Phe Thr Pro Val Val Thr Gly Ala Trp Asn
                405                 410                 415

Pro Gly Asn Ile Gly Val Arg Val Leu Pro Val Pro Val Ser Ala Ser
            420                 425                 430

Gly Asp Arg Tyr Thr Leu Leu Cys Tyr Ser Leu Gln Cys Thr Asn Ala
        435                 440                 445

Ser Ile Phe Asn Pro Ala Asn Ser Gly Thr Met Ile Val Gly Pro Val
    450                 455                 460

Leu Tyr Ser Cys Pro Ala Ala Ser Val Pro
465                 470

<210> SEQ ID NO 36
<211> LENGTH: 464
<212> TYPE: PRT
<213> ORGANISM: fowl adenovirus

<400> SEQUENCE: 36

Glu Thr Glu Ala Gly Pro Tyr Pro Ala Pro Ile Lys Arg Pro Lys Arg
1               5                   10                  15

Met Val Arg Ala Ser Gln Leu Asp Leu Val Tyr Pro Phe Asp Tyr Val
            20                  25                  30

Ala Asp Pro Val Gly Gly Leu Asn Pro Phe Leu Gly Gly Ser Gly
        35                  40                  45

Pro Leu Val Asp Gln Gly Gly Gln Leu Thr Leu Asn Val Thr Asp Pro
    50                  55                  60

Ile Ile Ile Lys Asn Arg Ser Val Asp Leu Ala His Asp Pro Ser Leu
65                  70                  75                  80

Asp Val Asn Ala Gln Gly Gln Leu Ala Val Ala Val Asp Pro Glu Gly
                85                  90                  95

Ala Leu Ala Ile Thr Pro Asp Gly Leu Asp Val Lys Val Asp Gly Val
            100                 105                 110

Thr Val Met Val Asn Asp Asp Trp Glu Leu Ala Val Lys Val Asp Pro

```
                   115                 120                 125
Ala Gly Gly Leu Asp Ser Thr Ala Gly Gly Leu Gly Val Ser Val Asp
            130                 135                 140

Asp Thr Leu Leu Val Asp Gln Gly Glu Leu Gly Val His Leu Asn Gln
145                 150                 155                 160

Gln Gly Pro Ile Thr Ala Asp Ser Ser Gly Ile Asp Leu Glu Ile Asn
                165                 170                 175

Pro Asn Met Phe Thr Val Asn Thr Ser Thr Gly Ser Gly Val Leu Glu
            180                 185                 190

Leu Asn Leu Lys Ala Gln Gly Gly Ile Gln Ala Asp Ser Ser Gly Val
                195                 200                 205

Gly Val Ser Val Asp Glu Ser Leu Gln Ile Val Asn Asn Thr Leu Glu
            210                 215                 220

Val Lys Pro Asp Pro Ser Gly Pro Leu Thr Val Ser Ala Asn Gly Leu
225                 230                 235                 240

Gly Leu Lys Tyr Asp Asn Asn Thr Leu Ala Val Thr Ala Gly Ala Leu
                245                 250                 255

Thr Val Val Gly Gly Gly Ser Val Ser Thr Pro Ile Ala Thr Phe Val
            260                 265                 270

Ser Gly Ser Pro Ser Leu Asn Thr Tyr Asn Ala Thr Val Asn Ser
                275                 280                 285

Ser Ala His Ala Phe Ser Cys Ala Tyr Tyr Leu Gln Gln Trp Asn Ile
            290                 295                 300

Gln Gly Leu Leu Phe Thr Ser Leu Tyr Leu Lys Leu Asp Ser Thr Thr
305                 310                 315                 320

Met Gly Thr Arg Pro Gly Asp Asn Ser Ser Val Asn Ala Lys Trp Phe
                325                 330                 335

Thr Phe Trp Val Ser Ala Tyr Leu Gln Gln Cys Asn Pro Ser Gly Ile
            340                 345                 350

Gln Ala Gly Thr Val Ser Pro Ser Thr Ala Thr Leu Thr Asp Phe Glu
                355                 360                 365

Pro Met Ala Asn Arg Ser Val Ser Ser Ser Trp Thr Tyr Ser Ala Asn
370                 375                 380

Ala Tyr Tyr Gln Pro Ser Ser Gly Glu Phe Gln Val Phe Thr Pro Val
385                 390                 395                 400

Val Thr Gly Ala Trp Asn Pro Gly Asn Ile Gly Val Arg Val Leu Pro
                405                 410                 415

Val Pro Val Ser Ala Ser Gly Asp Arg Tyr Thr Leu Leu Cys Tyr Ser
            420                 425                 430

Leu Gln Cys Thr Asn Ala Ser Ile Phe Asn Pro Ala Asn Ser Gly Thr
                435                 440                 445

Met Ile Val Gly Pro Val Leu Tyr Ser Cys Pro Ala Ala Ser Val Pro
            450                 455                 460

<210> SEQ ID NO 37
<211> LENGTH: 410
<212> TYPE: PRT
<213> ORGANISM: fowl adenovirus

<400> SEQUENCE: 37

Met Ala Asp Gln Lys Arg Lys Leu Ala Asp Pro Asp Ala Glu Ala Pro
1               5                   10                  15

Thr Gly Lys Met Ala Arg Ala Gly Pro Gly Glu Leu Asp Leu Val Tyr
                20                  25                  30
```

Pro Phe Trp Tyr Gln Val Ala Ala Pro Thr Glu Ile Thr Pro Pro Phe
                35                  40                  45

Leu Asp Pro Asn Gly Pro Leu Tyr Ser Thr Asp Gly Leu Leu Asn Val
 50                  55                  60

Arg Leu Thr Ala Pro Leu Val Ile Ile Arg Gln Ser Asn Gly Asn Ala
 65                  70                  75                  80

Ile Gly Val Lys Thr Asp Gly Ser Ile Thr Val Asn Ala Asp Gly Ala
                 85                  90                  95

Leu Gln Ile Gly Ile Ser Thr Ala Gly Pro Leu Thr Thr Ala Asn
                100                 105                 110

Gly Ile Asp Leu Asn Ile Asp Pro Lys Thr Leu Val Val Asp Gly Ser
                115                 120                 125

Ser Gly Lys Asn Val Leu Gly Val Leu Leu Lys Gly Gln Gly Ala Leu
                130                 135                 140

Gln Ser Ser Ala Gln Gly Ile Gly Val Ala Val Asp Glu Ser Leu Gln
145                 150                 155                 160

Ile Val Asp Asn Thr Leu Glu Val Lys Val Asp Ala Ala Gly Pro Leu
                165                 170                 175

Ala Val Thr Ala Ala Gly Val Gly Leu Gln Tyr Asp Asn Thr Gln Phe
                180                 185                 190

Lys Val Thr Asn Gly Thr Leu Gln Leu Tyr Gln Ala Pro Thr Ser Ser
                195                 200                 205

Val Ala Ala Phe Thr Ser Gly Thr Ile Gly Leu Ser Ser Pro Thr Gly
                210                 215                 220

Asn Phe Val Ser Ser Asn Asn Pro Phe Asn Gly Ser Tyr Phe Leu
225                 230                 235                 240

Gln Gln Ile Asn Thr Met Gly Met Leu Thr Thr Ser Leu Tyr Val Lys
                245                 250                 255

Val Asp Thr Thr Thr Met Gly Thr Arg Pro Thr Gly Ala Val Asn Glu
                260                 265                 270

Asn Ala Arg Tyr Phe Thr Val Trp Val Ser Ser Phe Leu Thr Gln Cys
                275                 280                 285

Asn Pro Ser Asn Ile Gly Gln Gly Thr Leu Glu Pro Ser Asn Ile Ser
290                 295                 300

Met Thr Ser Phe Glu Pro Ala Arg Asn Pro Ile Ser Pro Val Phe
305                 310                 315                 320

Asn Met Asn Gln Asn Ile Pro Tyr Tyr Ala Ser Arg Phe Gly Val Leu
                325                 330                 335

Glu Ser Tyr Arg Pro Ile Phe Thr Gly Ser Leu Asn Thr Gly Ser Ile
                340                 345                 350

Asp Val Arg Met Gln Val Thr Pro Val Leu Ala Thr Asn Asn Thr Thr
                355                 360                 365

Tyr Asn Leu Ile Ala Phe Thr Phe Gln Cys Ala Ser Ala Gly Leu Phe
370                 375                 380

Asn Pro Thr Val Asn Gly Thr Val Ala Ile Gly Pro Val His Thr
385                 390                 395                 400

Cys Pro Ala Ala Arg Ala Pro Val Thr Val
                405                 410

<210> SEQ ID NO 38
<211> LENGTH: 445
<212> TYPE: PRT
<213> ORGANISM: fowl adenovirus

<400> SEQUENCE: 38

```
Met Glu Arg Lys Arg Thr Ser Ala Ser Gly Phe Gly Ala Ala Pro
1               5                   10                  15

Lys Arg Pro Arg Ala Thr Ser Ala Gln Val Asp Leu Ile Tyr Pro Phe
            20                  25                  30

Trp Tyr Gln Ala Asp Ala Pro Ser Val Asn Pro Pro Phe Leu Asp Pro
        35                  40                  45

Ser Gly Pro Leu Phe Asp Lys Asp Gly Lys Leu Ser Ile Arg Leu Gln
50                  55                  60

Ala Pro Val Ala Glu Val Asn Lys Ser Val Gly Leu Leu Tyr Asp Gly
65                  70                  75                  80

Thr Met Gly Val Asn Asn Ala Gly Gln Leu Gly Met Arg Ile Asn Thr
            85                  90                  95

Thr Glu Gly Leu Glu Ala Thr Gly Thr Gly Leu Ala Ile Lys Thr Asp
            100                 105                 110

Leu Glu Ser Ile Gly Phe Asp Pro Thr Gly Asn Leu Gln Val Thr Leu
            115                 120                 125

Asp Pro Glu Gly Pro Ile Val Ala Ser Ala Asp Gly Leu Gln Leu Gln
            130                 135                 140

Leu Asp Gly Ala Thr Leu Glu Val Ala Asp Trp Glu Leu Gly Val Lys
145                 150                 155                 160

Leu Asp Pro Asn Glu Pro Ile Asp Ala Gly Ser Ala Gly Leu Lys Leu
            165                 170                 175

Asn Ile Asp Glu Thr Leu Leu Val Asp Ala Thr Gly Ser Gln Arg Ser
            180                 185                 190

Pro Leu Pro Asn Pro Lys Arg Pro Arg Thr His Arg Asn Gly Thr His
            195                 200                 205

Ser Gly Arg Leu Gln Arg Arg Pro Val Glu Ile Arg His His Thr Leu
210                 215                 220

Tyr Arg His Arg Arg Ala Glu Ser Arg Arg Thr Pro Ala Asn Leu
225                 230                 235                 240

Gly Tyr Thr Ser Ile Ser Tyr Val Ser Gly Ser Thr Ser Leu Asn Ser
            245                 250                 255

Asn Thr Ala Glu Ile Val Asn Ser Ser Asn Ser Phe Lys Cys Ser
            260                 265                 270

Tyr Tyr Val Lys Gln Val Asn Cys Met Gly Met Leu Phe Thr Ser Leu
            275                 280                 285

Tyr Ile Lys Leu Asp Ser Ala Thr Met Gly Thr Arg Pro Thr Gly Asn
            290                 295                 300

Thr Asn Val Asn Ala Lys Trp Phe Asn Phe Ile Val Ser Ser Tyr Leu
305                 310                 315                 320

Thr Asp Phe Asn Pro Ser Gln Met Asp Thr Gly Thr Leu Asn Pro Ala
            325                 330                 335

Val Ser Asn Gly Met Thr Tyr Met Glu Pro Ala Pro Asn Arg Thr Leu
            340                 345                 350

Pro Ser Asn Trp Asp Ala Asp Thr Asn Thr Tyr Tyr Glu Pro Ser Ser
            355                 360                 365

Gly Val Ser Gln Ser Leu Thr Ala Val Leu Thr Gly Ser Trp Ala Pro
            370                 375                 380

Gly Asn Ile Thr Val Val Ala Met Pro Val Ile Ala Gln Lys Asn Gln
385                 390                 395                 400

Glu Arg Tyr Thr Val Leu Cys Phe Ser Phe Arg Cys Thr Asn Gly Gly
            405                 410                 415
```

```
Leu Phe Asn Pro Ser Val Gln Gly Thr Ala Thr Ile Gly Pro Val Asn
                420                 425                 430

Tyr Ile Cys Glu Ala Ser Gln Ser Pro Asn Val Val Pro
            435                 440                 445

<210> SEQ ID NO 39
<211> LENGTH: 571
<212> TYPE: PRT
<213> ORGANISM: fowl adenovirus

<400> SEQUENCE: 39

Met Ala Lys Ser Thr Pro Phe Ala Phe Ser Met Gly Gln His Ser Ser
1               5                   10                  15

Arg Lys Arg Pro Ala Asp Ser Glu Asn Thr Gln Asn Ala Ser Lys Val
                20                  25                  30

Ala Lys Thr Gln Thr Ser Ala Thr Arg Ala Gly Val Asp Gly Asn Asp
            35                  40                  45

Asp Leu Asn Leu Val Tyr Pro Phe Trp Leu Gln Asn Ser Thr Ser Gly
        50                  55                  60

Gly Gly Gly Gly Gly Ser Gly Gly Asn Pro Ser Leu Asn Pro Pro Phe
65                  70                  75                  80

Ile Asp Pro Asn Gly Pro Leu Tyr Val Gln Asn Ser Leu Leu Tyr Val
                85                  90                  95

Lys Thr Thr Ala Pro Ile Glu Val Glu Asn Lys Ser Leu Ala Leu Ala
                100                 105                 110

Tyr Asp Ser Ser Leu Ala Val Asp Ala Gln Asn Gln Leu Gln Val Lys
            115                 120                 125

Val Asp Thr Glu Gly Pro Ile Arg Ile Ser Pro Asp Gly Leu Asp Ile
        130                 135                 140

Ala Val Asp Pro Ser Thr Leu Glu Val Asp Asp Glu Trp Glu Leu Ala
145                 150                 155                 160

Val Lys Leu Asp Pro Asn Gly Pro Leu Thr Ala Ser Ser Ala Gly Ile
                165                 170                 175

Asn Ile Asn Val Asp Asp Thr Leu Leu Ile Glu Asp Asp Asp Ala Asn
                180                 185                 190

Gln Ala Lys Glu Leu Gly Val His Leu Asn Pro Asn Gly Pro Ile Thr
            195                 200                 205

Ala Asp Arg Asp Gly Leu Asp Leu Glu Ile Asp Ser Gln Thr Met Val
        210                 215                 220

Val Lys Asp Ser Gly Thr Ser Gly Val Leu Gly Val Leu Leu Lys
225                 230                 235                 240

Pro Ser Gly Gly Leu Gln Ser Ser Ile Gln Gly Ile Gly Val Ala Val
                245                 250                 255

Ala Asp Thr Leu Thr Ile Thr Ser Asn Thr Val Glu Val Lys Thr Asp
                260                 265                 270

Pro Asn Gly Ser Ile Ser Tyr Ser Ala Asn Gly Ile Ala Val Lys Pro
            275                 280                 285

Asp Pro Ser Gly Pro Leu Thr Ser Ser Gly Thr Gly Leu Ser Val Val
        290                 295                 300

Thr Ala Ala Glu Gly Ser Ile Gln Ser Ser Asn Ala Gly Leu Ala Val
305                 310                 315                 320

Lys Thr Asp Pro Ser Gly Pro Ile Thr Ser Gly Ser Asn Gly Leu Asn
                325                 330                 335

Leu Ser Tyr Asn Ala Ser Asp Phe Thr Val Ser Gln Gly Val Leu Asn
                340                 345                 350
```

Ile Ile Arg Asn Pro Ser Thr Leu Pro Asp Ala Tyr Leu Glu Ser Gly
            355                 360                 365

Thr Asn Tyr Leu Asn Asn Phe Thr Ala Gln Ala Glu Asn Ser Ser Val
    370                 375                 380

Phe Lys Phe Asn Cys Ala Tyr Phe Leu Gln Ser Trp Tyr Ser Asn Gly
385                 390                 395                 400

Leu Val Thr Ser Ser Leu Tyr Leu Lys Ile Asp Arg Ala Gln Phe Ser
                405                 410                 415

Asn Met Pro Thr Gly Gln Ser Ala Glu Asn Ala Arg Tyr Phe Thr Phe
            420                 425                 430

Trp Val Pro Thr Tyr Glu Ser Leu Asn Leu Ser Arg Val Ser Thr Pro
            435                 440                 445

Thr Ile Thr Pro Asn Thr Val Gln Trp Gly Ala Phe Ser Pro Ala Gln
            450                 455                 460

Asn Cys Ser Gly Asn Pro Ala Phe Gln Tyr Asn Leu Thr Gln Pro Pro
465                 470                 475                 480

Ser Ile Tyr Phe Glu Pro Lys Ser Gly Ser Val Gln Thr Phe Gln Pro
                485                 490                 495

Val Leu Thr Gly Ala Trp Asn Thr Asp Thr Tyr Asn Pro Gly Thr Val
            500                 505                 510

Gln Val Cys Ile Leu Pro Gln Thr Val Val Gly Gly Gln Ser Thr Phe
            515                 520                 525

Val Asn Met Thr Cys Tyr Asn Phe Arg Cys Gln Asn Pro Gly Ile Phe
            530                 535                 540

Lys Val Ala Ala Ser Asn Gly Thr Phe Thr Ile Gly Pro Ile Phe Tyr
545                 550                 555                 560

Ser Cys Pro Thr Asn Glu Leu Thr Arg Pro Thr
            565                 570

<210> SEQ ID NO 40
<211> LENGTH: 523
<212> TYPE: PRT
<213> ORGANISM: fowl adenovirus

<400> SEQUENCE: 40

Met Ala Thr Ser Thr Pro His Ala Phe Ser Phe Gly Gln Ile Gly Ser
1               5                   10                  15

Arg Lys Arg Pro Ala Gly Gly Asp Gly Glu Arg Asp Ala Ser Lys Val
                20                  25                  30

Pro Lys Met Gln Thr Pro Ala Pro Ser Ala Thr Ala Asn Gly Asn Asp
            35                  40                  45

Glu Leu Asp Leu Val Tyr Pro Phe Trp Leu Gln Asn Gly Ser Thr Gly
    50                  55                  60

Gly Gly Gly Gly Gly Gly Ser Gly Gly Asn Pro Ser Leu Asn Pro
65                  70                  75                  80

Pro Phe Leu Asp Pro Asn Gly Pro Leu Ala Val Gln Asn Asn Leu Leu
                85                  90                  95

Lys Val Asn Thr Ala Ala Pro Ile Thr Val Ala Asn Lys Ala Leu Thr
            100                 105                 110

Leu Ala Tyr Glu Pro Asp Ser Leu Glu Leu Thr Asn Gln Gln Gln Leu
            115                 120                 125

Ala Val Lys Ile Asp Pro Glu Gly Pro Leu Lys Ala Thr Thr Glu Gly
        130                 135                 140

Ile Gln Leu Ser Val Asp Pro Thr Thr Leu Glu Val Asp Asp Val Asp

```
            145                 150                 155                 160
Trp Glu Leu Thr Val Lys Leu Asp Pro Asp Gly Pro Leu Asp Ser Ser
                165                 170                 175

Ala Thr Gly Ile Thr Val Arg Val Asp Glu Thr Leu Leu Ile Glu Asp
                180                 185                 190

Val Gly Ser Gly Gln Gly Lys Glu Leu Gly Val Asn Leu Asn Pro Thr
                195                 200                 205

Gly Pro Ile Thr Ala Asp Asp Gln Gly Leu Asp Leu Glu Ile Asp Asn
210                 215                 220

Gln Thr Leu Lys Val Asn Ser Val Thr Gly Gly Val Leu Ala Val
225                 230                 235                 240

Gln Leu Lys Ser Gln Gly Leu Thr Ala Gln Thr Asp Gly Ile Gln
                245                 250                 255

Val Asn Thr Gln Asn Ser Ile Thr Val Thr Asn Gly Ala Leu Asp Val
                260                 265                 270

Lys Val Ala Ala Asn Gly Pro Leu Glu Ser Thr Asp Thr Gly Leu Thr
                275                 280                 285

Leu Asn Tyr Asp Pro Gly Asp Phe Thr Val Asn Ala Gly Thr Leu Ser
                290                 295                 300

Ile Ile Arg Asp Pro Ala Leu Val Ala Asn Ala Tyr Leu Thr Ser Gly
305                 310                 315                 320

Ala Ser Thr Leu Gln Gln Phe Thr Ala Lys Ser Glu Asn Ser Ser Gln
                325                 330                 335

Phe Ser Phe Pro Cys Ala Tyr Tyr Leu Gln Gln Trp Leu Ser Asp Gly
                340                 345                 350

Leu Val Leu Ser Ser Leu Tyr Leu Lys Leu Asp Arg Ala Gln Phe Thr
                355                 360                 365

Asn Met Pro Thr Gly Ala Asn Tyr Gln Asn Ala Arg Tyr Phe Thr Phe
                370                 375                 380

Trp Val Gly Ala Gly Thr Ser Phe Asn Leu Ser Thr Leu Thr Glu Pro
385                 390                 395                 400

Thr Ile Thr Pro Asn Thr Thr Gln Trp Asn Ala Phe Ala Pro Ala Leu
                405                 410                 415

Asp Tyr Ser Gly Ala Pro Pro Phe Ile Tyr Asp Ala Ser Ser Val Val
                420                 425                 430

Thr Ile Tyr Phe Glu Pro Thr Ser Gly Arg Leu Glu Ser Tyr Leu Pro
                435                 440                 445

Val Leu Thr Asp Asn Trp Ser Gln Thr Tyr Asn Pro Gly Thr Val Thr
                450                 455                 460

Leu Cys Val Lys Thr Val Arg Val Gln Leu Arg Ser Gln Gly Thr Phe
465                 470                 475                 480

Ser Thr Leu Val Cys Tyr Asn Phe Arg Cys Gln Asn Thr Gly Ile Phe
                485                 490                 495

Asn Ser Asn Ala Thr Ala Gly Thr Met Thr Leu Gly Pro Ile Phe Phe
                500                 505                 510

Ser Cys Pro Ala Leu Ser Thr Ala Asn Ala Pro
                515                 520

<210> SEQ ID NO 41
<211> LENGTH: 554
<212> TYPE: PRT
<213> ORGANISM: fowl adenovirus

<400> SEQUENCE: 41
```

```
Met Ala Gln Pro Ser Gly Leu Leu Leu Gly Lys Arg Lys Arg Pro Glu
1               5                   10                  15

Ala Pro Leu Asp Asp Ser Ala Gly Val Ser Glu Gln Pro Leu Thr Ala
            20                  25                  30

Ser Lys Met Pro Lys Thr His Thr Tyr Ser Ser Pro Ile Gly Phe Tyr
            35                  40                  45

Gly Pro Thr Thr Gly Gln Leu Asp Leu Val Tyr Pro Phe Trp Phe Gln
50                  55                  60

Asn Ser Ser Gly Gly Gly Gly Thr Val Ile Pro Pro Val Asn Pro
65                  70                  75                  80

Pro Leu Leu Asp Pro Ala Gly Pro Leu Tyr Val Gln Asn Asn Met Leu
                85                  90                  95

Arg Met Arg Thr Gly Ala Pro Ile Val Val Ser Asn Gly Ala Leu Gly
                100                 105                 110

Leu Ser Tyr Asp Thr Ser Leu Gly Leu Ser Asp Gln Asn Gln Leu Gln
            115                 120                 125

Val Asn Leu Glu Pro Asn Gly Pro Leu Lys Ala Thr Asp Asp Gly Ile
    130                 135                 140

Glu Leu Thr Val Asp Pro Leu Thr Leu Glu Val Thr Asp Trp Glu Leu
145                 150                 155                 160

Gly Val Lys Ile Asp Pro Ala Gly Pro Leu Asp Ala Ser Thr Asp Gly
                165                 170                 175

Leu Thr Leu Arg Thr Asp Asp Thr Leu Ser Leu Gly Gln Asp Pro Thr
                180                 185                 190

Thr His Glu Tyr Glu Leu Gly Leu Lys Leu Asp Pro Ser Gly Pro Leu
        195                 200                 205

Glu Ala Ser Ala Asp Gly Leu Asn Leu Arg Leu Asp Asp Thr Leu Leu
        210                 215                 220

Val Glu Gln Asp Thr Thr Thr Gln Glu Tyr Glu Leu Gly Val His Leu
225                 230                 235                 240

Asn Pro Asn Gly Pro Val Thr Ala Asp Glu Asn Gly Ile Asp Leu Glu
                245                 250                 255

Ile Asn Thr Asp Thr Leu Thr Val Thr Ala Gly Ala Ala Gly Gly Gly
                260                 265                 270

Glu Leu Ser Val Leu Leu Asn Pro Gln Gly Ala Ile His Ala Thr Ala
            275                 280                 285

Ser Thr Gly Ile Gly Val Ala Val Gly Pro Gly Leu Gln Ile Thr Ser
            290                 295                 300

Asn Thr Val Ser Val Lys Pro Asp Pro Ala Gly Pro Leu Thr Ala Ser
305                 310                 315                 320

Pro Thr Gly Val Thr Leu Asn Tyr Asp Asn Ser Asp Phe Thr Ile Thr
                325                 330                 335

Asp Gly Lys Leu Thr Leu Tyr Lys Thr Pro Ala Val Thr Ser Asp Ala
            340                 345                 350

Tyr Leu Thr Ser Gly Asn Ser Ala Met Thr Thr Tyr Thr Ala Phe Phe
            355                 360                 365

Gly Asn Ser Ser Asn Tyr Arg Phe Lys Cys Ser Tyr Phe Leu Gln Gln
        370                 375                 380

Trp Leu Arg Asp Arg Leu Val Ile Thr Ser Leu Tyr Ile Lys Leu Asp
385                 390                 395                 400

Arg Ser Gln Leu Glu Asn Leu Ser Ser Asp Ala Ser Ala Gln Asn Ala
                405                 410                 415

Arg Tyr Phe Thr Phe Trp Val Ser Ser Asn Ala Leu Met Asn Leu Ser
```

```
                    420                 425                 430
Gly Ile Asp Glu Pro Val Val Thr Pro Ser Thr Val Thr Trp Ser Lys
                435                 440                 445

Phe Leu Pro Asp Val Asn Tyr Thr Asn Pro Thr Phe Asn Phe Asn
    450                 455                 460

Thr Ser Leu Tyr Phe Glu Pro Pro Ser Gly Glu Ile Leu Thr Phe Asn
465                 470                 475                 480

Pro Val Thr Thr Gly Asp Trp Ser Thr Thr Tyr Ser Pro Gly Thr Val
                485                 490                 495

Ser Val Cys Val Leu Pro Val Asn Val Arg Ala Ser Ser Gly Thr Gly
                500                 505                 510

Thr Leu Gln Thr Leu Leu Cys Phe Asn Phe Arg Cys Ala Asn Thr Gly
                515                 520                 525

Leu Phe Lys Thr Ala Ala Thr Thr Gly Thr Phe Tyr Val Gly Pro Ile
                530                 535                 540

Val Tyr Ser Cys Pro Gly Asn Pro Leu Ile
545                 550

<210> SEQ ID NO 42
<211> LENGTH: 434
<212> TYPE: PRT
<213> ORGANISM: fowl adenovirus

<400> SEQUENCE: 42

Met Ser Ala Leu Ile Ala Ser Ala Ala Asp Thr Val Ser Val Ser Gly
1               5                   10                  15

Lys Lys Arg Pro Arg Arg Ala Leu Ser Glu Pro Ile Arg Tyr Leu Ser
                20                  25                  30

Glu Gly Asp Glu Arg Arg Lys Pro Lys Arg Ala Pro Pro Ala Thr Arg
            35                  40                  45

Ala Asn Gly Pro Leu Leu Asp Leu Val Tyr Pro Phe Asp Phe Asn Ala
        50                  55                  60

Gly Gly Gly Gly Gly Ser Gly Gly Gly Gly Gly Gly Gly Gly Gly Gly
65                  70                  75                  80

Gly Gln Gln Ile Ala Val Asp Pro Asp Gly Pro Leu Glu Leu Thr Gly
                85                  90                  95

Asp Leu Leu Thr Leu Asn Thr Lys Thr Pro Ile Tyr Val Ser Asp Arg
            100                 105                 110

Ala Val Ser Leu Leu Ile Asp Asp Thr Leu Ala Thr Lys Gln Val
        115                 120                 125

Asn Gly Ala Leu Met Val Lys Thr Ala Ala Pro Leu Asn Ser Gly Thr
    130                 135                 140

Gly Gly Gly Val Thr Leu Gly Phe Asp Pro Arg Thr Met Ala Leu Asp
145                 150                 155                 160

Ser Val Thr Gly Val Leu Lys Val Leu Val Asp Ser Gln Gly Pro Leu
                165                 170                 175

Gln Ala Asp Thr Gly Gly Ile Thr Leu Gln Phe Asp Thr Gln Asp Phe
            180                 185                 190

Val Val Asn Asn Gly Thr Leu Ala Leu Ala Ser Ser Val Gly Pro Thr
        195                 200                 205

Tyr Leu Ser Pro Phe Ala Thr Tyr Glu Val Thr Pro Val Leu Gly Ile
    210                 215                 220

Ser Gln Arg Asn Gly Asn Val Lys Ser Lys Gly Leu Gln Asn Trp Ser
225                 230                 235                 240
```

-continued

```
Ile Gly Tyr Tyr Ile Tyr Met Val Ser Ser Ala Gly Ile Val Asn Gly
            245                 250                 255

Leu Ile Thr Leu Glu Leu Ala Gln Glu Leu Thr Gly Ala Ser Gly Glu
        260                 265                 270

Asn Ser Leu Thr Ser Gly Leu Asn Phe Thr Phe Val Leu Ser Pro Met
        275                 280                 285

Tyr Pro Ile Glu Thr Glu Val Asn Leu Ser Leu Ile Val Pro Pro Thr
        290                 295                 300

Val Ser Pro Thr Asn Gln Asn Arg Val Phe Val Pro Asn Ser Asn Gln
305                 310                 315                 320

Ser Asp Val Gly Tyr Leu Gly Leu Pro Ala Gln Thr Lys Asp Asp Trp
                325                 330                 335

Tyr Val Pro Ile Asn Ser Pro Gly Leu Arg Leu Val Ser Phe Met Pro
                340                 345                 350

Thr Ala Thr Gly Asn Glu Lys Phe Gly Gln Gly Thr Leu Gly Tyr Cys
                355                 360                 365

Ala Ala Thr Ile Gln Asn Thr Pro Ser Gly Thr Thr Pro Ser Asp Ala
            370                 375                 380

Ile Ala Phe Thr Val Ser Leu Pro Gln Thr Ser Gly Ser Asn Trp Phe
385                 390                 395                 400

Asp Gln Tyr Ala Pro Asp Thr Val Val Thr Gly Pro Ile Pro Phe
                405                 410                 415

Ser Tyr Gln Gly Tyr Val Tyr Ser Pro Asn Gly Asn His Ala Pro
                420                 425                 430

Ser Pro
```

<210> SEQ ID NO 43
<211> LENGTH: 432
<212> TYPE: PRT
<213> ORGANISM: fowl adenovirus

<400> SEQUENCE: 43

```
Met Ser Ala Leu Ile Ala Ser Ala Ala Asp Thr Val Ser Val Ser Gly
1               5                   10                  15

Lys Lys Arg Pro Arg Arg Ala Leu Ser Glu Pro Ile Arg Tyr Leu Ser
            20                  25                  30

Glu Gly Asp Glu Arg Arg Lys Pro Lys Arg Ala Pro Pro Ala Thr Arg
        35                  40                  45

Ala Asn Gly Pro Leu Leu Asp Leu Val Tyr Pro Phe Asp Phe Asn Ala
    50                  55                  60

Gly Gly Gly Gly Ser Gly Gly Gly Gly Gly Gly Gly Gly Gly Gly Gln
65                  70                  75                  80

Gln Ile Ala Val Asp Pro Asp Gly Pro Leu Glu Leu Thr Gly Asp Leu
                85                  90                  95

Leu Thr Leu Asn Thr Lys Thr Pro Ile Tyr Val Ser Asp Arg Ala Val
            100                 105                 110

Ser Leu Leu Ile Asp Asp Asp Thr Leu Ala Thr Lys Gln Val Asn Gly
        115                 120                 125

Ala Leu Met Val Lys Thr Ala Ala Pro Leu Asn Ser Gly Thr Gly Gly
    130                 135                 140

Gly Val Thr Leu Gly Phe Asp Pro His Thr Met Ala Leu Asp Ser Val
145                 150                 155                 160

Thr Gly Val Leu Lys Val Leu Val Asp Ser Gln Gly Pro Leu Gln Ala
                165                 170                 175
```

Asp Thr Gly Gly Ile Thr Leu Gln Phe Asn Thr Gln Asp Phe Val Val
                180                 185                 190

Asn Asn Gly Thr Leu Ala Leu Ala Ser Ser Val Gly Pro Thr Tyr Leu
            195                 200                 205

Ser Pro Phe Ala Thr Tyr Glu Val Thr Pro Val Leu Gly Ile Ser Gln
210                 215                 220

Arg Asn Gly Asn Val Lys Ser Lys Gly Leu Gln Asn Trp Ser Ile Gly
225                 230                 235                 240

Tyr Tyr Ile Tyr Met Val Ser Ser Ala Gly Ile Val Asn Gly Leu Ile
                245                 250                 255

Thr Leu Glu Leu Ala Gln Glu Leu Thr Gly Ala Ser Gly Glu Asn Ser
            260                 265                 270

Leu Thr Ser Gly Leu Asn Phe Thr Phe Val Leu Ser Pro Met Tyr Pro
        275                 280                 285

Ile Glu Thr Glu Val Asn Leu Ser Leu Ile Val Pro Pro Thr Val Ser
    290                 295                 300

Pro Thr Asn Gln Asn Arg Val Phe Val Pro Asn Ser Asn Gln Ser Asp
305                 310                 315                 320

Val Gly Tyr Leu Gly Leu Pro Pro Gln Thr Lys Asp Asn Trp Tyr Val
                325                 330                 335

Pro Ile Asp Ser Pro Gly Leu Arg Leu Val Ser Phe Met Pro Thr Ala
            340                 345                 350

Thr Gly Asn Glu Lys Phe Gly Gln Gly Thr Leu Gly Tyr Cys Ala Ala
        355                 360                 365

Thr Ile Gln Asn Thr Pro Ser Gly Thr Thr Pro Ser Asp Ala Leu Ala
    370                 375                 380

Phe Thr Val Ser Leu Pro Gln Thr Ser Gly Ser Asn Trp Phe Asp Gln
385                 390                 395                 400

Tyr Ala Pro Asp Thr Val Val Thr Thr Gly Pro Ile Pro Phe Ser Tyr
                405                 410                 415

Gln Gly Tyr Val Tyr Ser Pro Asn Gly Asn Asn His Ala Pro Ser Pro
            420                 425                 430

<210> SEQ ID NO 44
<211> LENGTH: 432
<212> TYPE: PRT
<213> ORGANISM: fowl adenovirus

<400> SEQUENCE: 44

Met Ser Ala Leu Ile Ala Ser Ala Ala Asp Thr Val Ser Val Ser Gly
1               5                   10                  15

Lys Lys Arg Pro Arg Arg Ala Leu Ser Glu Pro Ile Arg Tyr Leu Ser
            20                  25                  30

Glu Gly Asp Glu Arg Arg Lys Pro Lys Arg Ala Pro Pro Ala Thr Arg
        35                  40                  45

Ala Asn Gly Pro Leu Leu Asp Leu Val Tyr Pro Phe Asp Phe Asn Ala
    50                  55                  60

Gly Gly Gly Gly Ser Gly Gly Gly Gly Gly Gly Gly Gly Gly Gly Gln
65                  70                  75                  80

Gln Ile Ala Val Asp Pro Asp Gly Pro Leu Glu Leu Thr Gly Asp Leu
                85                  90                  95

Leu Thr Leu Asn Thr Lys Thr Pro Ile Tyr Val Ser Asp Arg Ala Val
            100                 105                 110

Ser Leu Leu Ile Asp Asp Asn Thr Leu Ala Thr Lys Gln Val Asn Gly
        115                 120                 125

```
Ala Leu Met Val Lys Thr Ser Ala Pro Leu Asn Ser Gly Thr Gly Gly
        130                 135                 140

Gly Val Thr Leu Gly Phe Asp Pro Arg Thr Met Ala Leu Asp Ser Val
145                 150                 155                 160

Thr Gly Val Leu Lys Val Leu Val Asp Ser Gln Gly Pro Leu Gln Ala
                165                 170                 175

Asp Thr Gly Gly Ile Thr Leu Gln Phe Asp Thr Gln Asp Phe Val Val
            180                 185                 190

Asn Asn Gly Thr Leu Ala Leu Ala Ser Ser Val Gly Pro Thr Tyr Leu
        195                 200                 205

Ser Pro Phe Ala Thr Tyr Glu Val Thr Pro Val Leu Gly Ile Ser Gln
    210                 215                 220

Arg Asn Gly Asn Val Lys Ser Lys Gly Leu Gln Asn Trp Ser Ile Gly
225                 230                 235                 240

Tyr Tyr Ile Tyr Met Val Ser Ser Ala Gly Leu Val Asn Gly Leu Ile
                245                 250                 255

Thr Leu Glu Leu Ala His Asp Leu Thr Gly Ala Ser Gly Glu Asn Ser
            260                 265                 270

Leu Thr Ser Gly Leu Asn Phe Thr Phe Val Leu Ser Pro Met Tyr Pro
        275                 280                 285

Ile Glu Thr Glu Val Asn Leu Ser Leu Ile Val Pro Pro Thr Val Ser
    290                 295                 300

Pro Thr Asn Gln Asn His Val Phe Val Pro Asn Ser Asn Gln Ser Asp
305                 310                 315                 320

Val Gly Tyr Leu Gly Leu Pro Ala Gln Thr Arg Asp Asn Trp Tyr Val
                325                 330                 335

Pro Ile Asn Ser Pro Gly Leu Arg Leu Val Ser Phe Met Pro Thr Ala
            340                 345                 350

Thr Gly Asn Glu Lys Phe Gly Gln Gly Thr Leu Gly Tyr Cys Ala Ala
        355                 360                 365

Thr Ile Gln Asn Thr Pro Ser Gly Thr Thr Pro Ser Asp Ala Leu Ala
    370                 375                 380

Phe Thr Val Ser Leu Pro Gln Thr Ser Gly Ser Asn Trp Phe Asp Gln
385                 390                 395                 400

Tyr Ala Pro Asp Thr Val Val Thr Thr Gly Pro Ile Pro Phe Ser Tyr
                405                 410                 415

Gln Gly Tyr Val Tyr Ser Pro Asn Gly Asn Asn Asn Ala Pro Ser Pro
            420                 425                 430

<210> SEQ ID NO 45
<211> LENGTH: 433
<212> TYPE: PRT
<213> ORGANISM: fowl adenovirus

<400> SEQUENCE: 45

Met Ser Ala Leu Ile Ala Ser Ala Asp Thr Val Ser Ala Ser Gly
1               5                   10                  15

Lys Lys Arg Pro Arg Arg Ala Leu Ser Glu Pro Ile Arg Tyr Leu Ser
                20                  25                  30

Glu Gly Asp Glu Arg Arg Lys Pro Lys Arg Ala Pro Pro Ala Thr Arg
            35                  40                  45

Ala Asn Gly Pro Leu Leu Asp Leu Val Tyr Pro Phe Asp Phe Asn Ala
        50                  55                  60

Gly Gly Gly Gly Ser Gly Gly Gly Gly Gly Gly Gly Gly Gly Gly
```

Gln Gln Ile Ala Val Asp Pro Asp Gly Pro Leu Glu Leu Thr Gly Asn
 65                  70                  75                  80

Leu Leu Thr Leu Asn Thr Lys Thr Pro Ile Tyr Val Ser Asp Arg Ala
                 85                  90                  95

Val Ser Leu Leu Ile Asp Asp Asn Thr Leu Ala Thr Lys Gln Ala Asn
            100                 105                 110

Gly Ala Leu Met Val Lys Thr Ser Ala Pro Leu Asn Ser Gly Thr Gly
        115                 120                 125

Gly Gly Val Thr Leu Gly Phe Asp Pro His Thr Met Ala Leu Asp Ser
    130                 135                 140

Val Thr Gly Val Leu Lys Val Leu Val Asp Ser Gln Gly Pro Leu Gln
145                 150                 155                 160

Ala Asp Thr Gly Gly Ile Thr Leu Gln Phe Asp Thr Gln Asp Phe Val
                165                 170                 175

Val Asn Asn Gly Val Leu Ala Leu Ala Ser Ser Val Gly Pro Thr Tyr
            180                 185                 190

Leu Ser Pro Phe Ala Thr Tyr Glu Val Thr Pro Val Leu Gly Ile Ser
        195                 200                 205

Gln Arg Asn Gly Asn Val Lys Ser Lys Gly Leu Gln Asn Trp Ser Ile
    210                 215                 220

Gly Tyr Tyr Ile Tyr Met Val Ser Ser Ala Gly Ile Val Asn Gly Leu
225                 230                 235                 240

Ile Thr Leu Glu Leu Ala Gln Glu Leu Thr Gly Ala Ser Gly Glu Asn
                245                 250                 255

Ser Leu Thr Ser Gly Leu Asn Phe Thr Phe Val Leu Ser Pro Met Tyr
            260                 265                 270

Pro Ile Glu Thr Glu Val Asn Leu Ser Leu Ile Val Pro Pro Thr Val
        275                 280                 285

Ser Pro Thr Asn Gln Asn Arg Val Phe Val Pro Asn Ser Asn Gln Ser
    290                 295                 300

Asp Val Gly Tyr Leu Gly Leu Pro Pro Gln Thr Lys Asp Asn Trp Tyr
305                 310                 315                 320

Val Pro Ile Asp Ser Pro Gly Leu Arg Leu Val Ser Phe Met Pro Thr
                325                 330                 335

Ala Thr Gly Asn Glu Lys Phe Gly Gln Gly Thr Leu Gly Tyr Cys Ala
            340                 345                 350

Ala Thr Ile Gln Asn Thr Pro Ser Gly Thr Thr Pro Ser Asp Ala Leu
        355                 360                 365

Ala Phe Thr Val Ser Leu Pro Gln Thr Ser Gly Ser Asn Trp Phe Asp
    370                 375                 380

Gln Tyr Ala Pro Asp Thr Val Val Thr Thr Gly Pro Ile Pro Phe Ser
385                 390                 395                 400

Tyr Gln Gly Tyr Val Tyr Ser Pro Asn Gly Asn Asn His Ala Pro Ser
                405                 410                 415

Pro

<210> SEQ ID NO 46
<211> LENGTH: 433
<212> TYPE: PRT
<213> ORGANISM: fowl adenovirus

<400> SEQUENCE: 46

Met Ser Ala Leu Ile Ala Ser Ala Ala Asp Thr Val Ser Ala Ser Gly

```
  1               5                    10                   15
Lys Lys Arg Pro Arg Ala Leu Ser Glu Pro Ile Arg Tyr Leu Ser
               20                   25                   30
Glu Gly Asp Glu Arg Arg Lys Pro Lys Arg Ala Pro Pro Ala Thr Arg
               35                   40                   45
Ala Asn Gly Pro Leu Leu Asp Leu Val Tyr Pro Phe Asp Phe Asn Ala
               50                   55                   60
Gly Gly Gly Gly Ser Gly Gly Gly Gly Gly Gly Gly Gly
 65                  70                   75                   80
Gln Gln Ile Ala Val Asp Pro Asp Gly Pro Leu Glu Leu Thr Gly Asn
                    85                   90                   95
Leu Leu Thr Leu Asn Thr Lys Thr Pro Ile Tyr Val Ser Asp Arg Ala
                   100                  105                  110
Val Ser Leu Leu Ile Asp Asp Asn Thr Leu Ala Thr Lys Gln Ala Asn
                   115                  120                  125
Gly Ala Leu Met Val Lys Thr Ser Ala Pro Leu Asn Ser Gly Thr Gly
                   130                  135                  140
Gly Gly Val Thr Leu Gly Phe Asp Pro His Thr Met Ala Leu Asp Ser
145                  150                  155                  160
Val Thr Gly Val Leu Lys Val Leu Val Asp Ser Gln Gly Pro Leu Gln
                   165                  170                  175
Ala Asp Thr Gly Gly Ile Thr Leu Gln Phe Asp Thr Gln Asp Phe Val
                   180                  185                  190
Val Asn Asn Gly Val Leu Ala Leu Ala Ser Ser Val Gly Pro Thr Tyr
                   195                  200                  205
Leu Ser Pro Phe Ala Thr Tyr Glu Val Thr Pro Val Leu Gly Ile Ser
                   210                  215                  220
Gln Arg Asn Gly Asn Val Lys Ser Lys Gly Leu Gln Asn Trp Ser Ile
225                  230                  235                  240
Gly Tyr Tyr Ile Tyr Met Val Ser Ser Ala Gly Ile Val Asn Gly Leu
                   245                  250                  255
Ile Thr Leu Glu Leu Ala Gln Glu Leu Thr Gly Ala Ser Gly Glu Asn
                   260                  265                  270
Ser Leu Thr Ser Gly Leu Asn Phe Thr Phe Val Leu Ser Pro Met Tyr
                   275                  280                  285
Pro Ile Glu Thr Glu Val Asn Leu Ser Leu Ile Val Pro Pro Thr Val
                   290                  295                  300
Ser Pro Thr Asn Gln Asn Arg Val Phe Val Pro Asn Ser Asn Gln Ser
305                  310                  315                  320
Asp Val Gly Tyr Leu Gly Leu Pro Pro Gln Thr Lys Asp Asn Trp Tyr
                   325                  330                  335
Val Pro Ile Asp Ser Pro Gly Leu Arg Leu Val Ser Phe Met Pro Thr
                   340                  345                  350
Ala Thr Gly Asn Glu Lys Phe Gly Gln Gly Thr Leu Gly Tyr Cys Ala
                   355                  360                  365
Ala Thr Ile Gln Asn Thr Pro Ser Gly Thr Thr Pro Ser Asp Ala Leu
                   370                  375                  380
Ala Phe Thr Val Ser Leu Pro Gln Thr Ser Gly Ser Asn Trp Phe Asp
385                  390                  395                  400
Gln Tyr Ala Pro Asp Thr Val Val Thr Thr Gly Pro Ile Pro Phe Ser
                   405                  410                  415
Tyr Gln Gly Tyr Val Tyr Ser Pro Asn Gly Asn Asn His Ala Pro Ser
                   420                  425                  430
```

Pro

```
<210> SEQ ID NO 47
<211> LENGTH: 436
<212> TYPE: PRT
<213> ORGANISM: fowl adenovirus

<400> SEQUENCE: 47
```

Met Ser Ala Leu Ile Ala Ser Ala Ala Asp Thr Val Ser Ala Ser Gly
1               5                   10                  15

Lys Lys Arg Pro Arg Arg Ala Leu Ser Glu Pro Ile Arg Tyr Leu Ser
            20                  25                  30

Glu Gly Asp Glu Arg Arg Lys Pro Lys Arg Ala Arg Pro Ala Thr Arg
        35                  40                  45

Ala Asn Gly Pro Leu Leu Asp Leu Val Tyr Pro Phe Asp Phe Asn Ala
    50                  55                  60

Gly Gly Gly Gly Ser Gly Gly Gly Gly Gly Gly Gly Gly Gly Gly Gly
65                  70                  75                  80

Gly Gly Gln Gln Ile Ala Val Asp Pro Asp Gly Pro Leu Glu Leu Thr
                85                  90                  95

Gly Asp Leu Leu Thr Leu Asn Thr Lys Thr Pro Ile Tyr Val Ser Asp
            100                 105                 110

Arg Ala Val Ser Leu Leu Ile Asp Asp Asn Thr Leu Ala Thr Lys Gln
        115                 120                 125

Ala Asn Gly Ala Leu Met Val Lys Thr Ser Ala Pro Leu Asn Ser Gly
    130                 135                 140

Thr Gly Gly Gly Val Thr Leu Gly Phe Asp Pro His Thr Met Ala Leu
145                 150                 155                 160

Asp Ser Val Thr Gly Val Leu Lys Val Leu Val Asp Ser Gln Gly Pro
                165                 170                 175

Leu Leu Ala Asp Thr Gly Gly Ile Thr Leu Gln Phe Asp Thr Gln Asp
            180                 185                 190

Phe Val Val Asn Asn Gly Val Leu Ala Leu Ala Ser Ser Val Gly Pro
        195                 200                 205

Thr Tyr Leu Ser Pro Phe Ala Thr Tyr Glu Val Thr Pro Val Leu Gly
    210                 215                 220

Ile Ser Gln Arg Asn Gly Asn Val Lys Ser Lys Gly Leu Gln Asn Trp
225                 230                 235                 240

Ser Ile Gly Tyr Tyr Ile Tyr Met Val Ser Ser Ala Gly Ile Val Asn
                245                 250                 255

Gly Leu Ile Thr Leu Glu Leu Ala Gln Glu Leu Thr Gly Ala Ser Gly
            260                 265                 270

Glu Asn Ser Leu Thr Ser Gly Leu Asn Phe Thr Phe Val Leu Ser Pro
        275                 280                 285

Met Tyr Pro Ile Glu Thr Glu Val Asn Leu Ser Leu Ile Val Pro Pro
    290                 295                 300

Thr Val Ser Pro Ser Asn Gln Asn His Val Phe Val Pro Asn Ser Asn
305                 310                 315                 320

Gln Ser Asp Val Gly Tyr Leu Gly Leu Pro Ala Gln Thr Arg Asp Asn
                325                 330                 335

Trp Tyr Val Pro Ile Asp Ser Pro Gly Leu Arg Leu Val Ser Phe Met
            340                 345                 350

Pro Thr Ala Thr Gly Asn Glu Lys Phe Gly Gln Gly Thr Leu Gly Tyr
        355                 360                 365

```
Cys Ala Ala Thr Ile Gln Asn Thr Pro Ser Gly Thr Thr Pro Ser Asp
        370                 375                 380

Ala Leu Ala Phe Thr Val Ser Leu Pro Gln Thr Ser Gly Ser Asn Trp
385                 390                 395                 400

Phe Asp Gln Tyr Ala Pro Asp Thr Val Val Thr Thr Gly Pro Ile Pro
                405                 410                 415

Phe Ser Tyr Gln Gly Tyr Val Tyr Ser Pro Thr Asn Gly Asn Asn His
                420                 425                 430

Ala Pro Ser Pro
        435

<210> SEQ ID NO 48
<211> LENGTH: 433
<212> TYPE: PRT
<213> ORGANISM: fowl adenovirus

<400> SEQUENCE: 48

Met Ser Ala Leu Ile Ala Ser Ala Asp Thr Val Ser Val Ser Gly
1               5                   10                  15

Lys Lys Arg Pro Arg Arg Ala Leu Ser Glu Pro Ile Arg Tyr Leu Ser
                20                  25                  30

Glu Gly Asp Glu Arg Arg Lys Pro Lys Arg Ala Pro Pro Ala Thr Arg
            35                  40                  45

Ala Asn Gly Pro Leu Leu Asp Leu Val Tyr Pro Phe Asp Phe Asn Ala
        50                  55                  60

Gly Gly Gly Gly Ser Gly Gly Gly Gly Gly Gly Gly Gly
65                  70                  75                  80

Gln Gln Ile Ala Val Asp Pro Asp Gly Pro Leu Glu Leu Thr Gly Asp
                85                  90                  95

Leu Leu Thr Leu Asn Thr Lys Thr Pro Ile Tyr Val Ser Asp Arg Ala
            100                 105                 110

Val Ser Leu Leu Ile Asp Asp Thr Leu Ala Thr Lys Gln Val Asn
        115                 120                 125

Gly Ala Leu Met Val Lys Thr Ala Ala Pro Leu Asn Ser Gly Thr Gly
    130                 135                 140

Gly Gly Val Thr Leu Gly Phe Asp Pro His Thr Met Ala Leu Asp Ser
145                 150                 155                 160

Val Thr Gly Val Leu Lys Val Leu Val Asp Ser Gln Gly Pro Leu Gln
                165                 170                 175

Ala Asp Thr Gly Gly Ile Thr Leu Gln Phe Asn Thr Gln Asp Phe Val
            180                 185                 190

Val Asn Asn Gly Val Leu Ala Leu Ala Ser Ser Val Ala Pro Thr Tyr
        195                 200                 205

Leu Ser Pro Phe Ala Thr Tyr Glu Val Thr Pro Val Leu Gly Ile Ser
    210                 215                 220

Gln Arg Asn Gly Asn Val Lys Ser Lys Gly Leu Gln Asn Trp Ser Ile
225                 230                 235                 240

Gly Tyr Tyr Ile Tyr Met Val Ser Ser Ala Gly Ile Val Asn Gly Leu
                245                 250                 255

Ile Thr Leu Glu Leu Ala Gln Glu Leu Thr Gly Ala Ser Gly Glu Asn
            260                 265                 270

Ser Leu Thr Ser Gly Leu Asn Phe Thr Phe Val Leu Ser Pro Met Tyr
        275                 280                 285

Pro Ile Glu Thr Glu Val Asn Leu Ser Leu Ile Val Pro Pro Thr Val
```

```
                 290                 295                 300
Ser Pro Thr Asn Gln Asn Arg Val Phe Val Pro Asn Ser Asn Gln Ser
305                 310                 315                 320

Asp Val Gly Tyr Leu Gly Leu Pro Pro Gln Thr Lys Asp Asn Trp Tyr
            325                 330                 335

Val Pro Ile Asp Ser Pro Gly Leu Arg Leu Val Ser Phe Met Pro Thr
            340                 345                 350

Ala Thr Gly Asn Glu Lys Phe Gly Gln Gly Thr Leu Gly Tyr Cys Ala
            355                 360                 365

Ala Thr Ile Gln Asn Thr Pro Ser Gly Thr Thr Pro Ser Asp Ala Leu
            370                 375                 380

Ala Phe Thr Val Ser Leu Pro Gln Thr Ser Gly Ser Asn Trp Phe Asp
385                 390                 395                 400

Gln Tyr Ala Pro Asp Thr Val Val Thr Thr Gly Pro Ile Pro Phe Ser
            405                 410                 415

Tyr Gln Gly Tyr Val Tyr Ser Pro Asn Gly Asn Asn Asn Ala Pro Gly
            420                 425                 430

Pro

<210> SEQ ID NO 49
<211> LENGTH: 434
<212> TYPE: PRT
<213> ORGANISM: fowl adenovirus

<400> SEQUENCE: 49

Met Ser Ala Leu Ile Ala Ser Ala Ala Asp Thr Val Ser Val Ser Gly
1               5                   10                  15

Lys Lys Arg Pro Arg Arg Ala Leu Ser Glu Pro Ile Arg Tyr Leu Ser
            20                  25                  30

Glu Gly Asp Glu Arg Arg Lys Pro Lys Arg Ala Pro Pro Ala Thr Arg
        35                  40                  45

Ala Asn Gly Pro Leu Leu Asp Leu Val Tyr Pro Phe Asp Phe Asn Ala
    50                  55                  60

Gly Gly Gly Gly Ser Gly Gly Gly Gly Gly Gly Gly Gly
65                  70                  75                  80

Gly Gly Gln Gln Ile Ala Val Asp Pro Asp Gly Pro Leu Glu Leu Thr
            85                  90                  95

Gly Asp Leu Leu Thr Leu Asn Thr Lys Thr Pro Ile Tyr Val Ser Asp
            100                 105                 110

Arg Ala Val Ser Leu Leu Ile Asp Asp Asn Thr Leu Ala Thr Lys Gln
            115                 120                 125

Ala Asn Gly Ala Leu Met Val Lys Thr Ser Ala Pro Leu Asn Ser Gly
            130                 135                 140

Thr Gly Gly Gly Ile Thr Leu Gly Phe Asp Pro His Thr Met Ala Leu
145                 150                 155                 160

Asp Ser Val Thr Gly Val Leu Lys Val Leu Val Asp Ser Gln Gly Pro
            165                 170                 175

Leu Gln Ala Asp Thr Gly Gly Ile Thr Leu Gln Phe Asp Thr Gln Asp
            180                 185                 190

Phe Val Val Asn Asn Gly Thr Leu Ala Leu Ala Ser Ser Val Ala Pro
            195                 200                 205

Ser Tyr Leu Ser Pro Phe Ala Thr Tyr Glu Val Thr Pro Val Leu Gly
            210                 215                 220

Ile Ser Gln Arg Asn Gly Asn Val Lys Ser Lys Gly Leu Gln Asn Trp
```

```
                225                 230                 235                 240
Ser Ile Gly Tyr Tyr Ile Tyr Met Val Ser Ser Ala Gly Leu Val Asn
                    245                 250                 255

Gly Leu Ile Thr Leu Glu Leu Ala His Asp Leu Thr Gly Ala Ser Gly
                260                 265                 270

Glu Asn Ser Leu Thr Ser Gly Leu Asn Phe Thr Phe Val Leu Ser Pro
            275                 280                 285

Met Tyr Pro Ile Glu Thr Glu Val Asn Leu Ser Leu Ile Val Pro Pro
        290                 295                 300

Thr Val Ser Pro Thr Asn Gln Asn Arg Val Phe Val Pro Asn Ser Asn
305                 310                 315                 320

Gln Ser Asp Val Gly Tyr Leu Gly Leu Pro Pro His Thr Arg Asp Asn
                325                 330                 335

Trp Tyr Val Pro Ile Asp Ser Pro Gly Leu Arg Leu Val Ser Phe Met
                340                 345                 350

Pro Thr Ala Thr Gly Asn Glu Lys Phe Gly Gln Gly Thr Leu Gly Tyr
                355                 360                 365

Cys Ala Ala Thr Ile Gln Asn Thr Pro Ser Gly Thr Thr Pro Ser Asp
            370                 375                 380

Ala Leu Ala Phe Thr Val Ser Leu Pro Gln Thr Ser Gly Ser Asn Trp
385                 390                 395                 400

Phe Asp Gln Asn Ala Pro Asp Thr Val Val Thr Thr Gly Pro Ile Pro
                405                 410                 415

Phe Ser Tyr Gln Gly Tyr Val Tyr Ser Pro Asn Gly Asn Asn Ala Pro
                420                 425                 430

Ser Pro

<210> SEQ ID NO 50
<211> LENGTH: 413
<212> TYPE: PRT
<213> ORGANISM: fowl adenovirus

<400> SEQUENCE: 50

Ile Ala Ser Ala Ala Asp Thr Val Ser Val Ser Gly Lys Lys Arg Pro
1               5                   10                  15

Arg Arg Ala Leu Ser Glu Pro Ile Arg Tyr Leu Ser Glu Gly Asp Glu
                20                  25                  30

Arg Arg Lys Pro Lys Arg Ala Pro Ala Thr Arg Ala Asn Gly Pro
            35                  40                  45

Leu Leu Asp Leu Val Tyr Pro Phe Asp Phe Asn Ala Gly Gly Gly Gly
        50                  55                  60

Gly Ser Gly Gly Gly Gly Gly Gly Gly Gly Gly Gly Gly Gly Gln Gln
65                  70                  75                  80

Ile Ala Val Asp Pro Asp Gly Pro Leu Glu Leu Thr Gly Asp Leu Leu
                85                  90                  95

Thr Leu Asn Thr Lys Thr Pro Ile Tyr Val Ser Asp Arg Ala Val Ser
            100                 105                 110

Leu Leu Ile Asp Asp Asn Thr Leu Ala Thr Lys Gln Ala Asn Gly Ala
        115                 120                 125

Leu Met Val Lys Thr Ser Ala Pro Leu Asn Ser Gly Thr Gly Gly Gly
    130                 135                 140

Ile Thr Leu Gly Phe Asp Pro His Thr Met Ala Leu Asp Ser Val Thr
145                 150                 155                 160

Gly Val Leu Lys Val Leu Val Asp Ser Gln Gly Pro Leu Gln Ala Asp
```

```
                  165                 170                 175
Thr Gly Gly Ile Thr Leu Gln Phe Asp Thr Gln Asp Phe Val Val Asn
                180                 185                 190

Asn Gly Thr Leu Ala Leu Ala Ser Ser Val Ala Pro Thr Tyr Leu Ser
            195                 200                 205

Pro Phe Ala Thr Tyr Glu Val Thr Pro Val Leu Gly Ile Ser Gln Arg
        210                 215                 220

Asn Gly Asn Val Lys Ser Lys Gly Leu Gln Asn Trp Ser Ile Gly Tyr
225                 230                 235                 240

Tyr Ile Tyr Met Val Ser Ser Ala Gly Leu Val Asn Gly Leu Ile Thr
                245                 250                 255

Leu Glu Leu Ala His Asp Leu Thr Gly Ala Ser Gly Glu Asn Ser Leu
            260                 265                 270

Thr Ser Gly Leu Asn Phe Thr Phe Val Leu Ser Pro Met Tyr Pro Ile
        275                 280                 285

Glu Thr Glu Val Asn Leu Ser Leu Ile Val Pro Pro Thr Val Ser Pro
        290                 295                 300

Thr Asn Gln Asn Arg Val Phe Val Pro Asn Ser Asn Gln Ser Asp Val
305                 310                 315                 320

Gly Tyr Leu Gly Leu Pro Pro His Thr Arg Asp Asn Trp Tyr Val Pro
                325                 330                 335

Ile Asp Ser Pro Gly Leu Arg Leu Val Ser Phe Met Pro Thr Ala Thr
            340                 345                 350

Gly Asn Glu Lys Phe Gly Gln Gly Thr Leu Gly Tyr Cys Ala Ala Thr
        355                 360                 365

Ile Gln Asn Thr Pro Ser Gly Thr Thr Pro Ser Asp Ala Leu Ala Phe
    370                 375                 380

Thr Val Ser Leu Pro Gln Thr Ser Gly Ser Asn Trp Phe Asp Gln Asn
385                 390                 395                 400

Ala Pro Asp Thr Val Val Thr Thr Gly Pro Ile Pro Phe
                405                 410

<210> SEQ ID NO 51
<211> LENGTH: 396
<212> TYPE: PRT
<213> ORGANISM: fowl adenovirus

<400> SEQUENCE: 51

Pro Arg Arg Ala Leu Ser Glu Pro Ile Arg Tyr Leu Ser Glu Gly Asp
1               5                   10                  15

Glu Arg Arg Lys Pro Lys Arg Ala Pro Pro Ala Thr Arg Ala Asn Gly
            20                  25                  30

Pro Leu Leu Asp Leu Val Tyr Pro Phe Asp Phe Asn Ala Gly Gly Gly
        35                  40                  45

Gly Ser Gly Gly Gly Gly Gly Gly Gly Gly Gln Gln Ile Ala
    50                  55                  60

Val Asp Pro Asp Gly Pro Leu Glu Leu Thr Gly Asp Leu Leu Thr Leu
65                  70                  75                  80

Asn Thr Lys Thr Pro Ile Tyr Val Ser Asp Arg Ala Val Ser Leu Leu
                85                  90                  95

Ile Asp Asp Asp Thr Leu Ala Thr Lys Gln Val Asn Gly Ala Leu Met
            100                 105                 110

Val Lys Thr Ala Ala Pro Leu Asn Ser Gly Thr Gly Gly Gly Val Thr
        115                 120                 125
```

```
Leu Gly Phe Asp Pro His Thr Met Ala Leu Asp Ser Val Thr Gly Val
    130                 135                 140

Leu Lys Val Leu Val Asp Ser Gln Gly Pro Leu Gln Ala Asp Thr Gly
145                 150                 155                 160

Gly Ile Thr Leu Gln Phe Asn Thr Gln Asp Phe Val Val Asn Asn Gly
                165                 170                 175

Val Leu Ala Leu Ala Ser Ser Val Ala Pro Thr Tyr Leu Ser Pro Phe
            180                 185                 190

Ala Thr Tyr Glu Val Thr Pro Val Leu Gly Ile Ser Gln Arg Asn Gly
        195                 200                 205

Asn Val Lys Ser Lys Gly Leu Gln Asn Trp Ser Ile Gly Tyr Ile
210                 215                 220

Tyr Met Val Ser Ser Ala Gly Ile Val Asn Gly Leu Ile Thr Leu Glu
225                 230                 235                 240

Leu Ala Gln Glu Leu Thr Gly Ala Ser Gly Glu Asn Ser Leu Thr Ser
                245                 250                 255

Gly Leu Asn Phe Thr Phe Val Leu Ser Pro Met Tyr Pro Ile Glu Thr
            260                 265                 270

Glu Val Asn Leu Ser Leu Ile Val Pro Pro Thr Val Ser Pro Thr Asn
        275                 280                 285

Gln Asn Arg Val Phe Val Pro Asn Ser Asn Gln Ser Asp Val Gly Tyr
    290                 295                 300

Leu Gly Leu Pro Pro Gln Thr Lys Asp Asn Trp Tyr Val Pro Ile Asp
305                 310                 315                 320

Ser Pro Gly Leu Arg Leu Val Ser Phe Met Pro Thr Ala Thr Gly Asn
                325                 330                 335

Glu Lys Phe Gly Gln Gly Thr Leu Gly Tyr Cys Ala Ala Ala Ile Gln
            340                 345                 350

Asn Thr Pro Ser Gly Thr Thr Pro Ser Asp Ala Leu Ala Phe Thr Val
        355                 360                 365

Ser Leu Pro Gln Thr Ser Gly Ser Asn Trp Phe Asp Gln Tyr Ala Pro
    370                 375                 380

Asp Thr Val Val Thr Thr Gly Pro Ile Pro Phe Pro
385                 390                 395

<210> SEQ ID NO 52
<211> LENGTH: 396
<212> TYPE: PRT
<213> ORGANISM: fowl adenovirus

<400> SEQUENCE: 52

Ala Glu Lys Arg Pro Arg Arg Ala Leu Ser Glu Pro Ile Arg Tyr Leu
1               5                   10                  15

Ser Glu Gly Asp Glu Arg Arg Lys Pro Lys Arg Ala Pro Pro Ala Thr
            20                  25                  30

Arg Ala Asn Gly Pro Leu Leu Asp Leu Val Tyr Pro Phe Asp Phe Asn
        35                  40                  45

Ala Gly Gly Gly Ser Gly Gly Gly Gly Gly Gly Gly Gln
    50                  55                  60

Gln Ile Thr Val Asp Pro Asp Gly Pro Leu Glu Leu Thr Gly Asp Leu
65                  70                  75                  80

Leu Thr Leu Asn Thr Lys Thr Pro Ile Tyr Val Ser Asp Arg Ala Val
                85                  90                  95

Ser Leu Leu Ile Asp Asp Asn Thr Leu Ala Thr Lys Gln Val Asn Gly
            100                 105                 110
```

Ala Leu Met Val Lys Thr Ser Ala Pro Leu Asn Ser Gly Thr Gly Gly
            115                 120                 125

Gly Val Thr Leu Gly Phe Asp Pro His Thr Met Ala Leu Asp Ser Val
            130                 135                 140

Thr Gly Val Leu Lys Val Leu Val Asp Ser Gln Gly Pro Leu Gln Ala
145                 150                 155                 160

Asp Thr Gly Gly Ile Thr Leu Gln Phe Asn Thr Gln Asp Phe Val Val
                165                 170                 175

Asn Asn Gly Thr Leu Ala Leu Ala Ser Ser Val Gly Pro Thr Tyr Leu
            180                 185                 190

Ser Pro Phe Ala Thr Tyr Glu Val Thr Pro Val Leu Gly Ile Ser Gln
            195                 200                 205

Arg Asn Gly Asn Val Lys Ser Lys Gly Leu Gln Asn Trp Ser Ile Gly
            210                 215                 220

Tyr Tyr Ile Tyr Met Val Ser Ala Gly Leu Val Asn Gly Leu Ile
225                 230                 235                 240

Thr Leu Glu Leu Ala His Asp Leu Thr Gly Ala Ser Gly Glu Asn Ser
                245                 250                 255

Leu Thr Ser Gly Leu Asn Phe Thr Phe Val Leu Ser Pro Met Tyr Pro
            260                 265                 270

Ile Glu Thr Glu Val Asn Leu Ser Leu Ile Val Pro Pro Thr Val Ser
            275                 280                 285

Pro Thr Asn Gln Asn Arg Val Phe Val Pro Asn Ser Asn Gln Ser Asp
            290                 295                 300

Val Gly Tyr Leu Gly Leu Pro Pro His Thr Arg Asp Asn Trp Tyr Val
305                 310                 315                 320

Ser Ile Asp Ser Pro Gly Leu Arg Leu Val Ser Phe Met Pro Thr Ala
                325                 330                 335

Thr Gly Asn Glu Lys Phe Gly Gln Gly Thr Leu Gly Tyr Cys Ala Ala
            340                 345                 350

Thr Ile Gln Asn Thr Pro Ser Gly Thr Thr Pro Ser Asp Ala Ile Ala
            355                 360                 365

Phe Thr Val Ser Leu Pro Gln Thr Ser Gly Ser Asn Trp Phe Asp Gln
            370                 375                 380

Asn Ala Pro Asp Thr Val Val Thr Thr Gly Pro Ile
385                 390                 395

<210> SEQ ID NO 53
<211> LENGTH: 394
<212> TYPE: PRT
<213> ORGANISM: fowl adenovirus

<400> SEQUENCE: 53

Pro Arg Arg Ala Leu Ser Glu Pro Ile Arg Tyr Leu Ser Glu Gly Asp
1               5                   10                  15

Glu Arg Arg Lys Pro Lys Arg Ala Pro Ala Thr Arg Ala Asn Gly
            20                  25                  30

Pro Leu Leu Asp Leu Val Tyr Pro Phe Asp Phe Asn Ala Gly Gly Gly
            35                  40                  45

Gly Ser Gly Gly Gly Gly Gly Gly Gly Gln Gln Ile Thr Val
            50                  55                  60

Asp Pro Asp Gly Pro Leu Glu Leu Thr Gly Asp Leu Leu Thr Leu Asn
65                  70                  75                  80

Thr Lys Thr Pro Ile Tyr Val Ser Asp Arg Ala Val Ser Leu Leu Ile

```
                85                  90                  95
Asp Asp Asn Thr Leu Ala Thr Lys Gln Val Asn Gly Ala Leu Met Val
            100                 105                 110
Lys Thr Ser Ala Pro Leu Asn Ser Gly Thr Gly Gly Val Thr Leu
            115                 120                 125
Gly Phe Asp Pro His Thr Met Ala Leu Asp Ser Val Thr Gly Val Leu
        130                 135                 140
Lys Val Leu Val Asp Ser Gln Gly Pro Leu Gln Ala Asp Thr Gly Gly
145                 150                 155                 160
Ile Thr Leu Gln Phe Asn Thr Gln Asp Phe Val Val Asn Asn Gly Thr
                165                 170                 175
Leu Ala Leu Ala Ser Ser Val Gly Pro Thr Tyr Leu Ser Pro Phe Ala
            180                 185                 190
Thr Tyr Glu Val Thr Pro Val Leu Gly Ile Ser Gln Arg Asn Gly Asn
            195                 200                 205
Val Lys Ser Lys Gly Leu Gln Asn Trp Ser Ile Gly Tyr Tyr Ile Tyr
        210                 215                 220
Met Val Ser Ser Ala Gly Leu Val Asn Gly Leu Ile Thr Leu Glu Leu
225                 230                 235                 240
Ala His Asp Leu Thr Gly Ala Ser Gly Glu Asn Ser Leu Thr Ser Gly
                245                 250                 255
Leu Asn Phe Thr Phe Val Leu Ser Pro Met Tyr Pro Ile Glu Thr Glu
            260                 265                 270
Val Asn Leu Ser Leu Ile Val Pro Pro Thr Val Ser Pro Thr Asn Gln
            275                 280                 285
Asn Arg Val Phe Val Pro Asn Ser Asn Gln Ser Asp Val Gly Tyr Leu
        290                 295                 300
Gly Leu Pro Pro His Thr Arg Asp Asn Trp Tyr Val Ser Ile Asp Ser
305                 310                 315                 320
Pro Gly Leu Arg Leu Val Ser Phe Met Pro Thr Ala Thr Gly Asn Glu
                325                 330                 335
Lys Phe Gly Gln Gly Thr Leu Gly Tyr Cys Ala Ala Thr Ile Gln Asn
            340                 345                 350
Thr Pro Ser Gly Thr Thr Pro Ser Asp Ala Ile Ala Phe Thr Val Ser
            355                 360                 365
Leu Pro Gln Thr Ser Gly Ser Asn Trp Phe Asp Gln Asn Ala Pro Asp
        370                 375                 380
Thr Val Val Thr Thr Gly Pro Ile Pro Phe
385                 390

<210> SEQ ID NO 54
<211> LENGTH: 393
<212> TYPE: PRT
<213> ORGANISM: fowl adenovirus

<400> SEQUENCE: 54

Pro Arg Arg Ala Leu Ser Glu Pro Ile Arg Tyr Leu Ser Glu Gly Asp
1               5                   10                  15
Glu Arg Arg Lys Pro Lys Arg Ala Pro Pro Ala Thr Arg Ala Asn Gly
            20                  25                  30
Pro Leu Leu Asp Leu Val Tyr Pro Phe Asp Phe Asn Ala Gly Gly Gly
        35                  40                  45
Gly Ser Gly Gly Gly Gly Gly Gly Gly Gly Gln Gln Ile Thr Val
    50                  55                  60
```

Asp Pro Asp Gly Pro Leu Glu Leu Thr Gly Asp Leu Leu Thr Leu Asn
 65                  70                  75                  80

Thr Lys Thr Pro Ile Tyr Val Ser Asp Arg Ala Val Ser Leu Leu Ile
             85                  90                  95

Asp Asp Asn Thr Leu Ala Thr Lys Gln Val Asn Gly Ala Leu Met Val
            100                 105                 110

Lys Thr Ser Ala Pro Leu Asn Ser Gly Thr Gly Gly Val Thr Leu
        115                 120                 125

Gly Phe Asp Pro His Thr Met Ala Leu Asp Ser Val Thr Gly Val Leu
130                 135                 140

Lys Val Leu Val Asp Ser Gln Gly Pro Leu Gln Ala Asp Thr Gly Gly
145                 150                 155                 160

Ile Thr Leu Gln Phe Asn Thr Gln Asp Phe Val Val Asn Asn Gly Thr
                165                 170                 175

Leu Ala Leu Ala Ser Ser Val Gly Pro Thr Tyr Leu Ser Pro Phe Ala
            180                 185                 190

Thr Tyr Glu Val Thr Pro Val Leu Gly Ile Ser Gln Arg Asn Gly Asn
        195                 200                 205

Val Lys Ser Lys Gly Leu Gln Asn Trp Ser Ile Gly Tyr Tyr Ile Tyr
210                 215                 220

Met Val Ser Ser Ala Gly Leu Val Asn Gly Leu Ile Thr Leu Glu Leu
225                 230                 235                 240

Ala His Asp Leu Thr Gly Ala Ser Gly Glu Asn Ser Leu Thr Ser Gly
                245                 250                 255

Leu Asn Phe Thr Phe Val Leu Ser Pro Met Tyr Pro Ile Glu Thr Glu
            260                 265                 270

Val Asn Leu Ser Leu Ile Val Pro Pro Thr Val Ser Pro Thr Asn Gln
        275                 280                 285

Asn Arg Val Phe Val Pro Asn Ser Asn Gln Ser Asp Val Gly Tyr Leu
290                 295                 300

Gly Leu Pro Pro His Thr Arg Asp Asn Trp Tyr Val Pro Ile Asp Ser
305                 310                 315                 320

Pro Gly Leu Arg Leu Val Ser Phe Met Pro Thr Ala Thr Gly Asn Glu
                325                 330                 335

Lys Phe Gly Gln Gly Thr Leu Gly Tyr Cys Ala Ala Thr Ile Gln Asn
            340                 345                 350

Thr Pro Ser Gly Thr Thr Pro Ser Asp Ala Ile Ala Phe Thr Val Ser
        355                 360                 365

Leu Pro Gln Thr Ser Gly Ser Asn Trp Phe Asp Gln Asn Ala Pro Asp
370                 375                 380

Thr Val Val Thr Thr Gly Pro Ile Pro
385                 390

<210> SEQ ID NO 55
<211> LENGTH: 394
<212> TYPE: PRT
<213> ORGANISM: fowl adenovirus

<400> SEQUENCE: 55

Pro Arg Arg Ala Leu Ser Glu Pro Ile Arg Tyr Leu Ser Glu Gly Asp
1               5                   10                  15

Glu Arg Arg Lys Pro Lys Arg Ala Pro Pro Ala Thr Arg Ala Asn Gly
            20                  25                  30

Pro Leu Leu Asp Leu Val Tyr Pro Phe Asp Phe Asn Ala Gly Gly Gly
        35                  40                  45

Gly Ser Gly Gly Gly Gly Gly Gly Gly Gln Gln Ile Thr Val
  50                  55                  60

Asp Pro Asp Gly Pro Leu Glu Leu Thr Gly Asp Leu Leu Thr Leu Asn
 65                  70                  75                  80

Thr Lys Thr Pro Ile Tyr Val Ser Asp Arg Ala Val Ser Leu Leu Ile
                 85                  90                  95

Asp Asp Asn Thr Leu Ala Thr Lys Gln Val Asn Gly Ala Leu Met Val
                100                 105                 110

Lys Thr Ser Ala Pro Leu Asn Ser Gly Thr Gly Gly Val Thr Leu
                115                 120                 125

Gly Phe Asp Pro His Thr Met Ala Leu Asp Ser Val Thr Gly Val Leu
                130                 135                 140

Lys Val Leu Val Asp Ser Gln Gly Pro Leu Gln Ala Asp Thr Gly Gly
145                 150                 155                 160

Ile Thr Leu Gln Phe Asn Thr Gln Asp Phe Val Val Asn Asn Gly Thr
                165                 170                 175

Leu Ala Leu Ala Ser Ser Val Gly Pro Thr Tyr Leu Ser Pro Phe Ala
                180                 185                 190

Thr Tyr Glu Val Thr Pro Val Leu Gly Ile Ser Gln Arg Asn Gly Asn
                195                 200                 205

Val Lys Ser Lys Gly Leu Gln Asn Trp Ser Ile Gly Tyr Tyr Ile Tyr
210                 215                 220

Met Val Ser Ser Ala Gly Leu Val Asn Gly Leu Ile Thr Leu Glu Leu
225                 230                 235                 240

Ala His Asp Leu Thr Gly Ala Ser Gly Glu Asn Ser Leu Thr Ser Gly
                245                 250                 255

Leu Asn Phe Thr Phe Val Leu Ser Pro Met Tyr Pro Ile Glu Thr Glu
                260                 265                 270

Val Asn Leu Ser Leu Ile Val Pro Pro Thr Val Ser Pro Thr Asn Gln
                275                 280                 285

Asn Arg Val Phe Val Pro Asn Ser Asn Gln Ser Asp Val Gly Tyr Leu
                290                 295                 300

Gly Leu Pro Pro His Thr Arg Asp Asn Trp Tyr Val Ser Ile Asp Ser
305                 310                 315                 320

Pro Gly Leu Arg Met Val Ser Phe Met Pro Thr Ala Thr Gly Asn Glu
                325                 330                 335

Lys Phe Gly Gln Gly Thr Leu Gly Tyr Cys Ala Ala Thr Ile Gln Asn
                340                 345                 350

Thr Pro Ser Gly Thr Thr Pro Ser Asp Ala Ile Ala Phe Thr Val Ser
                355                 360                 365

Leu Pro Gln Thr Ser Gly Ser Asn Trp Phe Asp Gln Asn Ala Pro Asp
                370                 375                 380

Thr Val Val Thr Thr Gly Pro Ile Pro Phe
385                 390

<210> SEQ ID NO 56
<211> LENGTH: 395
<212> TYPE: PRT
<213> ORGANISM: fowl adenovirus

<400> SEQUENCE: 56

Arg Pro Arg Arg Ala Leu Ser Glu Pro Ile Arg Tyr Leu Ser Glu Gly
 1                   5                  10                  15

Asp Glu Arg Arg Lys Pro Lys Arg Ala Pro Pro Ala Thr Arg Ala Asn

```
                 20                  25                  30
Gly Pro Leu Leu Asp Leu Val Tyr Pro Phe Asp Phe Asn Ala Gly Gly
             35                  40                  45

Gly Gly Ser Gly Gly Gly Gly Gly Gly Gly Gln Gln Ile Thr
 50                  55                  60

Val Asp Pro Asp Gly Pro Leu Glu Leu Thr Gly Asp Leu Leu Thr Leu
 65                  70                  75                  80

Asn Thr Lys Thr Pro Ile Tyr Val Ser Asp Arg Ala Val Ser Leu Leu
                 85                  90                  95

Ile Asp Asp Asn Thr Leu Ala Thr Lys Gln Val Asn Gly Ala Leu Met
            100                 105                 110

Val Lys Thr Ser Ala Pro Leu Asn Ser Gly Thr Gly Gly Gly Val Thr
            115                 120                 125

Leu Gly Phe Asp Pro His Thr Met Ala Leu Asp Ser Val Thr Gly Val
            130                 135                 140

Leu Lys Val Leu Val Asp Ser Gln Gly Pro Leu Gln Ala Asp Thr Gly
145                 150                 155                 160

Gly Ile Thr Leu Gln Phe Asn Thr Gln Asp Phe Val Val Asn Asn Gly
                165                 170                 175

Thr Leu Ala Leu Ala Ser Ser Val Gly Pro Thr Tyr Leu Ser Pro Phe
            180                 185                 190

Ala Thr Tyr Glu Val Thr Pro Val Leu Gly Ile Ser Gln Arg Asn Gly
            195                 200                 205

Asn Val Lys Ser Lys Gly Leu Gln Asn Trp Ser Ile Gly Tyr Tyr Ile
            210                 215                 220

Tyr Met Val Ser Ser Ala Gly Leu Val Asn Gly Leu Ile Thr Leu Glu
225                 230                 235                 240

Leu Ala His Asp Leu Thr Gly Ala Ser Gly Glu Asn Ser Leu Thr Ser
                245                 250                 255

Gly Leu Asn Phe Thr Phe Val Leu Ser Pro Met Tyr Pro Ile Glu Thr
            260                 265                 270

Glu Val Asn Leu Ser Leu Ile Val Pro Pro Thr Val Ser Pro Thr Asn
            275                 280                 285

Gln Asn Arg Val Phe Val Pro Asn Ser Asn Gln Ser Asp Val Gly Tyr
            290                 295                 300

Leu Gly Leu Pro Pro His Thr Arg Asp Asn Trp Tyr Val Ser Ile Asp
305                 310                 315                 320

Ser Pro Gly Leu Arg Leu Val Ser Phe Met Pro Thr Ala Thr Gly Asn
                325                 330                 335

Glu Lys Phe Gly Gln Gly Thr Leu Gly Tyr Cys Ala Ala Thr Ile Gln
            340                 345                 350

Asn Thr Pro Ser Gly Thr Thr Pro Ser Asp Ala Ile Ala Phe Thr Val
            355                 360                 365

Ser Leu Pro Gln Thr Ser Gly Ser Asn Trp Phe Asp Gln Asn Ala Pro
            370                 375                 380

Asp Thr Val Val Thr Thr Gly Pro Ile Pro Phe
385                 390                 395

<210> SEQ ID NO 57
<211> LENGTH: 397
<212> TYPE: PRT
<213> ORGANISM: fowl adenovirus

<400> SEQUENCE: 57
```

```
Ala Glu Lys Arg Pro Arg Arg Ala Leu Ser Glu Pro Ser Arg Tyr Leu
 1               5                  10                  15

Ser Glu Gly Asp Glu Arg Lys Pro Lys Arg Ala Arg Pro Ala Thr
             20                  25                  30

Arg Ala Asn Gly Pro Leu Leu Asp Leu Val Tyr Pro Phe Asp Phe Asn
             35                  40                  45

Ala Gly Gly Gly Gly Ser Gly Gly Gly Gly Gly Gly Gly Gly
 50                  55                  60

Gln Gln Ile Ala Val Asp Pro Asp Gly Pro Leu Glu Leu Thr Gly Asp
 65                  70                  75                  80

Leu Leu Thr Leu Asn Thr Lys Thr Pro Ile Tyr Val Ser Asp Arg Ala
                 85                  90                  95

Val Ser Leu Leu Ile Asp Asp Asn Thr Leu Ala Thr Lys Gln Ala Asn
                100                 105                 110

Gly Ala Leu Met Val Lys Thr Ala Ala Pro Leu Asn Ser Gly Thr Gly
                115                 120                 125

Gly Gly Val Thr Leu Gly Phe Asp Pro Arg Thr Met Ala Leu Asp Ser
    130                 135                 140

Val Thr Gly Val Leu Lys Val Leu Val Asp Ser Gln Gly Pro Leu Gln
145                 150                 155                 160

Ala Asp Thr Gly Gly Ile Thr Leu Gln Phe Asp Thr Gln Asp Phe Val
                165                 170                 175

Val Asn Asn Gly Val Leu Ala Leu Ala Ser Ser Val Gly Pro Thr Tyr
            180                 185                 190

Leu Ser Pro Phe Ala Thr Tyr Glu Val Thr Pro Val Leu Gly Ile Ser
        195                 200                 205

Gln Arg Asn Gly Asn Val Lys Ser Lys Gly Leu Gln Asn Trp Ser Ile
    210                 215                 220

Gly Tyr Tyr Ile Tyr Met Val Ser Ser Ala Gly Leu Val Asn Gly Leu
225                 230                 235                 240

Ile Thr Leu Glu Leu Ala His Asp Leu Thr Gly Ala Ser Gly Glu Asn
                245                 250                 255

Ser Leu Thr Ser Gly Leu Asn Phe Thr Phe Val Leu Ser Pro Met Tyr
            260                 265                 270

Pro Ile Glu Thr Glu Val Asn Leu Ser Leu Ile Val Pro Pro Thr Val
        275                 280                 285

Ser Pro Thr Asn Gln Asn His Val Phe Val Pro Asn Ser Asn Gln Ser
    290                 295                 300

Asp Val Gly Tyr Leu Gly Leu Pro Pro His Thr Arg Asp Asn Trp Tyr
305                 310                 315                 320

Val Pro Ile Asp Ser Pro Gly Leu Arg Leu Val Ser Phe Met Pro Thr
                325                 330                 335

Ala Thr Gly Asn Glu Lys Phe Gly Gln Gly Thr Leu Gly Tyr Cys Ala
            340                 345                 350

Ala Thr Ile Gln Asn Thr Ser Ser Gly Thr Thr Pro Ser Asp Ala Ile
        355                 360                 365

Ala Phe Thr Val Ser Leu Pro Gln Thr Ser Gly Ser Asn Trp Phe Asp
    370                 375                 380

Gln Asn Ala Pro Asp Thr Val Val Thr Thr Gly Pro Ile
385                 390                 395

<210> SEQ ID NO 58
<211> LENGTH: 393
<212> TYPE: PRT
```

<213> ORGANISM: fowl adenovirus

<400> SEQUENCE: 58

```
Pro Arg Arg Ala Leu Ser Glu Pro Ser Arg Tyr Leu Ser Glu Gly Asp
1               5                   10                  15

Glu Arg Arg Lys Pro Lys Arg Ala Arg Pro Ala Thr Arg Ala Asn Gly
            20                  25                  30

Pro Leu Leu Asp Leu Val Tyr Pro Phe Asp Phe Asn Ala Gly Gly Gly
        35                  40                  45

Gly Gly Ser Gly Gly Gly Gly Gly Gly Gly Gln Gln Ile Ala
    50                  55                  60

Val Asp Pro Asp Gly Pro Leu Glu Leu Thr Gly Asp Leu Leu Thr Leu
65                  70                  75                  80

Asn Thr Lys Thr Pro Ile Tyr Val Ser Asp Arg Ala Val Ser Leu Leu
                85                  90                  95

Ile Asp Asp Asn Thr Leu Ala Thr Lys Gln Ala Asn Gly Ala Leu Met
            100                 105                 110

Val Lys Thr Ala Ala Pro Leu Asn Ser Gly Thr Gly Gly Gly Val Thr
        115                 120                 125

Leu Gly Phe Asp Pro Arg Thr Met Ala Leu Asp Ser Val Thr Gly Val
130                 135                 140

Leu Lys Val Leu Val Asp Ser Gln Gly Pro Leu Gln Ala Asp Thr Gly
145                 150                 155                 160

Gly Ile Thr Leu Gln Phe Asp Thr Gln Asp Phe Val Val Asn Asn Gly
                165                 170                 175

Val Leu Ala Leu Ala Ser Ser Val Gly Pro Thr Tyr Leu Ser Pro Phe
            180                 185                 190

Ala Thr Tyr Glu Val Thr Pro Val Leu Gly Ile Ser Gln Arg Asn Gly
        195                 200                 205

Asn Val Lys Ser Lys Gly Leu Gln Asn Trp Ser Ile Gly Tyr Tyr Ile
210                 215                 220

Tyr Met Val Ser Ser Ala Gly Leu Val Asn Gly Leu Ile Thr Leu Glu
225                 230                 235                 240

Leu Ala His Asp Leu Thr Gly Ala Ser Gly Glu Asn Ser Leu Thr Ser
                245                 250                 255

Gly Leu Asn Phe Thr Phe Val Leu Ser Pro Met Tyr Pro Ile Glu Thr
            260                 265                 270

Glu Val Asn Leu Ser Leu Ile Val Pro Pro Thr Val Ser Pro Thr Asn
        275                 280                 285

Gln Asn His Val Phe Val Pro Asn Ser Asn Gln Ser Asp Val Gly Tyr
290                 295                 300

Leu Gly Leu Pro Pro His Thr Arg Asp Asn Trp Tyr Val Pro Ile Asp
305                 310                 315                 320

Ser Pro Gly Leu Arg Leu Val Ser Phe Met Pro Thr Ala Thr Gly Asn
                325                 330                 335

Glu Lys Phe Gly Gln Gly Thr Leu Gly Tyr Cys Ala Ala Thr Ile Gln
            340                 345                 350

Asn Thr Ser Ser Gly Thr Thr Pro Ser Asp Ala Ile Ala Phe Thr Val
        355                 360                 365

Ser Leu Pro Gln Thr Ser Gly Ser Asn Trp Phe Asp Gln Asn Ala Pro
370                 375                 380

Asp Thr Val Val Thr Thr Gly Pro Ile
385                 390
```

<210> SEQ ID NO 59
<211> LENGTH: 393
<212> TYPE: PRT
<213> ORGANISM: fowl adenovirus

<400> SEQUENCE: 59

```
Pro Arg Arg Ala Leu Ser Glu Pro Ser Arg Tyr Leu Ser Glu Gly Asp
1               5                   10                  15

Glu Arg Arg Lys Pro Lys Arg Ala Arg Pro Ala Thr Arg Ala Asn Gly
            20                  25                  30

Pro Leu Leu Asp Leu Val Tyr Pro Phe Asp Phe Asn Ala Gly Gly Gly
        35                  40                  45

Gly Gly Ser Gly Gly Gly Gly Gly Gly Gly Gly Gln Gln Ile Ala
    50                  55                  60

Val Asp Pro Asp Gly Pro Leu Glu Leu Thr Gly Asp Leu Leu Thr Leu
65                  70                  75                  80

Asn Thr Lys Thr Pro Ile Tyr Val Ser Asp Arg Ala Val Ser Leu Leu
                85                  90                  95

Ile Asp Asp Asn Thr Leu Ala Thr Lys Gln Ala Asn Gly Ala Leu Met
            100                 105                 110

Val Lys Thr Ala Ala Pro Leu Asn Ser Gly Thr Gly Gly Gly Val Thr
        115                 120                 125

Leu Gly Phe Asp Pro Arg Thr Met Ala Leu Asp Ser Val Thr Gly Val
    130                 135                 140

Leu Lys Val Leu Val Asp Ser Gln Gly Pro Leu Gln Ala Asp Thr Gly
145                 150                 155                 160

Gly Ile Thr Leu Gln Phe Asp Thr Gln Asp Phe Val Val Asn Asn Gly
                165                 170                 175

Val Leu Ala Leu Ala Ser Ser Val Gly Pro Thr Tyr Leu Ser Pro Phe
            180                 185                 190

Ala Thr Tyr Glu Val Thr Pro Val Leu Gly Ile Ser Gln Arg Asn Gly
        195                 200                 205

Asn Val Lys Ser Lys Gly Leu Gln Asn Trp Ser Ile Gly Tyr Tyr Ile
    210                 215                 220

Tyr Met Val Ser Ser Ala Gly Leu Val Asn Gly Leu Ile Thr Leu Glu
225                 230                 235                 240

Leu Ala His Asp Leu Thr Gly Ala Ser Gly Glu Asn Ser Leu Thr Ser
                245                 250                 255

Gly Leu Asn Phe Thr Phe Val Leu Ser Pro Met Tyr Pro Ile Glu Thr
            260                 265                 270

Glu Val Asn Leu Ser Leu Ile Val Pro Pro Thr Val Ser Pro Thr Asn
        275                 280                 285

Gln Asn His Val Phe Val Pro Asn Ser Asn Gln Ser Asp Val Gly Tyr
    290                 295                 300

Leu Gly Leu Pro Pro His Thr Arg Asp Asn Trp Tyr Val Pro Ile Asp
305                 310                 315                 320

Ser Pro Gly Leu Arg Leu Val Ser Phe Met Pro Thr Ala Thr Gly Asn
                325                 330                 335

Glu Lys Phe Gly Gln Gly Thr Leu Gly Tyr Cys Ala Ala Thr Ile Gln
            340                 345                 350

Asn Thr Ser Ser Gly Thr Thr Pro Ser Asp Ala Ile Ala Phe Thr Val
        355                 360                 365

Ser Leu Pro Gln Thr Ser Gly Ser Asn Trp Phe Asp Gln Asn Ala Pro
    370                 375                 380
```

```
Asp Thr Val Val Thr Thr Gly Pro Ile
385                 390
```

<210> SEQ ID NO 60
<211> LENGTH: 396
<212> TYPE: PRT
<213> ORGANISM: fowl adenovirus

<400> SEQUENCE: 60

```
Pro Arg Arg Ala Leu Ser Glu Pro Ser Arg Tyr Leu Ser Glu Gly Asp
1               5                   10                  15

Glu Arg Arg Lys Pro Lys Arg Ala Arg Pro Ala Thr Arg Ala Asn Gly
            20                  25                  30

Pro Leu Leu Asp Leu Val Tyr Pro Phe Asp Phe Asn Ala Gly Gly Gly
        35                  40                  45

Gly Gly Ser Gly Gly Gly Gly Gly Gly Gly Gln Gln Ile Ala
    50                  55                  60

Val Asp Pro Asp Gly Pro Leu Glu Leu Thr Gly Asp Leu Leu Thr Leu
65                  70                  75                  80

Asn Thr Lys Thr Pro Ile Tyr Val Ser Asp Arg Ala Val Ser Leu Leu
                85                  90                  95

Ile Asp Asp Asn Thr Leu Ala Thr Lys Gln Ala Asn Gly Ala Leu Met
            100                 105                 110

Val Lys Thr Ala Ala Pro Leu Asn Ser Gly Thr Gly Gly Gly Val Thr
        115                 120                 125

Leu Gly Phe Asp Pro Arg Thr Met Ala Leu Asp Ser Val Thr Gly Val
130                 135                 140

Leu Lys Val Leu Val Asp Ser Gln Gly Pro Leu Gln Ala Asp Thr Gly
145                 150                 155                 160

Gly Ile Thr Leu Gln Phe Asp Thr Gln Asp Phe Val Val Asn Asn Gly
                165                 170                 175

Val Leu Ala Leu Ala Ser Ser Val Gly Pro Thr Tyr Leu Ser Pro Phe
            180                 185                 190

Ala Thr Tyr Glu Val Thr Pro Val Leu Gly Ile Ser Gln Arg Asn Gly
        195                 200                 205

Asn Val Lys Ser Lys Gly Leu Gln Asn Trp Ser Ile Gly Tyr Tyr Ile
    210                 215                 220

Tyr Met Val Ser Ser Ala Gly Leu Val Asn Gly Leu Ile Thr Leu Glu
225                 230                 235                 240

Leu Ala His Asp Leu Thr Gly Ala Ser Gly Glu Asn Ser Leu Thr Ser
                245                 250                 255

Gly Leu Asn Phe Thr Phe Val Leu Ser Pro Met Tyr Pro Ile Glu Thr
            260                 265                 270

Glu Val Asn Leu Ser Leu Ile Val Pro Pro Thr Val Ser Pro Thr Asn
        275                 280                 285

Gln Asn His Val Phe Val Pro Asn Ser Asn Gln Ser Asp Val Gly Tyr
    290                 295                 300

Leu Gly Leu Pro Pro His Thr Arg Asp Asn Trp Tyr Val Pro Ile Asp
305                 310                 315                 320

Ser Pro Gly Leu Arg Leu Val Ser Phe Met Pro Thr Ala Thr Gly Asn
                325                 330                 335

Glu Lys Phe Gly Gln Gly Thr Leu Gly Tyr Cys Ala Ala Thr Ile Gln
            340                 345                 350

Asn Thr Ser Ser Gly Thr Thr Pro Ser Asp Ala Ile Ala Phe Thr Val
```

```
            355                 360                 365
Ser Leu Pro Gln Thr Ser Gly Ser Asn Trp Phe Asp Gln Asn Ala Pro
    370                 375                 380

Asp Thr Val Val Thr Thr Gly Pro Ile Pro Phe Pro
385                 390                 395

<210> SEQ ID NO 61
<211> LENGTH: 429
<212> TYPE: PRT
<213> ORGANISM: fowl adenovirus

<400> SEQUENCE: 61

Met Leu Ser Gly Leu Lys Arg Arg Gly Glu Arg Glu Asp Glu Glu Gly
1               5                   10                  15

Glu Arg Val Glu Ser Pro Pro Thr Ala Lys Thr Leu Arg Gly Gly Pro
            20                  25                  30

Thr Thr Ala Pro Ala Ala Arg Ala Tyr Pro Asn Asp Asp Gln Leu Asp
        35                  40                  45

Leu Val Tyr Pro Phe Gln Tyr Ala Ala Ser Gly Gly Gly Gly Gly Gly
    50                  55                  60

Gly Gly Gly Ser Ser Val Thr Val Asp Pro Asp Gly Pro Leu Thr Leu
65                  70                  75                  80

Val Asp Gly Val Leu Gly Leu Asn Val Lys Thr Pro Val Val Val Ser
                85                  90                  95

Asp Gly Ala Val Ala Leu Phe Phe Asp Gly Asp Thr Leu Ala Leu Lys
            100                 105                 110

Ser Val Asn Arg Ser Leu Met Val Lys Thr Ala Ala Pro Val Thr Ala
        115                 120                 125

Gly Thr Gly Gly Val Thr Leu Leu Phe Asp Ala Lys Gly Leu Thr
    130                 135                 140

Leu Asp Gly Thr Thr Gly Ala Leu Ser Leu Arg Leu Asp Thr Asn Gly
145                 150                 155                 160

Pro Leu Ala Val Gly Asn Asp Gly Leu Thr Leu Thr Val Asp Pro Gln
                165                 170                 175

Ser Phe Glu Ile Val Asn Arg Met Leu Arg Leu Lys Gly Gly Gly Thr
            180                 185                 190

Gly Pro Thr Tyr Leu Ser Pro Phe Ala Thr Tyr Thr Leu Glu Ser Asn
        195                 200                 205

Gly Gly Ile Thr Gly Tyr Ser Gly Ile Val Gln Ser Asp Gln Asp Pro
    210                 215                 220

Val Gly Thr Gln Pro Thr Glu Lys Lys Ser Thr Trp Asn Val Gly Tyr
225                 230                 235                 240

Tyr Val Phe Met Val Thr Ser Ala Ala Met Val Asn Gly Tyr Ile Asn
                245                 250                 255

Val Gln Leu Pro Arg Ile His Val Ala Ala Thr Ser Gly Thr Asp Ser
            260                 265                 270

Leu Thr Thr Gly Leu Asn Phe Thr Phe Val Leu Pro Pro Met Tyr Pro
        275                 280                 285

Gln Glu Thr Glu Gly Asn Leu Ser Asn Ile Ala Phe Pro Val Leu Gln
    290                 295                 300

Pro Thr Asn Thr Asn Ser Ala Phe Val Pro Asn Ala Gln Met Ser Asp
305                 310                 315                 320

Gly Asn Ser Tyr Leu Gly Leu Pro Asp Val Ser Gln Arg Asn Thr Thr
                325                 330                 335
```

```
Val Trp His Val Gly Ile Thr Asn Pro Gly Leu Arg Thr Gln Thr Phe
                340                 345                 350

Val Pro Thr Ala Gln Gly Ala Thr Phe Gly Pro Ser Ser Phe Gly Met
            355                 360                 365

Cys Pro Ala Thr Val Asn Thr Gly Ser Thr Gly Asn Thr Pro Arg Asp
        370                 375                 380

Val Leu Val Phe Thr Phe Ala Leu Lys Gln Thr Gly Gly Ser Asn Trp
385                 390                 395                 400

Phe Gln Lys Ala Thr Thr Glu Thr Glu Thr Val Thr Thr Gly Pro Ile
                405                 410                 415

Phe Phe Ser Tyr Gln Gly Tyr Pro Tyr Ser Pro Ser Pro
                420                 425

<210> SEQ ID NO 62
<211> LENGTH: 644
<212> TYPE: PRT
<213> ORGANISM: duck adenovirus

<400> SEQUENCE: 62

Met Lys Arg Leu Arg Leu Asp Pro Asp Pro Val Tyr Pro Phe Gly Thr
1               5                   10                  15

Ser Glu Thr Ile Pro Met Pro Pro Phe Ile Glu Ala Gly Ser Gly Leu
                20                  25                  30

Ala Val Asn Gly Leu Gln Leu Tyr Ile Thr Ala Gln Ala Pro Val Gly
            35                  40                  45

Phe Thr Asn Lys Ala Val Thr Leu Lys Tyr Gly Asp Gly Leu Glu Val
        50                  55                  60

Asn Glu Asn Gly Glu Leu Ile Ala Thr Ala Ser Ser Ala Val Lys Pro
65                  70                  75                  80

Pro Leu His Phe Asp Lys Gly Tyr Ile Val Leu Asn Leu Gln Asp Pro
                85                  90                  95

Leu Gly Val Ile Asp Gly Lys Leu Gly Val Lys Leu Gly Pro Gly Val
            100                 105                 110

His Ile Asn Gly Glu Gly Ala Val Ala Val Glu Ser Pro Val Asp Pro
        115                 120                 125

Ile Thr Leu Asp Thr Ala Gly Arg Ile Thr Leu Asn Tyr Gly Thr Gly
    130                 135                 140

Leu Asn Val Ser Asp Gly Lys Leu Arg Leu Val Ser Pro Glu Ser Pro
145                 150                 155                 160

Leu Thr Leu Leu Gly Asn Gly Lys Val Ala Leu Asn Phe Gly Asn Ser
                165                 170                 175

Met Glu Leu Val Gln Gly Thr Leu Gln Leu Lys Ala Pro Leu Asn Pro
            180                 185                 190

Leu Phe Met Thr Pro Ala Gly Ala Ile Gly Leu Arg Val Asp Asp Met
        195                 200                 205

Phe Asn Ile Ser Glu Gly Leu Leu Ser Phe Lys Met Pro Ser Asp Pro
    210                 215                 220

Ile Ser Phe Asn Ala Asp Gly Met Leu Ser Leu Asn Thr Asn Asp Thr
225                 230                 235                 240

Leu Gln Thr Thr Gly Gly Leu Leu Gly Leu Thr Glu Pro Ala Lys Pro
                245                 250                 255

Leu Lys Leu Ala Asp Gly Lys Leu Gly Val Asn Val Gly Leu Gly Leu
            260                 265                 270

Ala Val Ser Asn Gly Ser Leu Thr Val Asn Ala Gly Gln Gly Leu Thr
        275                 280                 285
```

```
Ile Arg Asn Asn Ala Val Ala Val Asn Gly Gly Asn Thr Leu Ala Phe
    290                 295                 300

Asn Asn Tyr Gly Glu Val Glu Ile Lys Asn Pro Arg Asn Pro Ile Ser
305                 310                 315                 320

Leu Thr Gln Asp Gly Glu Leu Ala Leu Ile Ile Gly Tyr Gly Leu Thr
                325                 330                 335

Thr Leu Asp Gly Arg Leu Thr Leu Leu Thr Ala Ser Thr Ser Pro Ile
            340                 345                 350

Ala Val Gly Pro Thr Gly Val Thr Phe Asn Val Thr Pro Ser Asp Phe
        355                 360                 365

Tyr Phe Leu Ser Ser Lys Leu Ala Leu Asn Val Glu Thr Arg Gly Gly
    370                 375                 380

Leu Glu Lys Ser Asp Thr Gly Leu Lys Ile Lys Arg Ala Ala Pro Leu
385                 390                 395                 400

Ser Ile Thr Ser Asp Gly Glu Leu Thr Leu Ala Tyr Asp Ser Thr Asp
                405                 410                 415

Phe Gln Val Thr Glu Asn Gly Leu Ala Leu Lys Val Ser Pro Thr Gln
            420                 425                 430

Thr Pro Leu Thr Arg Ile Ile Ser Met Gly Asn Asn Leu Phe Asp Ser
        435                 440                 445

Gly Tyr Glu Ile Phe Ala Ser Cys Pro Gln Asn Lys Ala Ala Lys Val
    450                 455                 460

Ala Gly Tyr Val Tyr Leu Thr Ser Val Gly Gly Leu Val His Gly Thr
465                 470                 475                 480

Ile Gln Ile Lys Ala Thr Ala Gly Tyr Trp Phe Thr Gly Gly Asn Ser
                485                 490                 495

Val Gln Glu Ser Ile Arg Phe Gly Leu Val Leu Cys Pro Phe Ser Ala
            500                 505                 510

Arg Asp Pro Thr Ala Asn Leu Ser Gly Trp Pro Ala Pro Val Val Trp
        515                 520                 525

Ser Gly Asp Ser Asn Thr Pro Leu Tyr Phe Ala Ala Asn Ala Ile Ser
    530                 535                 540

Tyr Thr Asn Asn Arg Val Asn Leu Ala Val Thr Gly Asn Phe Tyr Lys
545                 550                 555                 560

Glu Glu Thr Glu Leu Pro Gly Tyr Thr Arg His Ser Phe Cys Pro Thr
                565                 570                 575

Gly Thr Thr Gly Met Asn Phe Thr Gly Gly Asn Leu Tyr Val Cys Pro
            580                 585                 590

Cys Thr Val Asn Thr Gly Ala Thr Thr Leu Asn Ala Ile Tyr Met Val
        595                 600                 605

Phe Val Ile Thr Gln Ser Ala Leu Gly Thr Asn Phe Phe Ala Ser Asn
    610                 615                 620

Thr Pro Pro Asn Thr Phe Phe Leu Thr Pro Pro Ile Pro Phe Thr Tyr
625                 630                 635                 640

Val Gly Ala Gln

<210> SEQ ID NO 63
<211> LENGTH: 535
<212> TYPE: PRT
<213> ORGANISM: Bovine adenovirus type 1

<400> SEQUENCE: 63

Met Lys Arg Ala Arg Trp Asp Pro Val Tyr Pro Phe Thr Glu Glu Arg
1               5                   10                  15
```

```
Leu Ile Pro Leu Pro Pro Phe Ile Gln Ala Gly Asn Gly Leu Glu Ser
         20                  25                  30

Glu Gly Leu Ile Leu Ser Leu Lys Phe Thr Asp Pro Ile Thr Ile Asn
             35                  40                  45

Pro Gly Gly Phe Leu Thr Leu Lys Thr Gly Asp Gly Val Gln Ile Asn
 50                  55                  60

Lys Asn Gly Glu Leu Thr Thr Asp Ala Ala Val Gln Val Gln Glu Pro
 65                  70                  75                  80

Leu Glu Lys Asp Ser Asn Gly Ile Lys Ile Asn Leu Asp Ser Ala Leu
                 85                  90                  95

Ser Val Asp Ser Ala Gly Lys Leu Thr Val Ala Leu Asn Pro Leu
                100                 105                 110

Glu Asn Thr Leu Thr Gly Val Arg Leu Lys Leu Ser Asn Phe Phe Ser
             115                 120                 125

Ile Asp Asp Ser Gly Lys Leu Val Ile Thr Ser Pro Glu Leu Pro Leu
130                 135                 140

Ser Thr Thr Pro Glu Gly Lys Leu Phe Ile Gln Leu Ser Asn Cys Phe
145                 150                 155                 160

Ala Thr Asp Asn Gly Lys Leu Val Leu Thr Ser Pro Glu Leu Pro Leu
                165                 170                 175

Ser Val Thr Pro Glu Gly Lys Ile Phe Leu Gln Leu Ser Asn Ser Phe
                180                 185                 190

His Thr Asp Thr Asn Gly Asn Leu Ala Leu Ala Ser Pro Asn Pro Pro
             195                 200                 205

Leu Ser Val Asn Asn Glu Gly Lys Ile Tyr Leu Gln Leu Ser Asn Ser
             210                 215                 220

Phe Asn Ile Asp Asn Thr Gly Lys Leu Val Leu Ala Ser Pro Glu Leu
225                 230                 235                 240

Pro Leu Ser Val Thr Ser Glu Gly Lys Leu Phe Leu Lys Leu Gly Gln
                245                 250                 255

Pro Leu Thr Ile Thr Asp Ser Leu Leu Thr Leu Lys Thr Glu Asn Pro
                260                 265                 270

Leu Ala Val Thr Asp Gly Phe Leu Lys Ile Lys Leu Ser Asp Pro Phe
                275                 280                 285

Glu Glu Leu Asn Gly Asn Leu Ala Ile Lys Thr Asp Tyr Pro Leu Ala
 290                 295                 300

Val Thr Glu Gly Ser Leu Lys Ile Lys Leu Ser Asp Pro Phe Glu Glu
305                 310                 315                 320

Arg Asn Ser Asn Leu Thr Leu Lys Thr Asn Tyr Pro Leu Ser Val Asp
                325                 330                 335

Thr Gly Phe Leu Asn Ile Lys Leu Ala Glu Pro Phe Glu Val Leu Asn
                340                 345                 350

Asp Asn Leu Ala Leu Gly Leu Asn Asn Ser Leu Thr Val Glu Ser Gly
                355                 360                 365

Lys Leu Ala Val Lys Thr Ala Gly Pro Ile Gln Ser Thr Glu Gln Gly
 370                 375                 380

Ile Asn Leu Ser Val Ala Asn Pro Phe Ser Ile Ser Ser Asn Gln Leu
385                 390                 395                 400

Ser Leu Lys Leu Ala Phe Pro Leu Thr Ile Asn Thr Ala Gly Ala Leu
                405                 410                 415

Thr Thr Ser Thr Arg Gln Gly Ser Arg Val Val Gly Phe Met Asp Phe
                420                 425                 430
```

```
Ile Ile Ala Leu Gly Trp Gln Ile Pro Ser Asn Ile Arg Tyr Ile
            435                 440                 445

Tyr Ile Leu Asn Cys Ser Gln Phe Met Pro Thr Ser Asp Val Thr Thr
450                 455                 460

Ile Tyr Phe Gln Ala Asp Ser Gly Leu Glu Ser Ile Phe Val Met Asp
465                 470                 475                 480

Ser Pro Phe Tyr Ala Ser Cys Thr Gln Gln Leu Pro Asp Lys Thr Ile
                485                 490                 495

Lys Thr Tyr Gly Val Thr Ile Ser Lys Lys Gln Ser Ile Ile Ser Ile
                500                 505                 510

Asn Phe Ser Ser Ser Leu Glu Pro Asn Ile Met Val Ser Ala Trp Thr
            515                 520                 525

Ala Ser Ile Thr Arg Thr Gln
            530                 535

<210> SEQ ID NO 64
<211> LENGTH: 793
<212> TYPE: PRT
<213> ORGANISM: fowl adenovirus

<400> SEQUENCE: 64

Met Asn Glu Glu Val Pro Leu Lys Arg Val Ser Pro Asp Glu Thr Glu
1               5                   10                  15

Thr Val Pro Lys Lys Pro Arg Thr Asp Val Arg Asp Thr Val Arg Ala
                20                  25                  30

Gly Thr Asp Asp Thr Val Asp Leu Val Tyr Pro Phe Trp Trp Asn Leu
            35                  40                  45

Gly Thr Gly Gly Gly Gly Gly Gly Gly Gly Gly Gly Gly Gly Ser Gly
50                  55                  60

Thr Ser Leu Gln Pro Asn Asp Pro Leu Tyr Ala Ala Ser Gly Thr Ile
65                  70                  75                  80

Asn Leu Arg Met Thr Ser Pro Leu Thr Leu Ser Gln Arg Ala Leu Ala
                85                  90                  95

Leu Lys Thr Asp Ser Thr Leu Thr Leu Asn Thr Gln Gly Gln Leu Gly
                100                 105                 110

Val Ser Leu Thr Pro Gly Asp Gly Leu Val Leu Asn Thr Asn Gly Leu
            115                 120                 125

Ser Ile Asn Ala Asp Pro Gln Thr Leu Ala Phe Asn Asn Ser Gly Ala
        130                 135                 140

Leu Glu Val Asn Leu Asp Pro Asp Gly Pro Trp Ser Lys Thr Ala Thr
145                 150                 155                 160

Gly Ile Asp Leu Arg Leu Asp Pro Thr Thr Leu Glu Val Asp Asn Trp
                165                 170                 175

Glu Leu Gly Val Lys Leu Asp Pro Asp Glu Ala Ile Asp Ser Gly Pro
            180                 185                 190

Asp Gly Leu Cys Leu Asn Leu Asp Glu Thr Leu Leu Leu Ala Thr Asn
        195                 200                 205

Ser Thr Ser Gly Lys Thr Glu Leu Gly Val His Leu Asn Thr Ser Gly
210                 215                 220

Pro Ile Thr Ala Asp Asp Gln Gly Ile Asp Leu Asp Val Asp Pro Asn
225                 230                 235                 240

Thr Met Gln Val Asn Thr Gly Pro Ser Gly Met Leu Ala Val Lys
                245                 250                 255

Leu Lys Ser Gly Gly Gly Leu Thr Ala Asp Pro Asp Gly Ile Ser Val
            260                 265                 270
```

-continued

```
Thr Ala Thr Val Ala Pro Pro Ser Ile Ser Ala Thr Ala Pro Leu Thr
            275                 280                 285
Tyr Thr Ser Gly Thr Ile Ala Leu Thr Thr Asp Thr Gln Thr Met Gln
290                 295                 300
Val Asn Ser Asn Gln Leu Ala Val Lys Leu Lys Thr Gly Gly Gly Leu
305                 310                 315                 320
Thr Ala Asp Ala Asp Gly Ile Ser Val Ser Val Ala Pro Thr Pro Thr
                325                 330                 335
Ile Ser Ala Ser Pro Pro Leu Thr Tyr Thr Asn Gly Gln Ile Gly Leu
                340                 345                 350
Ser Ile Gly Asp Gln Ser Leu Gln Val Ser Ser Gly Gln Leu Gln Val
            355                 360                 365
Lys Leu Lys Ser Gln Gly Gly Ile Gln Gln Ser Thr Gln Gly Leu Gly
370                 375                 380
Val Ala Val Asp Gln Thr Leu Lys Ile Val Ser Asn Thr Leu Glu Val
385                 390                 395                 400
Asn Thr Asp Pro Ser Gly Pro Leu Thr Ser Gly Asn Asn Gly Leu Ser
                405                 410                 415
Leu Ala Ala Val Thr Pro Leu Ala Val Ser Ser Ala Gly Val Thr Leu
            420                 425                 430
Asn Tyr Gln Ser Pro Leu Thr Val Thr Ser Asn Ser Leu Gly Leu Ser
            435                 440                 445
Ile Ala Ala Pro Leu Gln Ala Gly Ala Gln Gly Leu Thr Val Asn Thr
450                 455                 460
Met Glu Pro Leu Ser Ala Ser Ala Gln Gly Ile Gln Leu His Tyr Gly
465                 470                 475                 480
Gln Gly Phe Gln Val Val Ala Gly Thr Leu Gln Leu Leu Thr Asn Pro
                485                 490                 495
Pro Ile Val Val Ser Ser Arg Gly Phe Thr Leu Leu Tyr Thr Pro Ala
                500                 505                 510
Phe Thr Val Ser Asn Asn Met Leu Gly Leu Asn Val Asp Gly Thr Asp
            515                 520                 525
Cys Val Ala Ile Ser Ser Ala Gly Leu Gln Ile Arg Lys Glu Ala Pro
            530                 535                 540
Leu Tyr Val Thr Ser Gly Ser Thr Pro Ala Leu Ala Leu Lys Tyr Ser
545                 550                 555                 560
Ser Asp Phe Thr Ile Thr Asn Gly Ala Leu Ala Leu Ala Asn Ser Gly
                565                 570                 575
Gly Gly Gly Ser Ser Thr Pro Glu Val Ala Thr Tyr His Cys Gly Asp
                580                 585                 590
Asn Leu Leu Glu Ser Tyr Asp Ile Phe Ala Ser Leu Pro Asn Thr Asn
            595                 600                 605
Ala Ala Lys Val Ala Ala Tyr Cys Arg Leu Ala Ala Ala Gly Gly Val
            610                 615                 620
Val Ser Gly Thr Ile Gln Val Thr Ser Tyr Ala Gly Arg Trp Pro Lys
625                 630                 635                 640
Val Gly Asn Ser Val Thr Asp Gly Ile Lys Phe Ala Ile Val Val Ser
                645                 650                 655
Pro Pro Met Asp Lys Asp Pro Arg Ser Asn Leu Ser Gln Trp Leu Gly
                660                 665                 670
Ala Thr Val Phe Pro Ala Gly Ala Thr Thr Ala Leu Phe Ser Pro Asn
            675                 680                 685
```

```
Pro Tyr Gly Ser Leu Asn Thr Ile Thr Thr Leu Pro Ser Ile Ala Ser
    690                 695                 700

Asp Trp Tyr Val Pro Glu Ser Asn Leu Val Thr Tyr Thr Lys Ile His
705                 710                 715                 720

Phe Lys Pro Thr Gly Ser Gln Gln Leu Gln Leu Ala Ser Gly Glu Leu
                725                 730                 735

Val Val Ala Ala Ala Lys Ser Pro Val Gln Thr Thr Lys Tyr Glu Leu
            740                 745                 750

Ile Tyr Leu Gly Phe Thr Leu Lys Gln Asn Ser Ser Gly Thr Asn Phe
                755                 760                 765

Phe Asp Pro Asn Ala Ser Ser Asp Leu Ser Phe Leu Thr Pro Pro Ile
770                 775                 780

Pro Phe Thr Tyr Leu Gly Tyr Tyr Gln
785                 790

<210> SEQ ID NO 65
<211> LENGTH: 543
<212> TYPE: PRT
<213> ORGANISM: Ovine adenovirus

<400> SEQUENCE: 65

Met Lys Arg Ala Arg Trp Asp Pro Val Tyr Pro Phe Ser Glu Glu Arg
1               5                   10                  15

Leu Val Pro Leu Pro Pro Phe Ile Glu Ala Gly Lys Gly Leu Lys Ser
                20                  25                  30

Glu Gly Leu Ile Leu Ser Leu Asn Phe Thr Asp Pro Ile Thr Ile Asn
            35                  40                  45

Gln Thr Gly Phe Leu Thr Val Lys Leu Gly Asp Gly Ile Phe Ile Asn
    50                  55                  60

Gly Glu Gly Gly Leu Ser Ser Thr Ala Pro Lys Val Lys Val Pro Leu
65                  70                  75                  80

Thr Val Ser Asp Glu Thr Leu Gln Leu Leu Ser Asn Ser Leu Thr
                85                  90                  95

Thr Glu Ser Asp Ser Leu Ala Leu Lys Gln Pro Gln Leu Pro Leu Lys
                100                 105                 110

Ile Asn Asp Glu Gly Ser Leu Val Leu Asn Leu Asn Thr Pro Leu Asn
            115                 120                 125

Leu Gln Asn Glu Arg Leu Ser Leu Asn Val Ser Asn Pro Leu Lys Ile
    130                 135                 140

Ala Ala Asp Ser Leu Thr Ile Asn Leu Lys Glu Pro Leu Gly Leu Gln
145                 150                 155                 160

Asn Glu Ser Leu Gly Leu Asn Leu Ser Asp Pro Met Asn Ile Thr Pro
                165                 170                 175

Glu Gly Asn Leu Gly Ile Lys Leu Lys Asn Pro Met Lys Val Glu Glu
            180                 185                 190

Ser Ser Leu Ala Leu Asn Tyr Lys Asn Pro Leu Ala Ile Ser Asn Asp
        195                 200                 205

Ala Leu Ser Ile Asn Ile Ala Asn Pro Leu Thr Val Asn Thr Ser Gly
210                 215                 220

Ser Leu Gly Ile Ser Tyr Ser Thr Pro Leu Arg Ile Ser Asn Asn Ala
225                 230                 235                 240

Leu Ser Leu Phe Ile Gly Lys Pro Leu Gly Leu Gly Thr Asp Gly Ser
                245                 250                 255

Leu Thr Val Asn Leu Thr Arg Pro Leu Val Cys Arg Gln Asn Thr Leu
            260                 265                 270
```

```
Ala Ile Asn Tyr Ser Ala Pro Leu Val Ser Leu Gln Asp Asn Leu Thr
            275                 280                 285

Leu Ser Tyr Ala Gln Pro Leu Thr Val Ser Asp Asn Ser Leu Arg Leu
        290                 295                 300

Ser Leu Asn Ser Pro Leu Asn Thr Asn Ser Asp Gly Lys Leu Ser Val
305                 310                 315                 320

Asn Tyr Ser Asn Pro Leu Val Val Thr Asp Ser Asn Leu Thr Leu Ser
            325                 330                 335

Val Lys Lys Pro Val Met Ile Asn Asn Thr Gly Asn Val Asp Leu Ser
        340                 345                 350

Phe Thr Ala Pro Ile Lys Leu Asn Asp Ala Glu Gln Leu Thr Leu Glu
            355                 360                 365

Thr Thr Glu Pro Leu Glu Val Ala Asp Asn Ala Leu Lys Leu Lys Leu
        370                 375                 380

Gly Lys Gly Leu Thr Val Ser Asn Asn Ala Leu Thr Leu Asn Leu Gly
385                 390                 395                 400

Asn Gly Leu Thr Phe Gln Gln Gly Leu Leu Gln Ile Lys Thr Asn Ser
            405                 410                 415

Ser Leu Gly Phe Asn Ala Ser Gly Glu Leu Ser Thr Ala Thr Lys Gln
        420                 425                 430

Gly Thr Ile Thr Val Asn Phe Leu Ser Thr Thr Pro Ile Ala Phe Gly
            435                 440                 445

Trp Gln Ile Ile Pro Thr Thr Val Ala Phe Ile Tyr Ile Leu Ser Gly
        450                 455                 460

Thr Gln Phe Thr Pro Gln Ser Pro Val Thr Ser Leu Gly Phe Gln Pro
465                 470                 475                 480

Pro Gln Asp Phe Leu Asp Phe Phe Val Leu Ser Pro Phe Val Thr Ser
            485                 490                 495

Val Thr Gln Ile Val Gly Asn Asp Val Lys Val Ile Gly Leu Thr Ile
        500                 505                 510

Ser Lys Asn Gln Ser Thr Ile Thr Met Lys Phe Thr Ser Pro Leu Ala
            515                 520                 525

Glu Asn Val Pro Val Ser Met Phe Thr Ala His Gln Phe Arg Gln
        530                 535                 540

<210> SEQ ID NO 66
<211> LENGTH: 429
<212> TYPE: PRT
<213> ORGANISM: Frog virus 3

<400> SEQUENCE: 66

Met Ala Gln Ser Ser Lys Arg Leu Arg Arg Asp Ala Glu Ala Ala Lys
1               5                   10                  15

Ser Asp Leu Asn Leu Val Tyr Pro Phe Phe Ala Pro Lys Ile Asn Ile
            20                  25                  30

Thr Pro Pro Phe Ile Asn Val Gly Glu Gly Leu Asp Val Ser Gly Leu
        35                  40                  45

Thr Leu Arg Leu Lys Ile Gly Ala Gly Leu Thr Phe Asn Ser Asp Gly
    50                  55                  60

Glu Leu Thr Val Ile Gly Gly Asp Glu Leu Lys Val Ser Ala Pro Leu
65                  70                  75                  80

Met Tyr Gln Gly Gly Val Leu Ala Leu Asn Lys Gly Ser Asn Leu Phe
            85                  90                  95

Val Gln Asn Gly Asp Leu Phe Gly Pro Ile Pro Ser Gly Pro Leu Tyr
```

```
            100                 105                  110
Ile Asp Asn Gln Lys Met Ser Val Lys Ile Gly Asp Gly Leu Lys Leu
            115                 120                 125
Asp Gly Asp Gln Leu Ala Leu Tyr Ile Asp Pro Val Phe Ser Ser Arg
    130                 135                 140
Asn Gly Val Cys Asp Leu Asn Thr Thr Pro Leu Thr Lys Ser Asp
145                 150                 155                 160
Asn Lys Leu Ser Val Ser Ile Gly Asn Gly Leu Lys Leu Asp Gly Gly
                165                 170                 175
Ala Leu Ala Ser Ala Trp Lys Phe Lys Tyr Pro Leu Lys Ser Val Asn
            180                 185                 190
Ser Asn Val Thr Leu Ser Leu Gly Ser Glu Phe Gln Thr Leu Asn Asn
        195                 200                 205
Glu Leu Arg Cys Lys Leu Leu Ser Pro Leu Ser Thr Ser Gln Gly
        210                 215                 220
Ile Ala Leu Asp Leu Gly Ala Gly Leu Gln Leu Lys Asn Asn Arg Leu
225                 230                 235                 240
Thr Leu Ala Val Ser Pro Pro Phe Ser Thr Gly Gly Leu Ser Leu
                245                 250                 255
Leu Leu Asp Pro Ser Leu Arg Leu Ile Ser Gly Ala Leu Gly Leu Lys
            260                 265                 270
Pro Ser Ser Ala Ser Cys Ile Val Ser Pro Ala Gly Val Glu Leu
            275                 280                 285
Lys Thr Gly Lys Gly Leu Gly Val Thr Gly Gly Ser Leu Glu Leu Lys
            290                 295                 300
Leu Ala Ala Ser Thr Phe Ser Leu Thr Ser Ala Thr Gly Gln Thr Ile
305                 310                 315                 320
Thr Ile Lys Leu Leu Gln Met Asp Ser Tyr Ile Cys Ile Ser Phe Leu
                325                 330                 335
Gly Ser Val Val Leu Gln Ala Ala Asp Phe Asn Val Asn Asp Leu Thr
                340                 345                 350
Leu Leu Lys Phe Thr Val Asn Phe Thr Glu Asn Ile Asp Leu Thr Phe
            355                 360                 365
Ser Gly Ser Ala Ile Ser Leu Ile Glu Phe Gly Thr Lys Val Leu Lys
        370                 375                 380
Thr Arg Glu Met Val Asn Val Thr Phe Ser Ser Glu Gly Gly Val Thr
385                 390                 395                 400
Gln Leu Ser Ile Asp Arg Thr Thr Pro Thr Ser Gly Ser Phe Asp Ser
                405                 410                 415
Val Gln Phe Ile Ser Thr Pro Phe Phe Ala Tyr Leu Gln
            420                 425

<210> SEQ ID NO 67
<211> LENGTH: 454
<212> TYPE: PRT
<213> ORGANISM: fowl adenovirus

<400> SEQUENCE: 67

Met Ala Thr Pro Gly Lys Arg Ser Ala Glu Glu Pro Asp Gln Gln Thr
1               5                   10                  15
Leu Lys Lys Ser Lys Gln Ser Asp Gln Ser Gln Gly Leu Asn Leu Ala
            20                  25                  30
Tyr Pro Phe Asp Lys Ile Thr Glu Phe Glu Ala Thr Pro Pro Phe Ile
        35                  40                  45
```

```
His Val Gly Gln Gly Leu Asp Ile Ser Asp Leu Ser Leu Asn Met Arg
 50                  55                  60

Ile Gly Lys Gly Leu Lys Phe Glu Asn Gly Asn Leu Val Val Ser Asp
 65                  70                  75                  80

Gln Gln Tyr Asn Val Thr Pro Pro Leu Ile Ala Asp Gln Ser Thr Leu
                 85                  90                  95

Gly Leu Lys Tyr Asn Pro Asp Val Leu Ser Leu Thr His Ser Gly Ala
                100                 105                 110

Leu Thr Leu Pro Thr Ile Gln His Pro Leu Gln Ala Ser Ala Gly Lys
            115                 120                 125

Phe Glu Leu Ala Leu Ser Ser Gly Leu Lys Ser Asp Asp Gln Gly Leu
130                 135                 140

Thr Leu Asp Leu Asp Pro Val Phe Ser Thr Glu Ser Ser Lys Phe Leu
145                 150                 155                 160

Leu Asn Cys Ser Leu Pro Leu Asp Lys Asn Ser Asp Lys Leu Thr Leu
                165                 170                 175

Lys Phe Gly Asn Gly Leu Gly Leu Asn Asn Asp Gln Leu Glu Asn Thr
                180                 185                 190

Met Thr Tyr Asn Leu Pro Leu Lys Arg Asp Gly Thr Asn Val Ser Leu
            195                 200                 205

Ser Phe Gly Thr Asn Phe Lys Ile Leu Asn Glu Met Leu Asp Leu Asn
210                 215                 220

Leu Val Ala Pro Met Ser Asn Ser Ala Gly Leu Ala Leu Gln Phe
225                 230                 235                 240

Lys Ser Pro Leu Ser Ala Asp Asp Gly Ile Leu Ser Ile Lys Thr Asp
                245                 250                 255

Thr Ser Leu Gly Ile Thr Gly Asn Lys Leu Gly Ile Arg Leu Ala Pro
            260                 265                 270

Asn Ser Gly Leu Gln Ile Thr Pro Asn Gly Leu Ala Val Ser Val Asn
        275                 280                 285

Ala Val Gln Ile Leu Ser Ser Pro Leu Ile Thr Ala Ala Ser Ile Gly
    290                 295                 300

Pro Pro Thr Thr Met Val Thr Gly Thr Val Ser Pro Gly Arg Ala Thr
305                 310                 315                 320

Asn Gly Gln Phe Val Thr Lys Thr Ala Lys Val Leu Arg Tyr Lys Phe
                325                 330                 335

Val Arg Trp Asp Ala Leu Leu Ile Ile Gln Phe Ile Asp Asn Ile Gly
            340                 345                 350

Val Ile Glu Asn Pro Thr Phe Tyr Arg Asn Lys Ser Ile Glu Leu Arg
        355                 360                 365

Ser Ala Asp Phe Leu Ser Pro Thr Leu Asn Asn Thr Tyr Ile Val Pro
    370                 375                 380

Leu Asn Gly Gly Val Arg Val Glu Ser Pro Thr Ile Pro Val Gln Leu
385                 390                 395                 400

Glu Val Ile Leu Glu Asn Asn Ser Ser Phe Ile Gln Val Gly Phe Val
                405                 410                 415

Arg Leu Thr Val Lys Asn Gly Asn Pro His Met Ile Ile Gln Cys Asn
            420                 425                 430

Pro Val Pro Gly Asn Ile Lys Met Ile Lys Ile Lys Ser Val Met Leu
        435                 440                 445

Phe Thr Cys Leu Ile Gly
    450
```

<210> SEQ ID NO 68
<211> LENGTH: 479
<212> TYPE: PRT
<213> ORGANISM: fowl adenovirus

<400> SEQUENCE: 68

| | | | | | | | | | | | | | | |
|---|---|---|---|---|---|---|---|---|---|---|---|---|---|---|
| Met | Leu | Arg | Ala | Pro | Lys | Arg | Arg | His | Ser | Glu | Asn | Gly | Gln | Pro | Glu |
| 1 | | | | 5 | | | | | 10 | | | | | 15 | |
| Ser | Glu | Ala | Gly | Pro | Ser | Pro | Ala | Pro | Ile | Lys | Arg | Ala | Lys | Arg | Met |
| | | | 20 | | | | | 25 | | | | | 30 | | |
| Val | Arg | Ala | Ser | Gln | Leu | Asp | Leu | Val | Tyr | Pro | Phe | Asp | Tyr | Val | Ala |
| | | 35 | | | | | 40 | | | | | 45 | | | |
| Asp | Pro | Val | Gly | Gly | Leu | Asn | Pro | Pro | Phe | Leu | Gly | Gly | Ser | Gly | Pro |
| | 50 | | | | | 55 | | | | | 60 | | | | |
| Leu | Val | Asp | Gln | Gly | Gly | Gln | Leu | Thr | Leu | Asn | Val | Thr | Asp | Pro | Ile |
| 65 | | | | | 70 | | | | | 75 | | | | | 80 |
| Ile | Ile | Lys | Asn | Arg | Ser | Val | Asp | Leu | Ala | His | Asp | Pro | Ser | Leu | Asp |
| | | | | 85 | | | | | 90 | | | | | 95 | |
| Val | Asn | Ala | Gln | Gly | Gln | Leu | Ala | Val | Ala | Val | Asp | Pro | Glu | Gly | Ala |
| | | | 100 | | | | | 105 | | | | | 110 | | |
| Leu | Asp | Ile | Thr | Pro | Asp | Gly | Leu | Asp | Val | Lys | Val | Asp | Gly | Val | Thr |
| | | 115 | | | | | 120 | | | | | 125 | | | |
| Val | Met | Val | Asn | Asp | Asp | Trp | Glu | Leu | Ala | Val | Lys | Val | Asp | Pro | Ser |
| | 130 | | | | | 135 | | | | | 140 | | | | |
| Gly | Gly | Leu | Asp | Ser | Thr | Ala | Gly | Gly | Leu | Gly | Val | Ser | Val | Asp | Asp |
| 145 | | | | | 150 | | | | | 155 | | | | | 160 |
| Thr | Leu | Leu | Val | Asp | Gln | Gly | Glu | Leu | Gly | Val | His | Leu | Asn | Gln | Gln |
| | | | | 165 | | | | | 170 | | | | | 175 | |
| Gly | Pro | Ile | Thr | Ala | Asp | Ser | Ser | Gly | Ile | Asp | Leu | Glu | Ile | Asn | Pro |
| | | | 180 | | | | | 185 | | | | | 190 | | |
| Asn | Met | Phe | Thr | Val | Asn | Thr | Ser | Thr | Gly | Ser | Gly | Val | Leu | Glu | Leu |
| | | 195 | | | | | 200 | | | | | 205 | | | |
| Asn | Leu | Lys | Ala | Gln | Gly | Gly | Ile | Gln | Ala | Gly | Ser | Ser | Gly | Val | Gly |
| | 210 | | | | | 215 | | | | | 220 | | | | |
| Val | Ser | Val | Asp | Glu | Ser | Leu | Glu | Ile | Val | Asn | Asn | Thr | Leu | Glu | Val |
| 225 | | | | | 230 | | | | | 235 | | | | | 240 |
| Lys | Pro | Asp | Pro | Ser | Gly | Pro | Leu | Thr | Val | Ser | Ala | Asn | Gly | Leu | Gly |
| | | | | 245 | | | | | 250 | | | | | 255 | |
| Leu | Lys | Tyr | Asp | Ser | Asn | Thr | Leu | Ala | Val | Thr | Ala | Gly | Ala | Leu | Thr |
| | | | 260 | | | | | 265 | | | | | 270 | | |
| Val | Val | Gly | Gly | Gly | Ser | Val | Ser | Thr | Pro | Ile | Ala | Thr | Phe | Val | Ser |
| | | 275 | | | | | 280 | | | | | 285 | | | |
| Gly | Ser | Pro | Ser | Leu | Asn | Thr | Tyr | Asn | Ala | Thr | Ile | Val | Asn | Ser | Ser |
| | 290 | | | | | 295 | | | | | 300 | | | | |
| Ser | His | Pro | Phe | Ser | Cys | Ala | Tyr | Tyr | Leu | Gln | Gln | Trp | Asn | Val | Gln |
| 305 | | | | | 310 | | | | | 315 | | | | | 320 |
| Gly | Leu | Leu | Phe | Thr | Ser | Leu | Tyr | Val | Lys | Leu | Asp | Ser | Thr | Thr | Met |
| | | | | 325 | | | | | 330 | | | | | 335 | |
| Gly | Thr | Arg | Pro | Gly | Asp | Asn | Ser | Ser | Ala | Asn | Ala | Lys | Trp | Phe | Thr |
| | | | 340 | | | | | 345 | | | | | 350 | | |
| Phe | Trp | Val | Ser | Ala | Tyr | Leu | Gln | Gln | Cys | Asn | Pro | Ser | Gly | Ile | Gln |
| | | 355 | | | | | 360 | | | | | 365 | | | |
| Ala | Gly | Thr | Val | Ser | Pro | Ser | Thr | Ala | Ala | Leu | Ala | Asp | Phe | Glu | Pro |
| | 370 | | | | | 375 | | | | | 380 | | | | |

Met Ala Asn Arg Ser Val Ser Ser Pro Trp Thr Tyr Ser Ala Asn Ala
385                 390                 395                 400

Tyr Tyr Gln Pro Ser Ser Gly Glu Phe Gln Val Phe Thr Pro Val Val
            405                 410                 415

Thr Gly Ala Trp Asn Pro Gly Asn Ile Gly Ile Arg Val Leu Pro Val
        420                 425                 430

Pro Val Thr Ala Ser Gly Asp Arg Tyr Thr Leu Leu Cys Tyr Ser Leu
    435                 440                 445

Gln Cys Thr Asn Ser Ser Ile Phe Asn Pro Ala Asn Ser Gly Thr Met
450                 455                 460

Ile Val Gly Pro Val Leu Tyr Ser Cys Pro Ala Ala Ser Val Pro
465                 470                 475

<210> SEQ ID NO 69
<211> LENGTH: 479
<212> TYPE: PRT
<213> ORGANISM: fowl adenovirus

<400> SEQUENCE: 69

Met Leu Arg Ala Pro Lys Arg Arg His Ser Glu Asn Gly Gln Pro Glu
1               5                   10                  15

Ser Glu Ala Gly Pro Ser Pro Ala Pro Ile Lys Arg Ala Lys Arg Met
            20                  25                  30

Val Arg Ala Ser Gln Leu Asp Leu Val Tyr Pro Phe Asp Tyr Val Ala
        35                  40                  45

Asp Pro Val Gly Gly Leu Asn Pro Pro Phe Leu Gly Gly Ser Gly Pro
    50                  55                  60

Leu Val Asp Gln Gly Gly Gln Leu Thr Leu Asn Val Thr Asp Pro Ile
65                  70                  75                  80

Ile Ile Lys Asn Arg Ser Val Asp Leu Ala His Asp Pro Ser Leu Asp
                85                  90                  95

Val Asn Ala Gln Gly Gln Leu Ala Val Ala Val Asp Pro Glu Gly Ala
            100                 105                 110

Leu Asp Ile Thr Pro Asp Gly Leu Asp Val Lys Val Asp Gly Val Thr
        115                 120                 125

Val Met Val Asn Asp Asp Trp Glu Leu Ala Val Lys Val Asp Pro Ser
130                 135                 140

Gly Gly Leu Asp Ser Thr Ala Gly Gly Leu Gly Val Ser Val Asp Asp
145                 150                 155                 160

Thr Leu Leu Val Asp Gln Gly Glu Leu Gly Val His Leu Asn Gln Gln
                165                 170                 175

Gly Pro Ile Thr Ala Asp Ser Ser Gly Ile Asp Leu Glu Ile Asn Pro
            180                 185                 190

Asn Met Phe Thr Val Asn Thr Ser Thr Gly Ser Gly Val Leu Glu Leu
        195                 200                 205

Asn Leu Lys Ala Gln Gly Gly Ile Gln Ala Gly Ser Ser Gly Val Gly
    210                 215                 220

Val Ser Val Asp Glu Ser Leu Glu Ile Val Asn Asn Thr Leu Glu Val
225                 230                 235                 240

Lys Pro Asp Pro Ser Gly Pro Leu Thr Val Ser Ala Asn Gly Leu Gly
                245                 250                 255

Leu Lys Tyr Asp Asn Asn Thr Leu Ala Val Thr Ala Gly Ala Leu Thr
            260                 265                 270

Val Val Gly Gly Gly Ser Ile Ser Thr Pro Ile Ala Thr Phe Val Ser
        275                 280                 285

Gly Ser Ala Ser Leu Asn Ala Tyr Asn Ala Arg Met Val Asn Ser Ser
        290                 295                 300
Ala His Ala Phe Ser Cys Ala Tyr Tyr Leu Gln Gln Trp Asn Ile Gln
305                 310                 315                 320
Gly Leu Leu Phe Thr Ser Leu Tyr Leu Lys Leu Asp Ser Ala Thr Met
                325                 330                 335
Gly Asn Arg Pro Gly Asp Asn Ser Val Asn Ala Lys Trp Phe Thr
                340                 345                 350
Phe Trp Val Ser Ala Tyr Leu Gln Gln Cys Asn Pro Ser Gly Ile Gln
                355                 360                 365
Ala Gly Thr Val Ser Pro Ser Thr Ala Thr Leu Ala Asp Phe Glu Pro
        370                 375                 380
Met Ala Asn Arg Ser Val Ser Ser Pro Trp Thr Tyr Ser Ala Asn Gly
385                 390                 395                 400
Tyr Tyr Glu Pro Pro Ser Gly Glu Phe Gln Leu Phe Thr Pro Val Val
                405                 410                 415
Thr Gly Ala Trp Thr Pro Gly Asn Ile Gly Ile Arg Val Leu Pro Val
                420                 425                 430
Pro Val Ser Ala Ser Gly Asp Arg Tyr Thr Leu Leu Cys Tyr Ser Leu
        435                 440                 445
Gln Cys Thr Asn Ala Ser Ile Phe Asn Pro Asn Asn Ser Gly Thr Met
        450                 455                 460
Ile Val Gly Pro Val Leu Tyr Ser Cys Pro Ala Gly Ser Leu Pro
465                 470                 475

<210> SEQ ID NO 70
<211> LENGTH: 474
<212> TYPE: PRT
<213> ORGANISM: fowl adenovirus

<400> SEQUENCE: 70

Met Leu Arg Ala Pro Lys Arg Arg His Ser Glu Thr Glu Ala Gly Pro
1               5                   10                  15
Tyr Pro Ala Pro Ile Lys Arg Pro Lys Arg Met Val Arg Ala Ser Gln
                20                  25                  30
Leu Asp Leu Val Tyr Pro Phe Asp Tyr Val Ala Asp Pro Val Gly Gly
            35                  40                  45
Leu Asn Pro Pro Phe Leu Gly Gly Ser Gly Pro Leu Val Asp Gln Gly
        50                  55                  60
Gly Gln Leu Thr Leu Asn Val Thr Asp Pro Ile Ile Ile Lys Asn Arg
65                  70                  75                  80
Ser Val Asp Leu Ala His Asp Pro Ser Leu Asp Val Asn Ala Gln Gly
                85                  90                  95
Gln Leu Ala Val Ala Val Asp Pro Glu Gly Ala Leu Ala Ile Thr Pro
                100                 105                 110
Asp Gly Leu Asp Val Lys Val Asp Gly Val Thr Val Met Val Asn Asp
            115                 120                 125
Asp Trp Glu Leu Ala Val Lys Val Asp Pro Ala Gly Gly Leu Asp Ser
        130                 135                 140
Thr Ala Gly Gly Leu Gly Val Ser Val Asp Thr Leu Leu Val Asp
145                 150                 155                 160
Gln Gly Glu Leu Gly Val His Leu Asn Gln Gln Gly Pro Ile Thr Ala
                165                 170                 175
Asp Ser Ser Gly Ile Asp Leu Glu Ile Asn Pro Asn Met Phe Thr Val

```
                180             185             190
Asn Thr Ser Thr Gly Ser Gly Val Leu Glu Leu Asn Leu Lys Ala Gln
            195                 200                 205
Gly Gly Ile Gln Ala Asp Ser Ser Gly Val Gly Val Ser Val Asp Glu
        210                 215                 220
Ser Leu Gln Ile Val Asn Asn Thr Leu Glu Val Lys Pro Asp Pro Ser
225                 230                 235                 240
Gly Pro Leu Thr Val Ser Ala Asn Gly Leu Gly Leu Lys Tyr Asp Asn
                245                 250                 255
Asn Thr Leu Ala Val Thr Ala Gly Ala Leu Thr Val Val Gly Gly Gly
            260                 265                 270
Ser Val Ser Thr Pro Ile Ala Thr Phe Val Ser Gly Ser Pro Ser Leu
        275                 280                 285
Asn Thr Tyr Asn Ala Thr Val Asn Ser Ser Ala His Ala Phe Ser
            290                 295                 300
Cys Ala Tyr Tyr Leu Gln Gln Trp Asn Ile Gln Gly Leu Leu Phe Thr
305                 310                 315                 320
Ser Leu Tyr Leu Lys Leu Asp Ser Thr Thr Met Gly Thr Arg Pro Gly
                325                 330                 335
Asp Asn Ser Ser Val Asn Ala Lys Trp Phe Thr Phe Trp Val Ser Ala
            340                 345                 350
Tyr Leu Gln Gln Cys Asn Pro Ser Gly Ile Gln Ala Gly Thr Val Ser
        355                 360                 365
Pro Ser Thr Ala Thr Leu Thr Asp Phe Glu Pro Met Ala Asn Arg Ser
370                 375                 380
Val Ser Ser Ser Trp Thr Tyr Ser Ala Asn Ala Tyr Tyr Gln Pro Ser
385                 390                 395                 400
Ser Gly Glu Phe Gln Val Phe Thr Pro Val Val Thr Gly Ala Trp Asn
                405                 410                 415
Pro Gly Asn Ile Gly Val Arg Val Leu Pro Val Pro Val Ser Ala Ser
            420                 425                 430
Gly Asp Arg Tyr Thr Leu Leu Cys Tyr Ser Leu Gln Cys Thr Asn Ala
        435                 440                 445
Ser Ile Phe Asn Pro Ala Asn Ser Gly Thr Met Ile Val Gly Pro Val
450                 455                 460
Leu Tyr Ser Cys Pro Ala Ala Ser Val Pro
465                 470

<210> SEQ ID NO 71
<211> LENGTH: 461
<212> TYPE: PRT
<213> ORGANISM: fowl adenovirus

<400> SEQUENCE: 71

Met Leu Arg Ala Pro Lys Arg Arg His Ser Glu Asn Gly Lys Pro Glu
1               5                   10                  15
Thr Glu Ala Gly Pro Ser Pro Ala Pro Ile Lys Arg Ala Lys Arg Met
            20                  25                  30
Val Arg Ala Ser Gln Leu Asp Leu Val Tyr Pro Phe Asp Tyr Val Ala
        35                  40                  45
Asp Pro Val Gly Gly Leu Asn Pro Phe Leu Gly Ser Gly Pro
    50                  55                  60
Leu Val Asp Gln Gly Gly Gln Leu Thr Leu Asn Val Thr Asp Pro Ile
65                  70                  75                  80
```

```
Ile Ile Lys Asn Arg Ser Val Asp Leu Ala His Asp Pro Ser Leu Asp
             85                  90                  95

Val Asn Ala Gln Gly Gln Leu Ala Val Ala Val Asp Pro Glu Gly Ala
            100                 105                 110

Leu Asp Ile Thr Pro Asp Gly Leu Asp Val Lys Val Asp Pro Ser Gly
            115                 120                 125

Gly Leu Asp Ser Thr Ala Gly Gly Leu Gly Val Ser Val Asp Asp Thr
130                 135                 140

Leu Leu Val Asp Gln Gly Glu Leu Gly Val His Leu Asn Gln Gln Gly
145                 150                 155                 160

Pro Ile Thr Ala Asp Ser Ser Gly Ile Asp Leu Glu Ile Asn Pro Asn
            165                 170                 175

Met Phe Thr Val Asn Thr Ser Thr Gly Ser Gly Val Leu Glu Leu Asn
            180                 185                 190

Leu Lys Ala Gln Gly Gly Ile Gln Ala Asp Ser Ser Gly Val Gly Val
            195                 200                 205

Ser Val Asp Glu Ser Leu Gln Ile Val Asn Asn Thr Leu Glu Val Lys
            210                 215                 220

Pro Asp Pro Ser Gly Pro Leu Thr Val Ser Ala Asn Gly Leu Gly Leu
225                 230                 235                 240

Lys Tyr Asp Thr Asn Thr Leu Ala Val Thr Ala Gly Ala Leu Thr Val
            245                 250                 255

Val Gly Gly Gly Ser Val Ser Thr Pro Asn Arg Tyr Phe Cys Leu Gly
            260                 265                 270

Lys Ser Gln Pro Gln His Leu Gln Cys His Ala Val Asn Ser Ser Ala
            275                 280                 285

Asn Ala Phe Ser Cys Ala Tyr Tyr Leu Gln Gln Trp Asn Ile Gln Gly
            290                 295                 300

Leu Leu Val Thr Ser Leu Tyr Leu Lys Leu Asp Ser Ala Thr Met Gly
305                 310                 315                 320

Asn Arg Pro Gly Asp Leu Asn Ser Ala Asn Ala Lys Trp Phe Thr Phe
            325                 330                 335

Trp Val Ser Ala Tyr Leu Gln Gln Cys Asn Ser Gly Ile Gln Ala Gly
            340                 345                 350

Thr Val Ser Pro Ser Thr Ala Thr Leu Thr Asp Phe Glu Pro Met Ala
            355                 360                 365

Asn Arg Ser Val Thr Ser Pro Trp Thr Tyr Ser Ala Asn Gly Tyr Tyr
            370                 375                 380

Glu Pro Ser Ile Gly Glu Phe Gln Val Phe Ser Pro Val Val Thr Gly
385                 390                 395                 400

Ala Trp Asn Pro Gly Asn Ile Gly Ile Arg Val Leu Pro Val Pro Val
            405                 410                 415

Ser Ala Ser Gly Glu Arg Tyr Thr Leu Leu Cys Tyr Ser Leu Gln Cys
            420                 425                 430

Thr Asn Ala Ser Ile Phe Asn Pro Asn Asn Ser Gly Thr Met Ile Val
            435                 440                 445

Gly Pro Val Leu Tyr Ser Cys Pro Ala Gly Ser Leu Pro
450                 455                 460
```

UNITED STATES PATENT AND TRADEMARK OFFICE
CERTIFICATE OF CORRECTION

PATENT NO. : 10,220,088 B2
APPLICATION NO. : 14/913204
DATED : March 5, 2019
INVENTOR(S) : Michael Hess et al.

Page 1 of 1

It is certified that error appears in the above-identified patent and that said Letters Patent is hereby corrected as shown below:

In the Claims

<u>Claim 3, Column 175, Line 30:</u>
Delete "QOGH78" and replace with -- Q0GH78 --.

<u>Claim 3, Column 175, Line 30:</u>
Delete "055281" and replace with -- O55281 --.

Signed and Sealed this
Fourteenth Day of May, 2019

Andrei Iancu
*Director of the United States Patent and Trademark Office*